(12) United States Patent
Scheib et al.

(10) Patent No.: US 7,980,443 B2
(45) Date of Patent: Jul. 19, 2011

(54) END EFFECTORS FOR A SURGICAL CUTTING AND STAPLING INSTRUMENT

(75) Inventors: Charles J. Scheib, Loveland, OH (US); Geoffrey C. Hueil, Mason, OH (US); Mark S. Ortiz, Milford, OH (US); Douglas B. Hoffman, Harrison, OH (US); Patrick A. Weizman, Liberty Township, OH (US); Dean B. Bruewer, Fairfield, OH (US); Kevin R. Doll, Mason, OH (US); Bret W. Smith, Kings Mills, OH (US); William D. Kelly, Mason, OH (US); Ronald J. Kolata, Raleigh, NC (US); Joshua R. Uth, Mason, OH (US); Frederick E. Shelton, IV, Hillsboro, OH (US); William B. Weisenburgh, II, Maineville, OH (US); Jerome R. Morgan, Cincinnati, OH (US); Kyle P. Moore, Mason, OH (US); Mark H. Ransick, West Chester, OH (US); Steven G. Hall, Cincinnati, OH (US); Randall J. Tanguay, Lebanon, OH (US); Jeffrey D. Messerly, Cincinnati, OH (US); Galen C. Robertson, Cincinnati, OH (US); Andrew M. Zwolinski, Cincinnati, OH (US); Jeffrey S. Swayze, Hamilton, OH (US); Thomas W. Huitema, Cincinnati, OH (US); Glen A. Armstrong, Hamilton, OH (US); Shailendra K. Parihar, Mason, OH (US); Donna L. Korvick, Maineville, OH (US); Richard W. Timm, Cincinnati, OH (US); Gregory B. Blair, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 270 days.

(21) Appl. No.: 12/031,873

(22) Filed: Feb. 15, 2008

(65) Prior Publication Data

US 2009/0206140 A1    Aug. 20, 2009

(51) Int. Cl.
*A61B 17/068*    (2006.01)
(52) U.S. Cl. ............... 227/180.1; 227/19; 227/176.1
(58) Field of Classification Search .............. 227/19, 227/176.1, 175.1, 180.1; 606/139, 219
See application file for complete search history.

(56) References Cited

U.S. PATENT DOCUMENTS 3,079,606 A    3/1963    Bobrov et al.
(Continued)

FOREIGN PATENT DOCUMENTS

CA    2458946 A1    3/2003
(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Scott A. Smith
(74) *Attorney, Agent, or Firm* — Dean Garner

(57) ABSTRACT

In various embodiments, an anvil of a disposable loading unit including a first member having staple pockets for deforming staples, a first cover plate secured to the first member, and a second cover plate secured to at least one of the first member and the first cover plate, wherein the first and second cover plates can be configured to support the first member. In at least one embodiment, an anvil can include a first member inserted into a second member, where at least one of the first and second members can be deformed to retain one to the other. In various embodiments, a surgical stapling instrument can include a disposable loading unit comprising a staple cartridge, an anvil, and a sleeve, wherein the sleeve can be configured to be slid relative to the staple cartridge and the anvil to hold the anvil in a closed position.

20 Claims, 88 Drawing Sheets

U.S. PATENT DOCUMENTS

| | | |
|---|---|---|
| 3,490,675 A | 1/1970 | Green et al. |
| 3,499,591 A | 3/1970 | Green |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,040,715 A | 8/1991 | Green et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,211,649 A | 5/1993 | Kohler et al. |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,332,142 A | 7/1994 | Robinson et al. |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,397,324 A | 3/1995 | Carroll et al. |
| 5,405,072 A | 4/1995 | Zlock et al. |
| 5,413,272 A | 5/1995 | Green et al. |
| 5,417,361 A | 5/1995 | Williamson, IV |
| 5,425,745 A | 6/1995 | Green et al. |
| 5,474,566 A | 12/1995 | Alesi et al. |
| 5,478,354 A | 12/1995 | Tovey et al. |
| 5,480,089 A | 1/1996 | Blewett |
| 5,484,451 A | 1/1996 | Akopov et al. |
| 5,485,947 A | 1/1996 | Olson et al. |
| 5,487,499 A | 1/1996 | Sorrentino et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,509,596 A | 4/1996 | Green et al. |
| 5,529,235 A | 6/1996 | Boiarski et al. |
| 5,535,934 A | 7/1996 | Boiarski et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,605,273 A | 2/1997 | Hamblin et al. |
| 5,607,094 A | 3/1997 | Clark et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,543 A | 12/1997 | Burdorff |
| 5,702,408 A | 12/1997 | Wales et al. |
| 5,704,534 A | 1/1998 | Huitema et al. |
| 5,707,392 A | 1/1998 | Kortenbach |
| 5,711,472 A | 1/1998 | Bryan |
| 5,715,987 A | 2/1998 | Kelley et al. |
| 5,716,366 A | 2/1998 | Yates |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |

| Patent No. | Date | Inventor |
|---|---|---|
| 5,868,760 A | 2/1999 | McGuckin, Jr. |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,919,198 A | 7/1999 | Graves, Jr. et al. |
| 5,941,442 A | 8/1999 | Geiste et al. |
| 5,954,259 A | 9/1999 | Viola et al. |
| 6,010,054 A | 1/2000 | Johnson et al. |
| 6,032,849 A | 3/2000 | Mastri et al. |
| 6,045,560 A | 4/2000 | McKean et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,119,913 A | 9/2000 | Adams et al. |
| 6,126,058 A | 10/2000 | Adams et al. |
| 6,171,330 B1 | 1/2001 | Benchetrit |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,330,965 B1 | 12/2001 | Milliman et al. |
| 6,387,113 B1 | 5/2002 | Hawkins et al. |
| RE37,814 E | 8/2002 | Allgeyer |
| 6,436,107 B1 | 8/2002 | Wang et al. |
| 6,443,973 B1 | 9/2002 | Whitman |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,644,532 B2 | 11/2003 | Green et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,769,594 B2 | 8/2004 | Orban, III |
| 6,773,438 B1 | 8/2004 | Knodel et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,108,709 B2 | 9/2006 | Cummins |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,730 B2 | 10/2008 | Viola |
| 7,438,209 B1 | 10/2008 | Hess et al. |
| 7,441,685 B1 | 10/2008 | Boudreaux |
| 7,481,347 B2 | 1/2009 | Roy |
| 7,490,749 B2 | 2/2009 | Schall et al. |
| 7,494,039 B2 | 2/2009 | Racenet et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,559,450 B2 | 7/2009 | Wales et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,631,793 B2 | 12/2009 | Rethy et al. |
| 7,658,311 B2 | 2/2010 | Boudreaux |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 7,699,204 B2 | 4/2010 | Viola |
| 7,717,312 B2 | 5/2010 | Beetel |
| 7,731,072 B2 | 6/2010 | Timm et al. |
| 7,735,703 B2 | 6/2010 | Morgan et al. |
| 7,753,245 B2 | 7/2010 | Boudreaux et al. |
| 7,766,209 B2 | 8/2010 | Baxter, III et al. |
| 7,784,662 B2 | 8/2010 | Wales et al. |
| 7,793,812 B2 | 9/2010 | Moore et al. |
| 7,798,386 B2 | 9/2010 | Schall et al. |
| 7,810,692 B2 | 10/2010 | Hall et al. |
| 7,810,693 B2 | 10/2010 | Broehl et al. |

| | | |
|---|---|---|
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2005/0054946 A1 | 3/2005 | Krzyzanowski |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0100643 A1 | 5/2006 | Laufer et al. |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0045379 A1 | 3/2007 | Shelton, IV |
| 2007/0073340 A1 | 3/2007 | Shelton, IV et al. |
| 2007/0073341 A1 | 3/2007 | Smith |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton IV et al. |
| 2007/0246505 A1 | 10/2007 | Pace-Floridia et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314957 A1 | 12/2008 | Boudreaux |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0108048 A1 | 4/2009 | Zemlok et al. |
| 2009/0114701 A1 | 5/2009 | Zemlok et al. |
| 2009/0206125 A1 | 8/2009 | Huitema et al. |
| 2009/0206126 A1 | 8/2009 | Huitema et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206141 A1 | 8/2009 | Huitema et al. |

| | | | | | | |
|---|---|---|---|---|---|---|
| 2009/0206142 | A1 | 8/2009 | Huitema et al. | EP | 0653189 A2 | 5/1995 |
| 2009/0206143 | A1 | 8/2009 | Huitema et al. | EP | 0669104 A1 | 8/1995 |
| 2009/0206144 | A1 | 8/2009 | Doll et al. | EP | 0511470 B1 | 10/1995 |
| 2009/0209946 | A1 | 8/2009 | Swayze et al. | EP | 0679367 A2 | 11/1995 |
| 2009/0218384 | A1 | 9/2009 | Aranyi | EP | 0392547 B1 | 12/1995 |
| 2009/0242610 | A1 | 10/2009 | Shelton, IV et al. | EP | 0685204 A1 | 12/1995 |
| 2009/0255974 | A1 | 10/2009 | Viola | EP | 0699418 A1 | 3/1996 |
| 2009/0255978 | A1 | 10/2009 | Viola et al. | EP | 0702937 A1 | 3/1996 |
| 2009/0289096 | A1 | 11/2009 | Shelton, IV et al. | EP | 0705571 A1 | 4/1996 |
| 2010/0032470 | A1 | 2/2010 | Hess et al. | EP | 0484677 B2 | 6/1996 |
| 2010/0065605 | A1 | 3/2010 | Shelton, IV et al. | EP | 0541987 B1 | 7/1996 |
| 2010/0069942 | A1 | 3/2010 | Shelton, IV | EP | 0667119 B1 | 7/1996 |
| 2010/0072252 | A1 | 3/2010 | Baxter, III et al. | EP | 0770355 A1 | 5/1997 |
| 2010/0072253 | A1 | 3/2010 | Baxter, III et al. | EP | 0503662 B1 | 6/1997 |
| 2010/0072256 | A1 | 3/2010 | Baxter, III et al. | EP | 0578425 B1 | 9/1997 |
| 2010/0076474 | A1 | 3/2010 | Yates et al. | EP | 0625335 B1 | 11/1997 |
| 2010/0076475 | A1 | 3/2010 | Yates et al. | EP | 0552423 B1 | 1/1998 |
| 2010/0089970 | A1 | 4/2010 | Smith et al. | EP | 0592244 B1 | 1/1998 |
| 2010/0089974 | A1 | 4/2010 | Shelton, IV | EP | 0648476 B1 | 1/1998 |
| 2010/0096435 | A1 | 4/2010 | Fuchs et al. | EP | 0676173 B1 | 9/1998 |
| 2010/0127042 | A1 | 5/2010 | Shelton, IV | EP | 0603472 B1 | 11/1998 |
| 2010/0133317 | A1 | 6/2010 | Shelton, IV et al. | EP | 0605351 B1 | 11/1998 |
| 2010/0133318 | A1 | 6/2010 | Boudreaux | EP | 0878169 A1 | 11/1998 |
| 2010/0179382 | A1 | 7/2010 | Shelton, IV et al. | EP | 0879742 A1 | 11/1998 |
| 2010/0181364 | A1 | 7/2010 | Shelton, IV et al. | EP | 0760230 B1 | 2/1999 |
| 2010/0193566 | A1 | 8/2010 | Scheib et al. | EP | 0537572 B1 | 6/1999 |
| 2010/0193567 | A1 | 8/2010 | Scheib et al. | EP | 0552050 B1 | 5/2000 |
| 2010/0193568 | A1 | 8/2010 | Scheib et al. | EP | 1090592 A1 | 4/2001 |
| 2010/0193569 | A1 | 8/2010 | Yates et al. | EP | 1256318 B1 | 5/2001 |
| 2010/0198220 | A1 | 8/2010 | Boudreaux et al. | EP | 0908152 B1 | 1/2002 |
| 2010/0200637 | A1 | 8/2010 | Beetel | EP | 0872213 B1 | 5/2002 |
| 2010/0213241 | A1 | 8/2010 | Bedi et al. | EP | 1238634 A2 | 9/2002 |
| 2010/0222901 | A1 | 9/2010 | Swayze et al. | EP | 0656188 B1 | 1/2003 |
| 2010/0224669 | A1 | 9/2010 | Shelton, IV et al. | EP | 0829235 B1 | 6/2003 |
| 2010/0237132 | A1 | 9/2010 | Measamer et al. | EP | 0813843 B1 | 10/2003 |
| 2010/0243709 | A1 | 9/2010 | Hess et al. | EP | 0741996 B1 | 2/2004 |
| 2010/0264193 | A1 | 10/2010 | Huang et al. | EP | 0705570 B1 | 4/2004 |
| 2010/0264194 | A1 | 10/2010 | Huang et al. | EP | 1086713 B1 | 5/2004 |
| 2010/0276471 | A1 | 11/2010 | Whitman | EP | 1426012 A1 | 6/2004 |
| 2010/0294829 | A1 | 11/2010 | Giordano et al. | EP | 0888749 B1 | 9/2004 |
| 2010/0301095 | A1 | 12/2010 | Shelton, IV et al. | EP | 1477119 A1 | 11/2004 |
| 2010/0301096 | A1 | 12/2010 | Moore et al. | EP | 1479345 A1 | 11/2004 |
| 2010/0305552 | A1 | 12/2010 | Shelton, IV et al. | EP | 1479347 A1 | 11/2004 |
| 2010/0308100 | A1 | 12/2010 | Boudreaux | EP | 1479348 A1 | 11/2004 |
| 2011/0006099 | A1 | 1/2011 | Hall et al. | EP | 1520521 A1 | 4/2005 |
| 2011/0006101 | A1 | 1/2011 | Hall et al. | EP | 1520523 A1 | 4/2005 |
| 2011/0006103 | A1 | 1/2011 | Laurent et al. | EP | 1520525 A1 | 4/2005 |
| 2011/0011914 | A1 | 1/2011 | Baxter, III et al. | EP | 1522264 A1 | 4/2005 |
| 2011/0011915 | A1 | 1/2011 | Shelton, IV | EP | 1523942 A2 | 4/2005 |
| 2011/0024477 | A1 | 2/2011 | Hall et al. | EP | 1550408 A1 | 7/2005 |
| 2011/0024478 | A1 | 2/2011 | Shelton, IV | EP | 1557129 A1 | 7/2005 |
| 2011/0024479 | A1 | 2/2011 | Swensgard et al. | EP | 1064883 B1 | 8/2005 |
| 2011/0042441 | A1 | 2/2011 | Shelton, IV et al. | EP | 1157666 B1 | 9/2005 |
| 2011/0060363 | A1 | 3/2011 | Hess et al. | EP | 1621138 A2 | 2/2006 |
| | | | | EP | 1621139 A2 | 2/2006 |
| | | FOREIGN PATENT DOCUMENTS | | EP | 1621141 A2 | 2/2006 |
| | | | | EP | 1621145 A2 | 2/2006 |
| CA | | 2512960 A1 | 1/2006 | EP | 1621151 A2 | 2/2006 |
| CA | | 2514274 A1 | 1/2006 | EP | 1652481 A2 | 5/2006 |
| DE | | 273689 C | 5/1914 | EP | 1382303 B1 | 6/2006 |
| DE | | 1775926 A | 1/1972 | EP | 1045672 B1 | 8/2006 |
| DE | | 3210466 A1 | 9/1983 | EP | 1617768 B1 | 8/2006 |
| DE | | 9412228 U | 9/1994 | EP | 1702567 A2 | 9/2006 |
| DE | | 19924311 A1 | 11/2000 | EP | 1129665 B1 | 11/2006 |
| DE | | 69328576 T2 | 1/2001 | EP | 1400206 B1 | 11/2006 |
| DE | | 20112837 U1 | 10/2001 | EP | 1256317 B1 | 12/2006 |
| DE | | 20121753 U1 | 4/2003 | EP | 1728473 A1 | 12/2006 |
| DE | | 10314072 A1 | 10/2004 | EP | 1728475 A2 | 12/2006 |
| EP | | 0122046 A1 | 10/1984 | EP | 1479346 B1 | 1/2007 |
| EP | | 0070230 B1 | 10/1985 | EP | 1484024 B1 | 1/2007 |
| EP | | 0033548 B1 | 5/1986 | EP | 1754445 A2 | 2/2007 |
| EP | | 0276104 A2 | 7/1988 | EP | 1759812 A1 | 3/2007 |
| EP | | 0639349 A2 | 2/1994 | EP | 1769756 A1 | 4/2007 |
| EP | | 0324636 B1 | 3/1994 | EP | 1769758 A1 | 4/2007 |
| EP | | 0593920 A1 | 4/1994 | EP | 1785097 A2 | 5/2007 |
| EP | | 0600182 A2 | 6/1994 | EP | 1790293 A2 | 5/2007 |
| EP | | 0630612 A1 | 12/1994 | EP | 1800610 A1 | 6/2007 |
| EP | | 0634144 A1 | 1/1995 | EP | 1300117 B1 | 8/2007 |
| EP | | 0646356 A2 | 4/1995 | EP | 1813199 A1 | 8/2007 |
| EP | | 0646357 A1 | 4/1995 | | | |

| | | | |
|---|---|---|---|
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1839596 A1 | 10/2007 |
| EP | 1402821 B1 | 12/2007 |
| EP | 1872727 A1 | 1/2008 |
| EP | 1897502 A1 | 3/2008 |
| EP | 1702568 B1 | 7/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 1759640 B1 | 12/2008 |
| EP | 2000102 A2 | 12/2008 |
| EP | 1749486 B1 | 3/2009 |
| EP | 2090256 A2 | 8/2009 |
| EP | 1813206 B1 | 4/2010 |
| EP | 1769754 B1 | 6/2010 |
| EP | 1702570 B1 | 10/2010 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/35464 A1 | 11/1996 |
| WO | WO 97/34533 A1 | 9/1997 |
| WO | WO 97/39688 A2 | 10/1997 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A1 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |
| WO | WO 2008/109125 A1 | 9/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

European Search Report, Application No. 09250360.6, published Jan. 26, 2010 (5 pages).

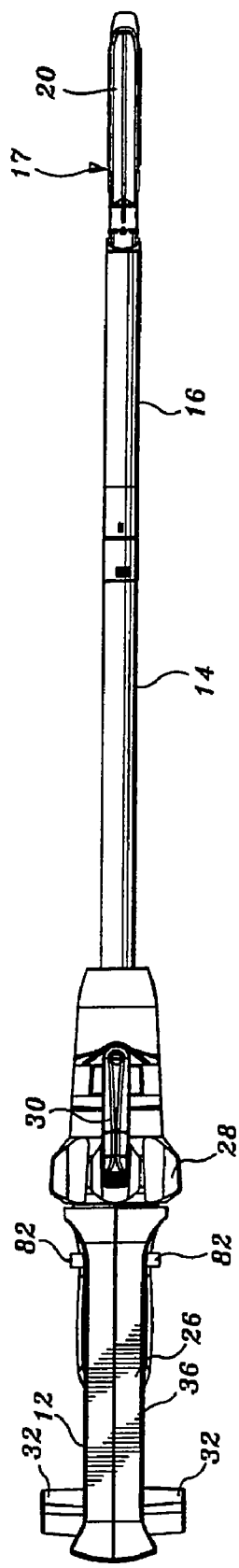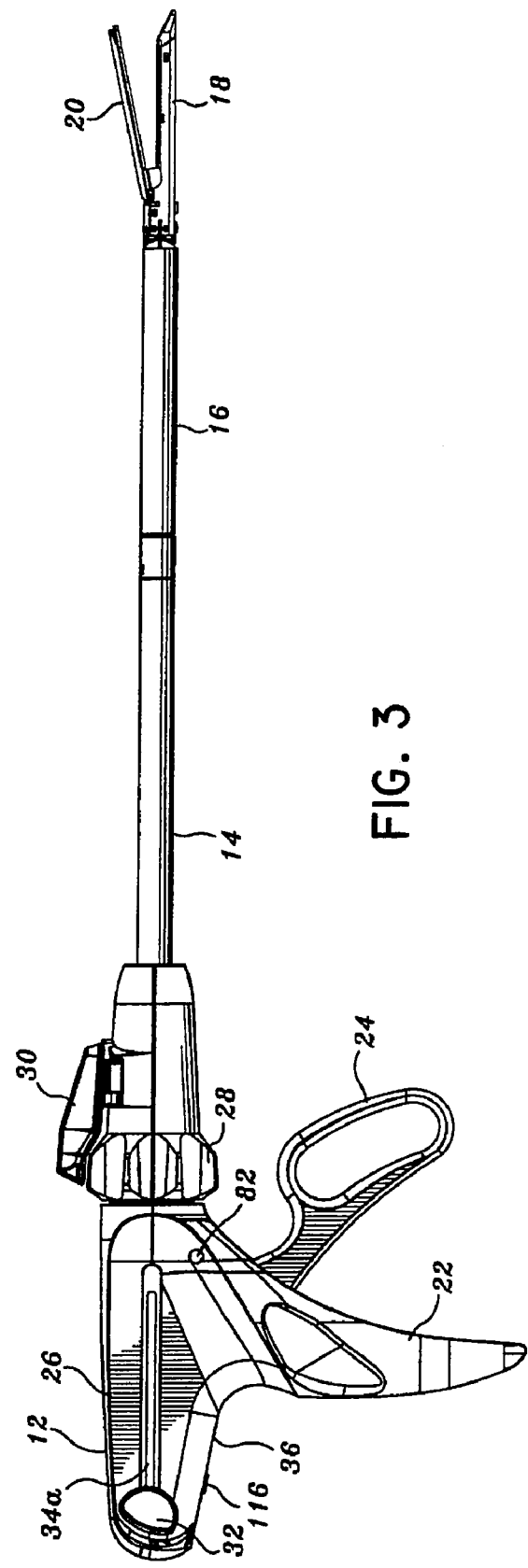
FIG. 2
FIG. 3

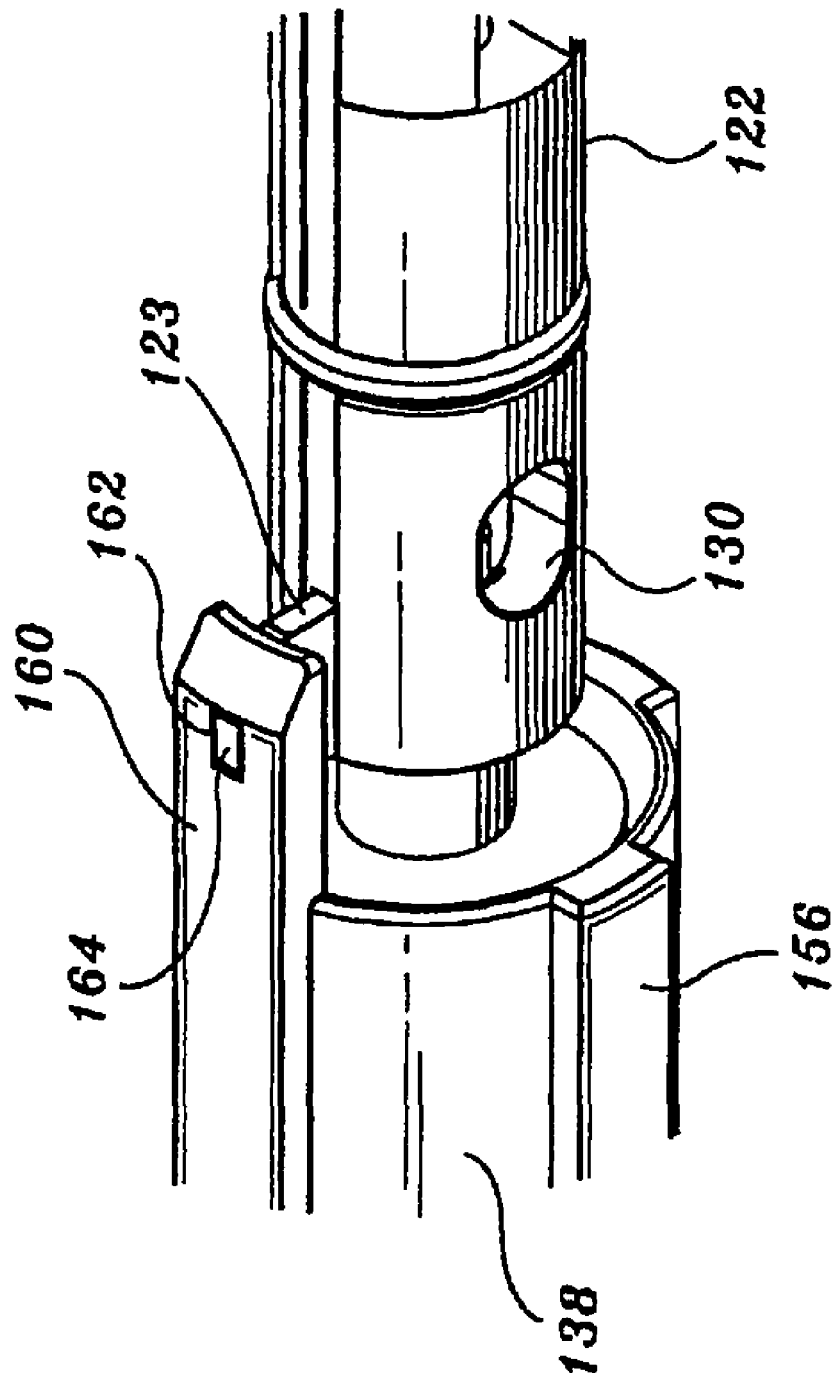

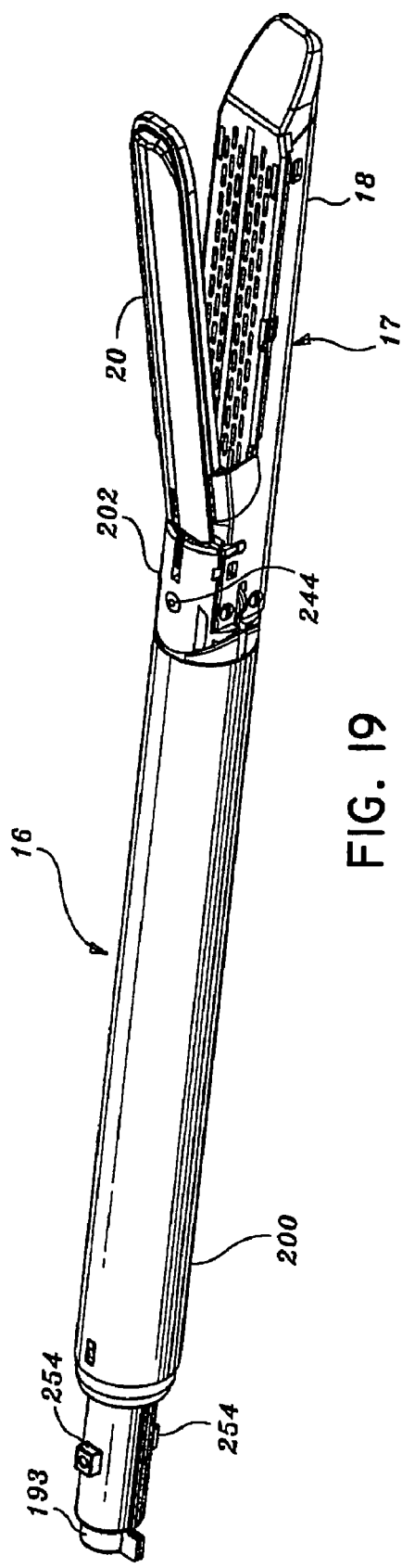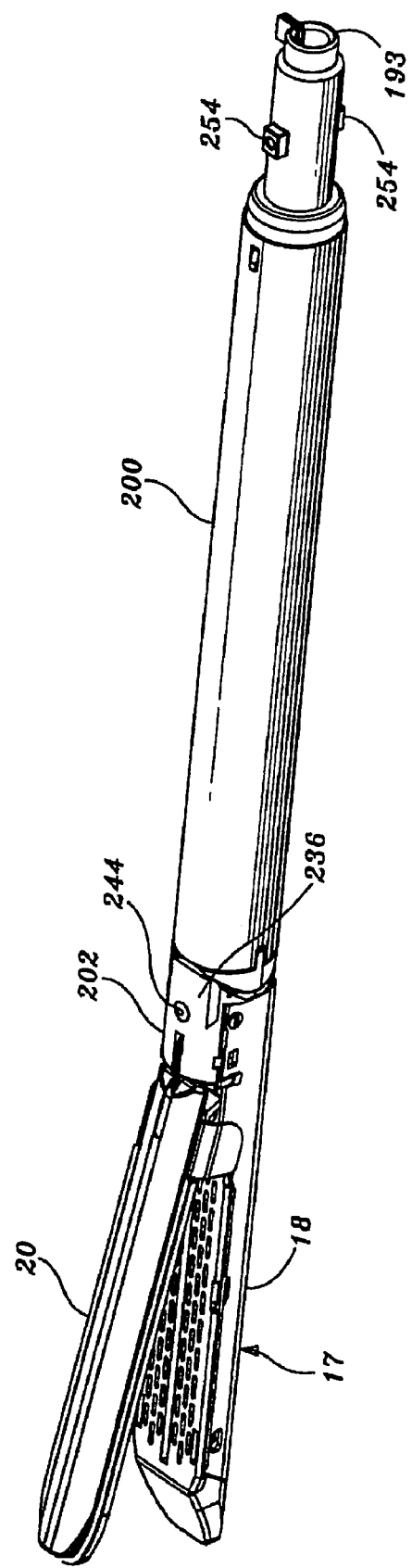

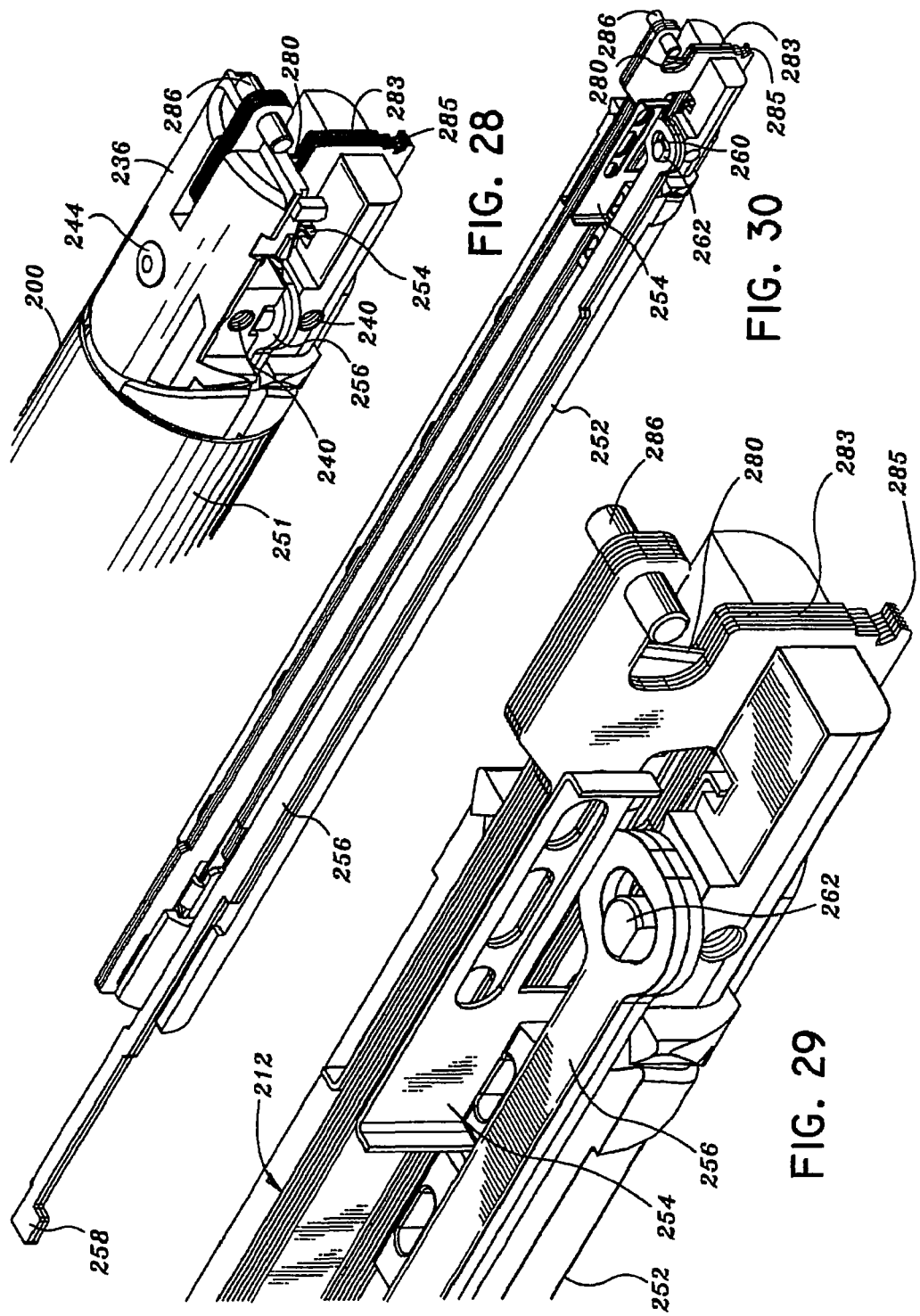

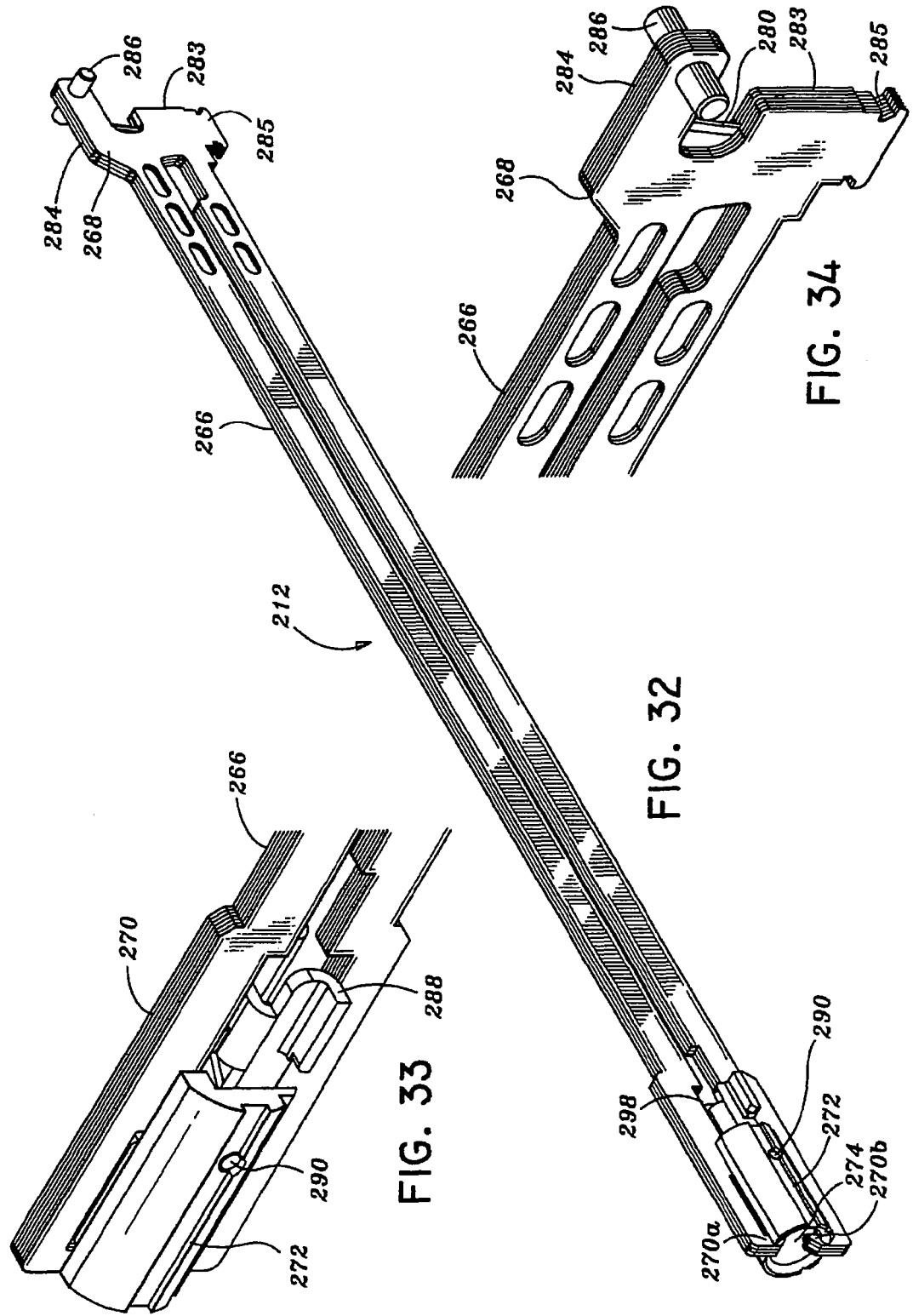

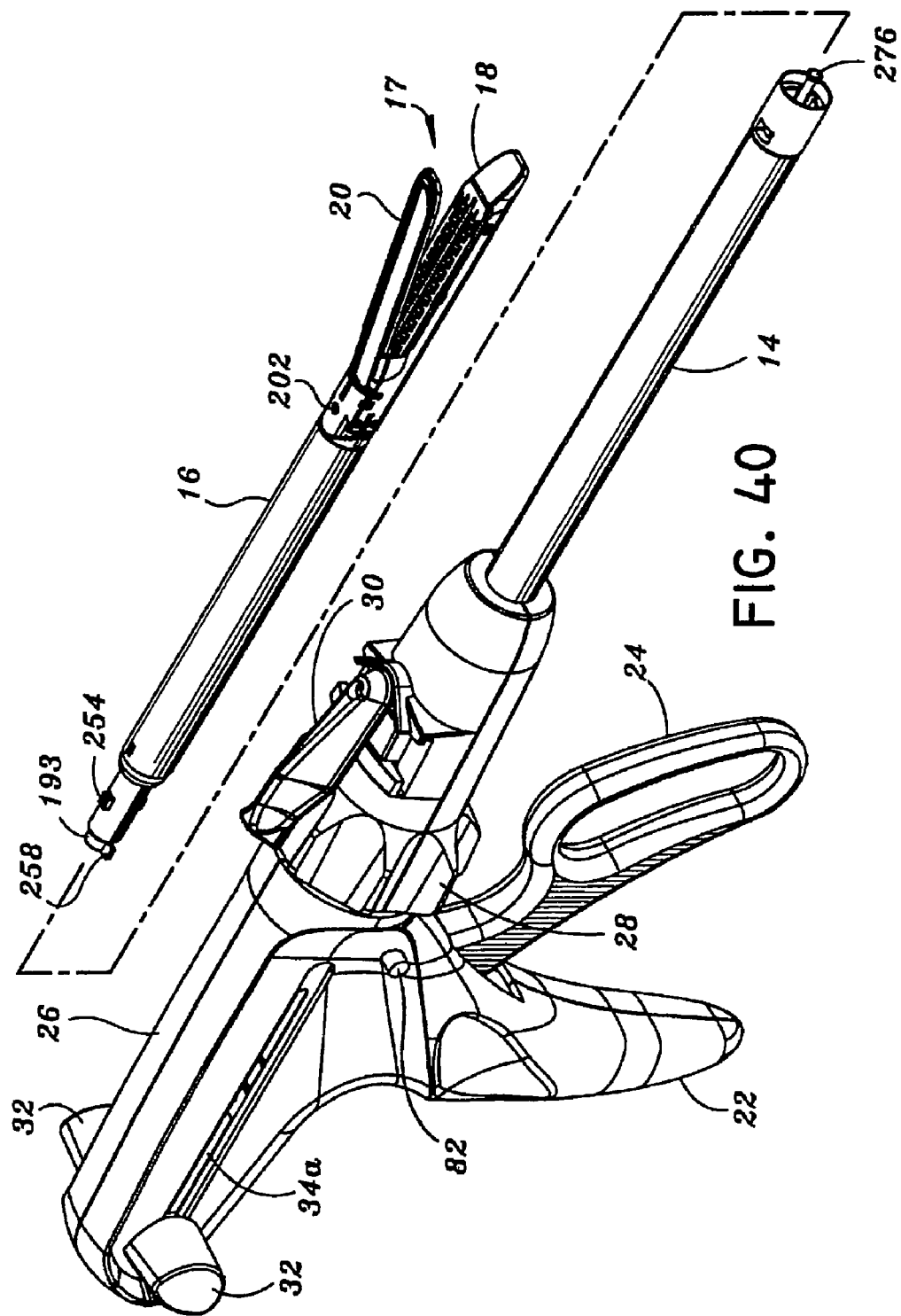

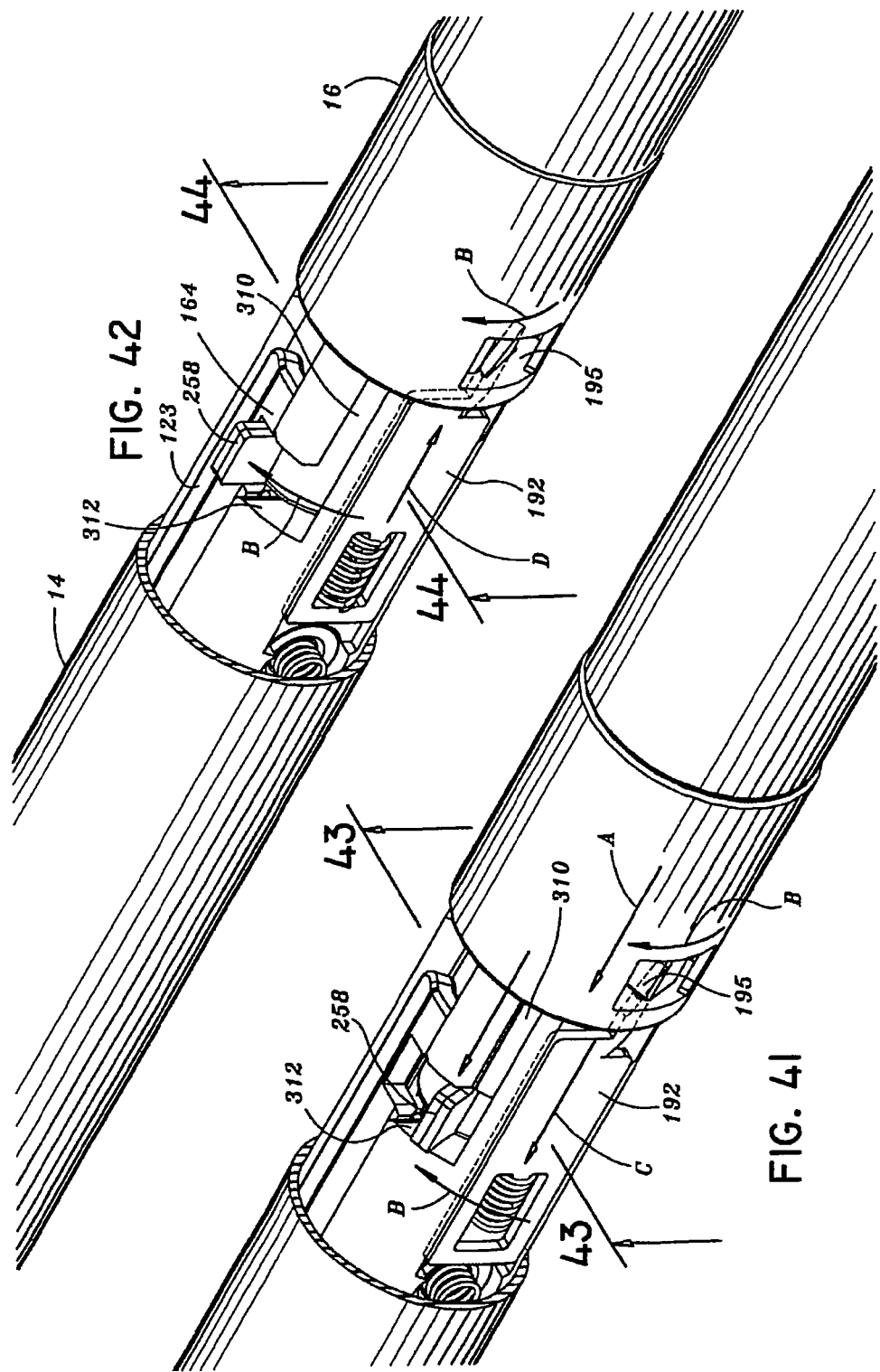

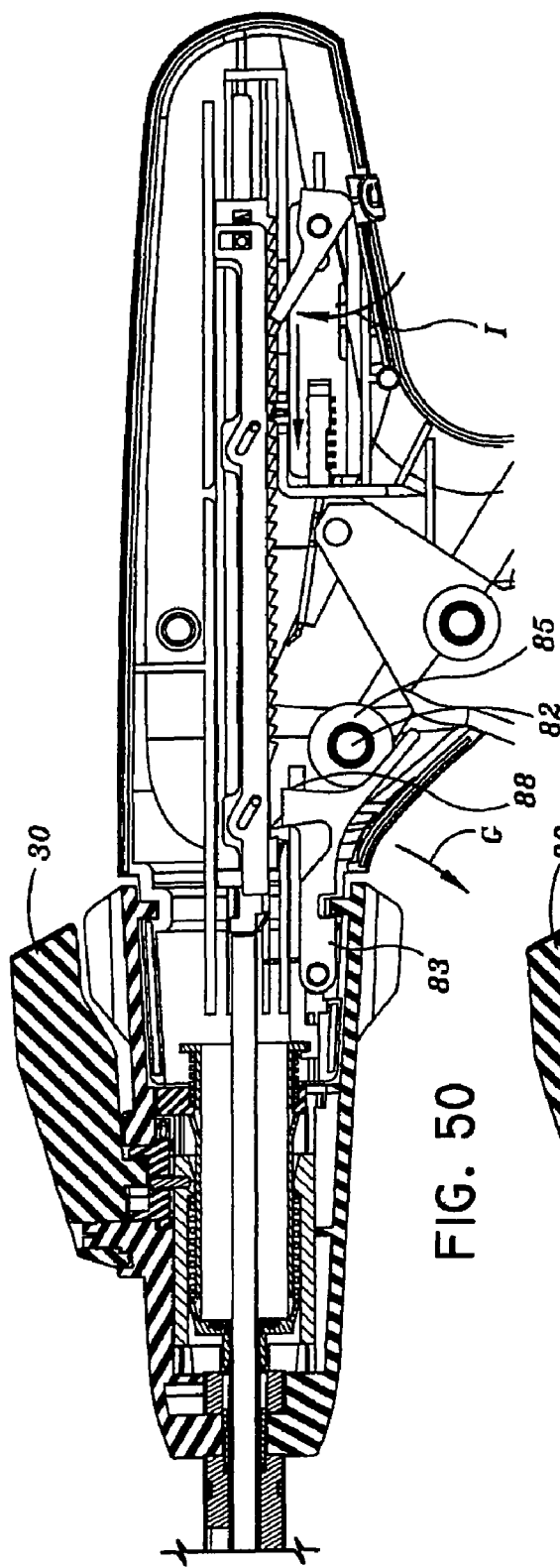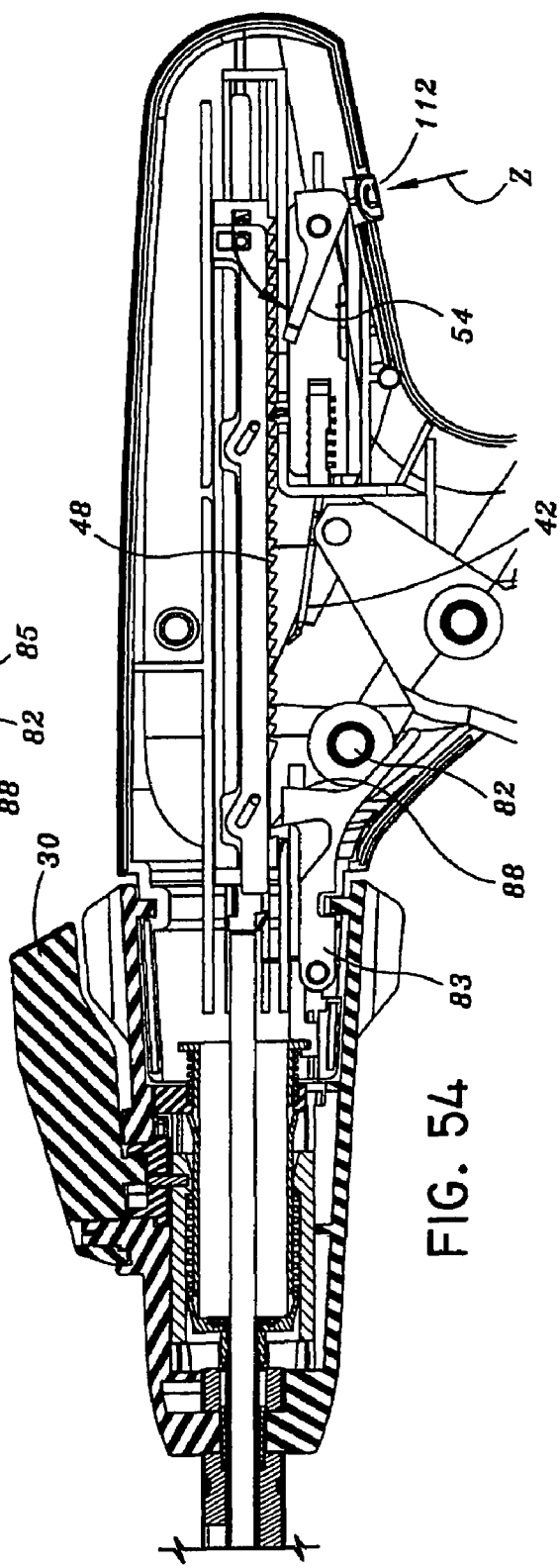

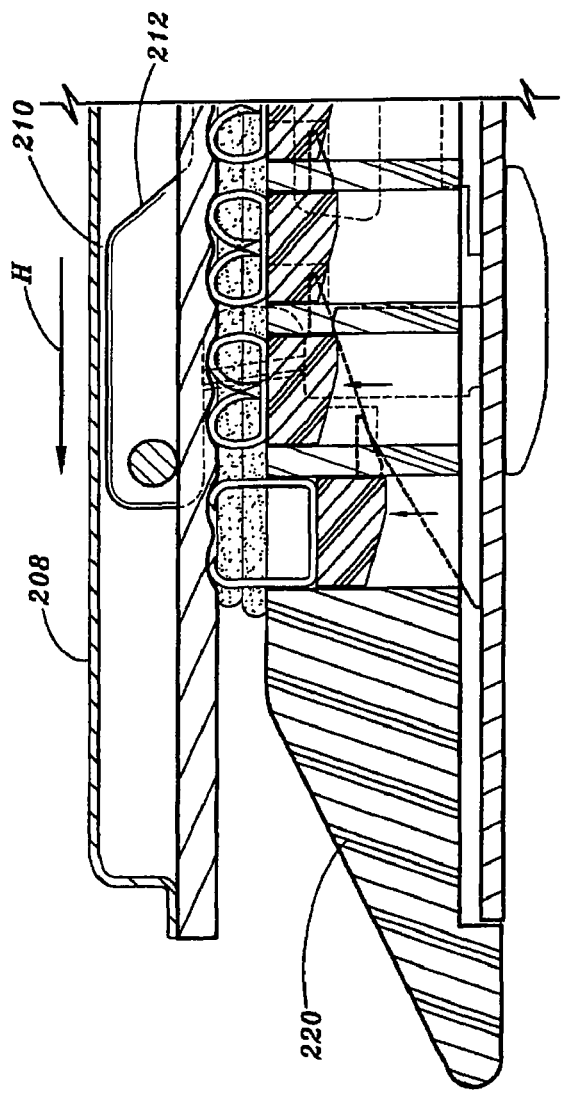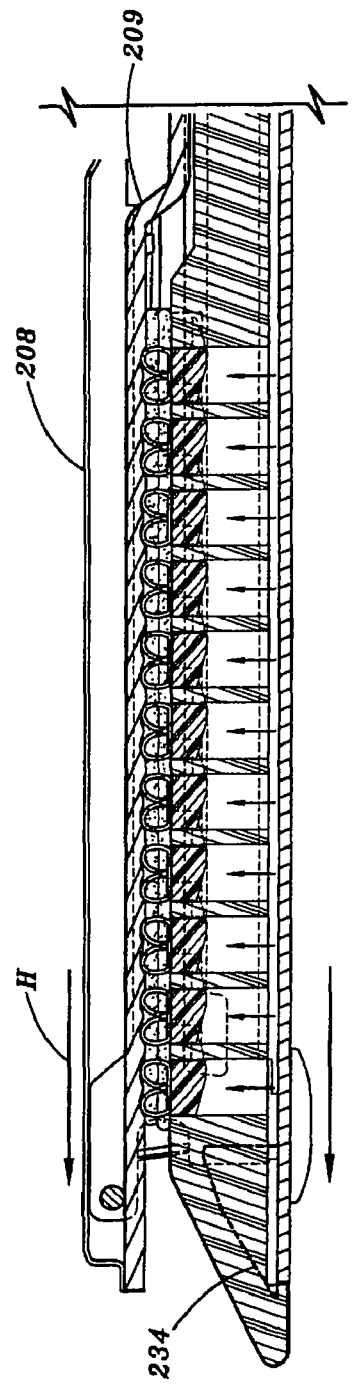
FIG. 51
FIG. 52

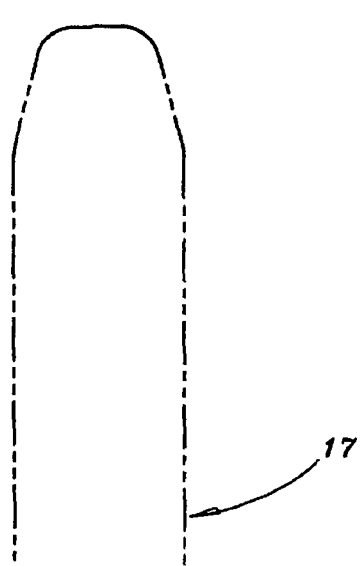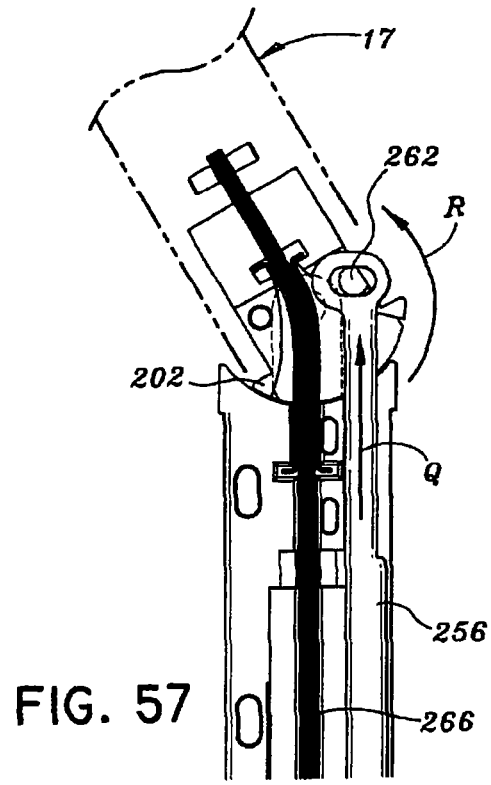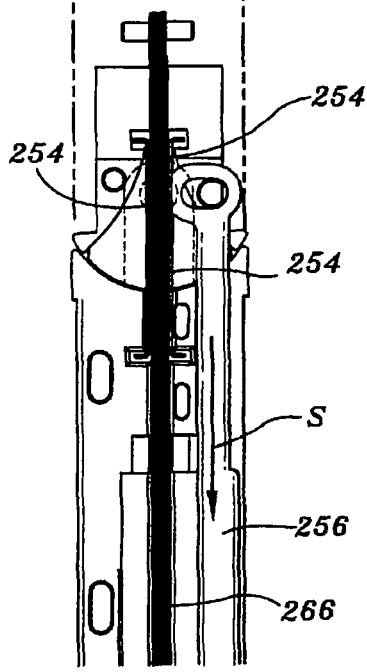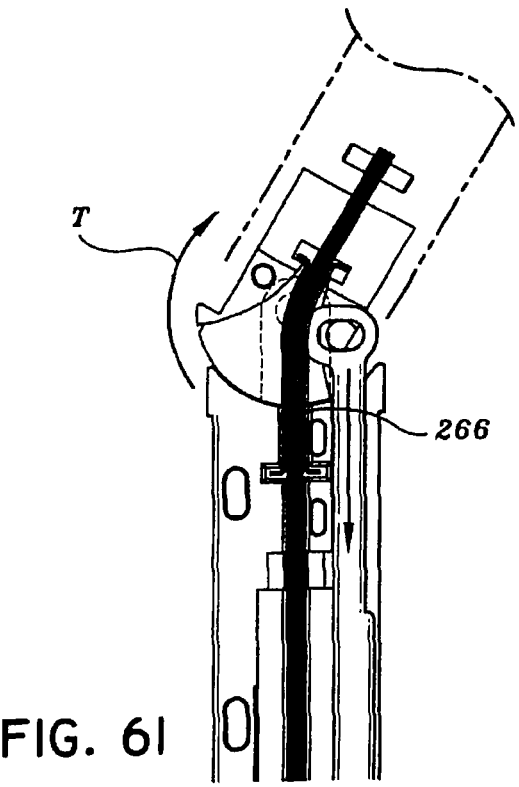
FIG. 57
FIG. 60
FIG. 61

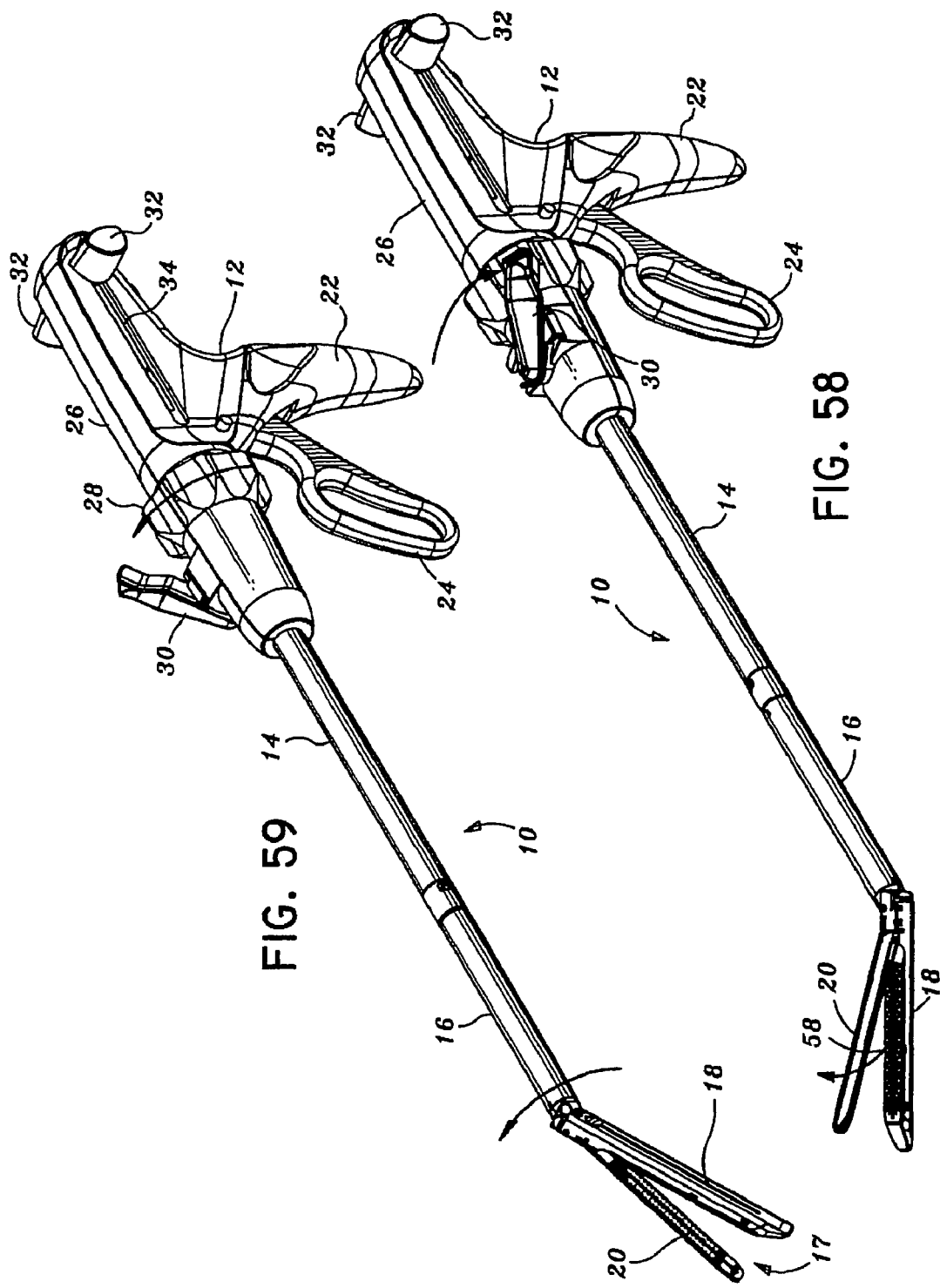

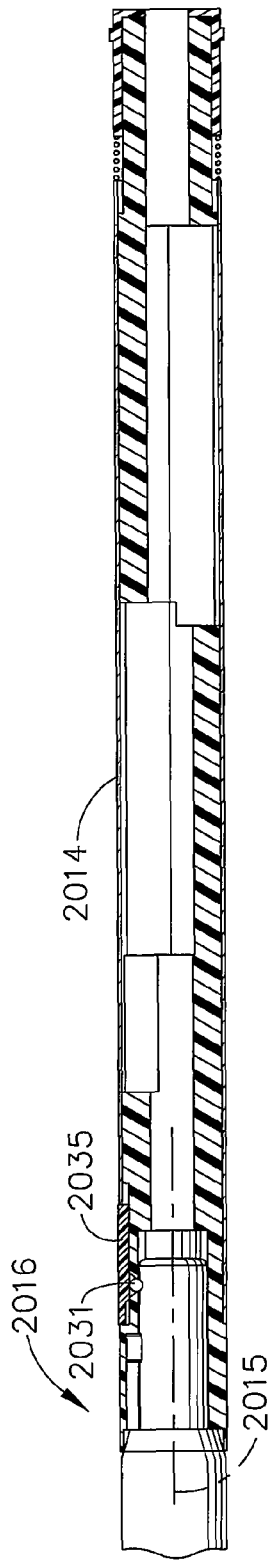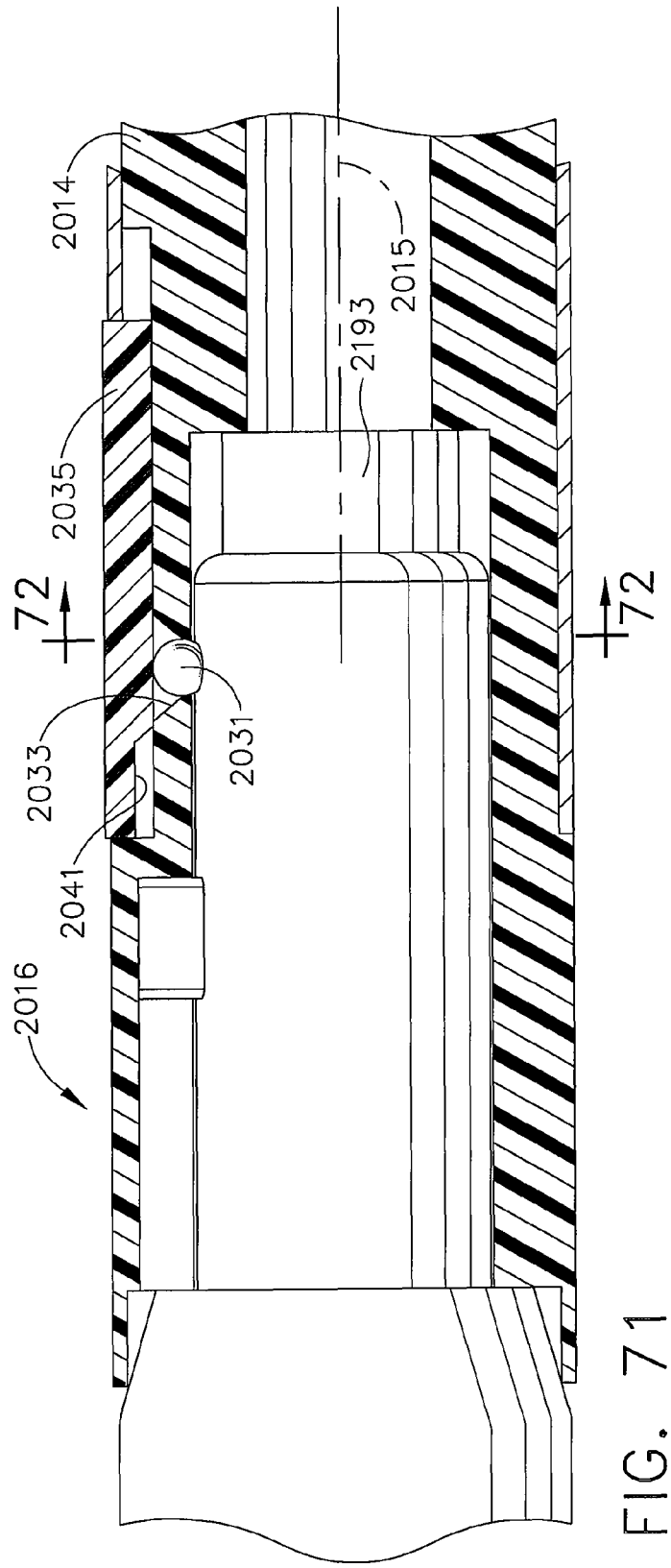
FIG. 70
FIG. 71

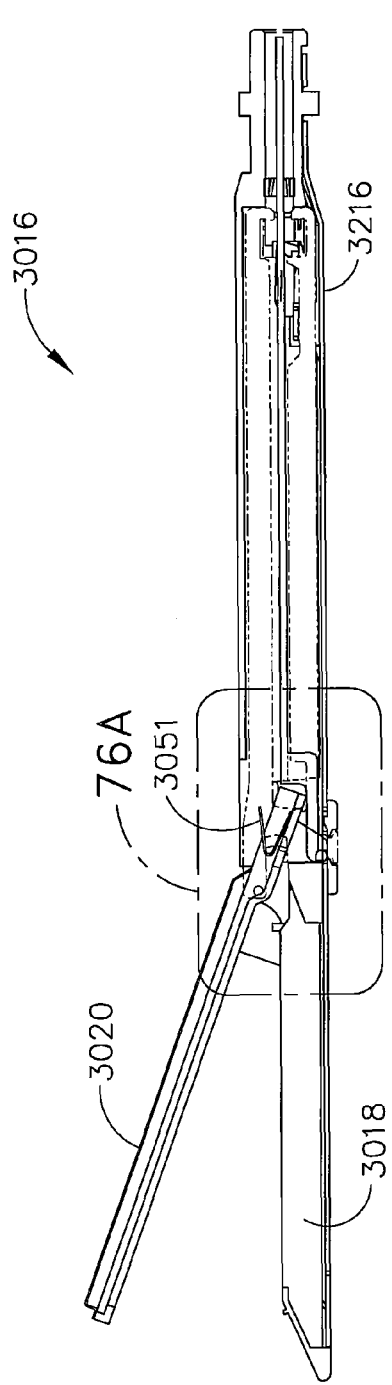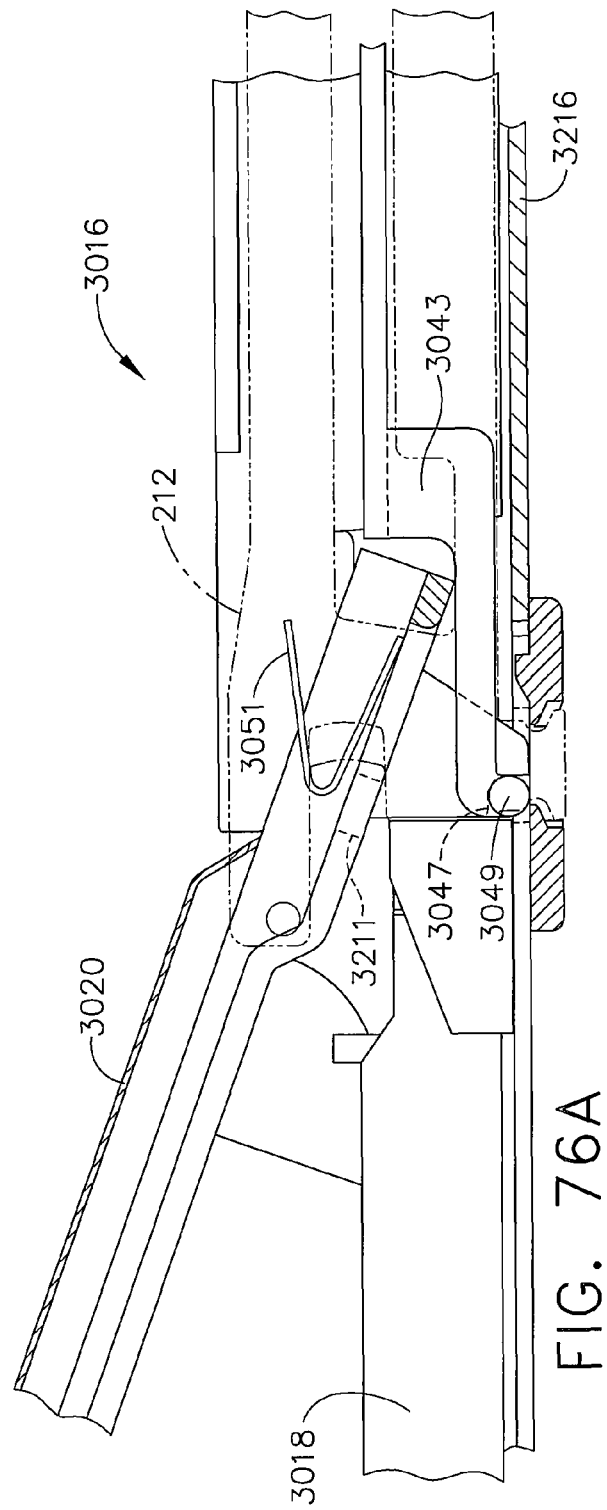

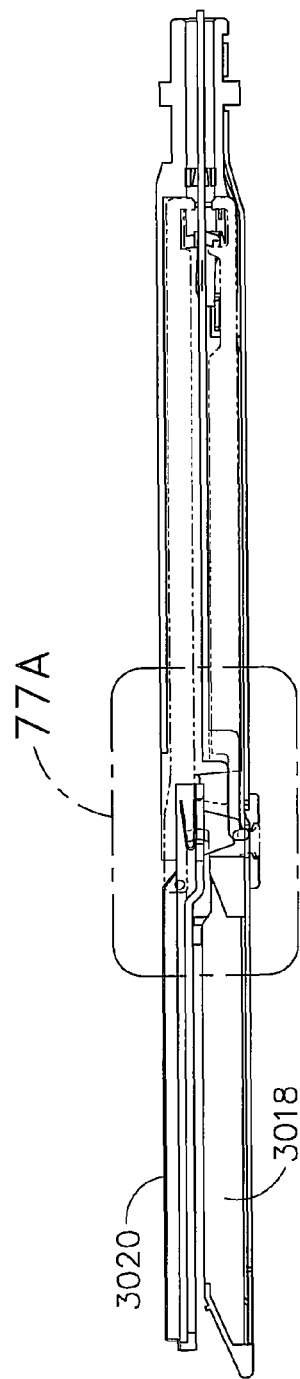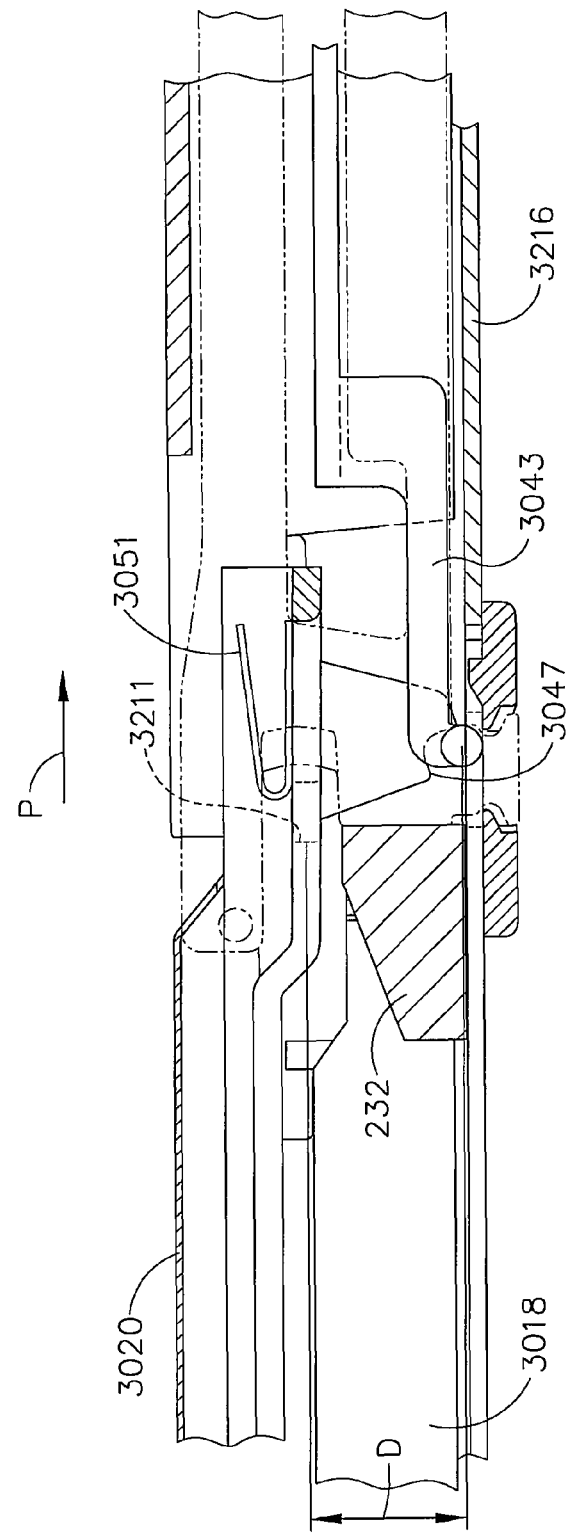

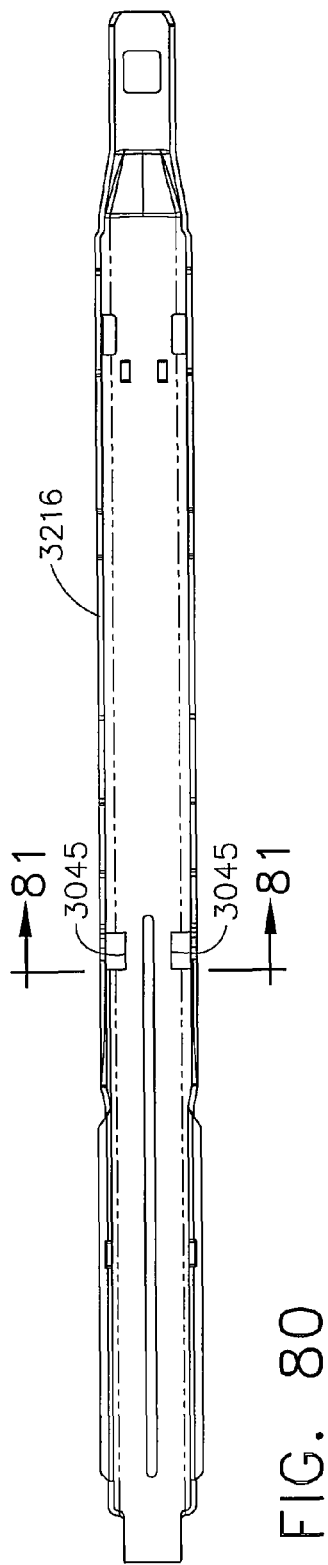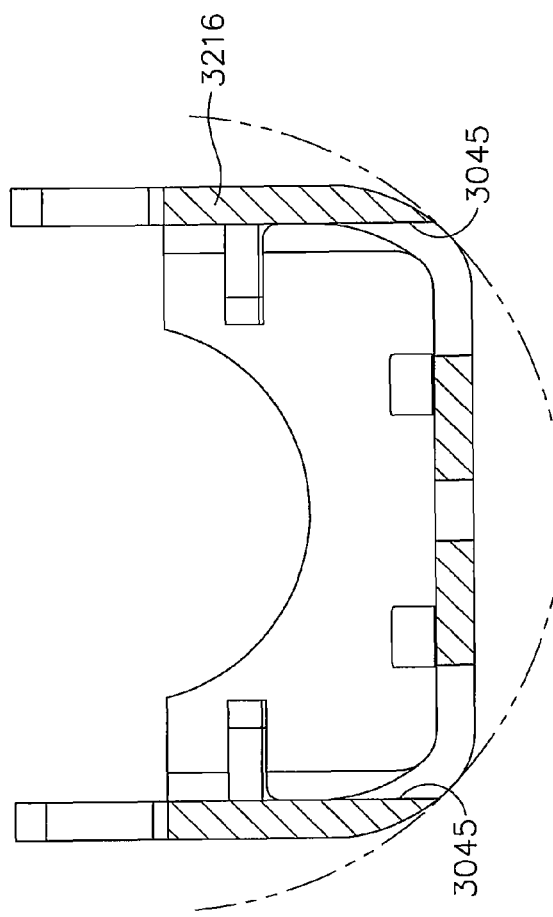

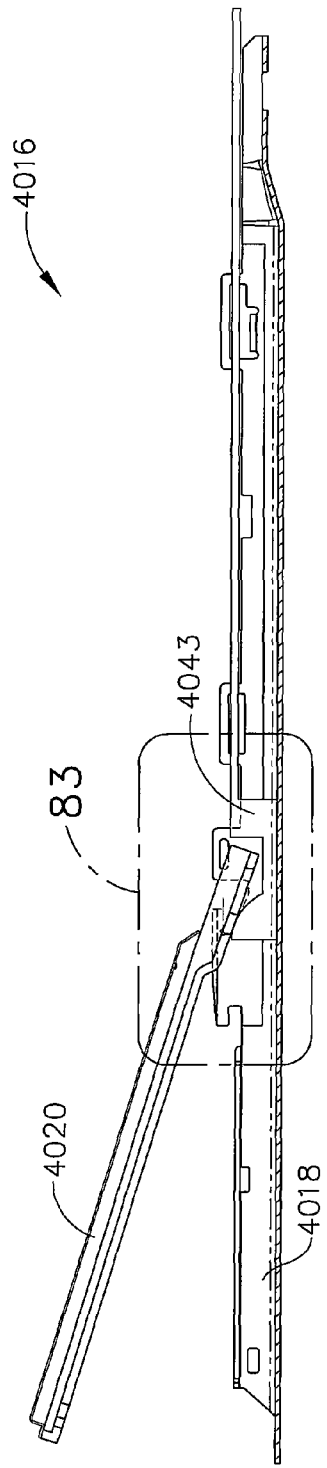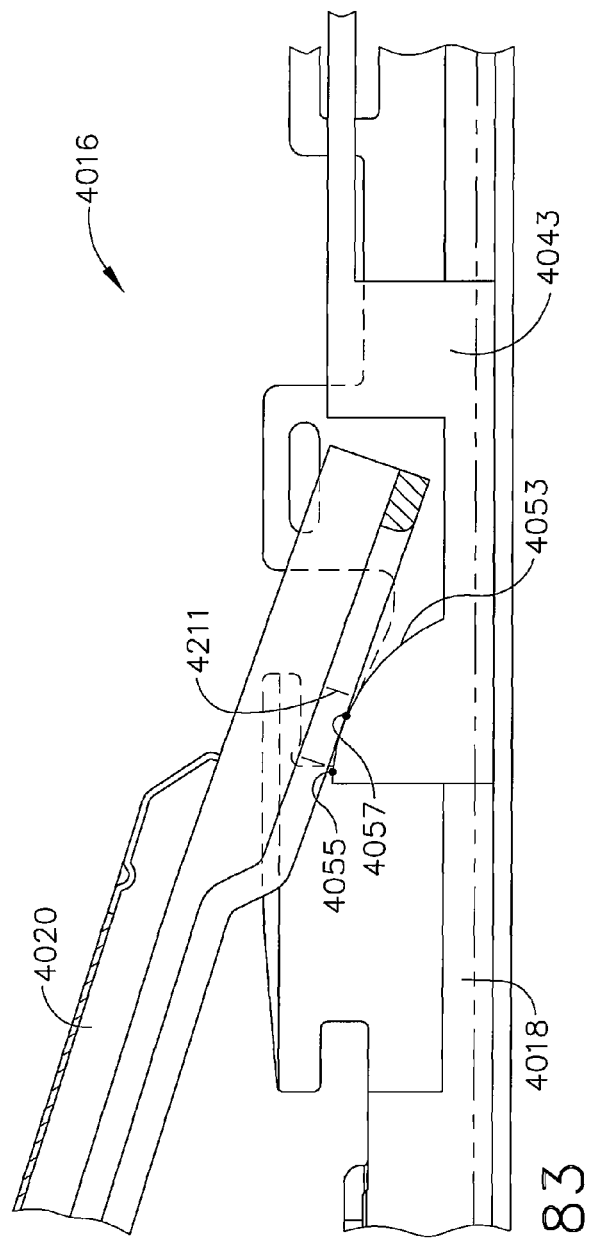

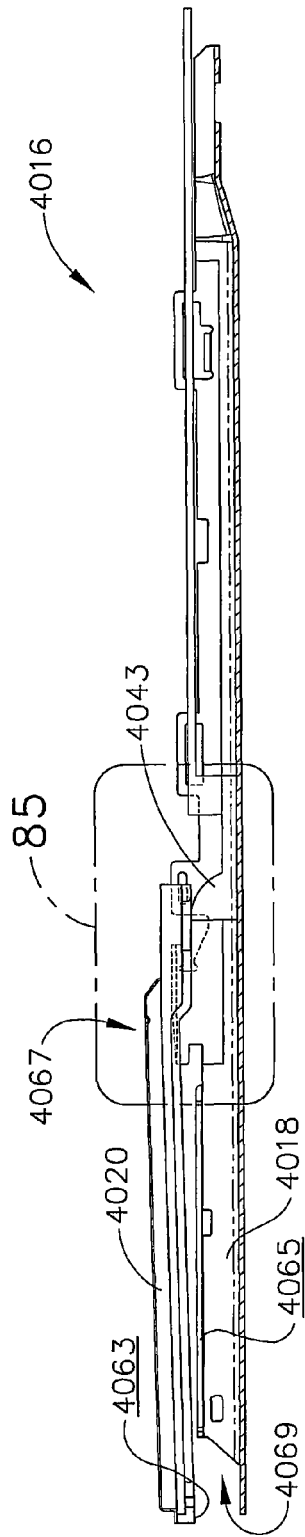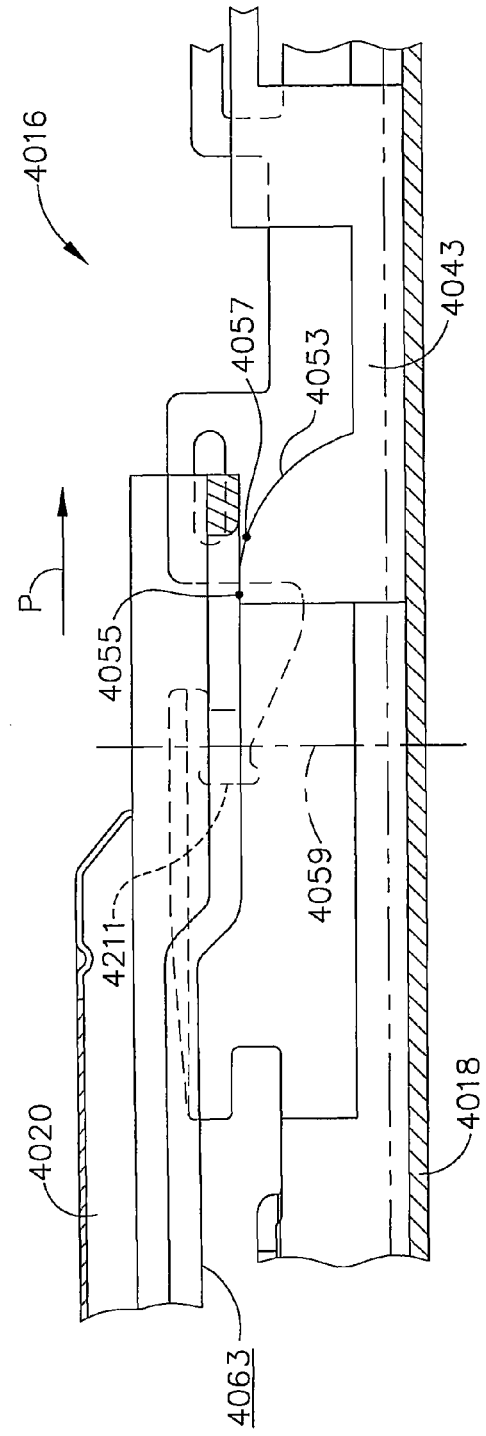

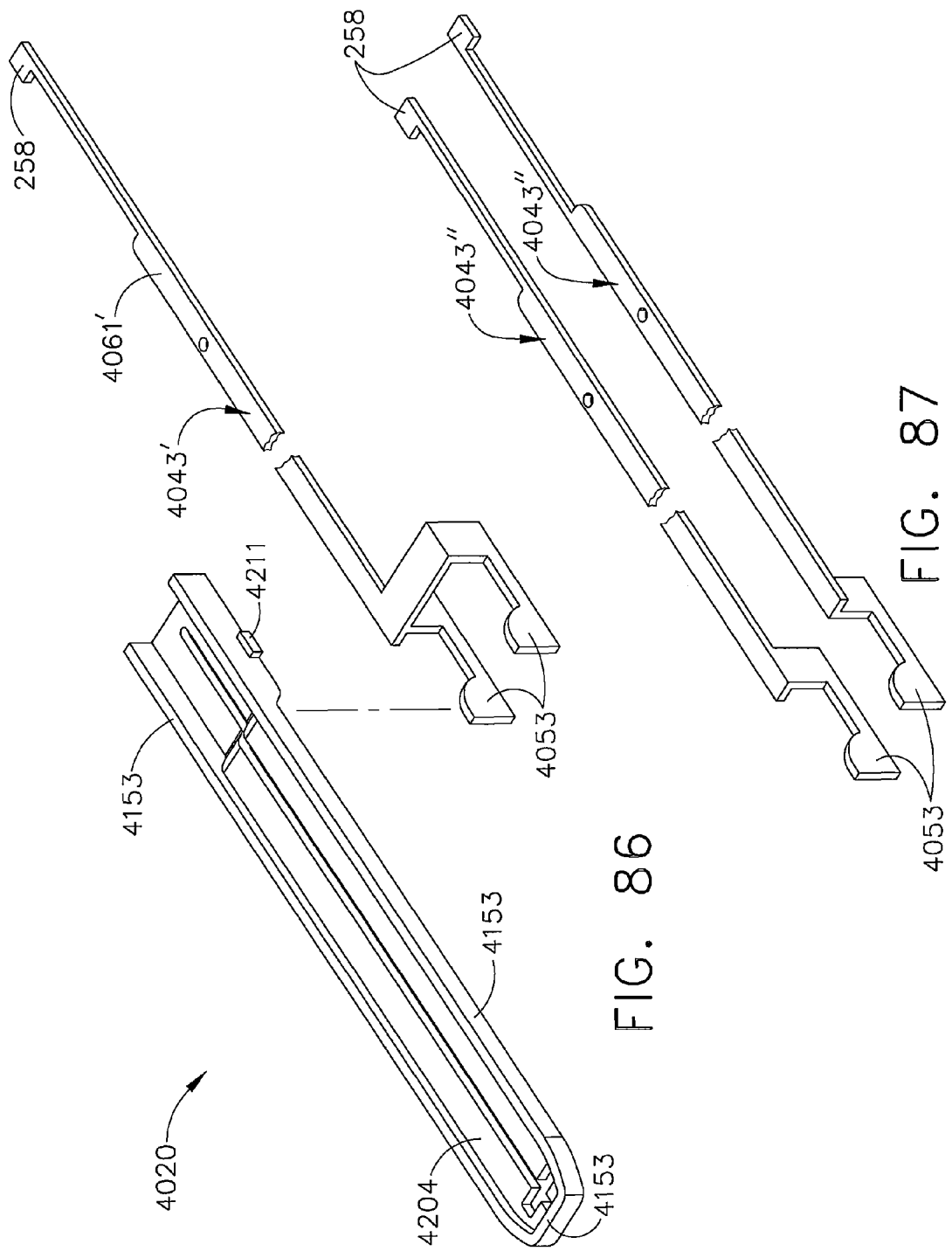

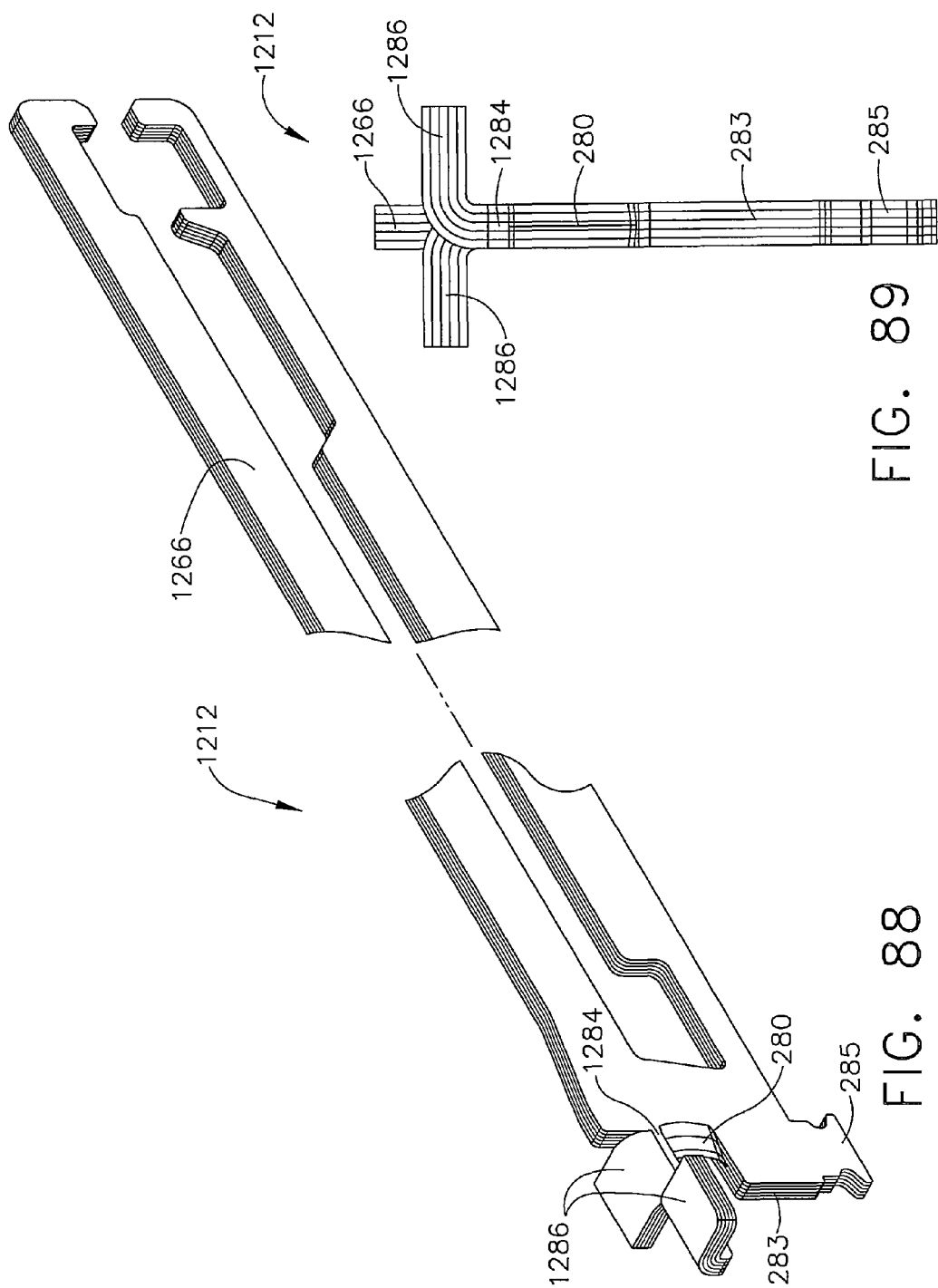

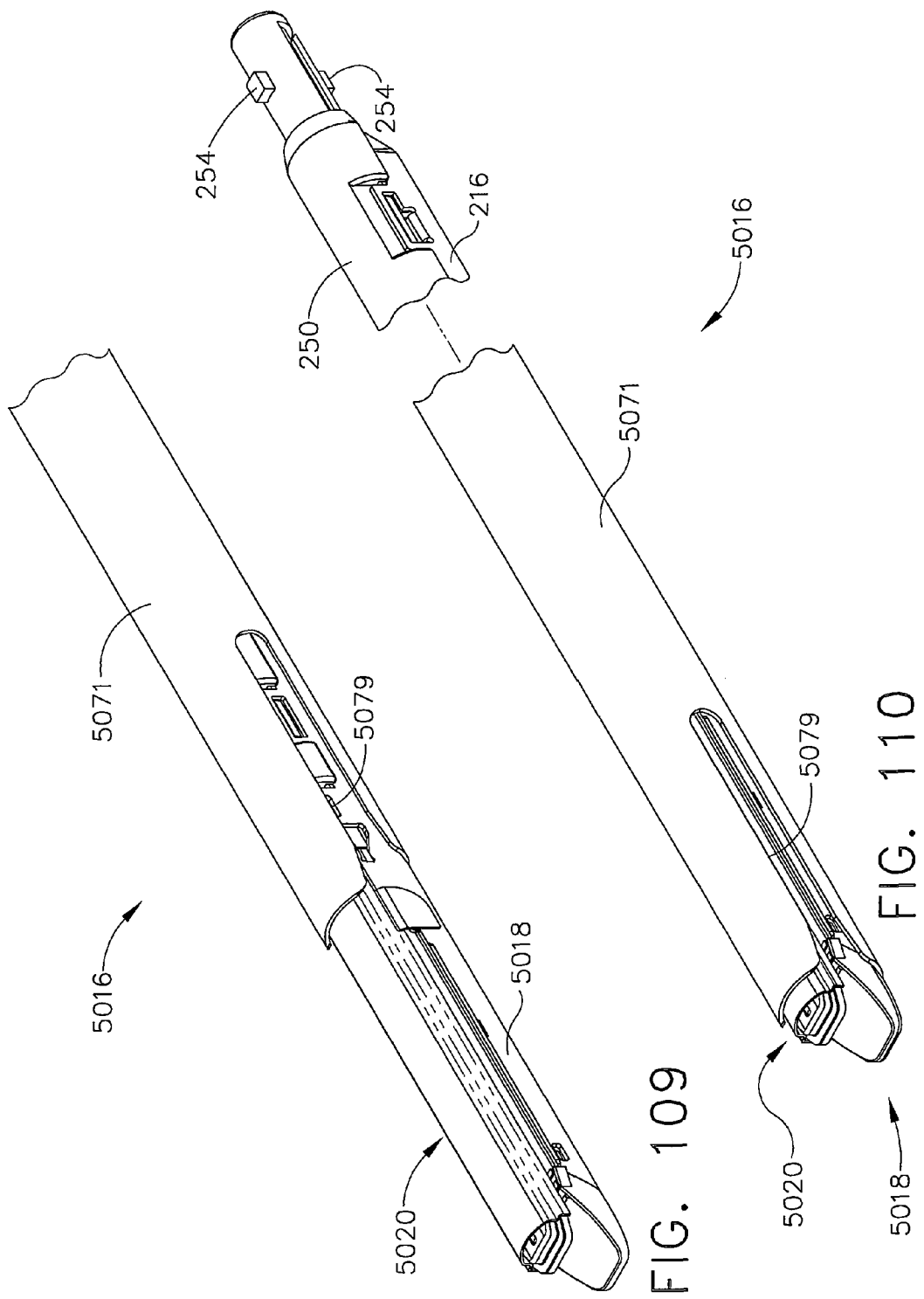

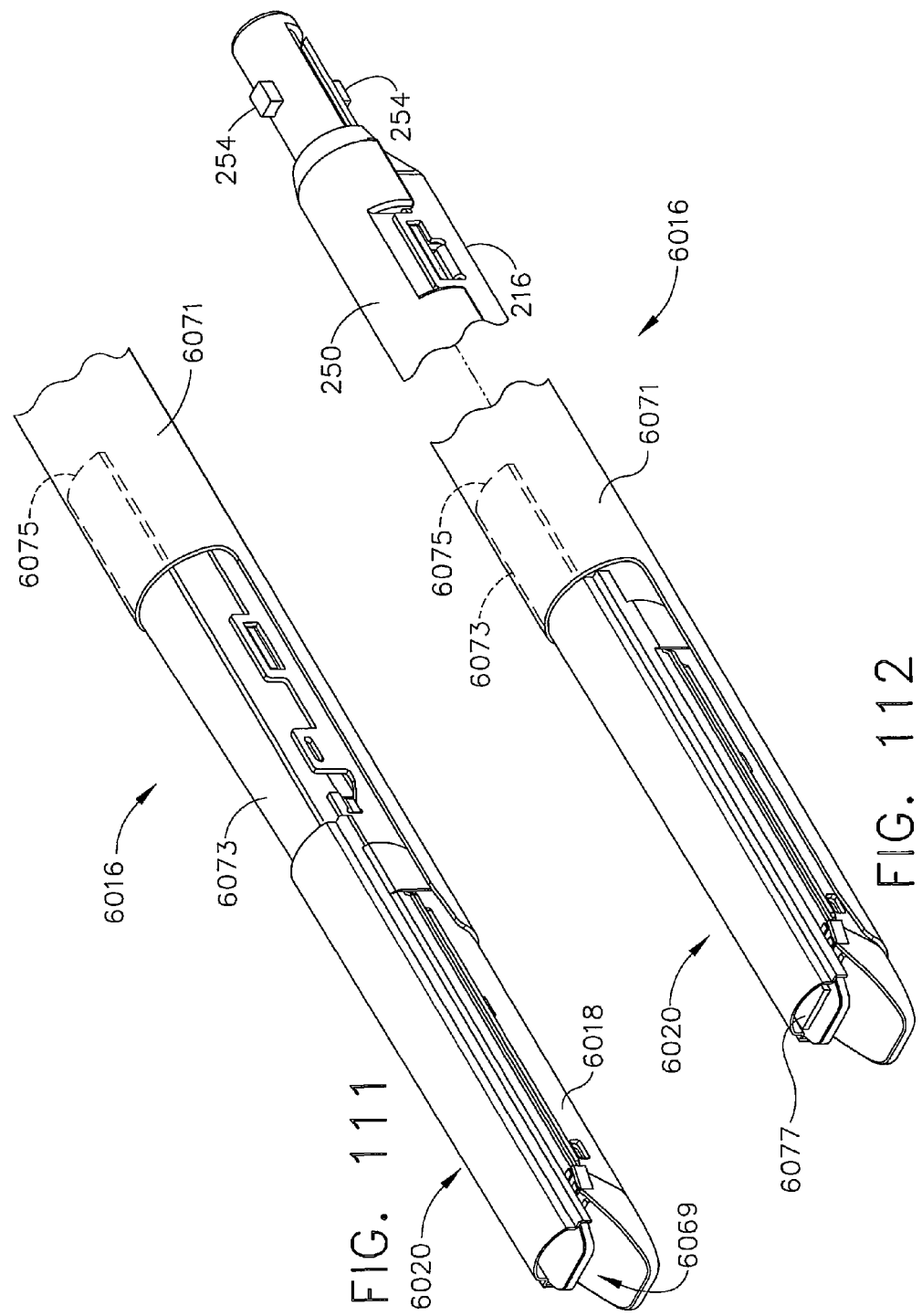

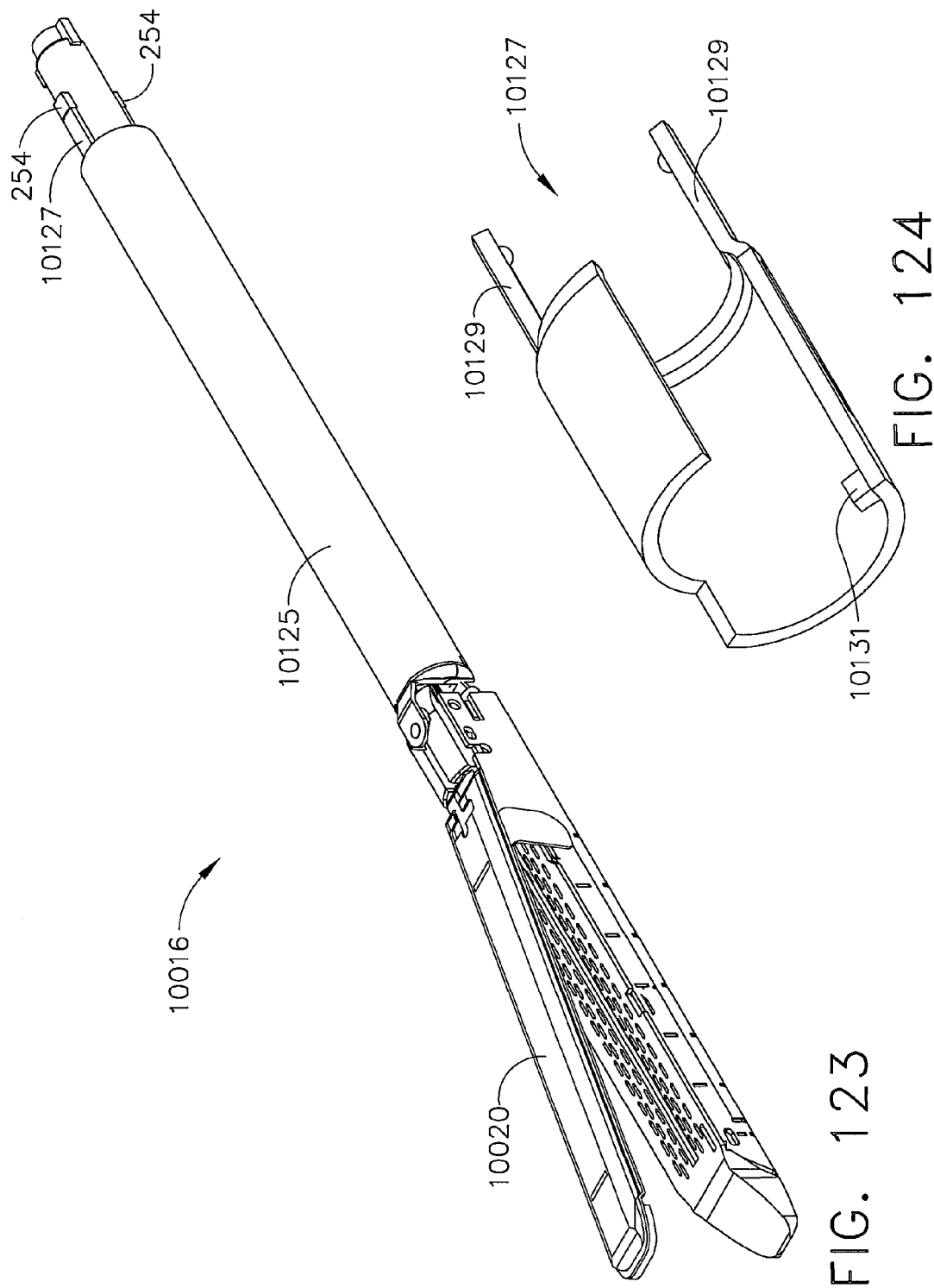

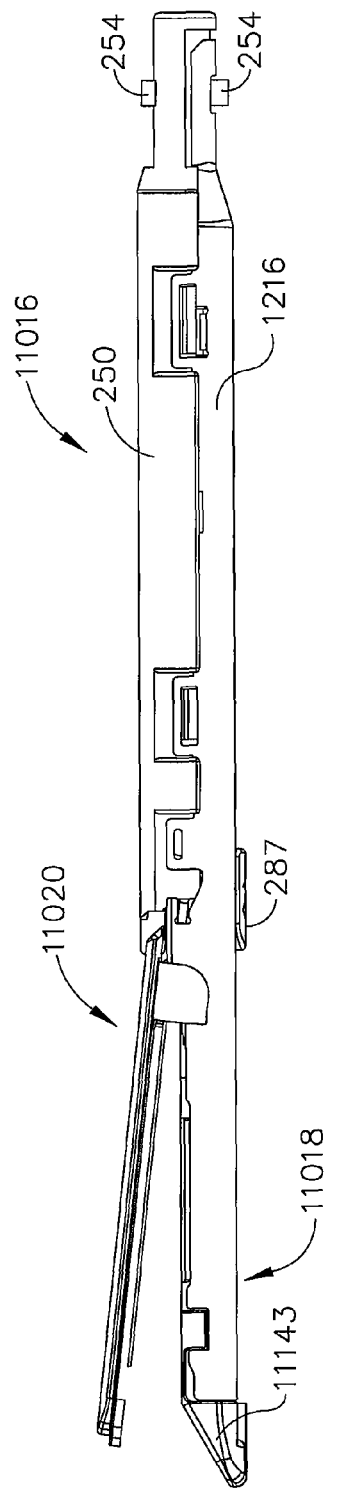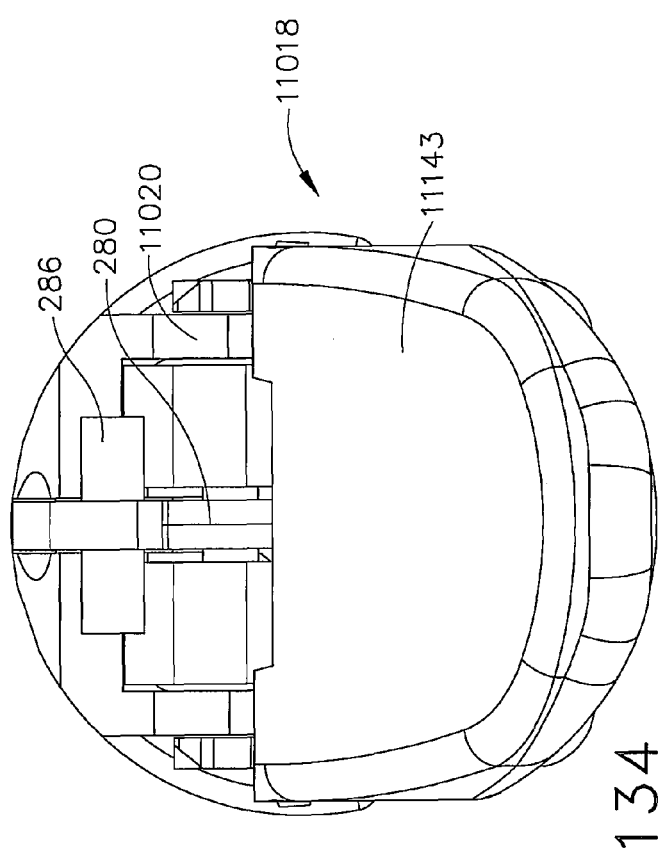
FIG. 133
FIG. 134

END EFFECTORS FOR A SURGICAL CUTTING AND STAPLING INSTRUMENT

BACKGROUND

1. Technical Field

This application relates to a surgical stapling apparatus and, in various embodiments, to an articulating mechanism for use with an endoscopic surgical stapling apparatus for sequentially applying a plurality of surgical fasteners to body tissue and optionally incising fastened tissue.

2. Background of Related Art

Surgical devices wherein tissue is first grasped or clamped between opposing jaw structures and then joined by surgical fasteners are well known in the art. In some instruments, a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675, the entire disclosures of which are hereby incorporated by reference herein.

A later stapler disclosed in U.S. Pat. No. 3,499,591, the entire disclosure of which is hereby incorporated by reference herein, applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929, the entire disclosures of which are hereby incorporated by reference herein.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. Nos. 5,040,715 (Green, et al.); 5,307,976 (Olson, et al.); 5,312,023 (Green, et al.); 5,318,221 (Green, et al.); 5,326,013 (Green, et al.); and 5,332,142 (Robinson, et al.), the entire disclosures of which are hereby incorporated by reference herein.

Many current laparoscopic linear stapling devices are configured to operate with disposable loading units and staple cartridges of only one size. For example, individual linear staplers are presently available for applying parallel rows of staples measuring 30 mm, 45 mm and 60 mm in length, for example. Thus, during a normal operation, a surgeon may be required to utilize several different stapling instruments to perform a single laparoscopic surgical procedure. Such practices increase the time, complexity and overall costs associated with laparoscopic surgical procedures. In addition, costs are greater in designing and manufacturing multiple stapler sizes, as opposed to creating a single, multipurpose stapler.

It would be extremely beneficial to provide a surgical device for use during laparoscopic and/or endoscopic surgical procedures that can be employed with several different sized disposable loading units to reduce the overall costs associated with such procedures. It would also be particularly beneficial if the device could perform multiple tasks, using disposable loading units of varying size and of varying purpose, such as, for example, to staple, clip, cut and/or articulate.

SUMMARY

In accordance with the present disclosure, improvements to a surgical stapling apparatus for sequentially applying a plurality of fasteners to body tissue and incising tissue are provided. In various embodiments, a surgical stapling apparatus includes a handle portion, an elongated body, or shaft, and a disposable loading unit, wherein the disposable loading unit is removably attachable to the elongated body. In at least one embodiment, the elongated body can include a connector portion which can be operably engaged with a connector portion of the disposable loading unit such that, when a trigger of the handle portion is actuated, the trigger can advance a driver within the disposable loading unit to deploy staples from the disposable loading unit and/or incise tissue. In previous surgical stapling devices, though, the disposable loading unit can become detached from the elongate body causing the surgical stapling instrument to malfunction or be rendered inoperable.

In various embodiments of the present disclosure, such problems can be ameliorated by utilizing a surgical stapling instrument having a handle, a shaft extending from the handle, wherein the shaft defines an axis, and a disposable loading unit which is assembled to the shaft in a direction which is transverse to the shaft axis. Such a connection between the disposable loading unit and the shaft, in at least one embodiment, can prevent, or at least inhibit, the disposable loading unit from being unintentionally displaced proximally and/or distally relative to the shaft of the surgical instrument. In at least one embodiment, the surgical stapling instrument and/or disposable loading unit can further include a collar configured to threadably engage the shaft and/or a portion of the disposable loading unit. In various embodiments, a disposable loading unit and/or elongated body can include a detent assembly for holding the disposable loading unit in place after it has been assembled to the elongated body.

After a disposable loading unit has been attached to a surgical stapling instrument, the instrument can be positioned relative to the soft tissue of a patient. In various circumstances, a surgical stapling instrument can include an anvil and a staple cartridge, where the anvil can be rotated relative to the staple cartridge to position the anvil and the staple cartridge with respect to the soft tissue. In some surgical stapling instruments, the anvil can be configured to clamp the soft tissue between the anvil and the staple cartridge as staples are discharged from the staple cartridge. In various circumstances, a portion of the soft tissue can flow, or move, out of the distal end of the disposable loading unit and, as a result, the soft tissue may not be properly treated by the surgical stapling instrument.

In various embodiments of the present disclosure, such problems can be ameliorated by utilizing a surgical stapling instrument which can clamp the soft tissue, for example, prior to the staples being deployed from the staple cartridge. In various embodiments, a surgical stapling instrument can include an actuator configured to be retracted relative to the distal end of the disposable loading unit where the actuator can be operably engaged with the anvil to rotate the anvil between an open position and a closed position. In at least one embodiment, the actuator can include a cam, where the cam can include an arcuate profile having an apex, and where the apex can be configured to be in contact with the anvil when the anvil is in a closed position. In at least one such embodiment, the anvil can apply a clamping force to the soft tissue prior to the staples being deployed and prevent, or at least inhibit, the soft tissue from flowing, or 'milking', out of the distal end of the disposable loading unit.

In various embodiments of the present disclosure, a surgical stapling instrument can include a disposable loading unit comprising a staple cartridge, an anvil, and a sleeve, wherein the sleeve can be configured to be slid relative to the staple cartridge and the anvil. In at least one embodiment, the sleeve can include an aperture wherein the sleeve can be slid over at least a portion of the anvil and the staple cartridge to hold the anvil in a closed position. In at least one such embodiment, the sleeve can be slid into position to apply a clamping force to the soft tissue before staples are deployed into the soft tissue. In various embodiments, a surgical stapling instrument can include a tongue configured to be slid relative to a staple cartridge and an anvil, wherein the tongue can be configured to engage the anvil and hold the anvil in a closed position. In at least one embodiment, the tongue can be configured such that it applies a force to the anvil at a distal end of the disposable loading unit so as to prevent, or at least reduce, soft tissue from milking out of the distal end.

After the anvil has been moved into a closed position, a drive beam can be advanced within the disposable loading unit to eject the staples therefrom and/or incise the soft tissue. In various circumstances, the anvil can include a slot defined therein which can be configured to receive at least a portion of the drive beam. In use, the drive beam can apply forces to the anvil which can cause the anvil to elastically and/or plastically deform and, as a result, affect the deployment of the surgical staples into the soft tissue. In various embodiments of the present disclosure, an anvil can include a first member having staple pockets for deforming the staples, a first cover plate secured to the first member, and a second cover plate secured to at least one of the first member and the first cover plate, wherein the first and second cover plates can be configured to support the first member. In at least one embodiment, an anvil can include a first member inserted into a second member, where the second member can be deformed such that the first member can be retained to and support the second member. In other various embodiments, the first member can be press-fit into the second member. In at least one embodiment, as a result of the above, the anvil can be better configured to withstand the forces applied thereto and eliminate, or at least reduce, undesirable deflections within the anvil.

In various circumstances, especially during endoscopic surgical procedures, at least a portion of a surgical stapling instrument is inserted through a cannula, or trocar, into a surgical site. Often, an anvil of a disposable loading unit is moved into its closed position before it is inserted into the trocar and then reopened after it has been inserted therethrough. Some disposable loading units having large anvils and/or staple cartridges may not fit, or easily fit, through the trocar. In various embodiments of the present disclosure, a surgical stapling instrument can include a disposable loading unit having an anvil which can be moved between open, closed, and/or collapsed positions to facilitate the insertion of the disposable loading unit through the trocar. More particularly, in at least one embodiment, an anvil can be moved between a closed position in which the anvil is a first distance away from the staple cartridge, for example, and a collapsed position in which the anvil is closer to the staple cartridge such that the disposable loading unit can be more easily inserted through the trocar.

After the disposable loading unit has been used, or expended, it can be removed from the elongated body of the surgical instrument and a new disposable loading unit can be assembled to the elongated body. Thereafter, the surgical instrument can be reinserted into a surgical site to perform additional steps of a surgical technique. In various circumstances, though, a surgeon, or other clinician, may become confused as to whether a disposable loading unit has been previously expended. In various embodiments of the present disclosure, a disposable loading unit can include a lockout feature which can prevent, or at least inhibit, an expended disposable loading unit from being reassembled to the elongated body of the surgical instrument.

BRIEF DESCRIPTION OF THE DRAWINGS

Various preferred embodiments are described herein with reference to the drawings:

FIG. 2 is a top view of the surgical apparatus shown in FIG. 1;

FIG. 3 is a side view of the surgical apparatus shown in FIG. 1;

FIG. 10a is a perspective view of the translation member of the articulating mechanism and the proximal end of the elongated body of the surgical stapling apparatus shown in FIG. 1;

FIG. 19 is a perspective view of a disposable loading unit usable with the surgical stapling apparatus of FIG. 1;

FIG. 20 is another perspective view of a disposable loading unit usable with the surgical stapling apparatus of FIG. 1;

FIG. 28 is an enlarged perspective view of the mounting assembly of the disposable loading unit shown in FIG. 19 mounted to a distal end portion of the proximal housing portion;

FIG. 29 is an enlarged perspective view of the proximal housing portion and the mounting assembly of the disposable loading unit shown in FIG. 19 with the upper housing half removed;

FIG. 30 is a perspective view of the proximal housing portion and the mounting assembly of the disposable loading unit shown in FIG. 19 with the upper housing half removed;

FIG. 32 is an enlarged perspective view of the axial drive assembly shown in FIG. 31;

FIG. 33 is an enlarged perspective view of the proximal end of the axial drive assembly shown in FIG. 31 including the locking device;

FIG. 34 is an enlarged perspective view of the distal end of the axial drive assembly shown in FIG. 31;

FIG. 40 is a perspective view of the surgical stapling apparatus shown in FIG. 1 with the disposable loading unit of FIG. 19 detached from the elongated body;

FIG. 41 is an enlarged perspective view of the disposable loading unit of FIG. 19 during attachment to the elongated body of the surgical stapling apparatus shown in FIG. 1;

FIG. 42 is another enlarged perspective view of the disposable loading unit of FIG. 19 during attachment to the elongated body of the surgical stapling apparatus shown in FIG. 1;

FIG. 50 is a cross-sectional view of the handle assembly of the stapling apparatus of FIG. 1 during the clamping stroke of the apparatus;

FIG. 51 is a side cross-sectional view of the distal end of the tool assembly of the stapling apparatus shown in FIG. 1 during firing of the apparatus;

FIG. 52 is a side cross-sectional view of the distal end of the tool assembly of the stapling apparatus shown in FIG. 1 after firing of the apparatus;

FIG. 54 is a side cross-sectional view of the handle assembly of the stapling apparatus during actuation of the emergency release button;

FIG. 57 is a top view of the distal end of the elongated body, the mounting assembly, and the proximal end of the tool assembly during articulation of the stapling apparatus;

FIG. 58 is a perspective view of the surgical stapling apparatus during articulation of the tool assembly;

FIG. 59 is a perspective view of the surgical stapling apparatus during articulation and rotation of the tool assembly;

FIG. 60 is a top view of the distal end of the disposable loading unit immediately prior to articulation;

FIG. 61 is a top view of the distal end of the elongated body, the mounting assembly, and the proximal end of the tool assembly during articulation of the stapling apparatus;

FIG. 70 is a cross-sectional view of a connector portion of a disposable loading unit assembled to a connector portion of an elongated body of an alternative embodiment of a surgical stapling apparatus;

FIG. 71 is a detail view of the connector portions of FIG. 70;

FIG. 76 is a cross-sectional view of the disposable loading unit of FIG. 74 including an anvil in an open position;

FIG. 76A is a detail view of the disposable loading unit of FIG. 74 illustrating an actuator operably engaged with the anvil;

FIG. 77 is a cross-sectional view of the disposable loading unit of FIG. 74 illustrating the anvil in a closed position;

FIG. 77A is a detail view of the anvil and actuator of the disposable loading unit of FIG. 76A;

FIG. 80 is a bottom plan view of the disposable loading unit of FIG. 74;

FIG. 81 is a cross-sectional view of a staple cartridge carrier of the disposable loading unit of FIG. 74;

FIG. 82 is a cross-sectional elevational view of an alternative embodiment of a disposable loading unit with some components removed, the disposable loading unit including an anvil in an open position;

FIG. 83 is a detail view of the disposable loading unit of FIG. 82 including an actuator for closing the anvil;

FIG. 84 is another cross-sectional elevational view of the disposable loading unit of FIG. 82 illustrating the anvil in a closed position;

FIG. 85 is a detail view of the actuator and the anvil of FIG. 83;

FIG. 86 is a perspective view of an anvil and an actuator of an alternative embodiment of a disposable loading unit;

FIG. 87 is a perspective view of an actuator of a further alternative embodiment of a disposable loading unit;

FIG. 88 is a perspective view of a drive beam of an alternative embodiment of a disposable loading unit;

FIG. 89 is an end view of the drive beam of FIG. 88;

FIG. 109 is a perspective view of an alternative embodiment of a disposable loading unit including an anvil in a closed position and a sleeve in a retracted position;

FIG. 110 is a perspective view of the disposable loading unit of FIG. 109 illustrating the sleeve in an extended position to support the anvil;

FIG. 111 is a perspective view of an alternative embodiment of a disposable loading unit including an anvil in a closed position and a tongue in a retracted position;

FIG. 112 is a perspective view of the disposable loading unit of FIG. 11 illustrating the tongue in an extended position to support the anvil;

FIG. 113 is a cross-sectional view of the disposable loading unit of FIG. 111;

FIG. 114 is an exploded view of an alternative embodiment of a disposable loading unit;

FIG. 115 is a cross-sectional view of the disposable loading unit of FIG. 114 illustrating an anvil in an open position;

FIG. 116 is a detail view of the disposable loading unit of FIG. 114;

FIG. 117 is a cross-sectional view of the disposable loading unit of FIG. 114 illustrating the anvil in a closed position;

FIG. 118 is a detail view of the disposable loading unit of FIG. 116;

FIG. 119 is a cross-sectional view of the disposable loading unit of FIG. 114 illustrating the anvil in a collapsed position;

FIG. 120 is a detail view of the disposable loading unit of FIG. 114;

FIG. 121 is a cross-sectional view of the disposable loading unit of FIG. 114 illustrating the anvil in its collapsed position;

FIG. 122 is a cross-sectional view of the disposable loading unit of FIG. 114 illustrating the anvil returned to its closed position;

Figure 125:
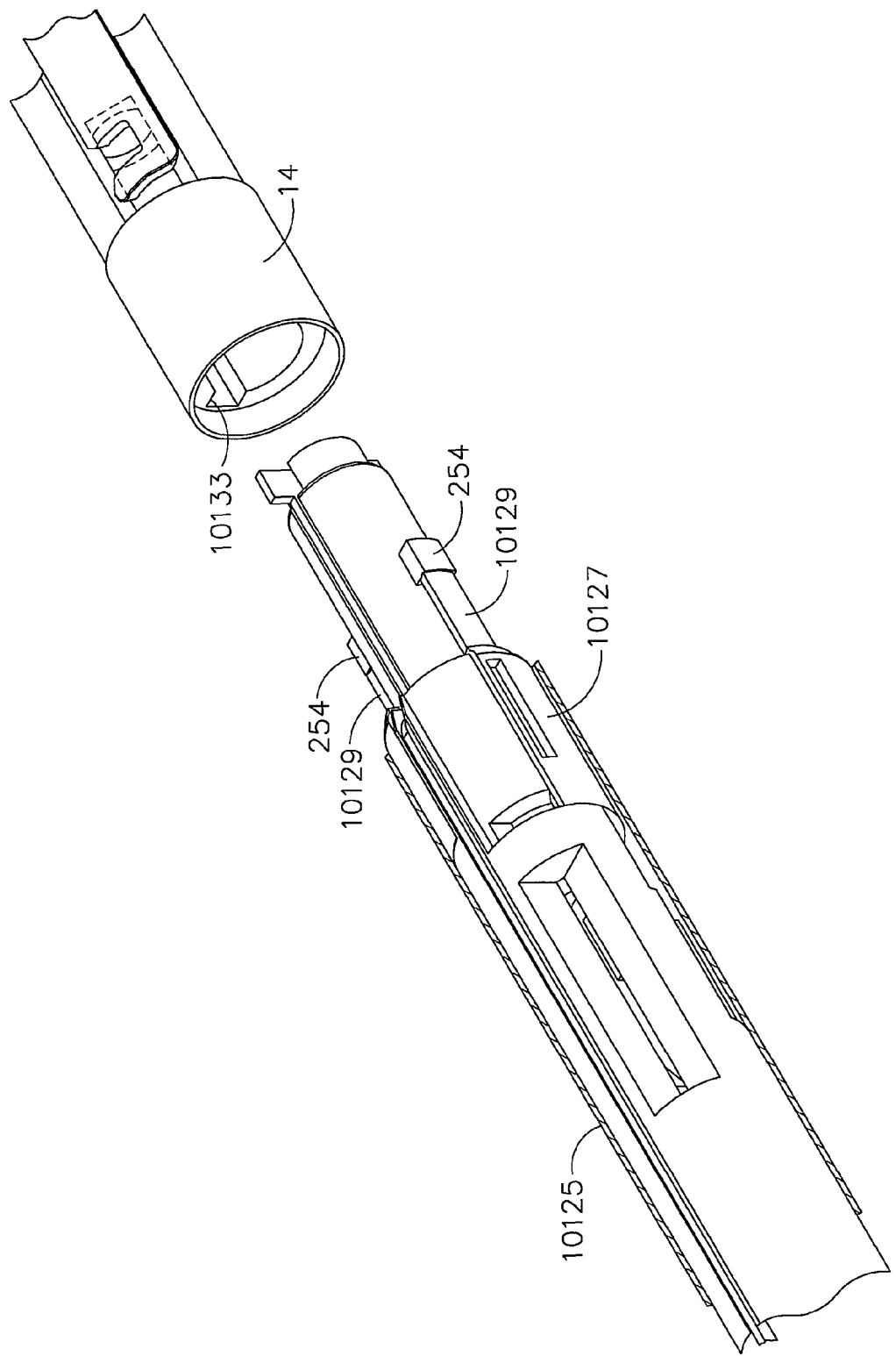
Figure 126:
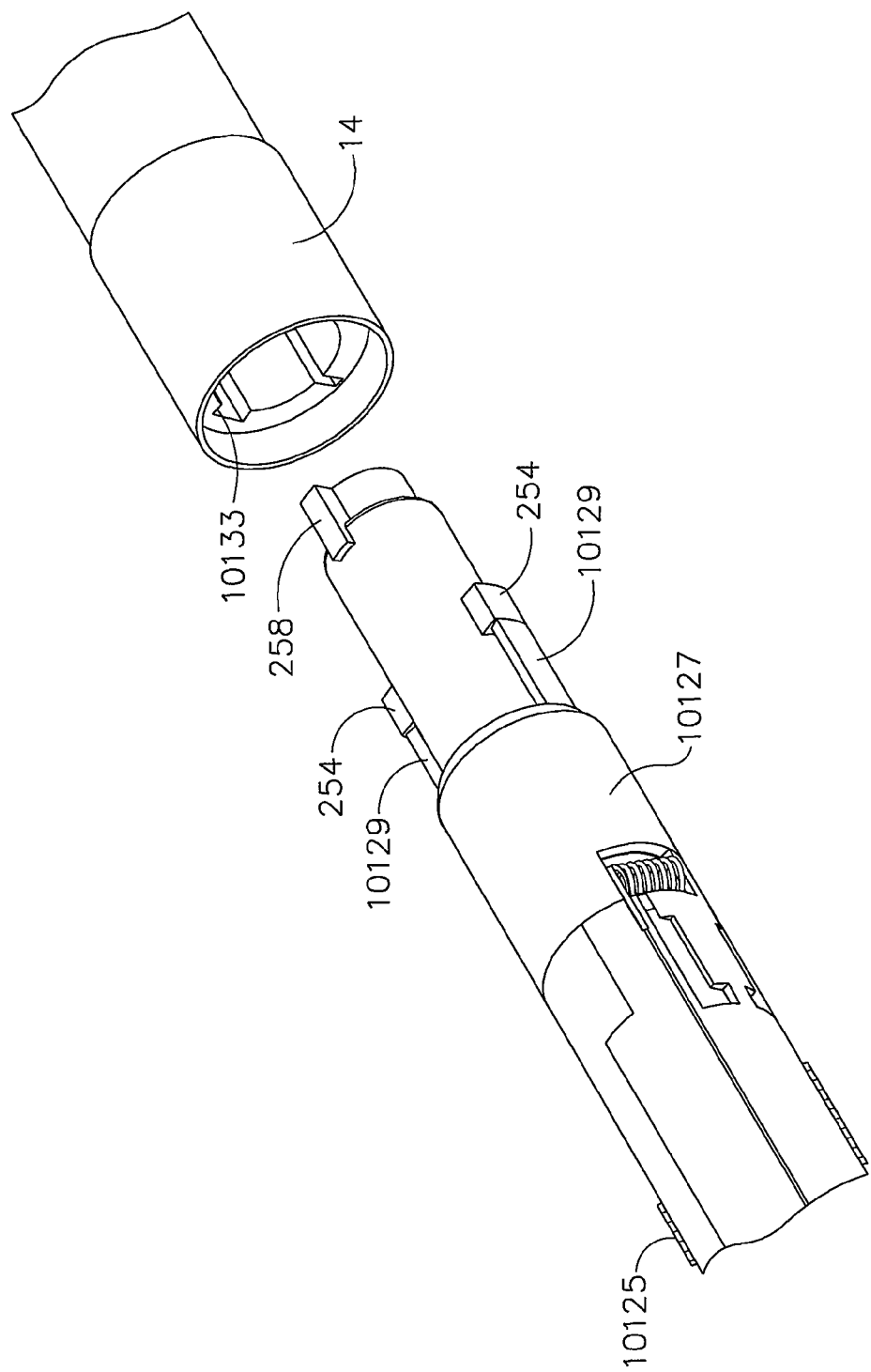
Figure 127:
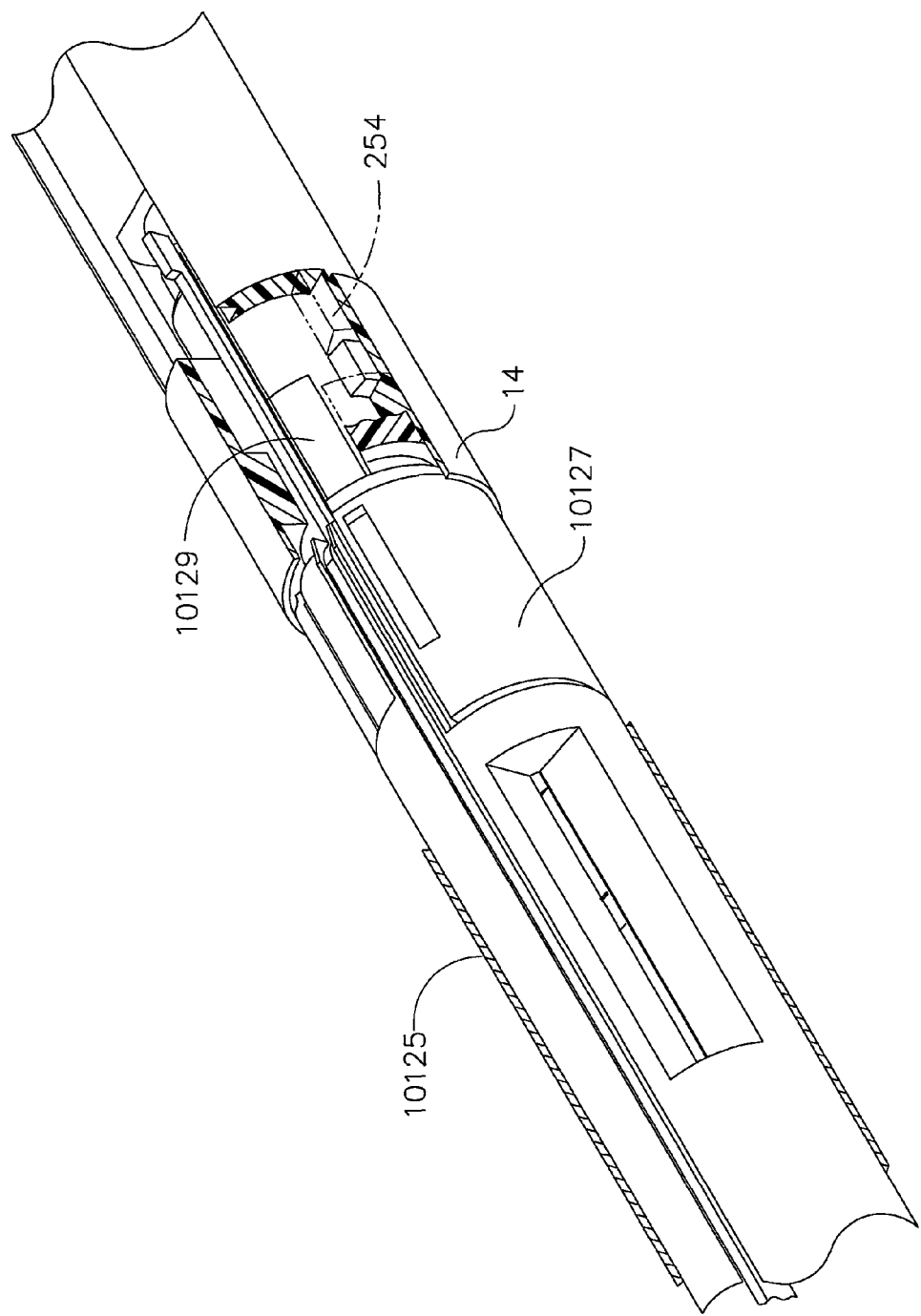
Figure 128:
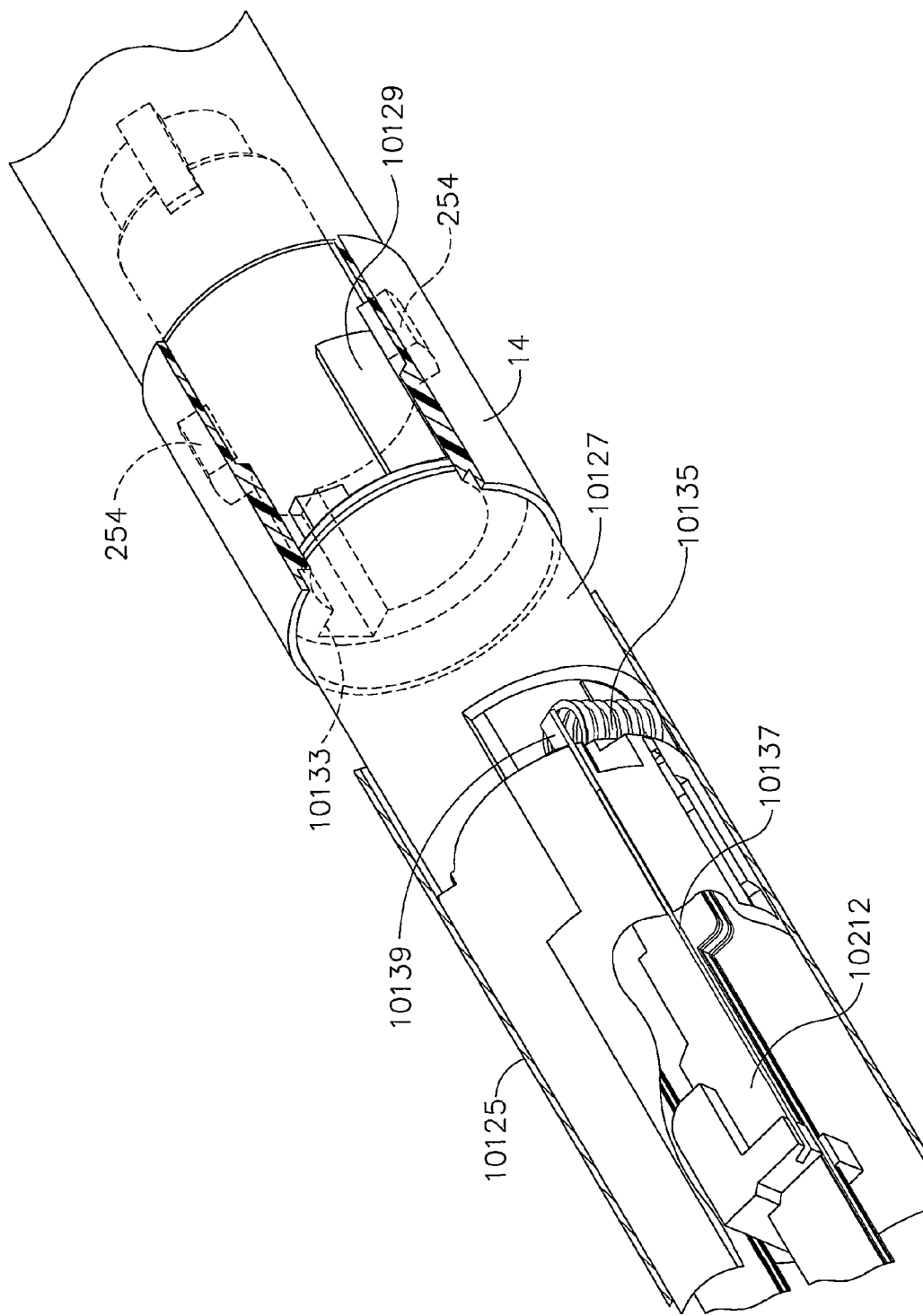
Figure 129:
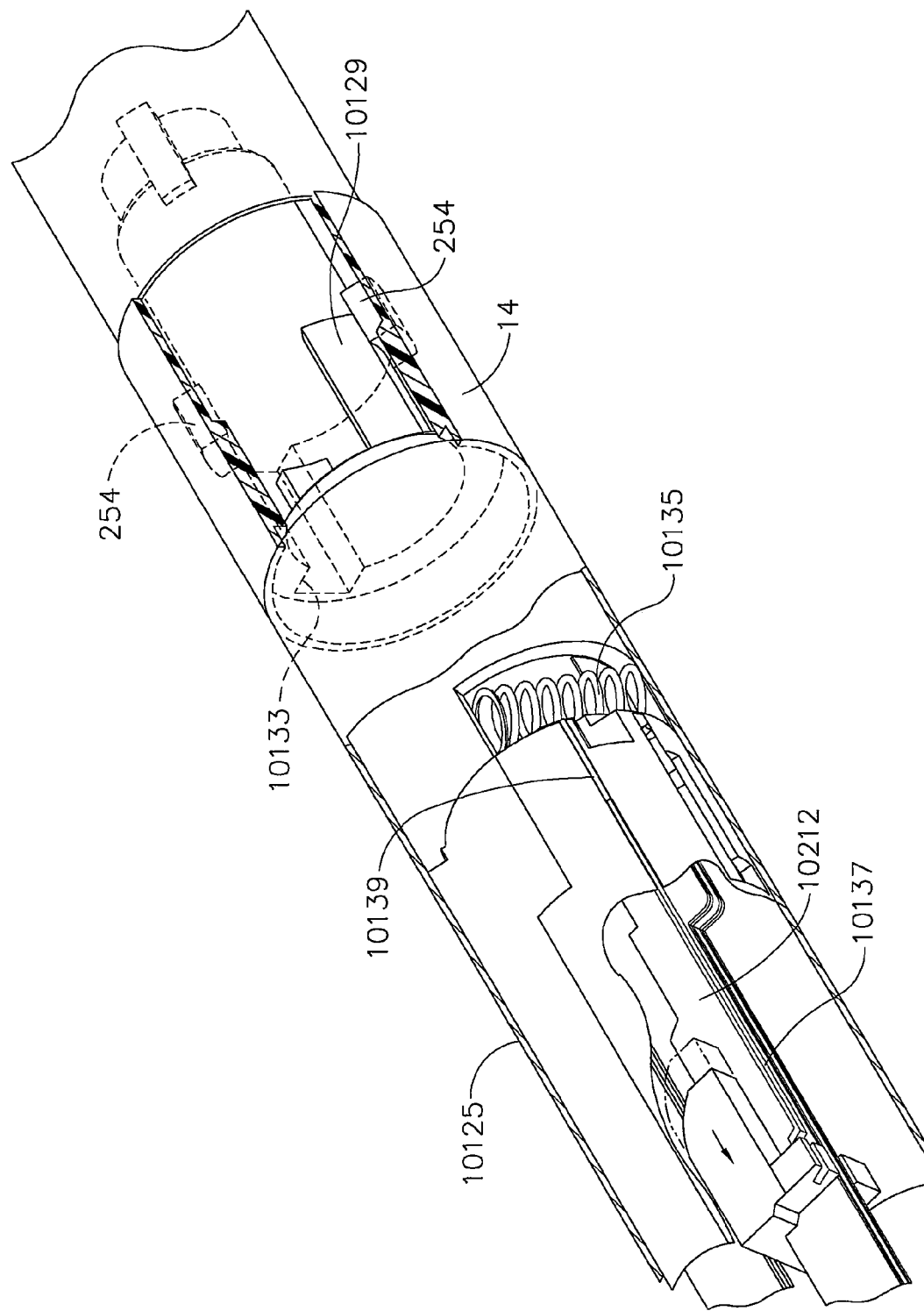
Figure 130:
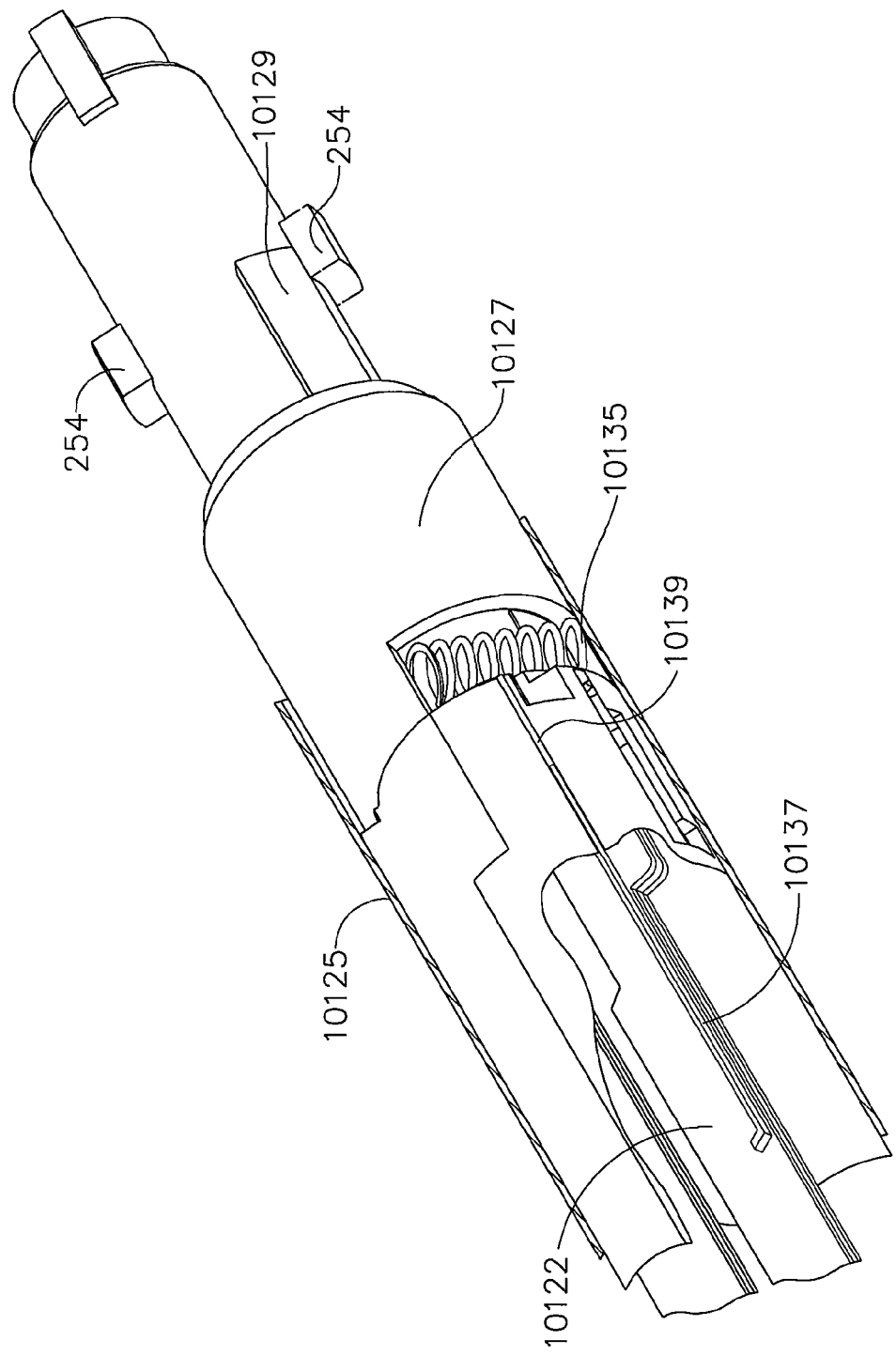
Figure 131:
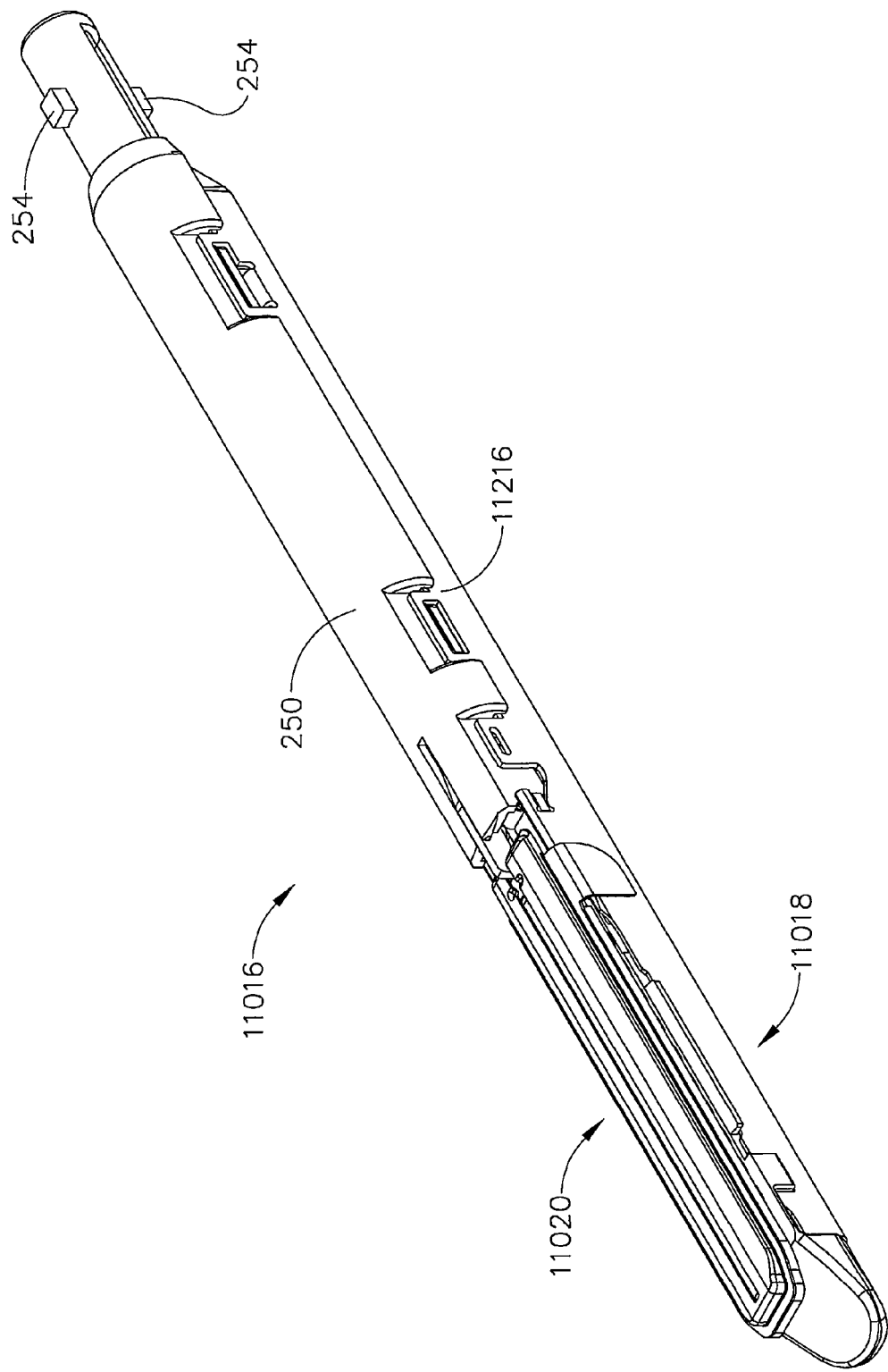
Figure 132:
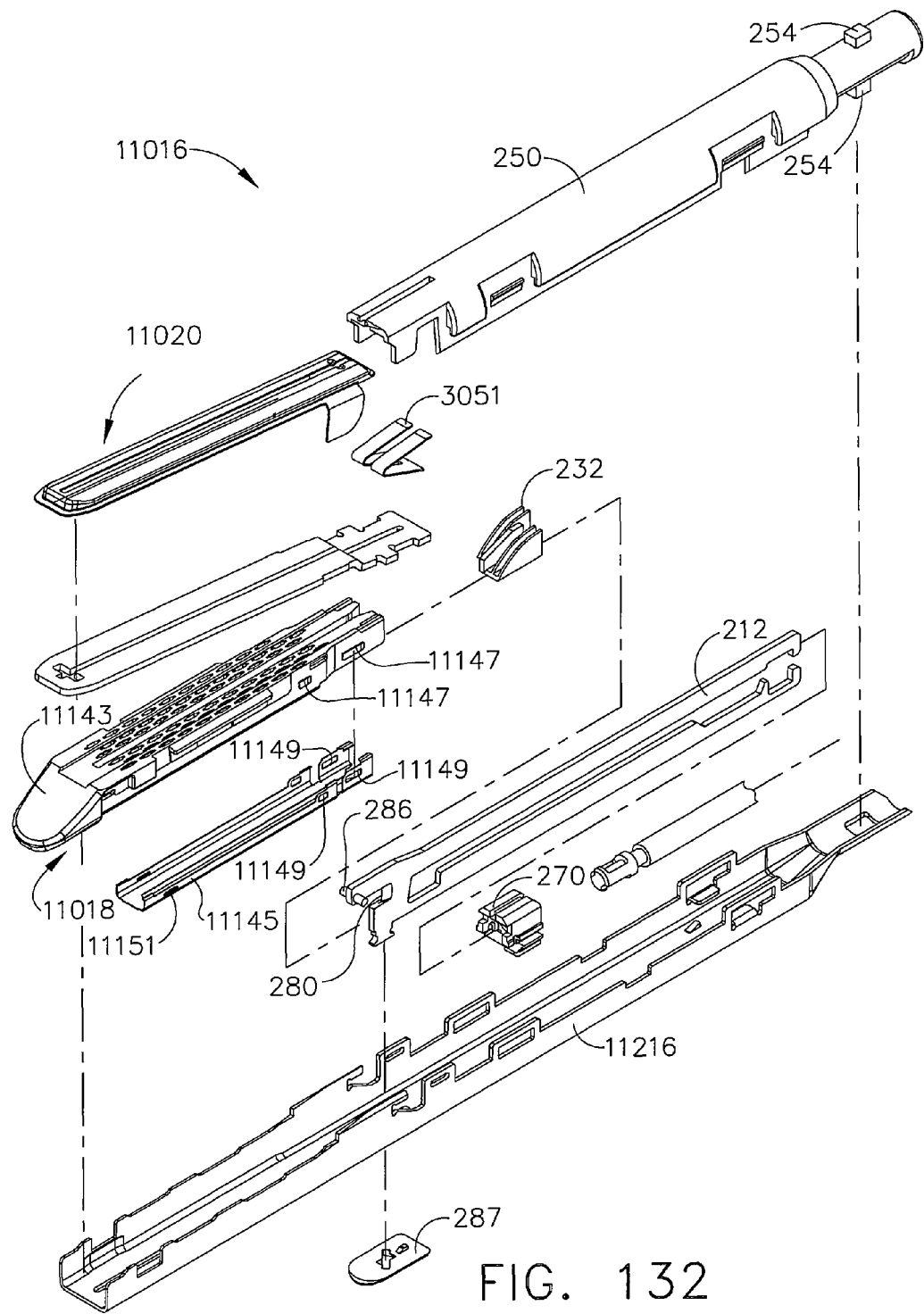

FIG. 123 is a perspective view of an alternative embodiment of a disposable loading unit;

FIG. 124 is a perspective view of a knife lockout of the disposable loading unit of FIG. 123;

FIG. 125 is a perspective view of the disposable loading unit of FIG. 123 with some components removed and a connector portion of an elongated body of a surgical stapling apparatus;

FIG. 126 is another perspective view of the disposable loading unit of FIG. 123;

FIG. 127 is another perspective view of the disposable loading unit of FIG. 123 with some components of the elongated body connector portion removed;

FIG. 128 is a perspective view of the disposable loading unit of FIG. 123 prior to a drive beam of the surgical apparatus being advanced within the disposable loading unit and a retention plate engaged with a biasing spring;

FIG. 129 is a perspective view of the disposable loading unit of FIG. 123 after the drive beam has been advanced the retention plate has been disengaged from the biasing spring;

FIG. 130 is a perspective view of the disposable loading unit of FIG. 123 after it has been disengaged from the connector portion of the elongated body illustrating the knife lockout biased into a locked-out position by the biasing spring;

FIG. 131 is a perspective view of an alternative embodiment of a disposable loading unit;

FIG. 132 is an exploded view of the disposable loading unit of FIG. 131 illustrating a removable staple cartridge;

FIG. 133 is an elevational view of the disposable loading unit of FIG. 131;

FIG. 134 is an end view of the disposable loading unit of FIG. 131; and

Figure 135:
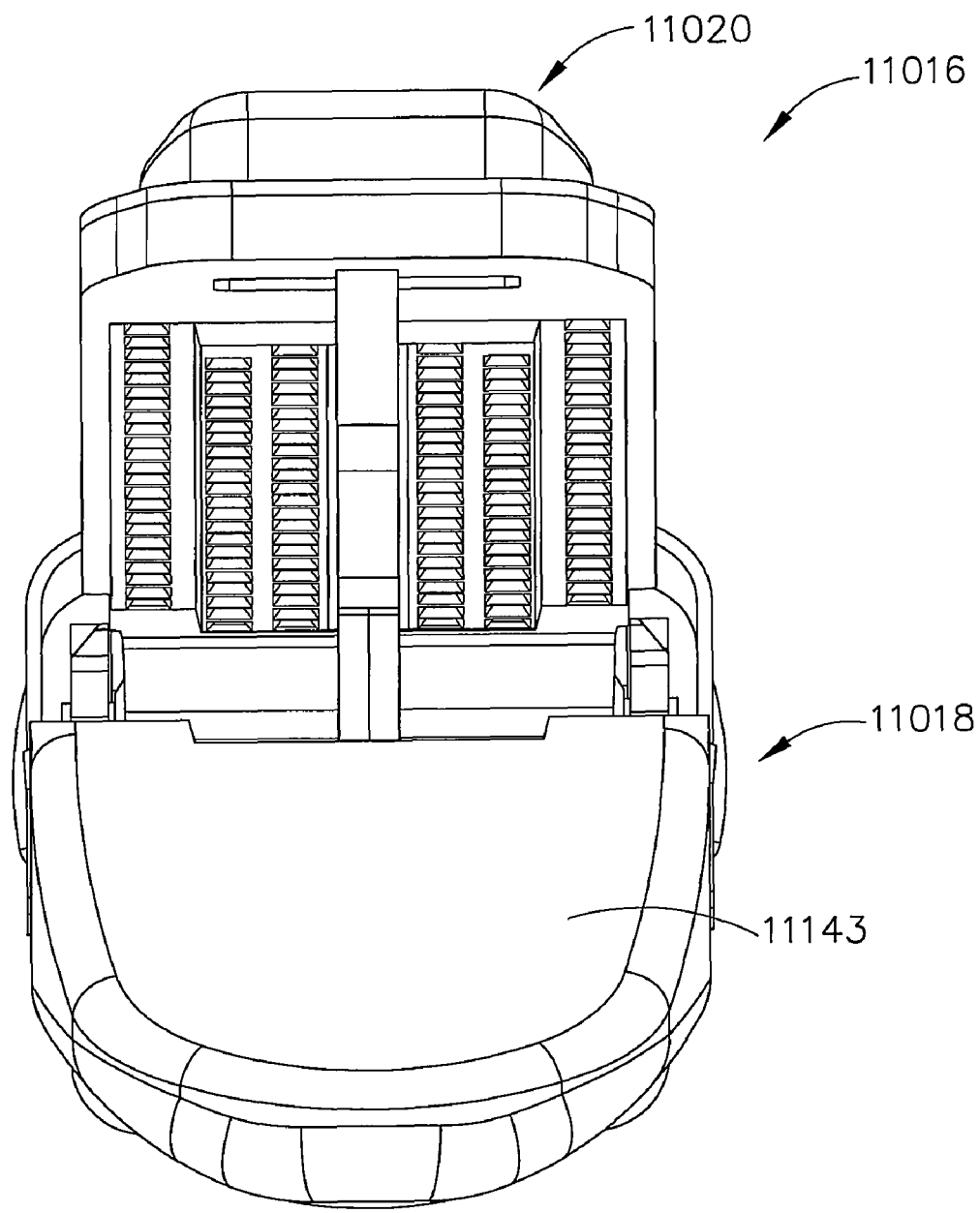

FIG. 135 is another end view of the disposable loading unit of FIG. 131 illustrating an anvil in an open position.

DETAILED DESCRIPTION OF PREFERRED EMBODIMENTS

Preferred embodiments of the presently disclosed endoscopic surgical stapling apparatus will now be described in detail with reference to the drawings, in which like reference numerals designate identical or corresponding elements in each of the several views. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

In the drawings and in the description that follows, the term "proximal", as is traditional, will refer to the end of the stapling apparatus which is closest to the operator, while the term distal will refer to the end of the apparatus which is furthest from the operator.

Figure 1:
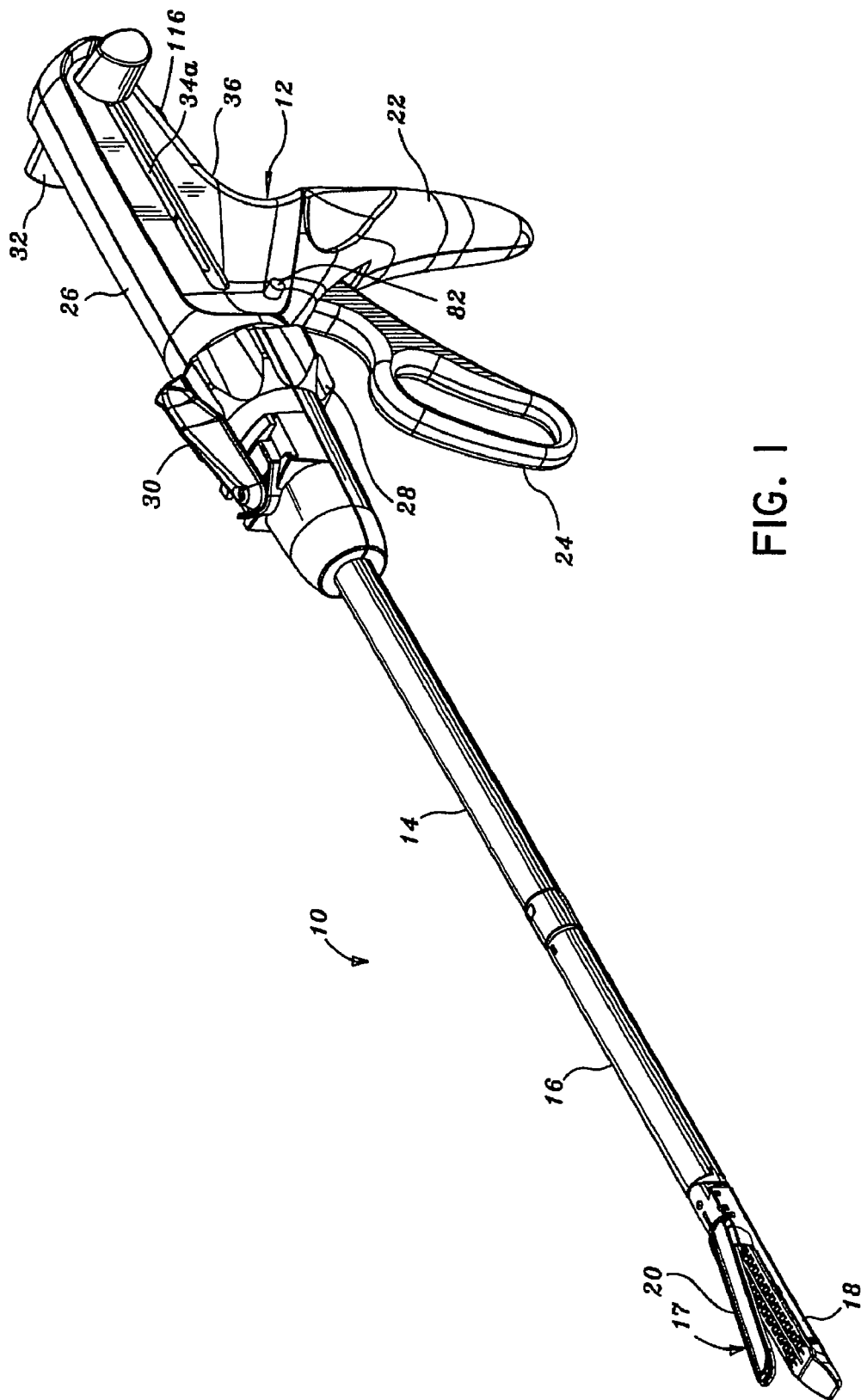
FIG. 1 is a perspective view of one preferred embodiment of the presently disclosed surgical stapling apparatus.

FIGS. 1-3 illustrate one embodiment of the presently disclosed surgical stapling apparatus shown generally as 10. Briefly, surgical stapling apparatus 10 includes a handle assembly 12 and an elongated body 14. A disposable loading unit or DLU 16 is releasably secured to a distal end of elongated body 14. Disposable loading unit 16 includes a tool assembly 17 having a cartridge assembly 18 housing a plurality of surgical staples and an anvil assembly 20 movably secured in relation to cartridge assembly 18. Disposable loading unit 16 is configured to apply linear rows of staples measuring from about 30 mm to about 60 mm in length. Disposable loading units having linear rows of staples of other lengths are also envisioned, e.g., 45 mm. Handle assembly 12 includes a stationary handle member 22, a movable handle member 24, and a barrel portion 26. A rotatable member 28 is preferably mounted on the forward end of barrel portion 26 to facilitate rotation of elongated body 14 with respect to handle assembly 12. An articulation lever 30 is also preferably mounted on the forward end of barrel portion 26 adjacent rotatable knob 28 to facilitate articulation of tool assembly 17. A pair of retraction knobs 32 are movably positioned along barrel portion 26 to return surgical stapling apparatus 10 to a retracted position, as will be described in detail below.

Figure 4:
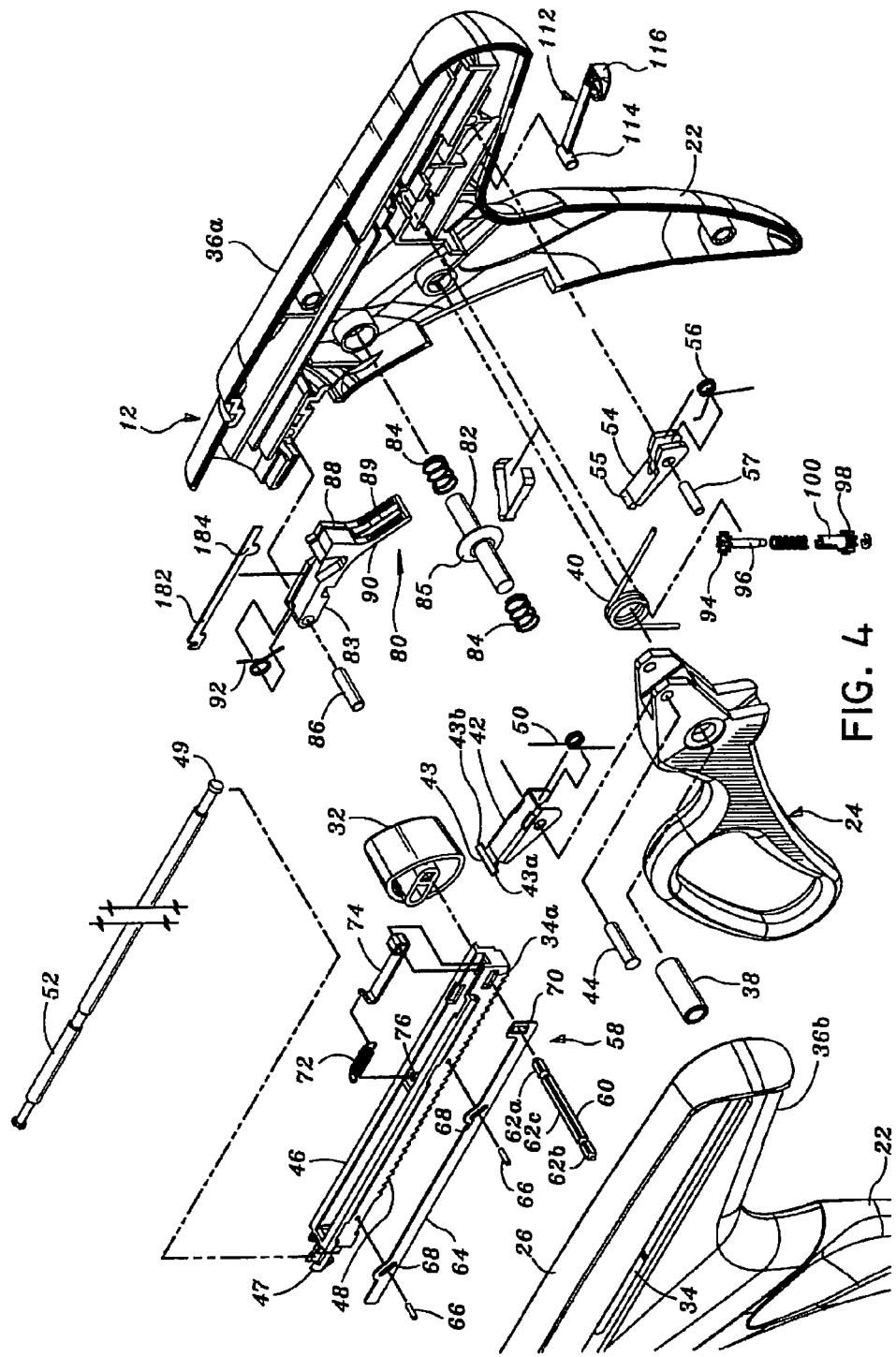
FIG. 4 is a perspective view with parts separated of the handle assembly of the surgical apparatus shown in FIG. 1.

Referring to FIG. 4, handle assembly 12 includes housing 36, which is preferably formed from molded housing half-sections 36a and 36b, which forms stationary handle member 22 and barrel portion 26 of handle assembly 12 (See FIG. 1). Movable handle member 24 is pivotably supported between housing half-sections 36a and 36b about pivot pin 38. A biasing member 40, which is preferably a torsion spring, biases movable handle 24 away from stationary handle 22. An actuation shaft 46 is supported within barrel portion 26 of housing 36 and includes a toothed rack 48. A driving pawl 42 having a rack engagement finger 43 with laterally extending wings 43a and 43b is pivotably mounted to one end of movable handle 24 about a pivot pin 44. A biasing member 50, which is also preferably a torsion spring, is positioned to urge engagement finger 43 of driving pawl 42 towards toothed rack 48 of actuation shaft 46. Movable handle 24 is pivotable to move engagement finger 43 of driving pawl 42 into contact with toothed rack 48 of actuation shaft 46 to advance the actuation shaft linearly in the distal direction. The forward end of actuation shaft 46 rotatably receives the proximal end 49 of a control rod 52 such that linear advancement of actuation shaft 46 causes corresponding linear advancement of control rod 52. A locking pawl 54 having a rack engagement member 55 is pivotably mounted within housing 36 about pivot pin 57 and is biased towards toothed rack 48 by biasing member 56, which is also preferably a torsion spring. Engagement member 55 of locking pawl 54 is movable into engagement with toothed rack 48 to retain actuation shaft 46 in a longitudinally fixed position.

A retraction mechanism 58 which includes a pair of retractor knobs 32 (See FIG. 1) is connected to the proximal end of actuation shaft 46 by a coupling rod 60. Coupling rod 60 includes right and left engagement portions 62a and 62b for receiving retractor knobs 32 and a central portion 62c which is dimensioned and configured to translate within a pair of longitudinal slots 34a formed in actuation shaft 46 adjacent the proximal end thereof. A release plate 64 is operatively associated with actuation shaft 46 and is mounted for movement with respect thereto in response to manipulation of retractor knobs 32. A pair of spaced apart pins 66 extend outwardly from a lateral face of actuation shaft 46 to engage a pair of corresponding angled cam slots 68 formed in release plate 64. Upon rearward movement of retractor knobs 32, pins 66 can release plate 64 downwardly with respect to actuation shaft 46 and with respect to toothed rack 48 such that the bottom portion of release plate 64 extends below toothed rack 48 to disengage engagement finger 43 of driving pawl 42 from toothed rack 48. A transverse slot 70 is formed at the proximal end of release plate 64 to accommodate the central portion 62c of coupling rod 60, and elongated slots 34 (See FIG. 1) are defined in the barrel section 26 of handle assembly 12 to accommodate the longitudinal translation of coupling rod 60 as retraction knobs 32 are pulled rearwardly to retract actuation shaft 46 and thus retract control rod 52 rearwardly. Actuation shaft 46 is biased proximally by spring 72 which is secured at one end to coupling rod portion 62 via connector 74 and at the other end to post 76 on actuation shaft 46.

Figure 5:
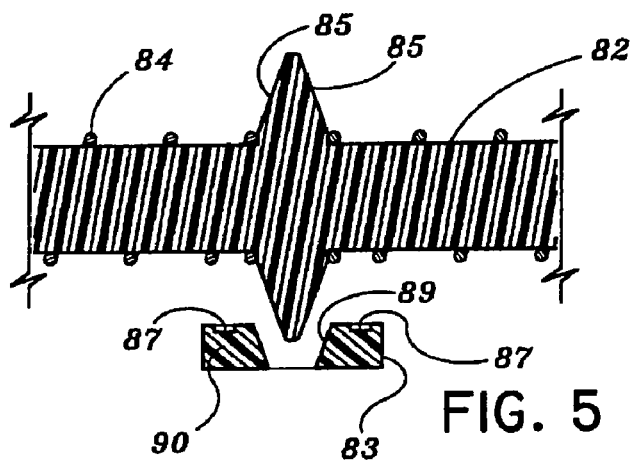
FIG. 5 is a cross-sectional view of a portion of the firing lockout mechanism shown in FIG. 4.

Referring also to FIG. 5, handle assembly 12 includes a firing lockout assembly 80 which includes a plunger 82 and a pivotable locking member 83. Plunger 82 is biased to a central position by biasing springs 84 and includes annular tapered camming surfaces 85. Each end of plunger 82 extends through housing 36 (See FIG. 1) adjacent an upper end of stationary handle 22. Pivotable locking member 83 is pivotably attached at its distal end between housing half-sections 36a and 36b about pivot pin 86 and includes a locking surface 88 and proximal extension 90 having a slot 89 formed therein. Locking member 83 is biased by spring 92 counter-clockwise (as viewed in FIG. 4) to move locking surface 88 to a position to abut the distal end of actuation shaft 46 to prevent advancement of shaft 46 and subsequent firing of stapling apparatus 10. Annular tapered camming surface 85 is positioned to extend into tapered slot 89 in proximal extension 90. Lateral movement of plunger 82 in either direction against the bias of either spring 84 moves tapered camming surface 85 into engagement with the sidewalls of tapered slot 89 to pivot locking member 83 clockwise about pivot pin 86, as viewed in FIG. 4, to move blocking surface 88 to a position to permit advancement of actuation shaft 46 and thus firing of stapling apparatus 10. Blocking surface 88 is retained in this position by recesses 87 which receive the tapered tip of camming surface 85 to lock locking member 83 in a counter-clockwise position. Operation of firing lockout assembly 80 will be further illustrated below.

Figure 6:
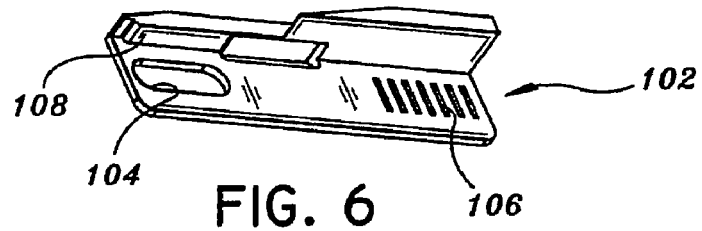
FIG. 6 is a perspective of the slide plate of the anti-reverse clutch mechanism of the surgical apparatus.
Figure 7:
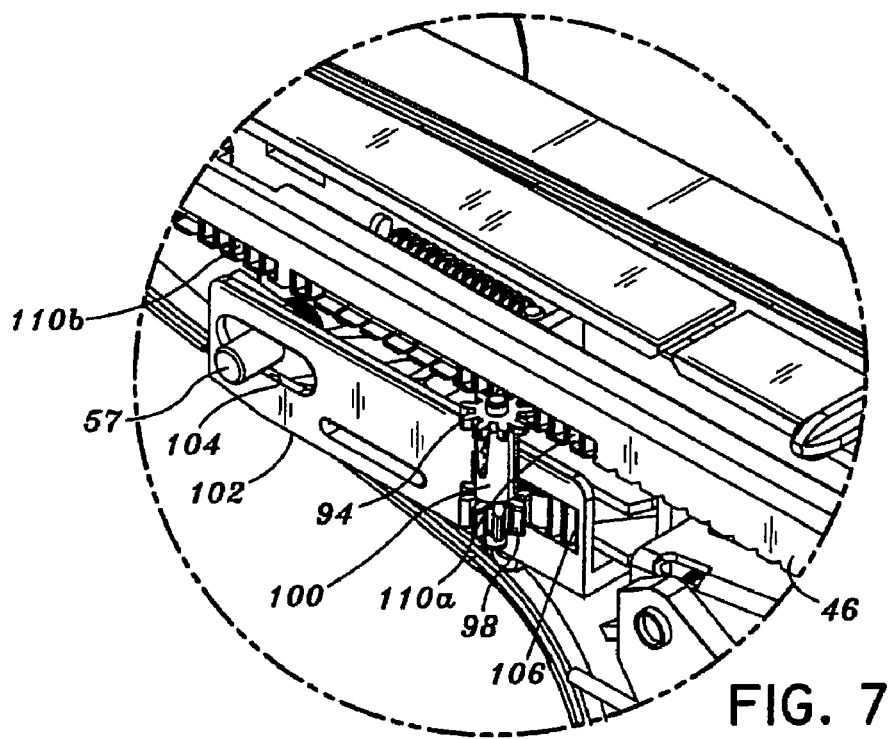
FIG. 7 is an enlarged perspective view of the anti-reverse clutch mechanism shown in FIG. 1.

Referring to FIGS. 4, 6, and 7, handle mechanism 12 also includes an anti-reverse clutch mechanism which includes a first gear 94 rotatably mounted on a first shaft 96, and second gear 98 mounted on a second shaft 100, and a slide plate 102 (FIGS. 6 and 7) slidably mounted within housing 36. Slide plate 102 includes an elongated slot 104 dimensioned and configured to be slidably positioned about locking pawl pivot pin 57, a gear plate 106 configured to mesh with the teeth of second gear 98, and a cam surface 108. In the retracted position, cam surface 108 of slide plate 102 engages locking pawl 54 to prevent locking pawl 54 from engaging toothed rack 48. Actuation shaft 46 includes a distal set of gear teeth 110a spaced from a proximal set of gear teeth 110b positioned to engage first gear 94 of actuation shaft 46 during movement of actuation shaft 46. When actuation shaft 46 is advanced by pivoting movable handle 24 about pivot pin 38, distal gear teeth 110a on actuation shaft 46 mesh with and rotate first gear 94 and first shaft 96. First shaft 96 is connected to second shaft 100 by spring clutch assembly such that rotation of first shaft 96 will cause corresponding rotation of second shaft 100. Rotation of second shaft 100 causes corresponding rotation of second gear 98 which is engaged with gear plate 106 on slide plate 102 to cause linear advancement of slide plate 102. Linear advancement of slide plate 102 is limited to the length of elongated slot 104. When slide plate has been advanced the length of slot 104, cam surface 108 releases locking pawl 54 such that it is moved into engagement with toothed rack 48. Continued advancement of actuation shaft 46 eventually moves gear teeth 110b into engagement with gear plate 106. However, since slide plate 102 is longitudinally fixed in position, the spring clutch is forced to release, such that continued distal advancement of actuation shaft 46 is permitted.

When actuation shaft 46 is returned to the retracted position (by pulling retraction knobs 34 proximally, as discussed above) gear teeth 110b engage first gear 94 to rotate second gear 98 in the reverse direction to retract slide member 102 proximally within housing 36. Proximal movement of slide member 102 advances cam surface 108 into locking pawl 54 prior to engagement between locking pawl 54 and toothed rack 48 to urge locking pawl 54 to a position to permit retraction of actuation shaft 46.

Referring again to FIG. 4, handle assembly 12 includes an emergency return button 112 pivotally mounted within housing 36 about a pivot member 114 supported between housing half-sections 36a and 36b. Return button 112 includes an externally positioned member 116 positioned on the proximal end of barrel portion 26. Member 116 is movable about pivot member 114 into engagement with the proximal end of locking pawl 54 to urge rack engagement member 55 out of engagement with toothed rack 48 to permit retraction of actuation shaft 46 during the firing stroke of the stapling apparatus 10. As discussed above, during the clamping portion of advancement of actuation shaft 46, slide plate 102 disengages pawl 54 from rack 48 and thus actuation of return button 112 is not necessary to retract the actuation shaft 46.

Figure 8:
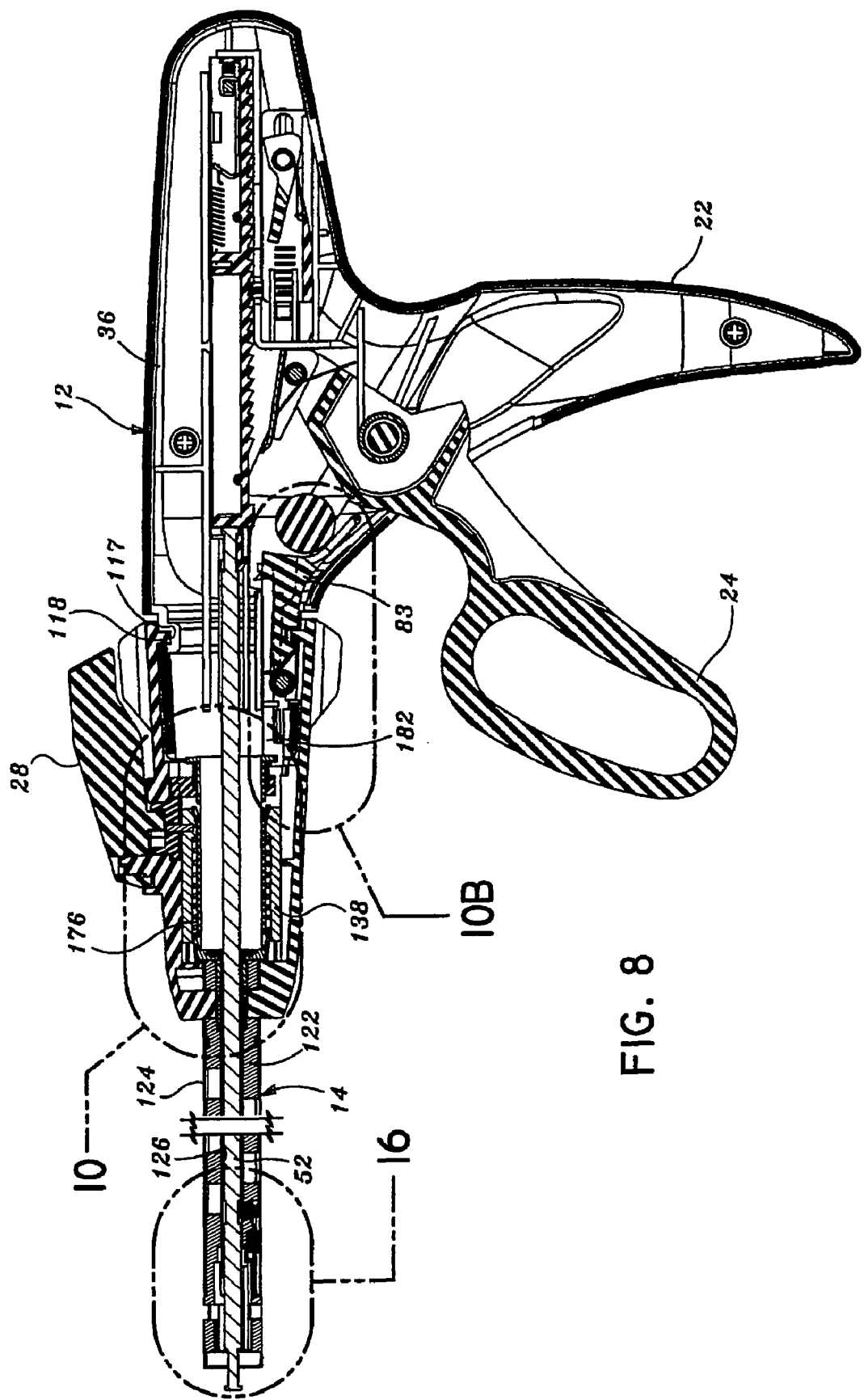
FIG. 8 is a side cross-sectional view of the surgical stapling apparatus shown in FIG. 1 in the non-actuated position with the disposable loading unit removed.
Figure 9:
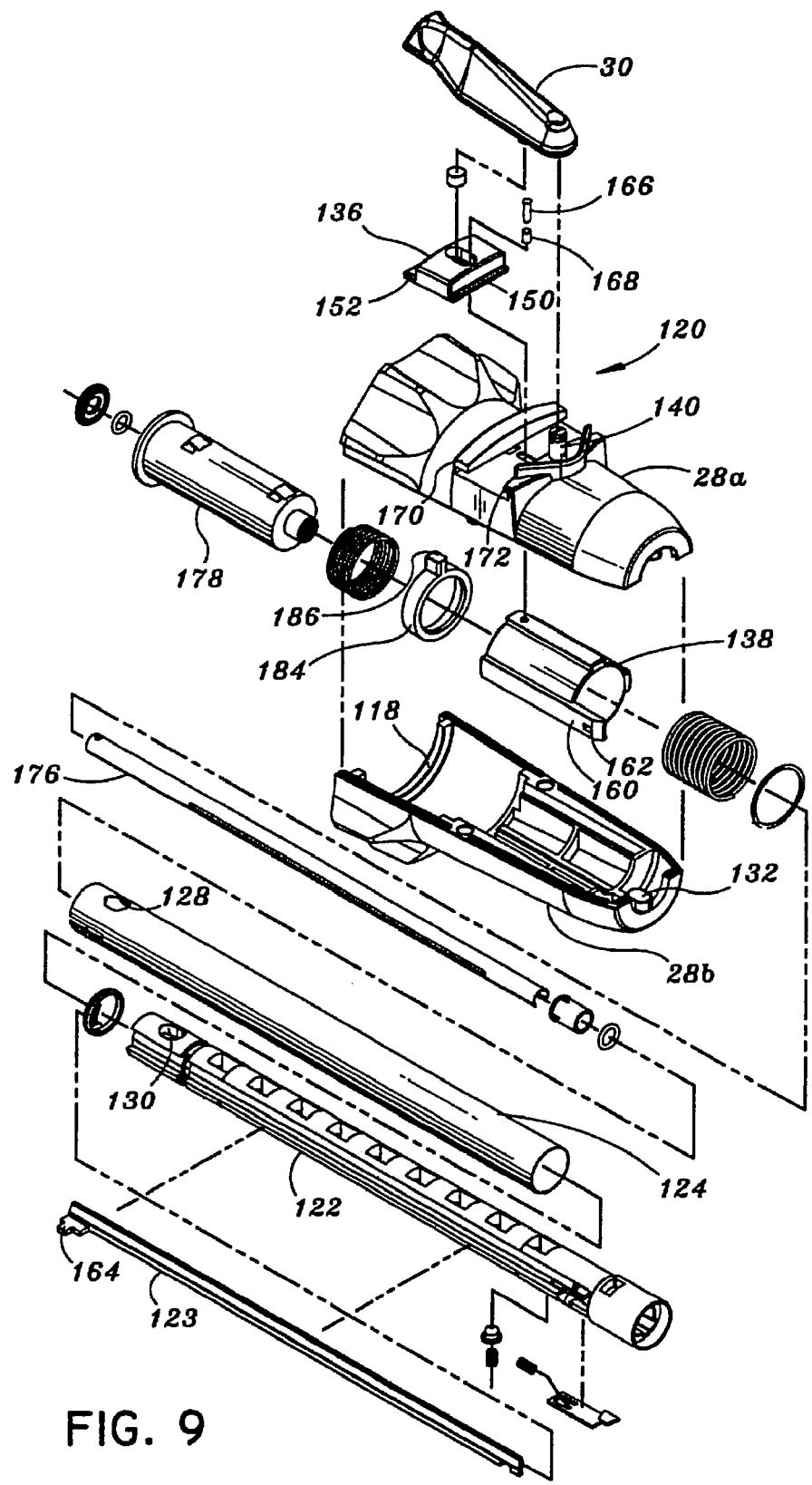
FIG. 9 is a perspective view with parts separated of the rotation member, the articulation mechanism, and the elongated body of the surgical stapling apparatus shown in FIG. 1.
Figure 10:
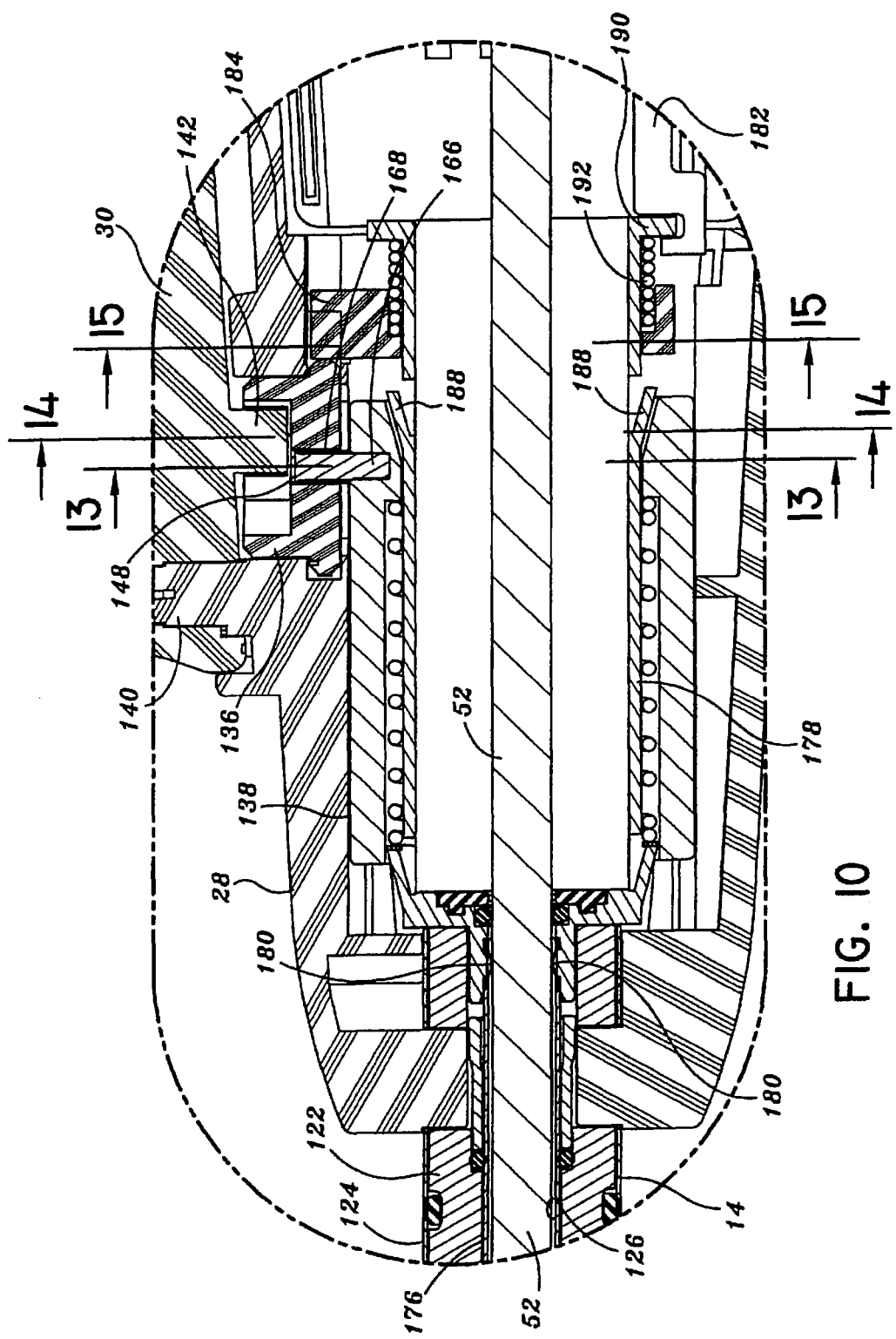
FIG. 10 is an enlarged view of the indicated area of detail shown in FIG. 8.
Figure 10B:
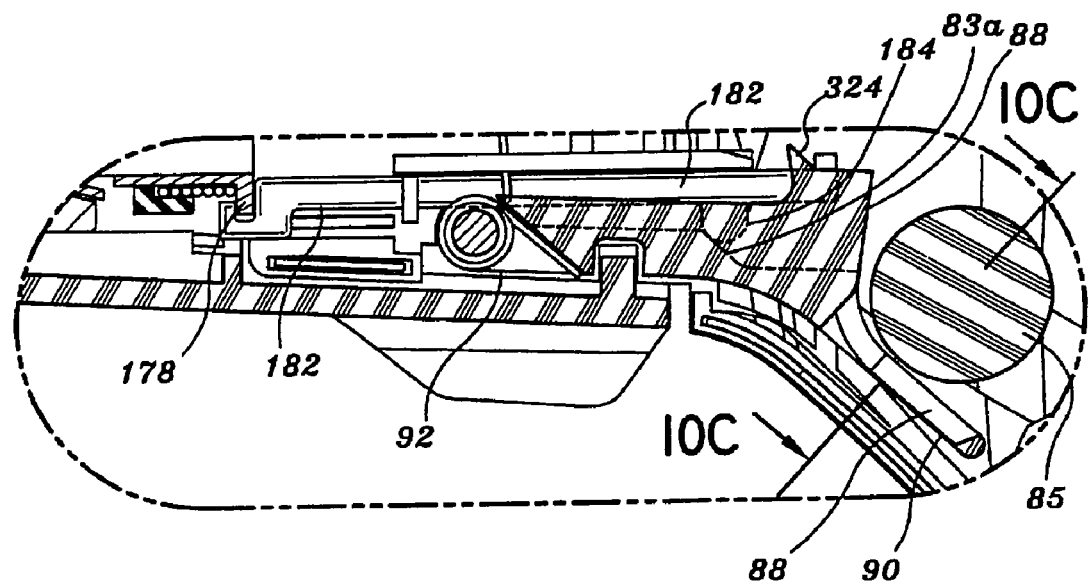
FIG. 10b is an enlarged cross-sectional view of the indicated area of detail of FIG. 8.
Figure 10C:
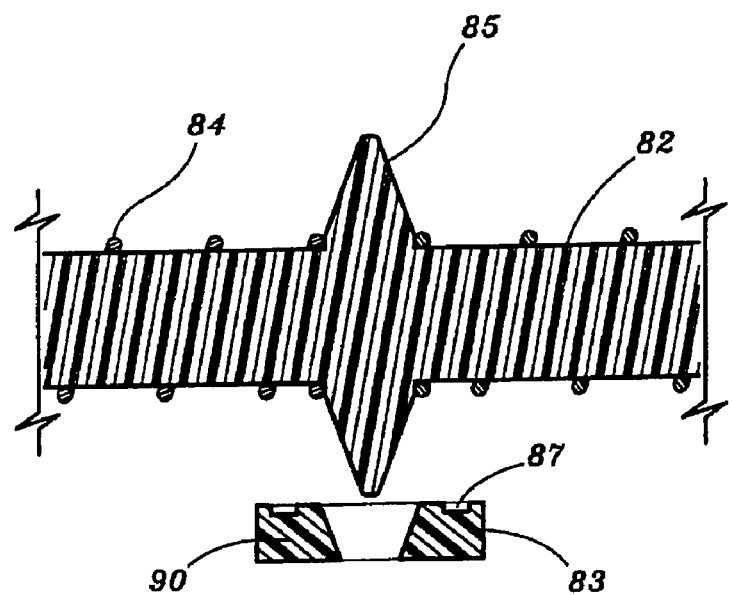
FIG. 10c is a cross-sectional view along section line 10c-10c of FIG. 8.

FIG. 8 illustrates the interconnection of elongated body 14 and handle assembly 12. Referring to FIGS. 8-10, housing 36 includes an annular channel 117 configured to receive an annular rib 118 formed on the proximal end of rotation member 28, which is preferably formed from molded half-sections 28a and 28b. Annular channel 117 and rib 118 permit relative rotation between rotation member 28 and housing 36. Elongated body 14 includes inner housing 122 and an outer casing 124. Inner housing 122 is dimensioned to be received within outer casing 124 and includes an internal bore 126 (FIG. 8) which extends therethrough and is dimensioned to slidably receive a first articulation link 123 and control rod 52. The proximal end of housing 122 and casing 124 each include a pair of diametrically opposed openings 130 and 128, respectively, which are dimensioned to receive radial projections 132 formed on the distal end of rotation member 28. Projections 132 and openings 128 and 130 fixedly secure rotation member 28 and elongated body 14 in relation to each other, both longitudinally and rotatably. Rotation of rotation knob 28 with respect to handle assembly 12 thus results in corresponding rotation of elongated body 14 with respect to handle assembly 12.

An articulation mechanism 120 is supported on rotatable member 28 and includes articulation lever 30, a cam member 136, a translation member 138, and first articulation link 123 (FIG. 9). Articulation lever 30 is pivotably mounted about pivot member 140 which extends outwardly from rotation member 28 and is preferably formed integrally therewith. A projection 142 extends downwardly from articulation lever 30 for engagement with cam member 136.

Figure 12:
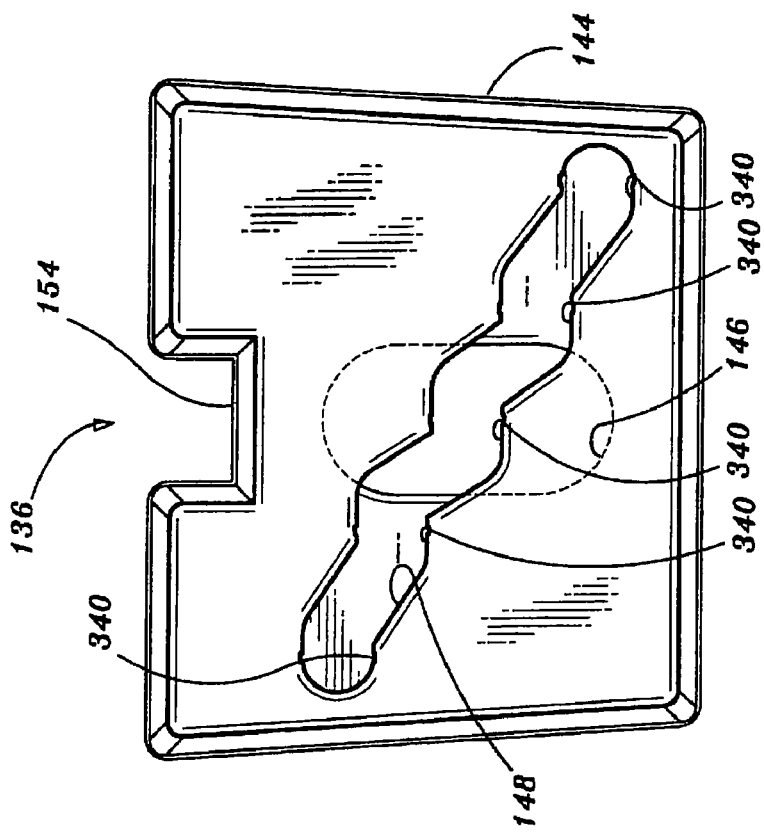
FIG. 12 is a top view of the cam member of the articulation mechanism of the surgical stapling apparatus shown in FIG. 1.
Figure 11:
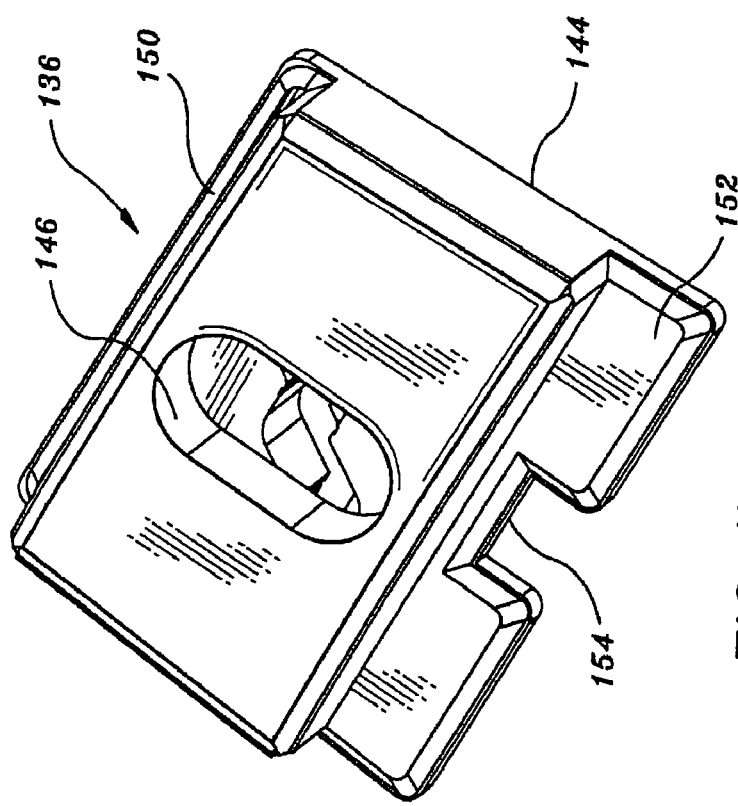
FIG. 11 is a perspective view of the cam member of the articulation mechanism of the surgical stapling apparatus shown in FIG. 1.

Referring temporarily to FIGS. 11 and 12, cam member 136 includes a housing 144 having an elongated slot 146 extending through one side thereof and a stepped canning surface 148 formed in the other side thereof. Each step of camming surface 148 corresponds to a particular degree of articulation of stapling apparatus 10. Although five steps are illustrated, fewer or more steps may be provided. Elongated slot 146 is configured to receive projection 142 formed on articulation lever 30. Housing 144 includes a distal stepped portion 150 and a proximal stepped portion 152. Proximal stepped portion 152 includes a recess 154.

Figure 13:
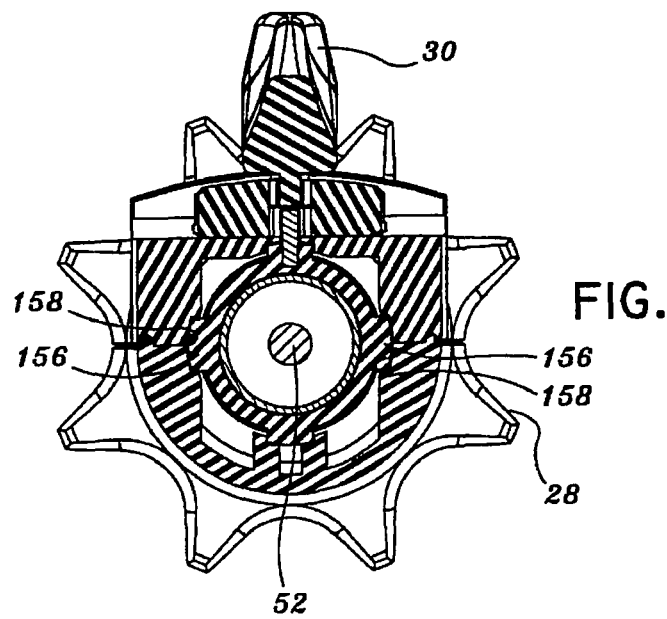
FIG. 13 is a cross-sectional view taken along section line 13-13 of FIG. 10.
Figure 14:
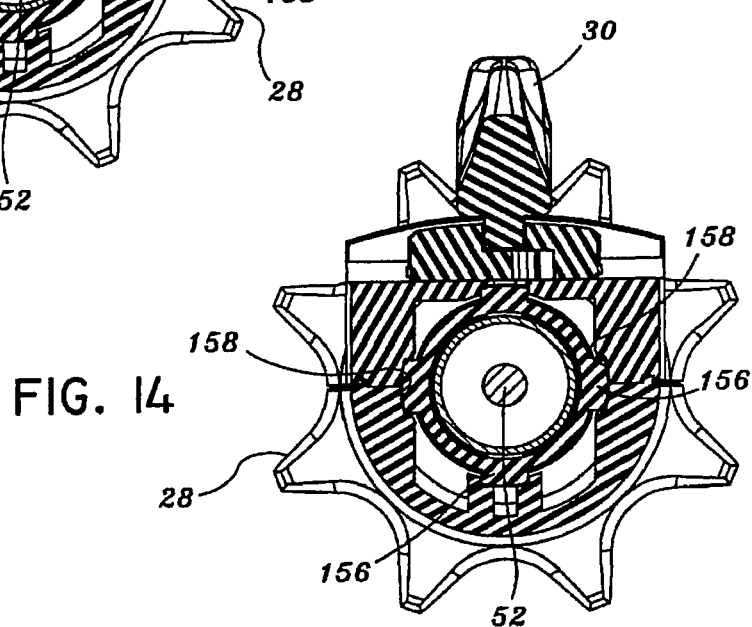
FIG. 14 is a cross-sectional view taken along section line 14-14 of FIG. 10.
Figure 15:
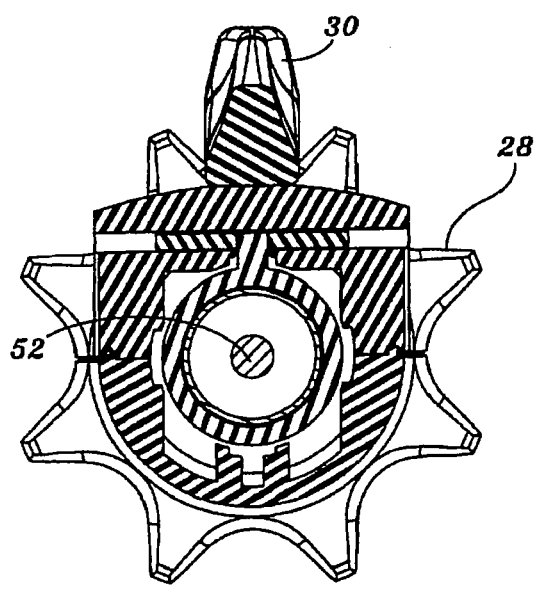
FIG. 15 is a cross-sectional view taken along section line 15-15 of FIG. 10.

Referring again to FIGS. 8-10 and also to FIGS. 13-15, translation member 138 includes a plurality of ridges 156 which are configured to be slidably received within grooves 158 formed along the inner walls of rotation member 28. Engagement between ridges 156 and grooves 158 prevent relative rotation of rotation member 28 and translation member 138 while permitting relative linear movement. The distal end of translation member 138 includes arm 160 which includes an opening 162 configured to receive a finger 164 extending from the proximal end of articulation link 123 (See FIG. 10a). A pin 166 having a housing 168 constructed from a non-abrasive material, e.g., Teflon, is secured to translation member 138 and dimensioned to be received within stepped camming surface 148.

In an assembled condition, proximal and distal stepped portions 150 and 152 of cam member 136 are positioned beneath flanges 170 and 172 formed on rotation member 28 to restrict cam member 136 to transverse movement with respect to the longitudinal axis of stapling apparatus 10. When articulation lever 30 is pivoted about pivot member 140, cam member 136 is moved transversely on rotation member 28 to move stepped camming surface 148 transversely relative to pin 166, forcing pin 166 to move proximally or distally along stepped cam surface 148. Since pin 166 is fixedly attached to translation member 138, translation member 138 is moved proximally or distally to effect corresponding proximal or distal movement of first actuation link 123.

Referring to FIGS. 8-10 and 16, a disposable loading unit sensing mechanism extends within stapling apparatus 10 from elongated body 14 into handle assembly 12. The sensing mechanism includes a sensor tube 176 which is slidably supported within bore 26 of elongated body 14. The distal end of sensor tube 176 is positioned towards the distal end of elongated body 14 and the proximal end of sensor tube 176 is secured within the distal end of a sensor cylinder 176 via a pair of nubs 180. The distal end of a sensor link 182 is secured to the proximal end of sensor cylinder 178. Sensor link 182 (See FIGS. 8a and 8c) has a bulbous end 184 which engages a camming surface 83a on pivotable locking member 83. When a disposable loading unit (not shown) is inserted in the distal end of elongated body 14, the disposable loading unit engages the distal end 177 of sensor tube 176 to drive sensor tube 176 proximally, and thereby drive sensor cylinder 178 and sensor link 182 proximally. Movement of sensor link 182 proximally causes bulbous end 184 of sensor link 182 to move distally of camming surface 83a to allow locking member 83 to pivot under the bias of spring 92 from a position permitting firing of stapling apparatus 10 to a blocking position, wherein blocking member 83 is positioned to engage actuation shaft 46 and prevent firing of stapling apparatus 10. Sensor link 182 and locking member 83 function to prevent firing of surgical stapling apparatus 10 after a disposable loading unit has been secured to elongated body 14, without first operating firing lockout assembly 80. It is noted that movement of link 182 proximally permits locking member 83 to move to its position shown in FIG. 5.

Figure 12A:
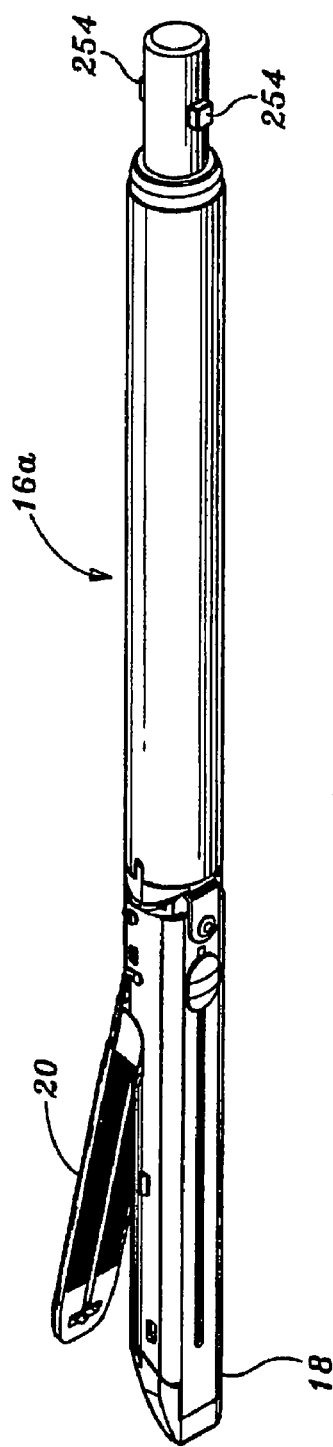
FIG. 12a is a perspective view of a non-articulating disposable loading unit usable with the surgical stapling apparatus shown in FIG. 1.
Figure 12B:
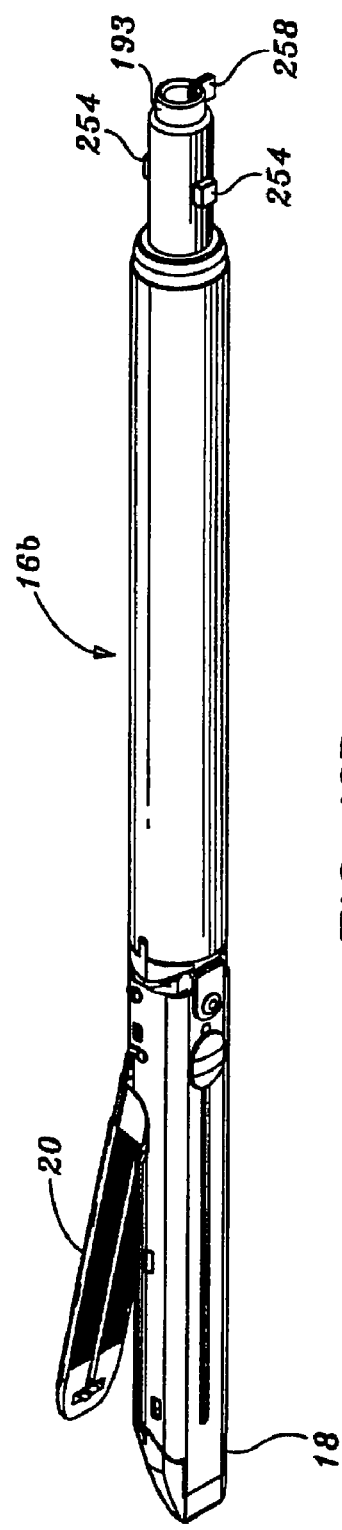
FIG. 12b is a perspective view of the preferred articulating disposable loading unit of the surgical stapling apparatus shown in FIG. 1.

Referring again to FIGS. 9-12, cam member 136 includes recess 154. A locking ring 184 having a nub portion 186 configured to be received within recess 154 is positioned about sensor cylinder 178 between a control tab portion 188 and a proximal flange portion 190. A spring 192 positioned between flange portion 190 and locking ring 184 urges locking ring distally about sensor cylinder 178. When an articulating disposable loading unit 16b having an extended insertion tip 193 is inserted into the distal end of elongated body 14 of stapling apparatus 10, insertion tip 193 causes tab portion 188 to move proximally into engagement with locking ring 184 to urge locking ring 184 and nub 186 proximally of recess 154 in cam member 136 (See FIG. 12b). With nub 186 positioned proximally of recess 154, cam member 136 is free to move transversely to effect articulation of stapling apparatus 10. A non-articulating disposable loading unit does not have an extended insertion tip (See FIG. 12a). As such, when a non-articulating disposable loading unit is inserted in elongated body 14, sensor cylinder 178 is not retracted proximally a sufficient distance to move nub 186 from recess 154. Thus, cam member 136 is prevented from moving transversely by nub 186 of locking ring 184 which is positioned in recess 154 and articulation lever 30 is locked in its central position.

Figure 16:
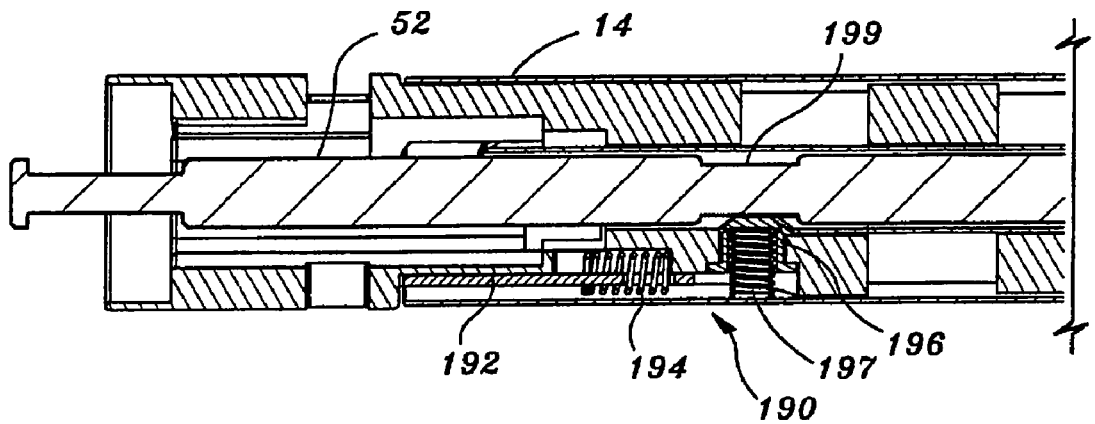
FIG. 16 is an enlarged view of the indicated area of detail shown in FIG. 8.
Figure 17:
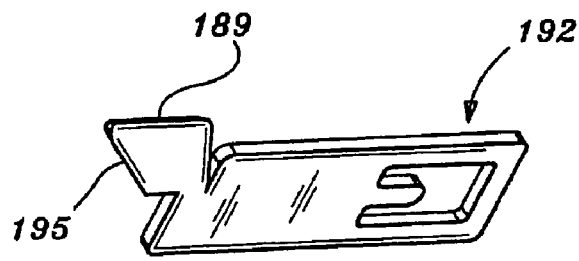
FIG. 17 is a side perspective view of the blocking plate of the surgical stapling apparatus shown in FIG. 1.
Figure 18:
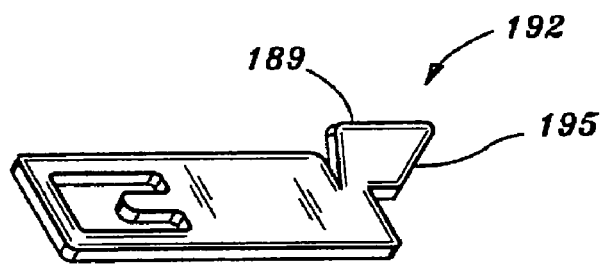
FIG. 18 is a top perspective view of the blocking plate of the surgical stapling apparatus shown in FIG. 1.
Figure 21:
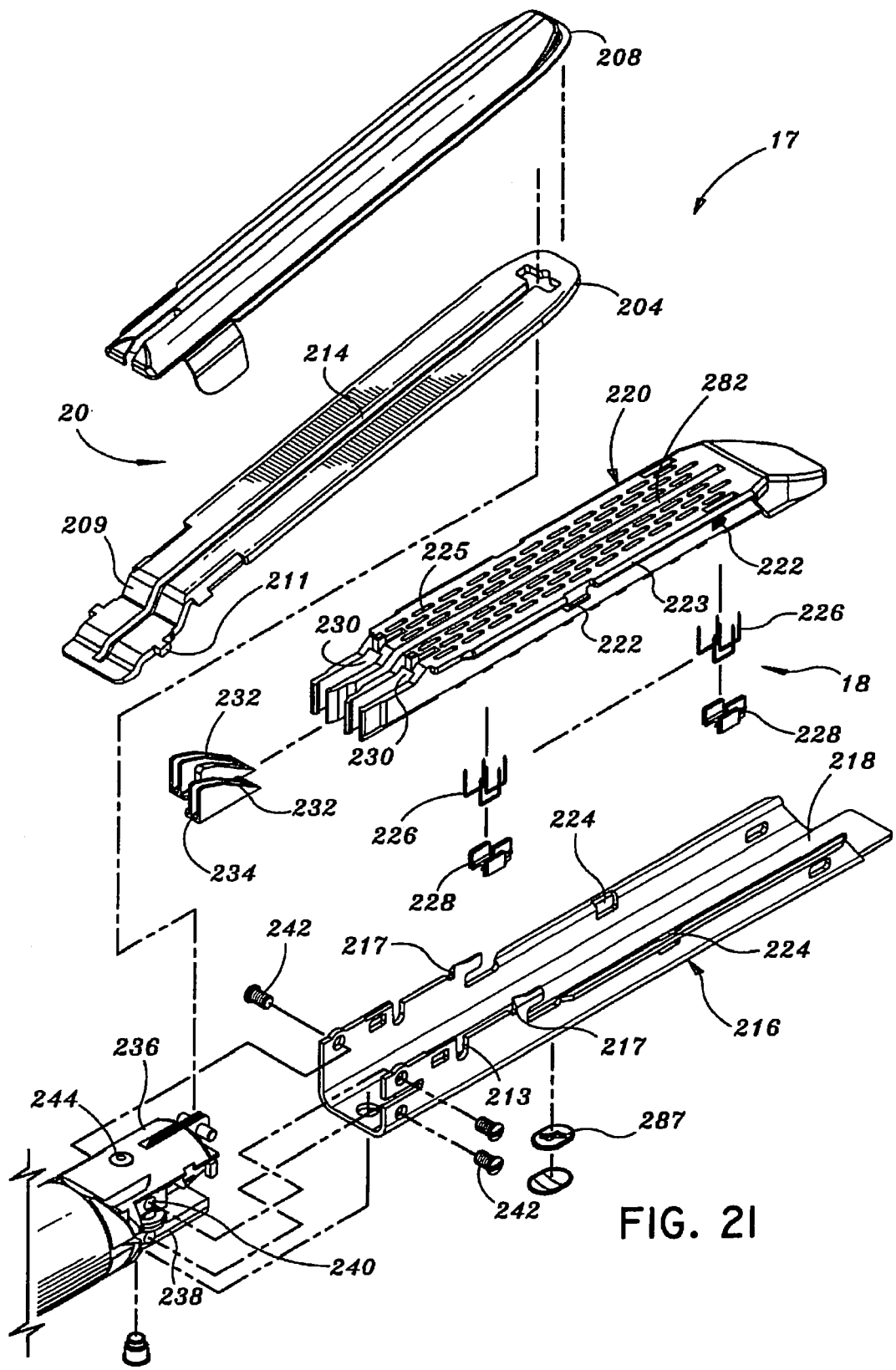
FIG. 21 is a perspective view of the tool assembly of the surgical stapling apparatus of FIG. 1 with parts separated.
Figure 22:
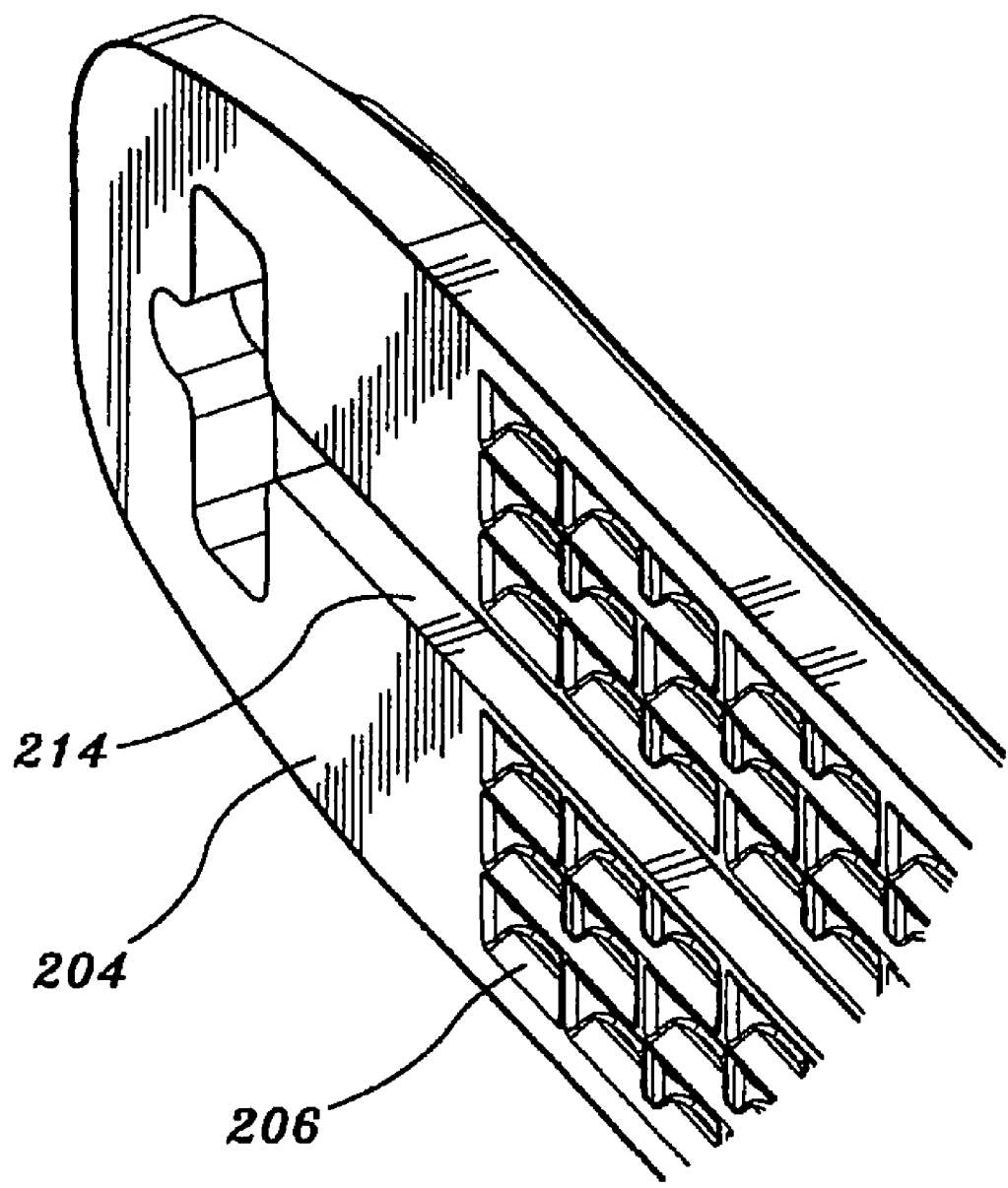
FIG. 22 is an enlarged perspective view of the distal end of the anvil assembly showing a plurality of staple deforming cavities.
Figure 23:
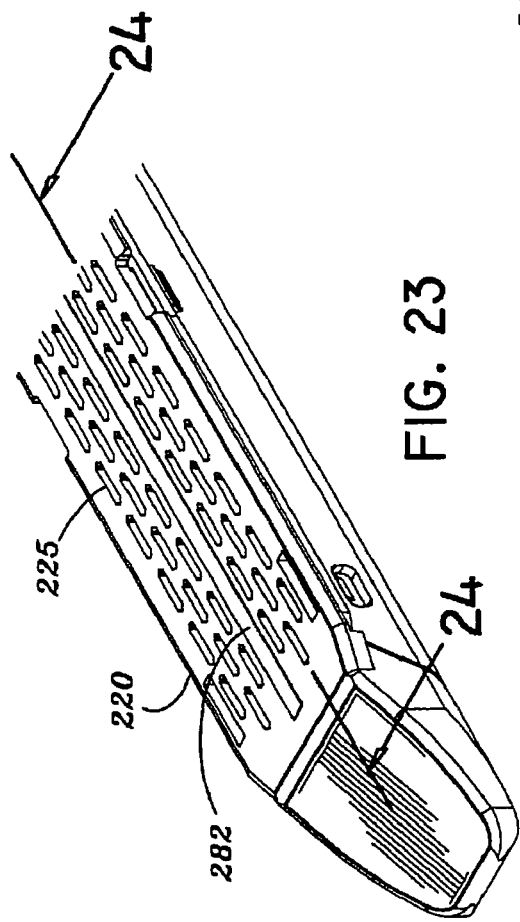
FIG. 23 is an enlarged perspective view of the distal end of the staple cartridge of the surgical stapling apparatus shown in FIG. 1.
Figure 24:
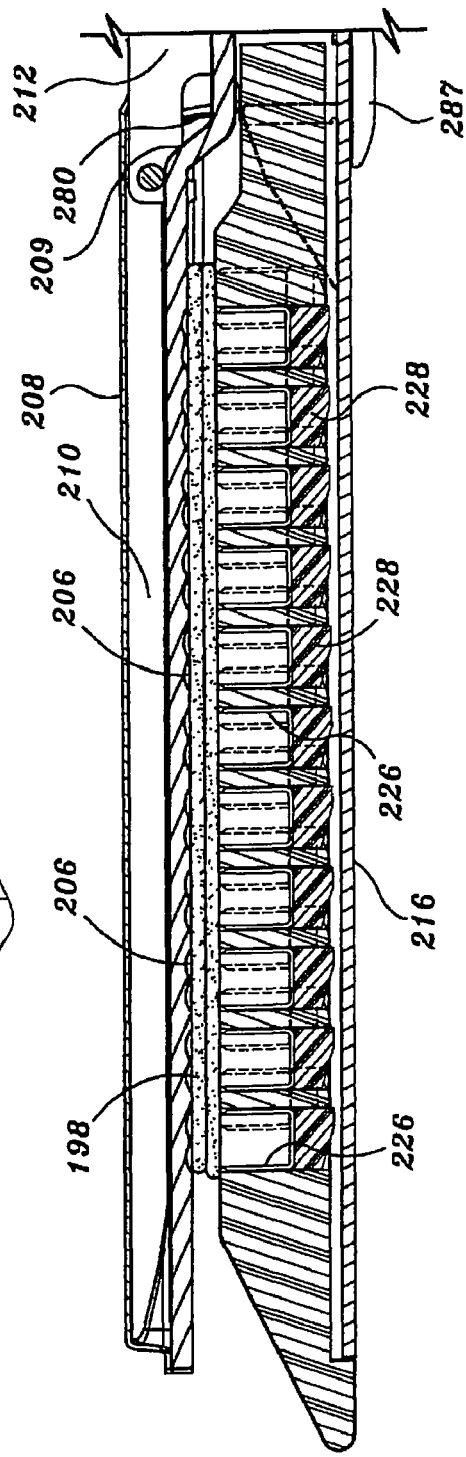
FIG. 24 is a side cross-sectional view taken along section line 24-24 of FIG. 23.
Figure 25:
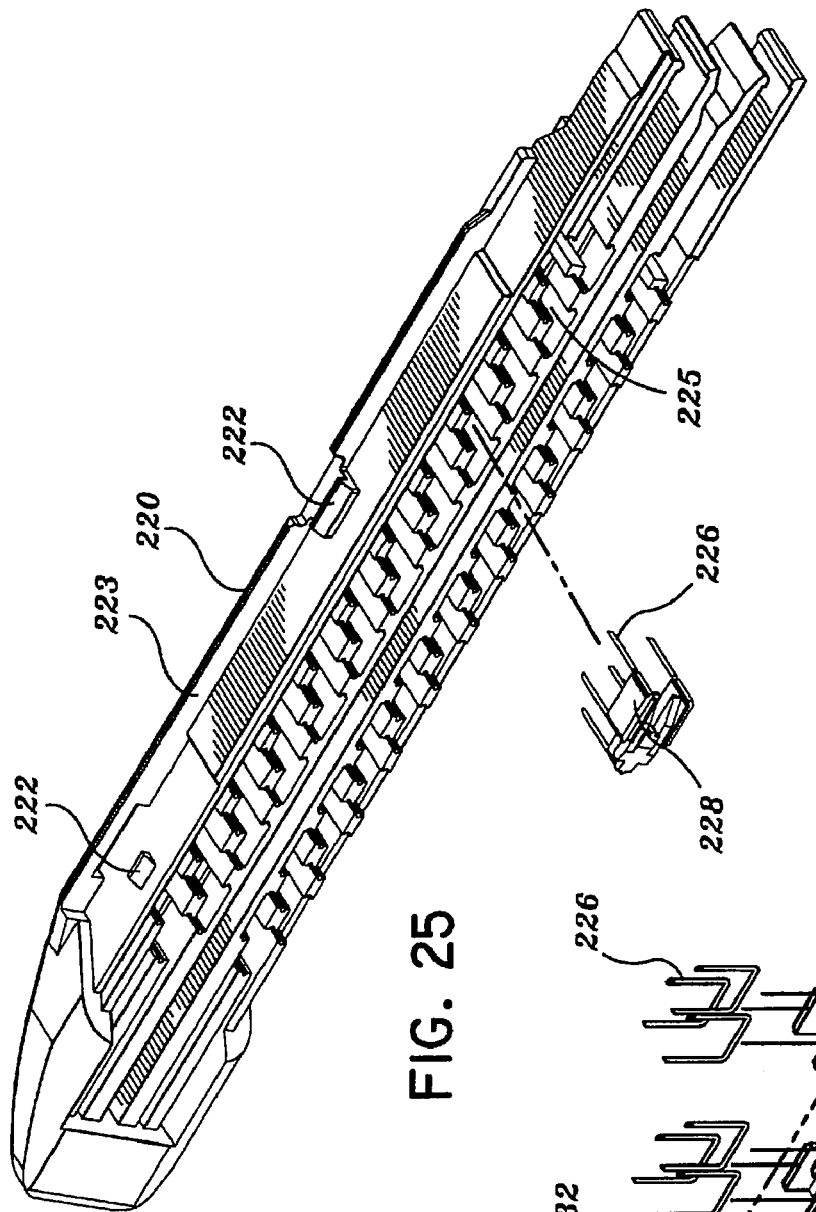
FIG. 25 is a bottom perspective view of the staple cartridge shown in FIG. 21.
Figure 26:
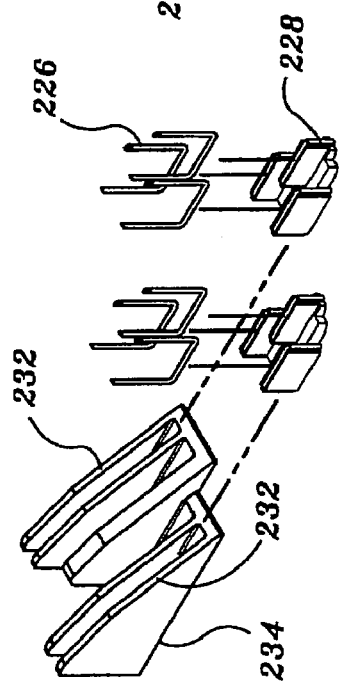
FIG. 26 is an enlarged perspective view of the actuation sled, the pushers and the fasteners shown in FIG. 21.

Referring to FIGS. 16-18, the distal end of elongated body 14 includes a control rod locking mechanism 190 which is activated during insertion of a disposable loading unit into elongated body 14. Control rod locking mechanism 190 includes a blocking plate 192 which is biased distally by a spring 194 and includes a proximal finger 189 having angled cam surface 195. A semi-circular engagement member 196 is biased transversely towards control rod 52 by a spring 197. Control rod 52 includes an annular recess 199 configured to receive engagement member 196. Blocking plate 192 is movable from a distal position spaced from engagement member 196 to a proximal position located behind engagement member 196. In the proximal position, engagement member 196 is prevented from being biased from recess 199 by engagement with blocking plate 192. During insertion of a disposable loading unit 16 (See FIG. 1) into the distal end of elongated body 14, as will be described in further detail below, cam surface 195 of blocking plate 192 is engaged by a nub 254 (FIG. 30) on the disposable loading unit 16 as the disposable loading unit is rotated into engagement with elongated body 14 to urge plate 192 to the proximal position. Engagement member 196, which is positioned within recess 199, is retained therein by blocking plate 192 while nub 254 engages cam surface 195 to prevent longitudinal movement of control rod 52 during assembly. When the disposable loading unit 16 is properly positioned with respect to the elongated body 14, nub 254 on the proximal end of the disposable loading unit 16 passes off cam surface 195 allowing spring 194 to return blocking plate 192 to its distal position to permit subsequent longitudinal movement of control rod 52. It is noted that when the disposable loading unit nub passes off cam surface 195, an audible clicking sound is produced indicating that the disposable loading unit 16 is properly fastened to the elongated body 14.

Referring to FIGS. 19 and 20, disposable loading unit 16 includes a proximal housing portion 200 adapted to releasably engage the distal end of body portion 14 (FIG. 1). A mounting assembly 202 is pivotally secured to the distal end of housing portion 200, and is configured to receive the proximal end of tool assembly 17 such that pivotal movement of mounting assembly 202 about an axis perpendicular to the longitudinal axis of housing portion 200 effects articulation of tool assembly 17.

Referring to FIGS. 21-26, tool assembly 17 preferably includes anvil assembly 20 and cartridge assembly 18. Anvil assembly 20 includes anvil portion 204 having a plurality of staple deforming concavities 206 (FIG. 22) and a cover plate 208 secured to a top surface of anvil portion 204 to define a cavity 210 (FIG. 24) therebetween. Cover plate 208 is provided to prevent pinching of tissue during clamping and firing of stapling apparatus 10. Cavity 210 is dimensioned to receive a distal end of an axial drive assembly 212 (See FIG. 27). A longitudinal slot 214 extends through anvil portion 204 to facilitate passage of retention flange 284 of axial drive assembly 212 into the anvil cavity 210. A camming surface 209 formed on anvil portion 204 is positioned to engage axial drive assembly 212 to facilitate clamping of tissue 198. A pair of pivot members 211 formed on anvil portion 204 are positioned within slots 213 formed in carrier 216 to guide the anvil portion between the open and clamped positions. A pair of stabilizing members 215 engage a respective shoulder 217 formed on carrier 216 to prevent anvil portion 204 from sliding axially relative to staple cartridge 220 as camming surface 209 is deformed.

Cartridge assembly 18 includes a carrier 216 which defines an elongated support channel 218. Elongated support channel 218 is dimensioned and configured to receive a staple cartridge 220. Corresponding tabs 222 and slots 224 formed along staple cartridge 220 and elongated support channel 218 function to retain staple cartridge 220 within support channel 218. A pair of support struts 223 formed on staple cartridge 220 are positioned to rest on side walls of carrier 216 to further stabilize staple cartridge 220 within support channel 218.

Staple cartridge 220 includes retention slots 225 for receiving a plurality of fasteners 226 and pushers 228. A plurality of spaced apart longitudinal slots 230 extend through staple cartridge 220 to accommodate upstanding cam wedges 232 of actuation sled 234. A central longitudinal slot 282 extends along the length of staple cartridge 220 to facilitate passage of a knife blade 280. During operation of surgical stapler 10, actuation sled 234 translates through longitudinal slots 230 of staple cartridge 220 to advance cam wedges 232 into sequential contact with pushers 228, to cause pushers 228 to translate vertically within slots 224 and urge fasteners 226 from slots 224 into the staple deforming cavities 206 of anvil assembly 20.

Figure 27:
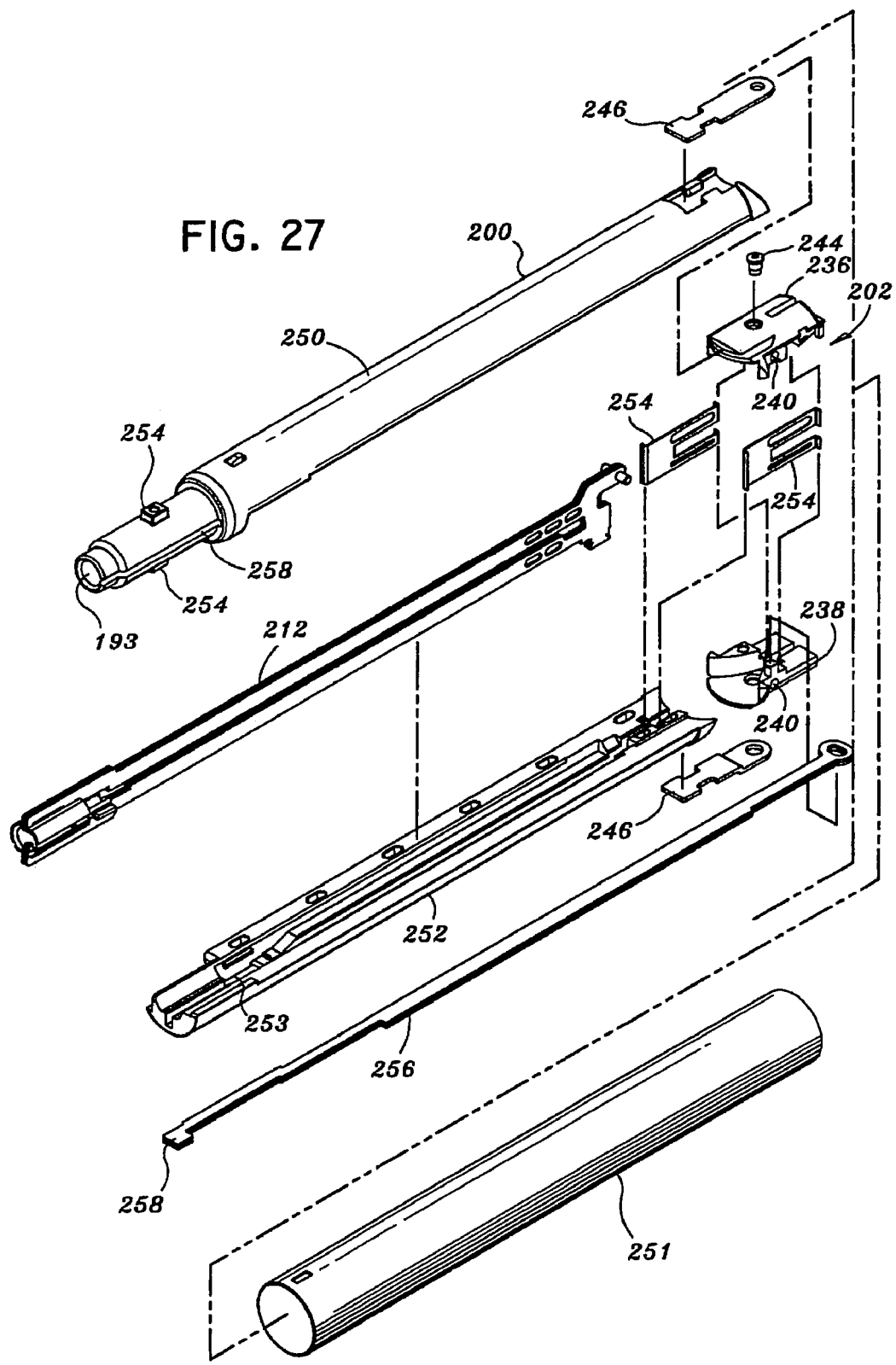
FIG. 27 is an enlarged perspective view with parts separated of the proximal housing portion and mounting assembly of the disposable loading unit shown in FIG. 19.
Figure 31:
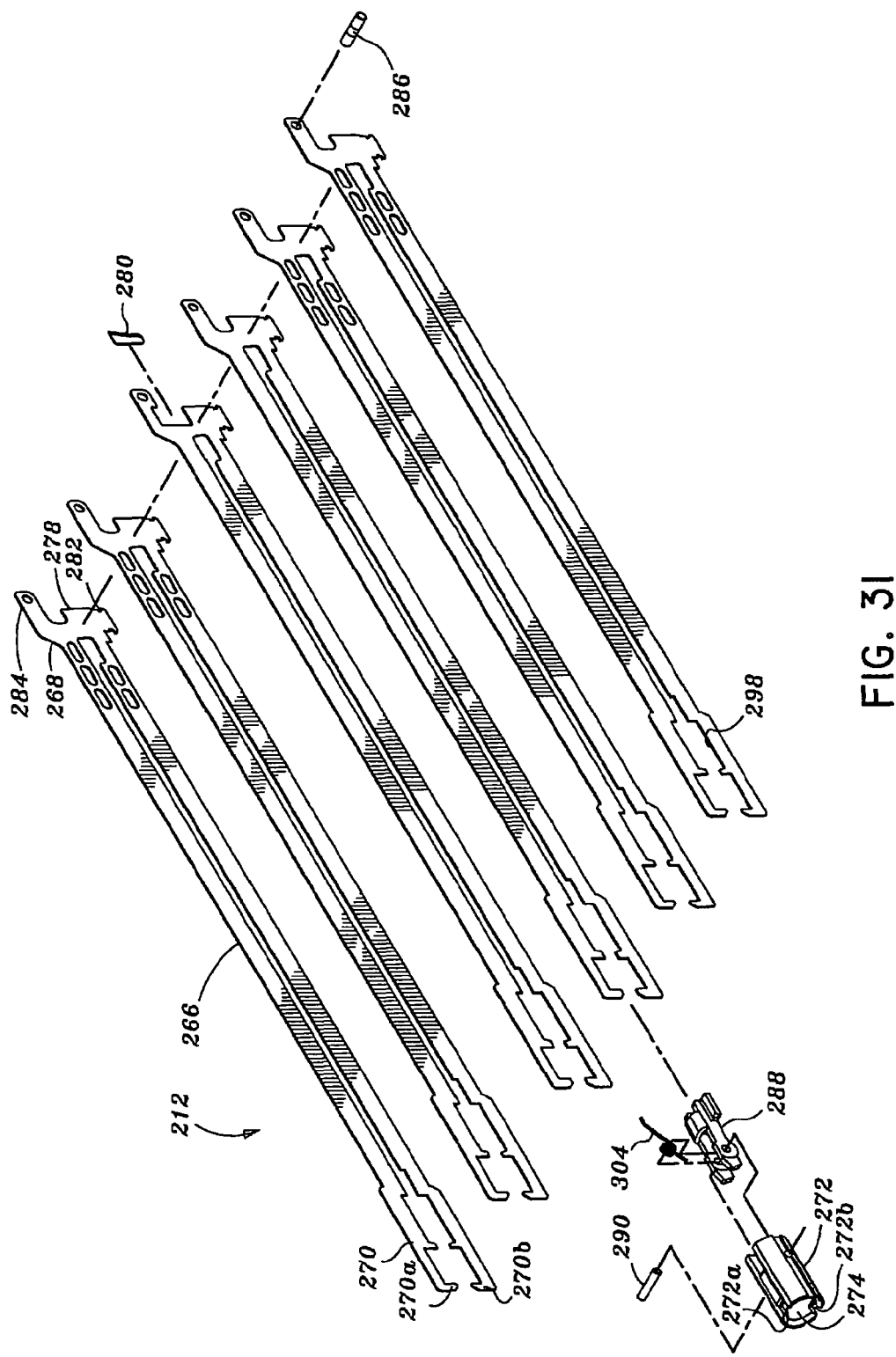
FIG. 31 is a perspective view with parts separated of the axial drive assembly.

Referring to FIGS. 27 and 28, mounting assembly 202 includes upper and lower mounting portions 236 and 238. Each mounting portion includes a threaded bore 240 on each side thereof dimensioned to receive threaded bolts 242 (See FIG. 21) for securing the proximal end of carrier 216 thereto. A pair of centrally located pivot members 244 (See FIG. 21) extends between upper and lower mounting portions via a pair of coupling members 246 which engage the distal end of housing portion 200. Coupling members 246 each include an interlocking proximal portion 248 configured to be received in grooves 250 formed in the proximal end of housing portion 200 to retain mounting assembly 202 and housing portion 200 in a longitudinally fixed position in relation thereto.

Housing portion 200 of disposable loading unit 16 includes an upper housing half 250 and a lower housing half 252 contained within an outer casing 251. The proximal end of housing half 250 includes engagement nubs 254 for releasably engaging elongated body 14 and an insertion tip 193. Nubs 254 form a bayonet type coupling with the distal end of body 14 which will be discussed in further detail below. Housing halves 250 and 252 define a channel 253 for slidably receiving axial drive assembly 212. A second articulation link 256 is dimensioned to be slidably positioned within a slot 258 formed between housing halves 250 and 252. A pair of blow out plates 254 are positioned adjacent the distal end of housing portion 200 adjacent the distal end of axial drive assembly 212 to prevent outward bulging of drive assembly 212 during articulation of tool assembly 17.

Referring to FIGS. 29-30, second articulation link 256 includes at least one elongated metallic plate. Preferably, two or more metallic plates are stacked to form link 256. The proximal end of articulation link 256 includes a hook portion 258 configured to engage first articulation link 123 (See FIG. 9) and the distal end includes a loop 260 dimensioned to engage a projection 262 formed on mounting assembly 202. Projection 262 is laterally offset from pivot pin 244 such that linear movement of second articulation link 256 causes mounting assembly 202 to pivot about pivot pins 244 to articulate tool assembly 17.

Figure 35:
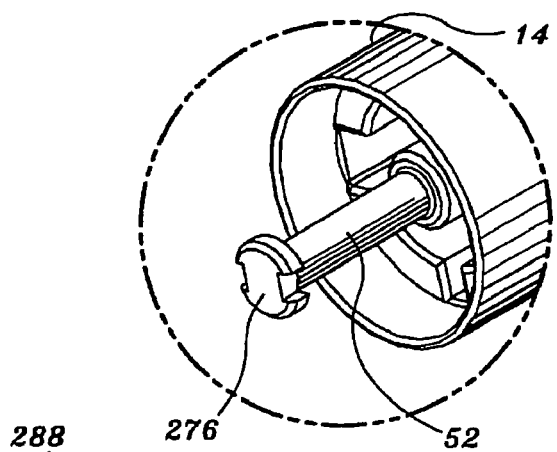
FIG. 35 is an enlarged perspective view of the distal end of the elongated body of the stapling apparatus shown in FIG. 1.
Figure 36:
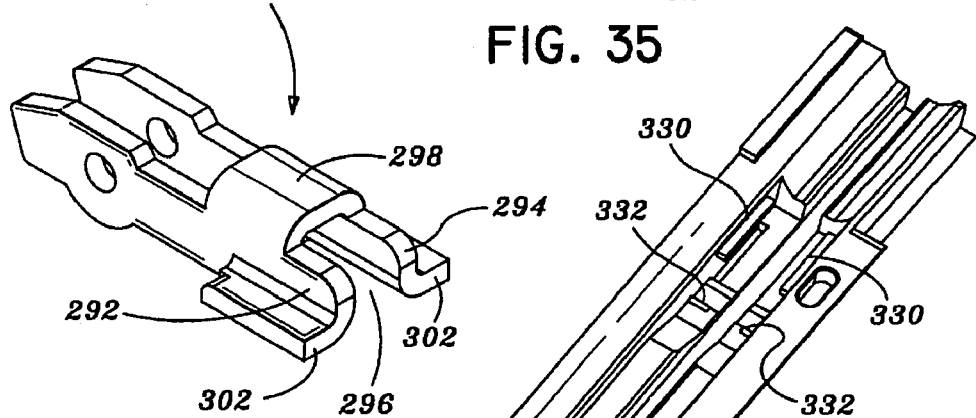
FIG. 36 is an enlarged perspective view of the locking device shown in FIG. 33.

Referring also to FIGS. 31-34, axial drive assembly 212 includes an elongated drive beam 266 including a distal working head 268 and a proximal engagement section 270. Drive beam 266 may be constructed from a single sheet of material or, preferably, multiple stacked sheets. Engagement section 270 includes a pair of engagement fingers 270a and 270b which are dimensioned and configured to mountingly engage a pair of corresponding retention slots 272a and 272b formed in drive member 272. Drive member 272 includes a proximal porthole 274 configured to receive the distal end 276 of control rod 52 (See FIG. 35) when the proximal end of disposable loading unit 16 is engaged with elongated body 14 of surgical stapling apparatus 10.

The distal end of drive beam 266 is defined by a vertical support strut 278 which supports a knife blade 280, and an abutment surface 283 which engages the central portion of actuation sled 234 during a stapling procedure. Surface 285 at the base of surface 283 is configured to receive a support member 287 slidably positioned along the bottom of the staple cartridge 220. Knife blade 280 is positioned to translate slightly behind actuation sled 234 through a central longitudinal slot 282 in staple cartridge 220 (FIG. 30) to form an incision between rows of stapled body tissue. A retention flange 284 projects distally from vertical strut 278 and supports a cylindrical cam roller 286 at its distal end. Cam roller 286 is dimensioned and configured to engage cam surface 209 on anvil body 204 to clamp anvil portion 204 against body tissue.

Referring also to FIGS. 36-39, a locking device 288 is pivotally secured to drive member 270 about a pivot pin 290. Locking device 288 includes a pair of elongate glides 292 and 294 which define a channel 296. A web 298 joins a portion of the upper surfaces of glides 292 and 294, and is configured and dimensioned to fit within elongated slot 298 formed in drive beam 266 at a position distal of drive member 270. Horizontal cams 300 and 302 extend from glides 292 and 294 respectively, and are accommodated along an inner surface of lower housing half 252. As best shown in FIG. 42, a torsion spring 304 is positioned adjacent drive member 270 and engages horizontal cams 300 and 302 of locking device 288 to normally bias locking device 288 downward toward lower housing half 252 onto ledge 310. Locking device 288 translates through housing portion 200 with axial drive assembly 212. Operation of locking device 288 will be described below.

Sequence of Operation

Referring to FIGS. 40-44, to use stapling instrument 10, a disposable loading unit 16 is first secured to the distal end of elongated body 14. As discussed above, stapling instrument 10 can be used with articulating and non-articulating disposable loading units having linear rows of staples between about 30 mm and about 60 mm. To secure disposable loading unit 16 to elongated body 14, the distal end 276 of control rod 52 is inserted into insertion tip 193 of disposable loading unit 16, and insertion tip 193 is slid longitudinally into the distal end of elongated body 14 in the direction indicated by arrow "A" in FIG. 41 such that hook portion 258 of second articulation link 256 slides within a channel 310 in elongated body 314. Nubs 254 will each be aligned in a respective channel (not shown) in elongated body 14. When hook portion 258 engages the proximal wall 312 of channel 310, disposable loading unit 16 is rotated in the direction indicated by arrow "B" in FIGS. 41-44 to move hook portion 258 of second articulation link 256 into engagement with finger 164 of first articulation link 123. Nubs 254 also forms a bayonet type coupling within annular channel 314 in body 14. During rotation of loading unit 16, nubs 254 engage cam surface 195 (FIG. 41) of block plate 192 to initially move plate 192 in the direction indicated by arrow "C" in FIGS. 41 and 43 to lock engagement member 196 in recess 199 of control rod 52 to prevent longitudinal movement of control rod 52 during attachment of disposable loading unit 16. During the final degree of rotation, nubs 254 disengage from cam surface 195 to allow blocking plate 192 to move in the direction indicated by arrow "D" in FIGS. 42 and 44 from behind engagement member 196 to once again permit longitudinal movement of control rod 52.

Figure 43:
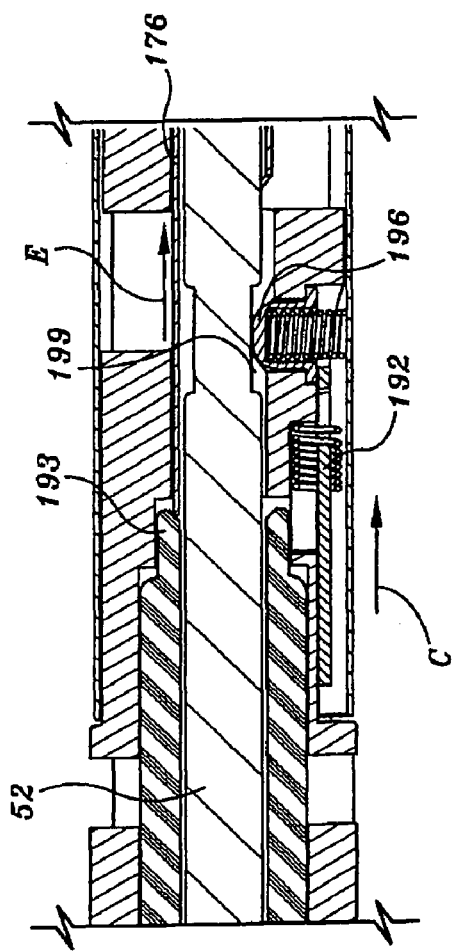
FIG. 43 is a cross-sectional view taken along section line 43-43 of FIG. 41.
Figure 44:
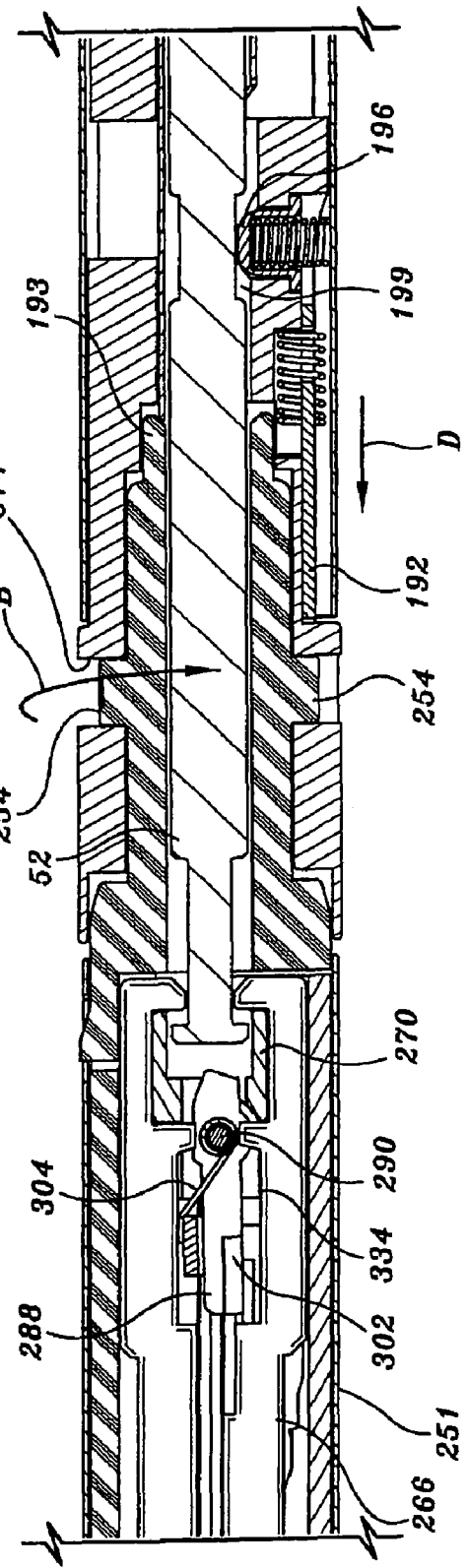
FIG. 44 is a cross-sectional view taken along section line 44-44 of FIG. 42.
Figure 43A:
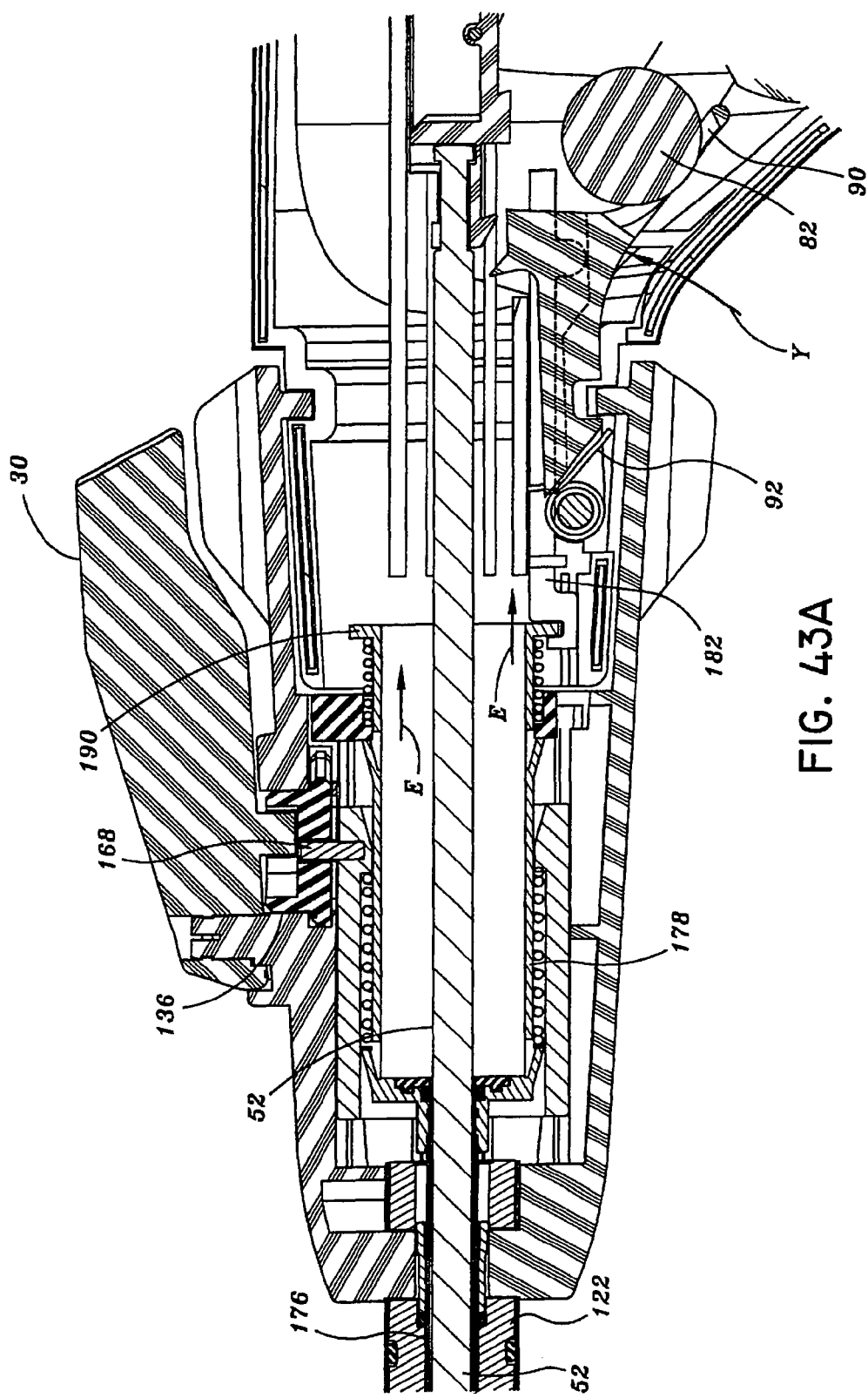
FIG. 43a is a side cross-sectional view of the rotation knob, articulation mechanism, and sensing mechanism during insertion of a disposable loading unit into the elongated body of the surgical stapling apparatus.

Referring to FIGS. 43 and 43a, when insertion tip 193 engages the distal end of sensor tube 176, the disposable loading unit sensing mechanism is actuated. Insertion tip 193 engages and moves sensor tube 176 proximally in the direction indicated by arrow "E" in FIG. 43. As discussed above, proximal movement of sensor tube 176 effects proximal movement of sensor cylinder 178 and sensor link 182 in the direction indicated by arrow "E" in FIG. 43a to pivot locking member 83 counter-clockwise, as indicated by arrow "Y" in FIG. 43a, from a non-blocking position to a position blocking movement of actuation shaft 46.

Figure 45:
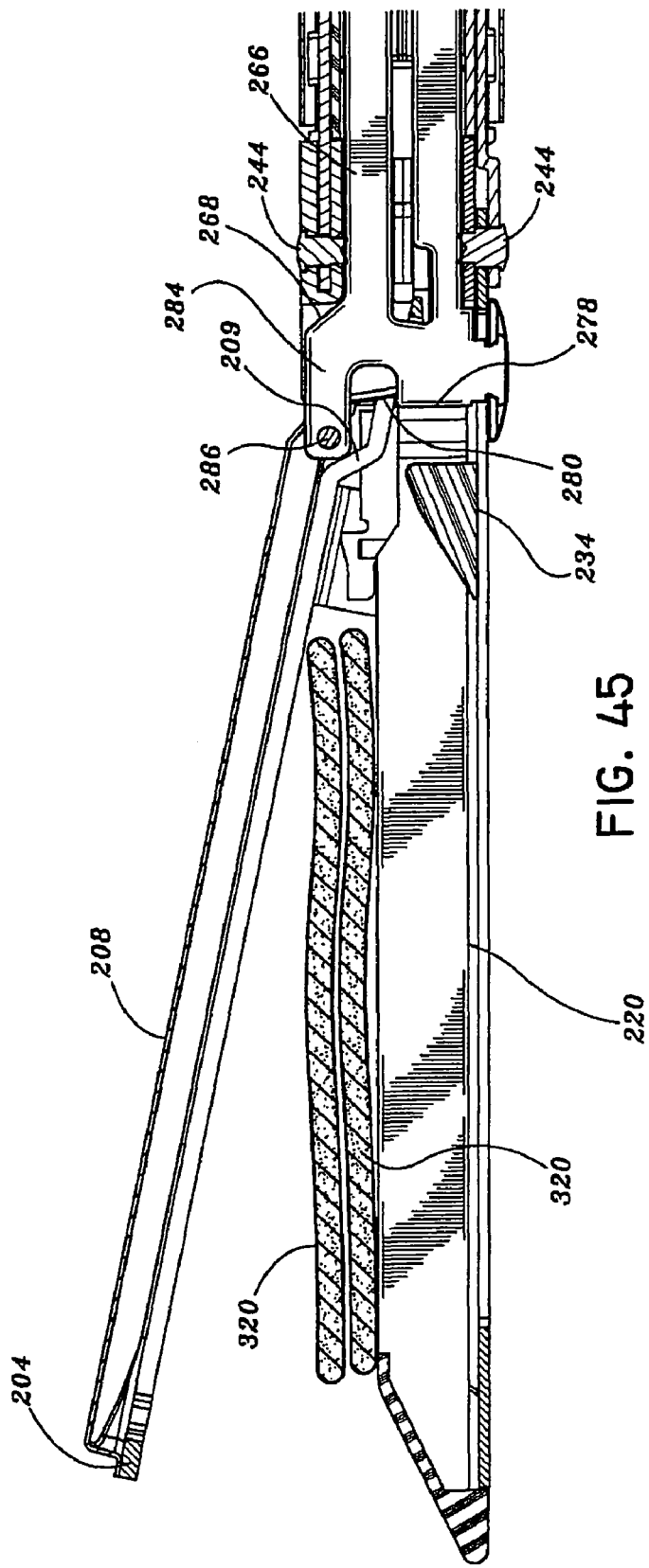
FIG. 45 is a side cross-sectional view of the distal end of the disposable loading unit of FIG. 1 with tissue positioned between the anvil and clamp assemblies.
Figure 46:
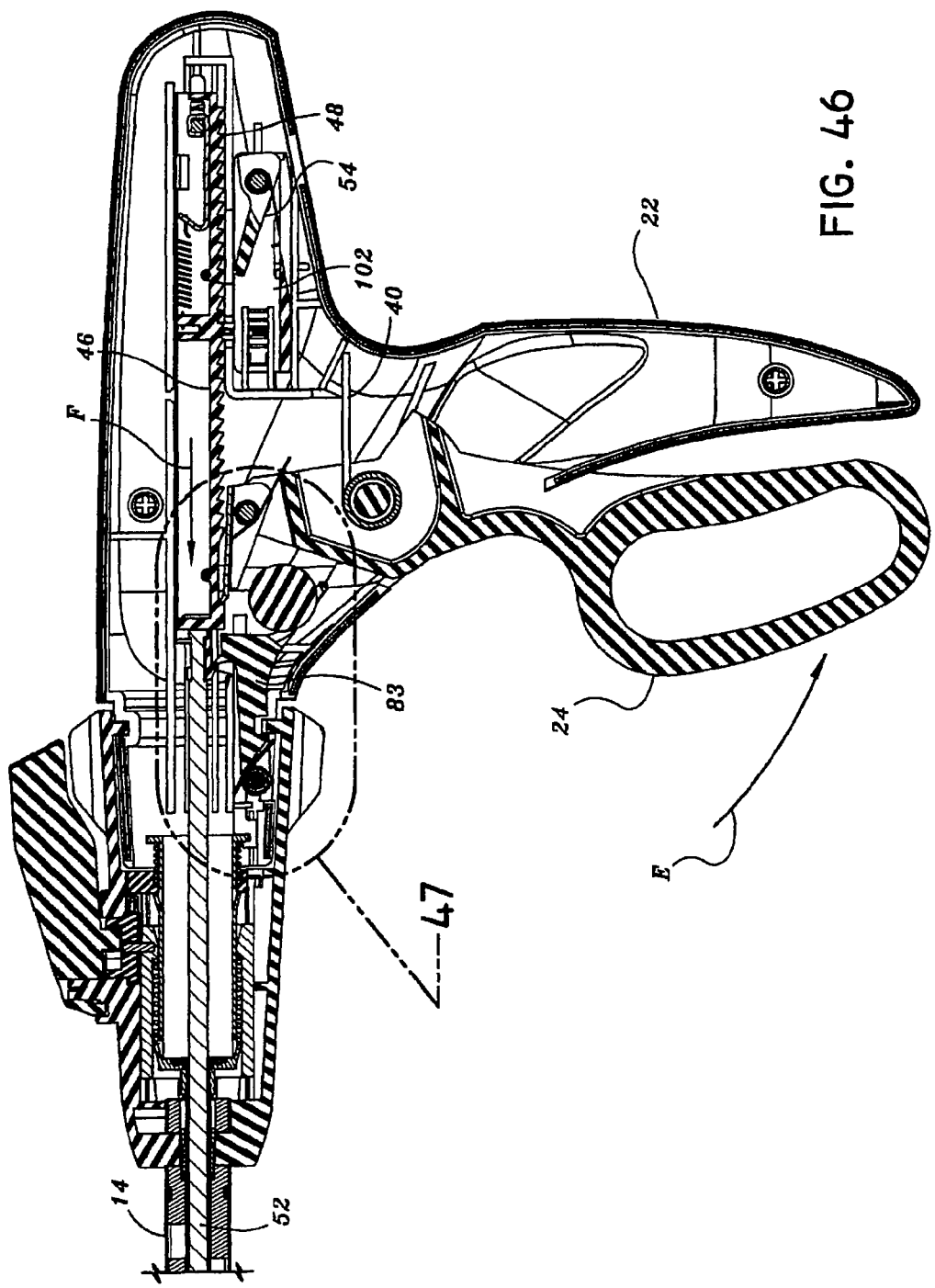
FIG. 46 is a side cross-sectional view of the handle assembly with the movable handle in an actuated position.
Figure 47:
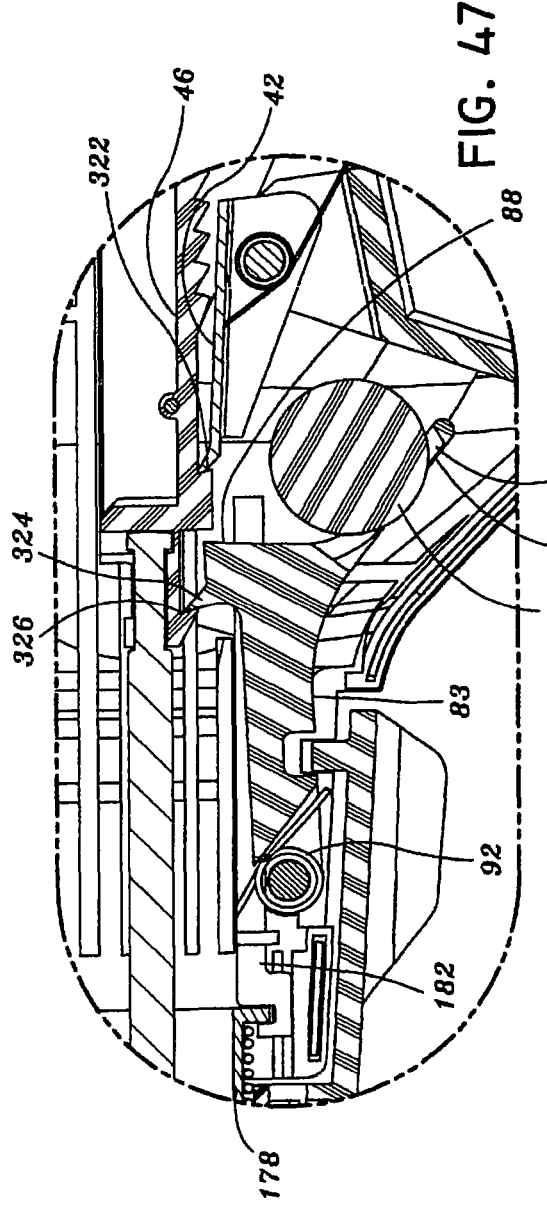
FIG. 47 is an enlarged view of the indicated area of detail shown in FIG. 46.
Figure 48:
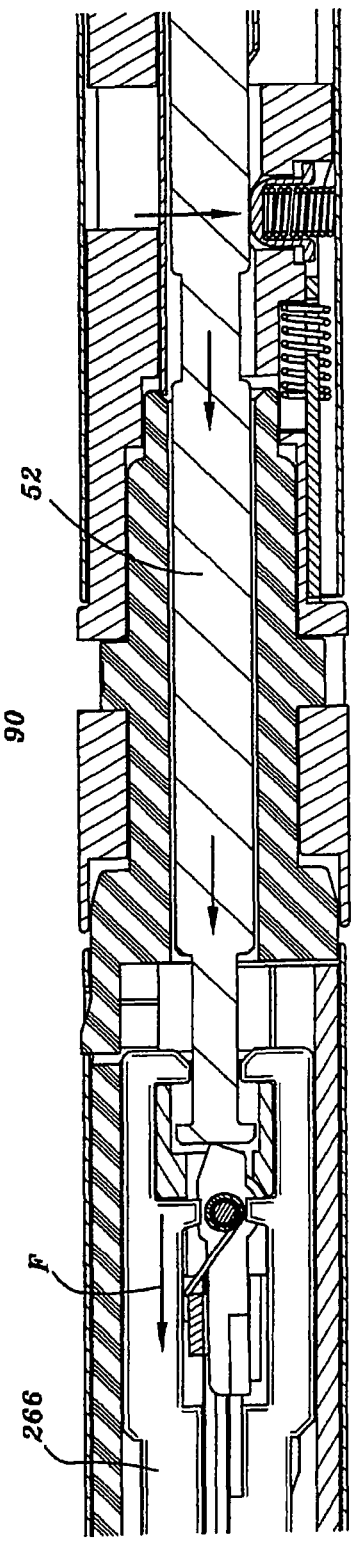
FIG. 48 is a cross-sectional view of the proximal end of the disposable loading unit of FIG. 19 and the distal end of the elongated body of the surgical stapling apparatus shown in FIG. 1 with the control rod in a partially advanced position.

Referring to FIGS. 46-49, with a disposable loading unit attached to stapling instrument 10, tool assembly 17 can be positioned about tissue 320 (FIG. 45). To clamp tissue between anvil assembly 20 and cartridge assembly 18, stationary handle 24 is moved in the direction indicated by arrow "E" in FIG. 46 against the bias of torsion spring 40 to move driving pawl 42 into engagement with shoulder 322 on actuation shaft 46. Engagement between shoulder 322 and driving pawl 42 advances actuation shaft 46 and thus advances control rod 52 distally. Control rod 52 is connected at its distal end to axial drive assembly 212 (FIG. 48), including drive beam 266, such that distal movement of control rod 52 effects distal movement of drive beam 266 in the direction indicated by arrow "F" in FIGS. 48 and 49, moving cam roller 286 into engagement with cam surface 209 on anvil portion 204 to urge anvil portion 204 in the direction indicated by arrow "G" in FIG. 49. It is noted that one complete stroke of movable handle 24 advances actuation shaft 46 approximately 15 mm which is sufficient to clamp tissue during the first stroke but not to fire staples.

As discussed above with respect to the anti-reverse clutch mechanism, during the first (clamping) stroke of movable handle 24, slide plate 102 (FIG. 46) prevents locking pawl 54 from engaging toothed rack 48. To maintain actuation shaft 46 in its longitudinal position after handle 24 is released, an engagement member 324 (FIG. 47) is provided on locking member 83 to engage shoulder 326 on actuation shaft 46 and retain shaft 46 in its longitudinal position (See FIG. 47). Upon release of movable handle 24, drive pawl 42 moves over rack 48 as torsion spring 40 returns handle 24 to a position spaced from stationary handle 22. In this position, driving pawl 42 is urged into engagement with toothed rack 48 to retain actuation shaft 46 in its longitudinal fixed position.

In order to fire staples, movable handle 24 is actuated again, i.e., moved through another stroke. As discussed above, stapling apparatus 10 is capable of receiving disposable loading units having linear rows of staples of between about 30 mm and about 60 mm. Since each stroke of the movable handle 24 preferably advances actuation shaft 46 15 mm, and one stroke is required to clamp tissue, the movable handle must be actuated (n+1) strokes to fire staples, where n is the length of the linear rows of staples in the disposable loading unit attached to stapling instrument 10 divided by 15 mm.

Referring to FIG. 50, prior to being able to fire staples, firing lockout assembly 80 (FIG. 4) must be actuated to move locking surface 88 from its blocking position (FIG. 47) to a non-blocking position. This is accomplished by pressing down on plunger 82 to move camming surface 85 into engagement with sidewalls of slot 89 of locking member 83 to pivot locking member 83 in the direction indicated by arrow "G" in FIG. 50 (see also FIG. 5). Thereafter, movable handle 24 may be actuated an appropriate number of strokes to advance actuation shaft 46, and thus control rod 52 and drive beam 266, distally in the direction indicated by arrow "H" in FIGS. 51 and 52 to advance actuation sled 234 through staple cartridge 220 to effect ejection of staples. It is noted that after the first or clamping stroke of movable handle 54 (during the second stroke), slide 102 passes over locking pawl 54 allowing torsion spring 56 to move locking pawl 54 in the direction indicated by arrow "I" in FIG. 50 into engagement with toothed rack 48 to retain actuation shaft 46 in its longitudinal position.

Figure 53:
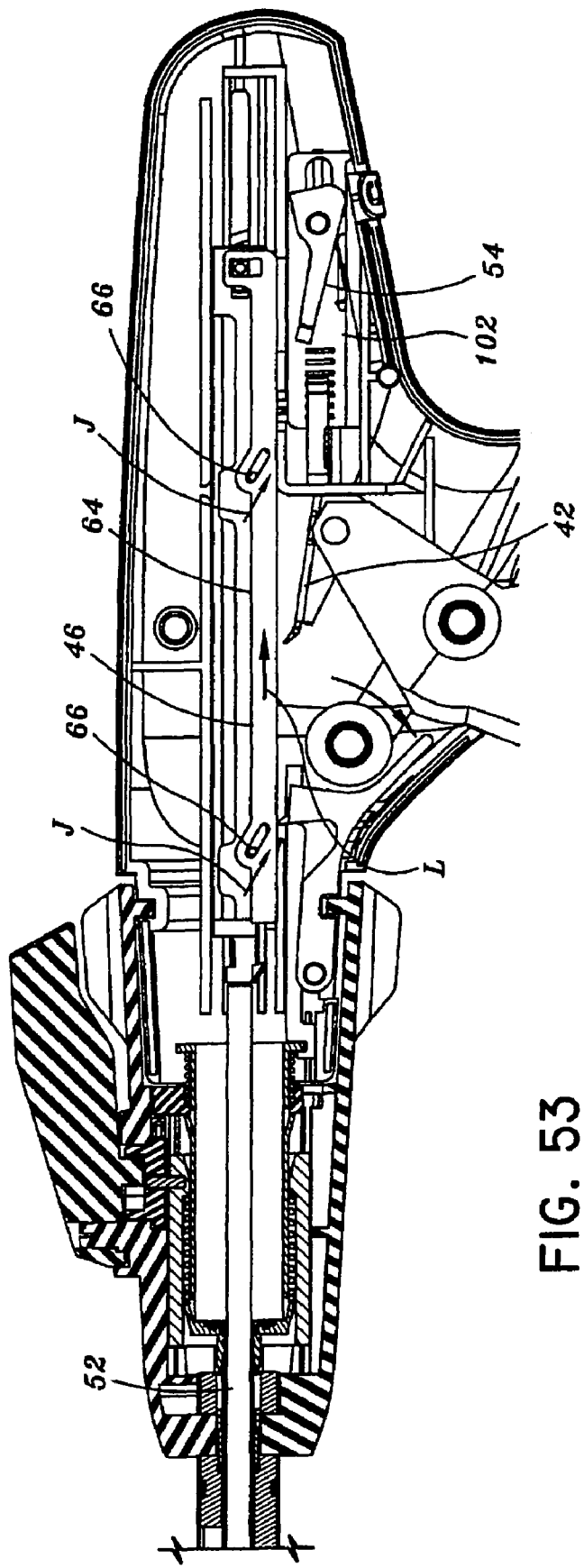
FIG. 53 is a side cross-sectional view of the handle assembly of the apparatus during retraction of the actuation shaft.

Referring to FIG. 53, to retract actuation shaft 46 and thus control rod 52 and drive member 266 after firing staples, retraction knobs 32 (see FIG. 1) are pulled proximally causing pins 66 to move release plate 64 in the direction indicated by arrow "J" in FIG. 53 over teeth 48 to disengage drive pawl 42 from engagement with teeth 48. As discussed above, with respect to the anti-reverse clutch mechanism, locking pawl 54 is urged by slide plate 102 out of engagement with toothed rack 48 (not shown) to permit actuation shaft 46 to be moved proximally, in the direction indicated by arrow "L", after drive pawl 42 is disengaged from teeth 48.

Referring to FIG. 54, in order to retract actuation shaft 46 prior to firing stapling apparatus, i.e., when locking pawl is currently engaged with toothed racked 48, emergency return button 112 is pushed in the direction indicated by arrow "Z" in FIG. 54 to disengage locking pawl 54 from toothed rack 48. Retraction knobs 32 (FIG. 1) must also be concurrently pulled rearwardly, as discussed above, to release drive pawl 42 from rack 48.

Figure 55:
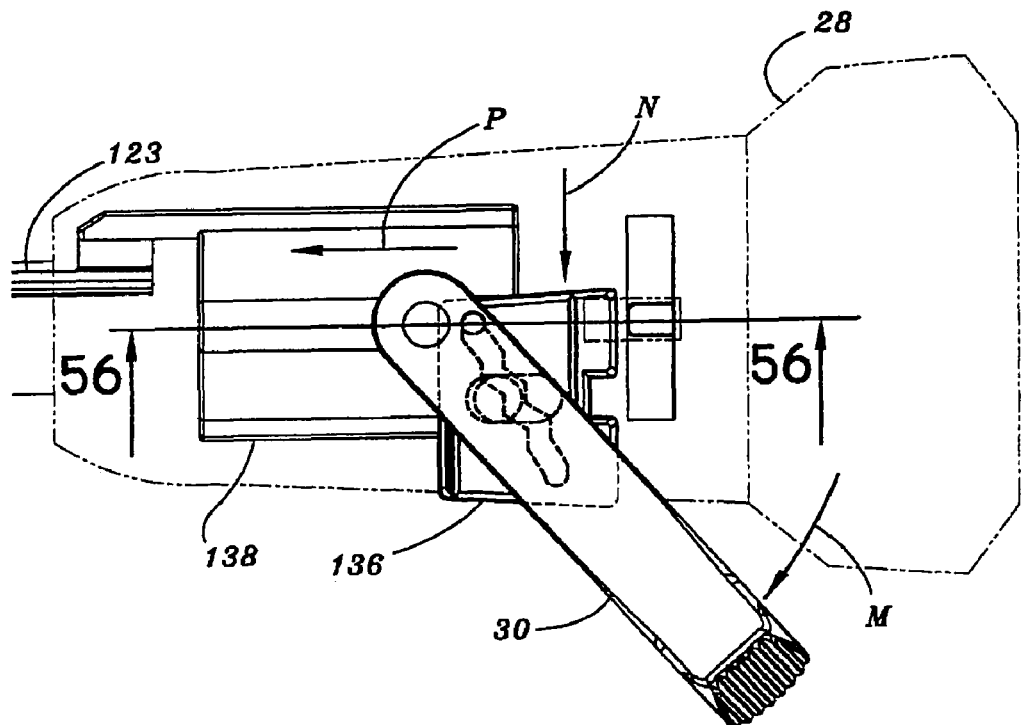
FIG. 55 is a top view of the articulation mechanism of the surgical stapling apparatus.
Figure 56:
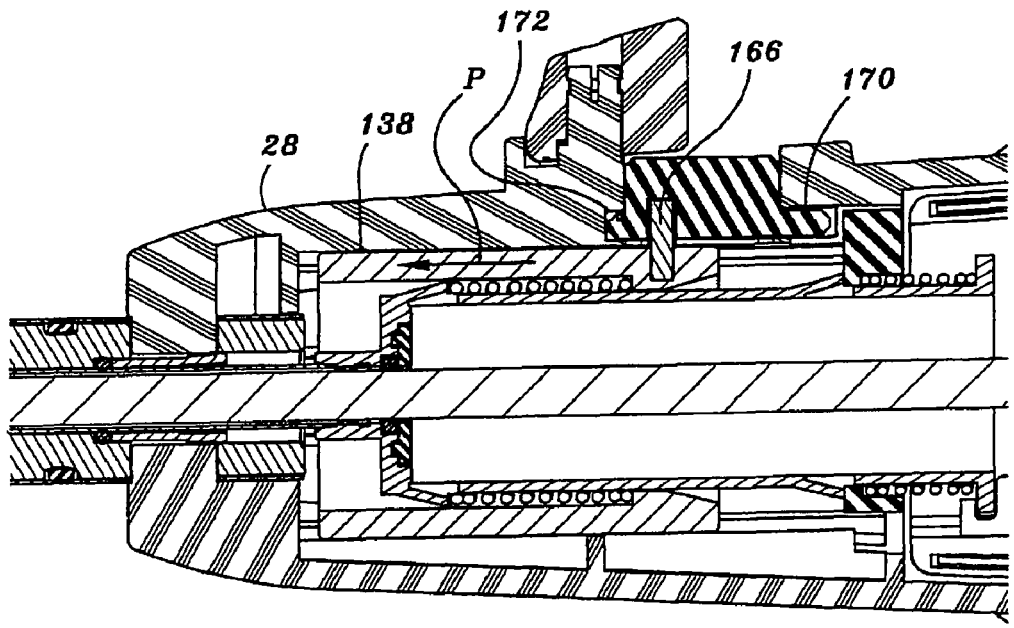
FIG. 56 is a side cross-sectional view of the articulation mechanism and rotation member of the surgical stapling apparatus shown in FIG. 1.

Referring to FIGS. 55-61, when an articulating disposable loading unit is secured to elongated body 14 and articulation lever 30 is pivoted in the direction indicated by arrow "M" in FIG. 55, cam member 136 is moved transversely by projection 142 (FIG. 10) in the direction indicated by arrow "N" between flanges 170 and 172 of rotation knob 28. Since translation member 138 is prevented from rotating by ridges 156 (FIG. 13), pin 166, which is fixedly secured to translation member 138, is forced to move along stepped cam surface 148. Movement of pin 166 causes corresponding movement of translation member 138 in the direction indicated by arrow "P" in FIGS. 55 and 56 to advance first articulation link 123 in the distal direction. The distal end of first articulation link 123 engages the proximal end of second articulation link 256 (FIG. 42) which is connected to projection 262 on mounting assembly 202 to advance second link 256 in the direction indicated by arrow "Q" in FIG. 57. Projection 262 is laterally offset from pivot members 244, such that distal advancement of second articulation link 256 causes mounting assembly 202 and thus tool assembly 17 to pivot in the direction indicated by arrow "R" in FIGS. 57 and 58. Note in FIG. 59 that rotation member 28 can be rotated to rotate elongated body 14 about its longitudinal axis while tool assembly 17 is articulated.

FIGS. 60-61 illustrate articulation of tool assembly 17 in the opposite direction to that described above. When second articulation link 256 is retracted by rotating articulation lever 30 in a counter-clockwise direction (not shown) as viewed in FIG. 55, pin 66 is forced to move proximally along stepped camming surface 148, moving translation member 138 and first articulation link 123 proximally. Movement of first articulation link 123 proximally, causes second articulation link 256 to move proximally as indicated by arrow "S" in FIG. 58, to rotate tool assembly 17 in a clockwise direction, as indicated by arrow "T" in FIG. 61.

Referring to FIG. 12, movement of pin 166 (FIG. 9) between adjacent step portions 340 causes tool assembly 17 to articulate 22.5 degrees. Camming surface 148 includes five step portions 340. The third step portion corresponds to the non-articulated tool assembly position, whereas the first and the fifth step portions correspond to articulation of tool assembly 17 to forty-five degrees. Each step portion is flat to retain articulation lever 30 in a fixed position when pin 166 is engaged therewith.

Figure 37:
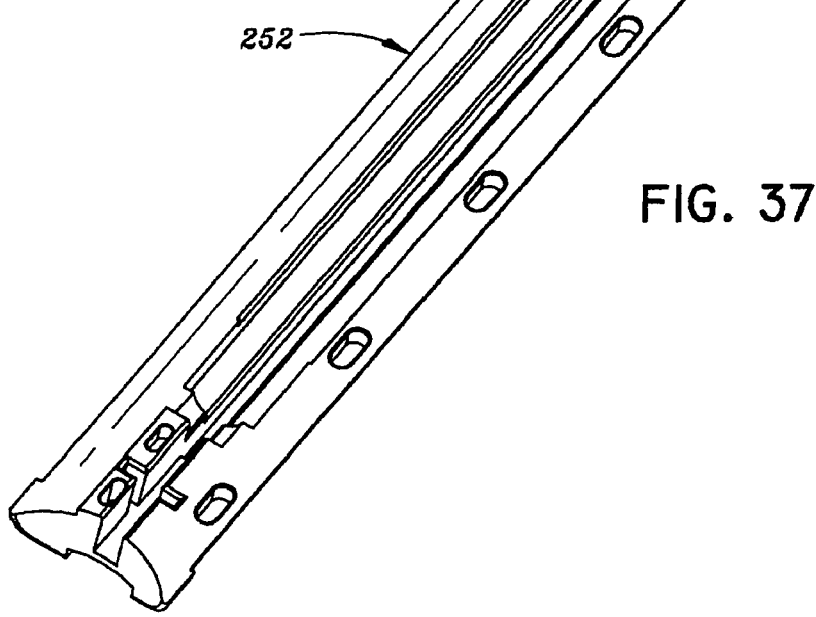
FIG. 37 is an enlarged perspective view of a lower housing half of the proximal housing portion of the disposable loading unit shown in FIG. 27.
Figure 38:
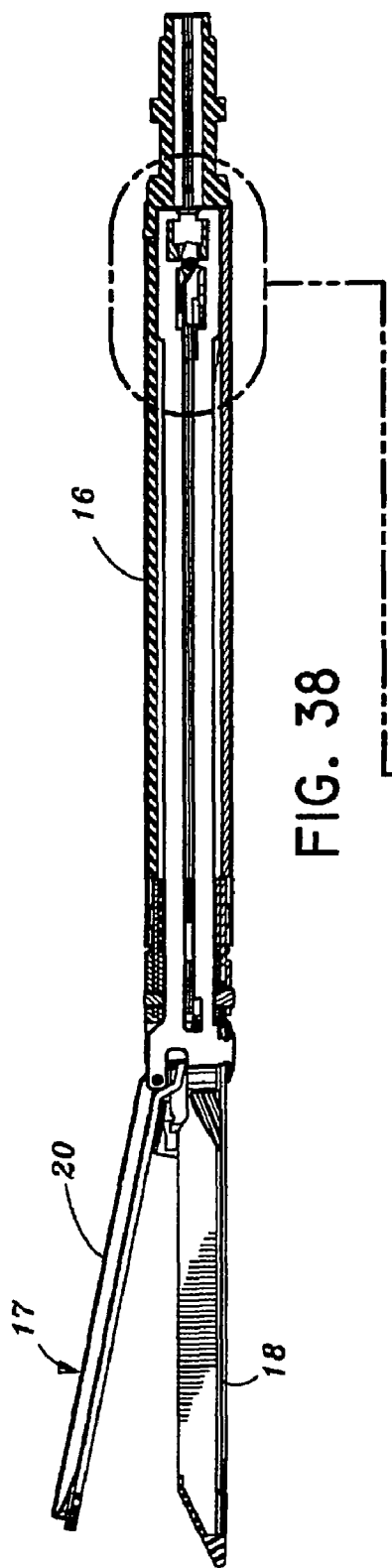
FIG. 38 is a side cross-sectional view of the disposable loading unit shown in FIG. 20.
Figure 39:
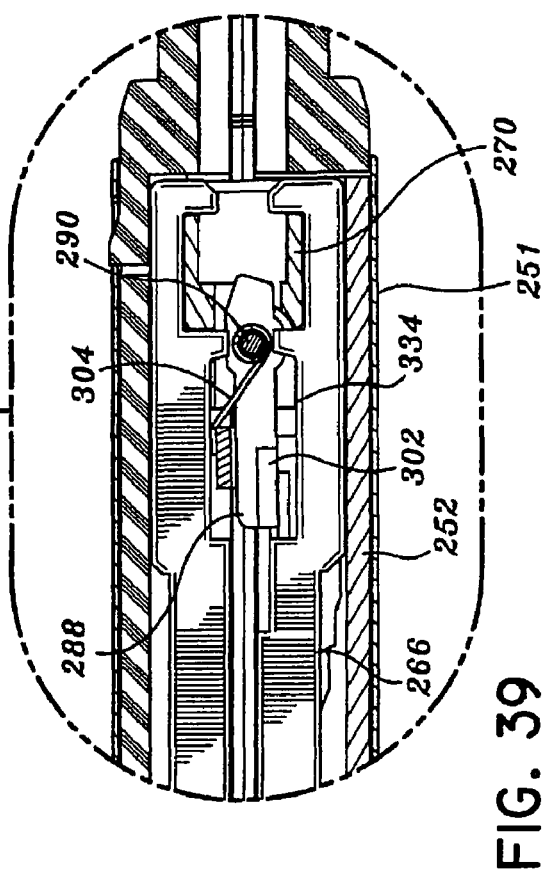
FIG. 39 is an enlarged view of the indicated area of detail shown in FIG. 38.

Referring now to FIGS. 37, 39, 62 and 63, the sequence of lockout operation will be described in detail. In FIG. 39, lockout device 288 is shown in its prefered position with horizontal cams 300 and 302 resting on top of projections 330 formed in the sidewalls of lower housing half 252 (FIG. 37). In this position, locking device 288 is held up out of alignment with projection 332 formed in the bottom surface of lower housing half 252, and web 298 is in longitudinal juxtaposition with shelf 334 defined in drive beam 266. This configuration permits the anvil 20 (FIG. 38) to be opened and repositioned onto the tissue to be stapled until the surgeon is satisfied with the position without activating locking device 288 to disable the disposable loading unit 16.

Figure 62:
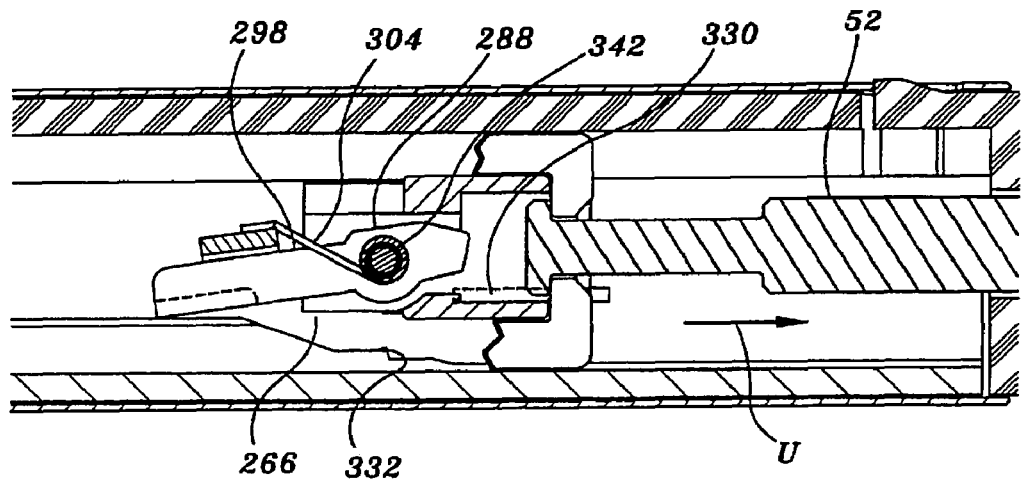
FIG. 62 is a partial cross-sectional view of a portion of the disposable loading unit during retraction of the locking device.
Figure 63:
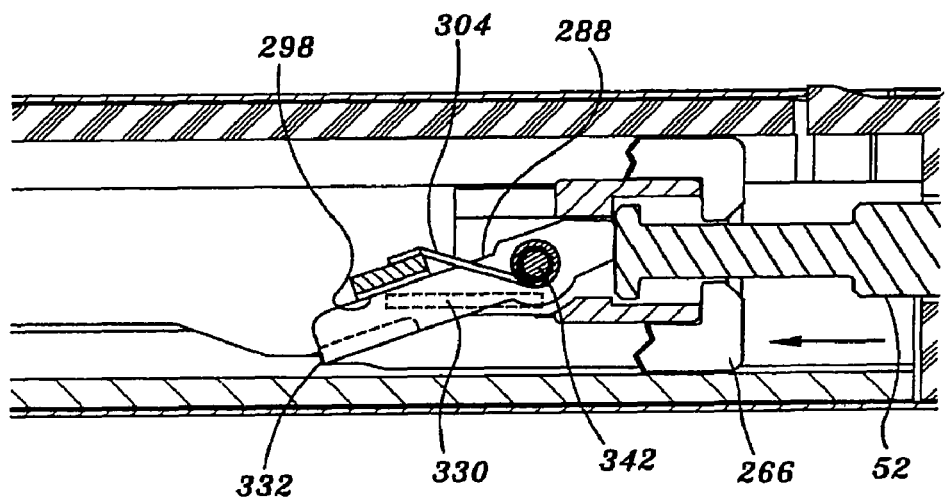
FIG. 63 is a partial cross-sectional view of a portion of the disposable loading unit with the locking device in the locked position.

As shown in FIG. 62, upon distal movement of drive beam 266, locking device 288 rides off of projections 330 (not shown) and is biased into engagement with base lower housing half 252 by spring 304, distal to projection 332. Locking device 288 remains in this configuration throughout firing of the apparatus.

Upon retraction of the drive beam 266 in the direction indicated by arrow "U" in FIG. 62, locking device 288 passes under projections 330 and rides over projection 332 until the distalmost portion of locking device 288 is proximal to projection 332. Spring 304 biases locking device 288 into juxtaposed alignment with projection 332, effectively disabling the disposable loading unit. If an attempt is made to reactuate the apparatus, the control rod 52 will abut a proximal end surface of locking device 288 which surface is diagonally sloped to impart a moment about pivot pin 342 such that the distal end of locking device 288 is rotationally urged into contact with projection 332. Continued distal force in the direction indicated by arrow "W" in FIG. 63, will only serve to increase the moment applied to the locking device thus the locking device will abut projection 332 and inhibit distal movement of the control rod 52.

Referring again to FIGS. 41-44, the disabled or locked disposable loading unit can be removed from the distal end of elongated body 14 by rotating disposable loading unit 16 in the direction opposite to the direction indicated by arrow "B" in FIGS. 41, 42 and 44, to disengage hook portion 258 of second articulation link 256 from finger 164 of first articulation link 123, and to disengage nubs 254 from within channel 314 of elongated body 14. After rotation, disposable loading unit 16 can be slid in the direction opposite to that indicated by arrow "A" in FIG. 41 to detach body 14 from disposable loading unit 16. Subsequently, additional articulating and/or non-articulating disposable loading units can be secured to the distal end of elongated body, as described above, to perform additional surgical stapling and/or cutting procedures. As discussed above, each disposable loading unit may include linear rows of staples which vary from about 30 mm to about 60 mm.

Figure 65:
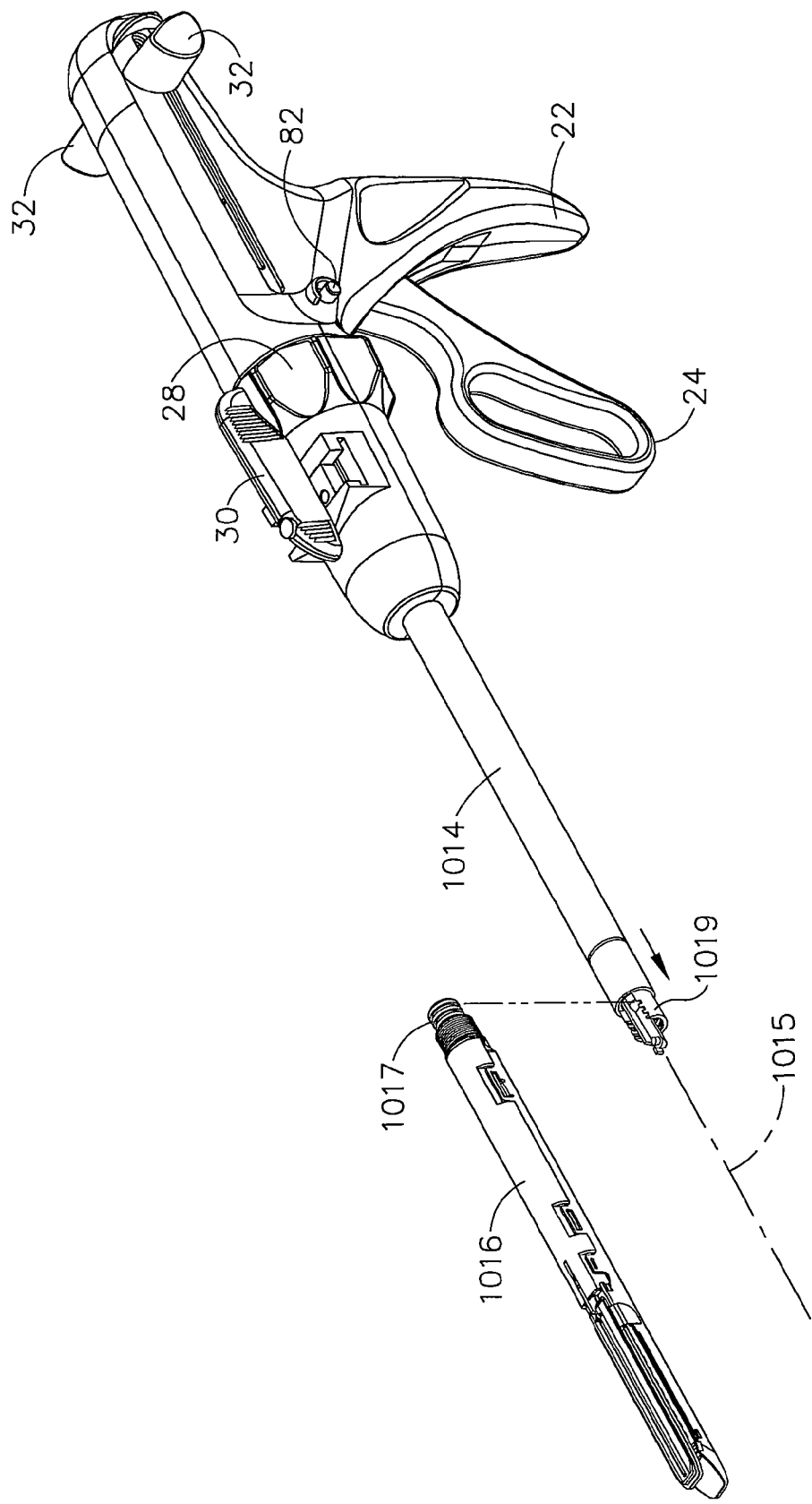
FIG. 65 is a perspective view of an embodiment of a surgical stapling apparatus including an elongated body defining an axis and a disposable loading unit.

Although the above-described surgical stapling instruments may be suitable for their intended purpose, improvements to these instruments are provided below. As described above, surgical stapling instruments can include a handle portion, an elongated body, or shaft, and a disposable loading unit, wherein the disposable loading unit can be removably attached to the elongated body. As described above in connection with disposable loading unit 16 illustrated in FIGS. 40-42, elongated body 14 of the surgical stapling instrument can define an axis along which disposable loading unit 16 can be assembled thereto. In various circumstances, though, disposable loading unit 16 can become unintentionally detached from elongated body 14 causing the surgical stapling instrument to malfunction or be rendered inoperable. Such circumstances can particularly arise when the disposable loading unit becomes detached and separated from the elongated body along the axis defined by the elongated body, i.e., the axis along which the disposable loading unit was assembled to the elongated body. In various embodiments of the present invention, a disposable loading unit can be assembled to an elongated body of a surgical instrument in a direction which is not collinear with or parallel to the elongated body axis. In at least one embodiment, referring to FIG. 65, disposable loading unit 1016 can be assembled to elongated body 1014 in a direction which is transverse, perpendicular, or oblique to axis 1015 defined by elongated body 1014.

Figure 66:
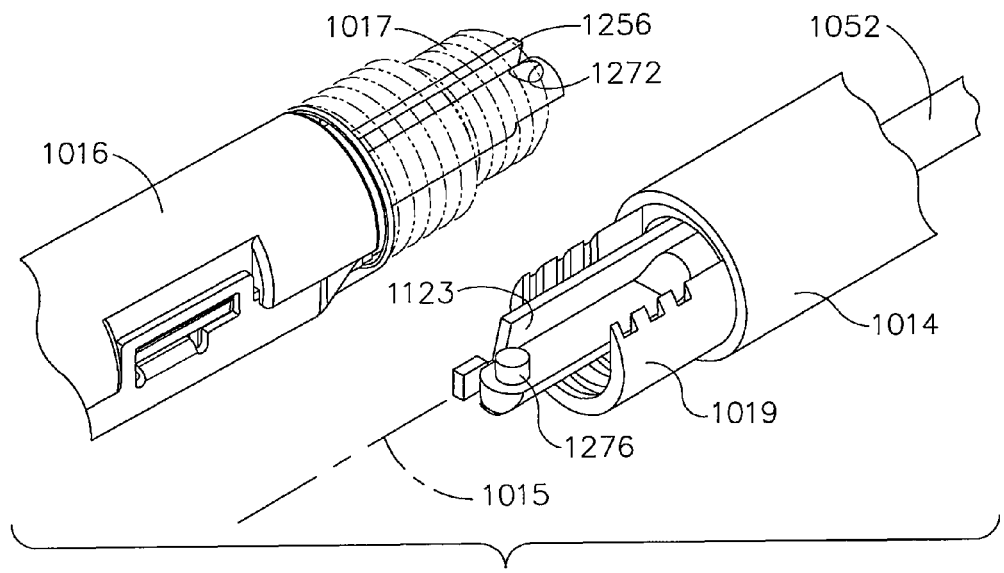
FIG. 66 is a perspective view of a connector portion of the disposable loading unit of FIG. 65 and a connector portion of the elongated body of FIG. 65.
Figure 67:
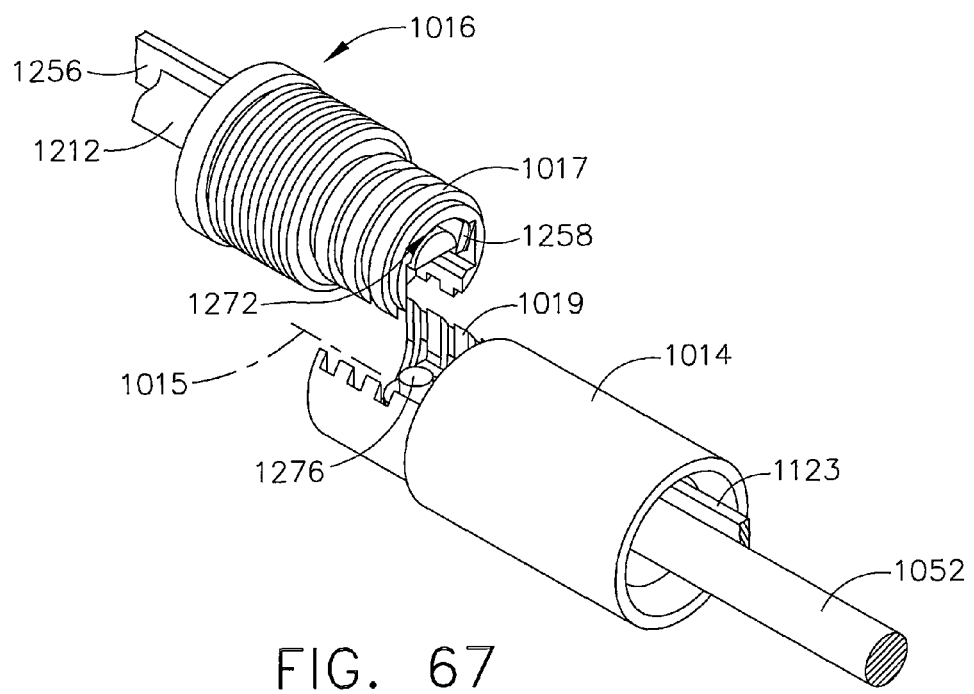
FIG. 67 is another perspective view of the connector portions of FIG. 66 with additional components of the disposable loading unit removed.

In various embodiments, referring to FIGS. 66 and 67, disposable loading unit 1016 can include connector portion 1017 which can be configured to be engaged with connector portion 1019 of elongated body 1014. In at least one embodiment, connector portion 1017 can include at least one projection and/or groove which can be mated with at least one projection and/or groove of connector portion 1019. In at least one such embodiment, the connector portions can include co-operating dovetail portions. In various embodiments, the connector portions can be configured to interlock with one another and prevent, or at least inhibit, distal and/or proximal movement of disposable loading unit 1016 along axis 1015. In at least one embodiment, similar to the devices described above, the surgical stapling instrument can include control rod 1052 which can be operably connected to drive member 1212 of disposable loading unit 1016 such that drive member 1212 can be advanced distally to deploy staples therefrom and/or incise tissue, for example, upon an actuation of handle member 24 (FIG. 1). In at least one such embodiment, drive member 1212 can include aperture 1272 which can be configured to receive projection 1276 extending from control rod 1052. In various embodiments, such an arrangement can allow disposable loading unit 1016 to be assembled to elongated member 1014 in a direction which is not collinear with or parallel to axis 1015. Although not illustrated, drive member 1212 and control rod 1052 can include any other suitable arrangement of projections and apertures to operably connect them to each other. Also similar to the devices described above, the surgical instrument can include first articulation link 1123 which can be operably engaged with second articulation link 1256 such that the operation of articulation lever 1030 can be transmitted to disposable loading unit 1016.

Figure 68:
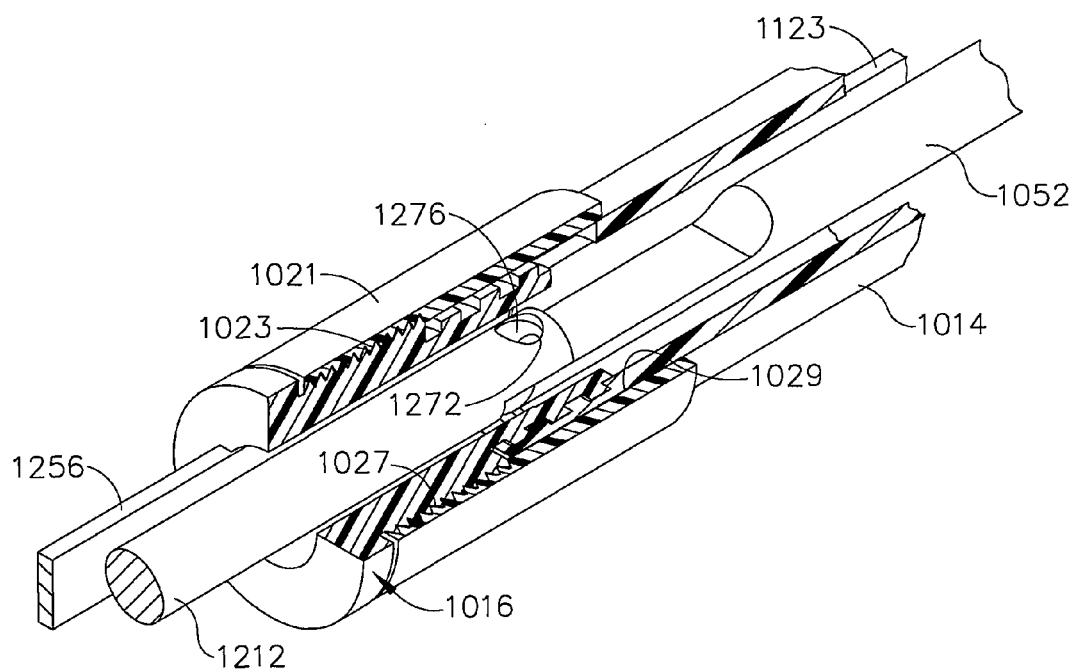
FIG. 68 is a cross-sectional perspective view of the connector portions of FIG. 66 assembled together and retained in position by a threaded collar.
Figure 69:
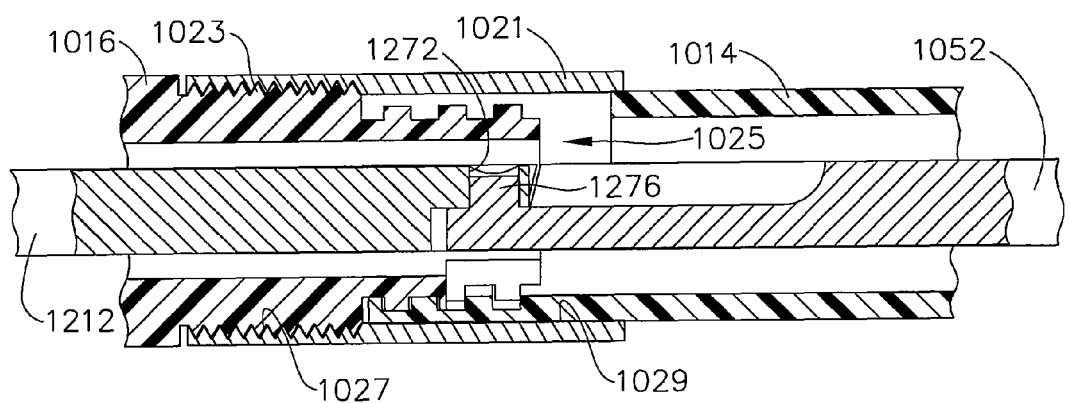
FIG. 69 is a cross-sectional elevational view of the connector portions of FIG. 66 and the threaded collar of FIG. 68.

In various embodiments, further to the above, the projections and/or grooves of connector portions 1017 and 1019 can be configured such that they can be press-fit together to prevent, or at least inhibit, disposable loading unit 1016 from moving in a direction which is transverse to axis 1015. In at least one embodiment, referring primarily to FIGS. 68 and 69, a sleeve, or collar, can be utilized to retain the disposable loading unit to the elongated member. In various embodiments, collar 1021 can be threadably engaged with threaded portion 1023 of disposable loading unit 1016 to prevent connector portions 1017 and 1019 from being disengaged from one another. In at least one embodiment, collar 1021 can include aperture 1025 having, first, a threaded portion 1027 which can threadably engage threaded portion 1023 and, second, a second portion 1029 which can closely receive elongated member 1014 so as to prevent, or at least limit, relative movement between disposable loading unit 1016 and elongated member 1014. Alternatively, although not illustrated, a collar can be configured to threadably engage elongated member 1014 and closely receive disposable loading unit 1016. In at least one embodiment, a collar can be configured to threadably engage both the elongated member and the disposable loading unit.

In various embodiments, a detent mechanism can be utilized to retain a disposable loading unit to an elongated member of a surgical stapling instrument. In at least one embodiment, referring to FIGS. 70-72, elongated member 2014 can include at least one ball detent 2031 which can be configured to engage disposable loading unit 2016 and hold disposable loading unit 2016 in position. In various embodiments, elongated member can include at least one aperture 2033 for receiving ball detents 2031 and at least one retention member 2035 for retaining ball detents 2031 in apertures 2033. In at least one embodiment, retention members 2035 can also be configured to bias ball detents 2031 into recesses 2037 in disposable loading unit 2016 such that the movement of disposable loading unit 2016 along axis 2015 can be prevented, or at least inhibited. In use, insertion tip 2193 of disposable loading unit 2016 can be inserted into elongated member 2014 such that the end of disposable loading unit 2016 can contact ball detents 2031 and displace them radially within apertures 2033. Once disposable loading unit 2016 has been inserted to its proper depth, recesses 2037 can be substantially aligned with apertures 2033 and retention members 2035 can position at least a portion of ball detents within recesses 2037.

Figure 72:
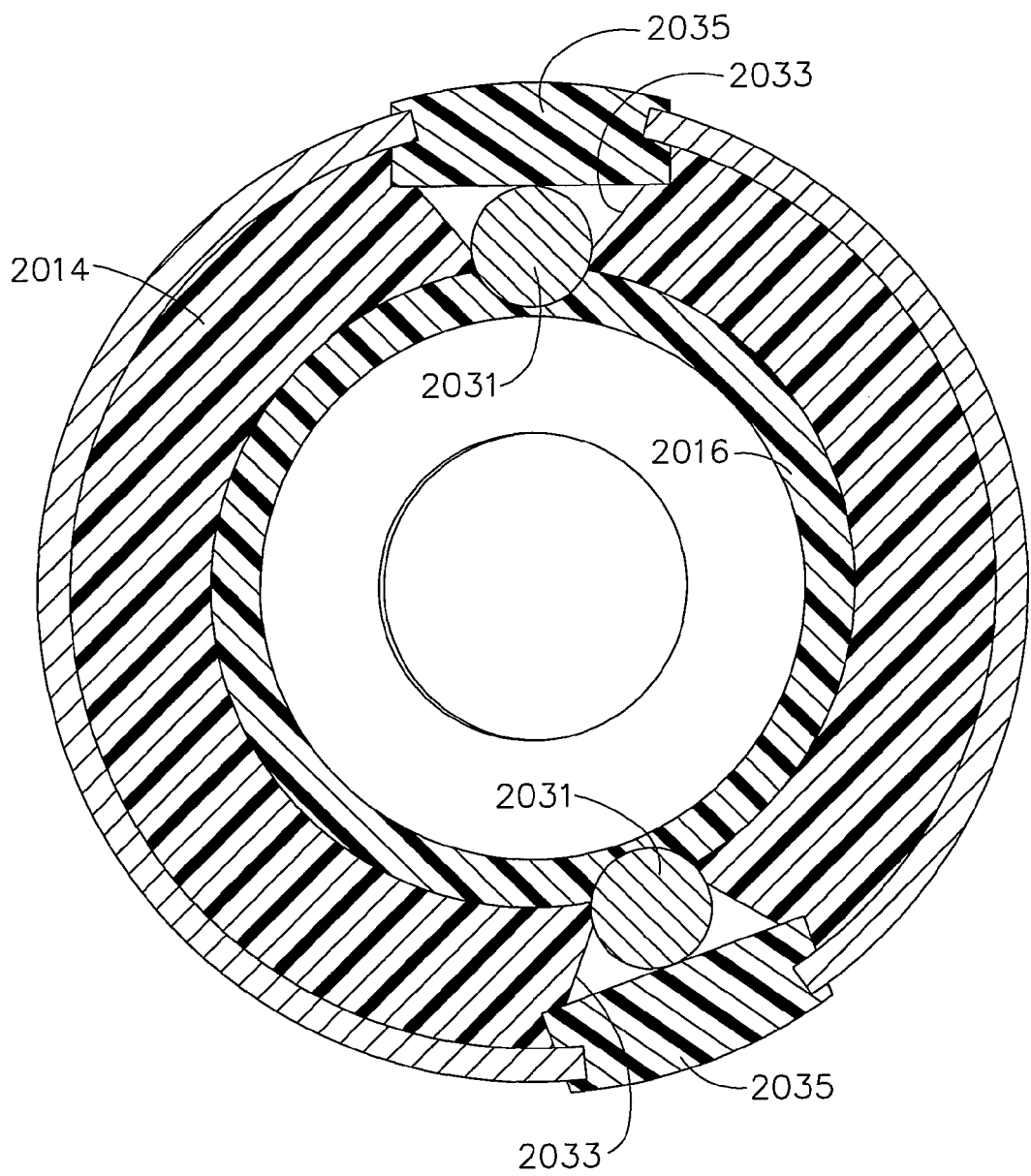
FIG. 72 is a cross-sectional view of the surgical stapling apparatus of FIG. 70 taken along line 72-72 in FIG. 71.
Figure 73:
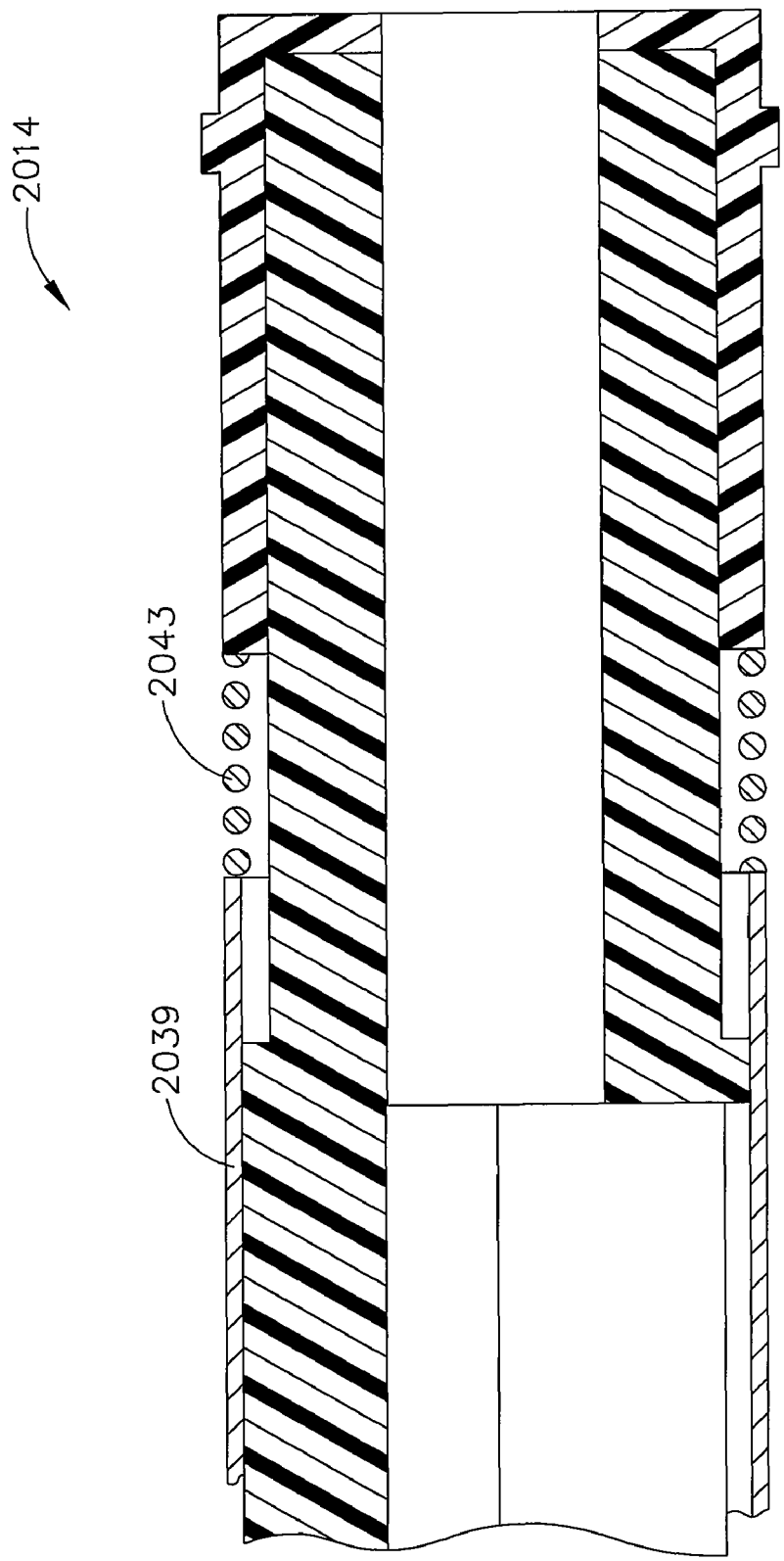
FIG. 73 is a detail view of an actuator of the elongated body of FIG. 70.
Figure 74:
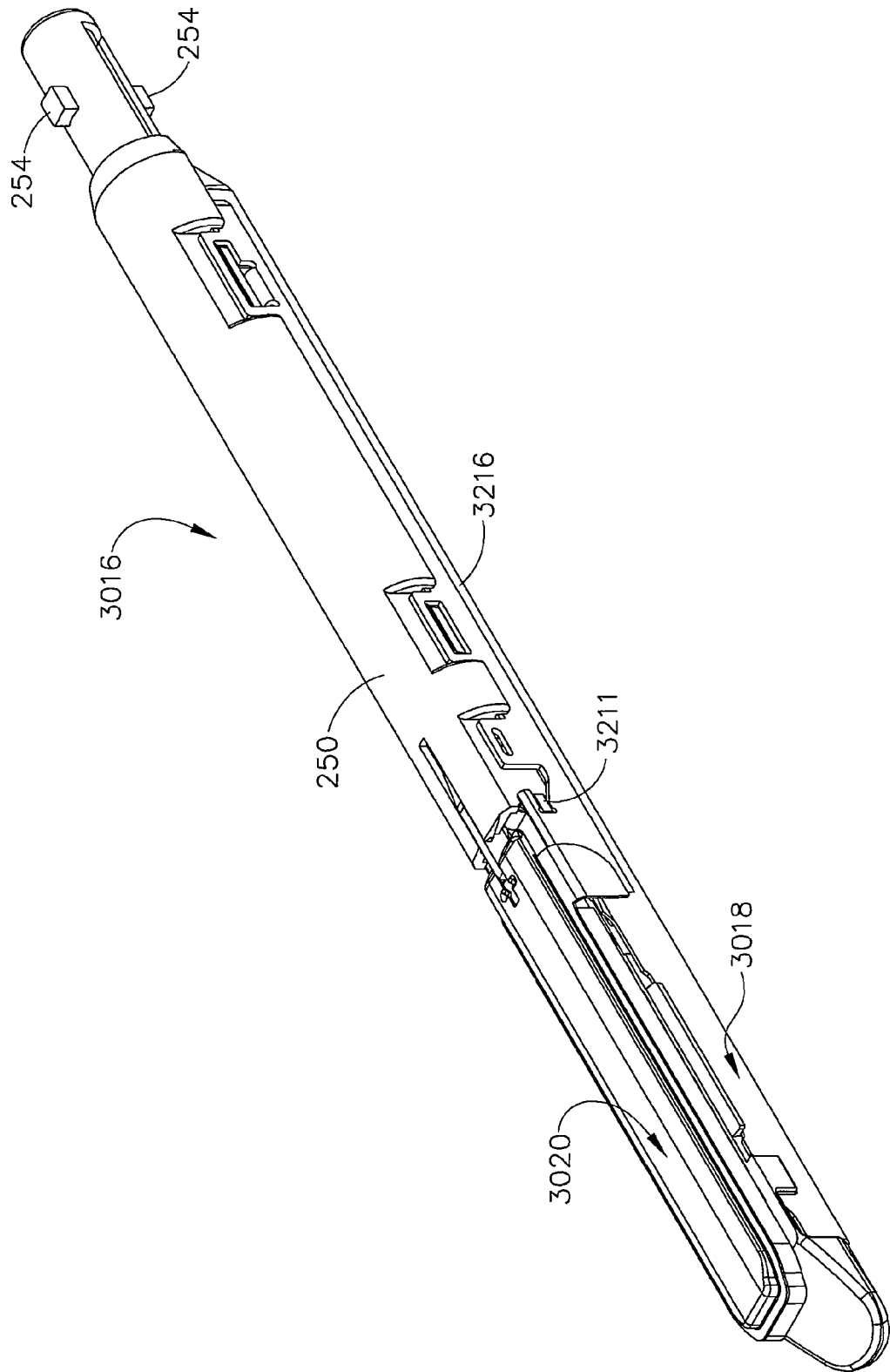
FIG. 74 is a perspective view of a disposable loading unit of an alternative embodiment of a surgical stapling apparatus.

In various embodiments, further to the above, at least one of retention members 2035 can be comprised of a resilient material. In at least one embodiment, ball detents 2031 and retention members 2035 can be structured and arranged such that retention members 2035 are deflected outwardly by ball detents 2031 and, as a result, resilient members 2035 can apply a biasing force to ball detents 2031. In order to release disposable loading unit 2016 from elongated member 2014, elongated member 2016 can further include actuator 2039 which can be manipulated to retract retention members 2035 proximally such that undercut 2041 of resilient members 2035 can be aligned, or at least substantially aligned, with ball detents 2031. In various embodiments, the alignment of undercut 2041 with ball detents 2031 can allow ball detents 2031 to be displaced radially and out of engagement with recesses 2037 when disposable loading unit 2016 is pulled out of the aperture in elongated member 2014. In at least one embodiment, referring to FIGS. 70 and 73, elongated member 2014 can further include return spring 2043 which can be configured to advance actuator 2039 and retention members 2035 distally and reposition retention members 2035 relative to ball detents 2031. In various embodiments, as illustrated in FIGS. 71 and 72, ball detents 2031 can be spherical, or at least substantially spherical, and can be comprised of any suitable material such as stainless steel, for example. In other various embodiments, although not illustrated, detents 2031 can have any suitable non-spherical shape.

In various embodiments, a disposable loading unit and an elongated member of a surgical instrument can include co-operating snap-fit features for retaining the disposable loading unit to the surgical stapling instrument. In at least one embodiment, although not illustrated, a disposable loading unit can include arms extending therefrom which can be at least partially received within apertures or recess in an elongated assembly. In use, the arms can be configured to flex inwardly toward each other as they are inserted into the elongated member and then resiliently spring outwardly when the arms are aligned with the apertures. In various embodiments, the surgical instrument can include a lock which can be slid intermediate the arms to hold the arms in the apertures and prevent, or at least inhibit, the disposable loading unit from becoming detached from the surgical instrument. In at least one embodiment, the lock could be slid distally upon an actuation of a trigger. In various alternative embodiments, the lock can include one or more cams configured to engage the arms and retain them in the apertures when the lock is rotated.

After a disposable loading unit has been attached to a surgical stapling instrument, the instrument can be positioned relative to the soft tissue of a patient. In various circumstances, a surgical stapling instrument can include an anvil and a staple cartridge, where the anvil can be rotated relative to the staple cartridge to position the anvil and the staple cartridge with respect to the soft tissue. As described above in connection with disposable loading unit 16 illustrated in FIGS. 38 and 40, disposable loading unit 16 can include anvil assembly 20 and cartridge assembly 18, where anvil assembly 20 can be pivoted between an open and closed positions. In some such devices, as outlined above and referring to FIG. 24, axial drive assembly 212 can be configured to contact camming surface 209 of anvil assembly 20 and move anvil assembly 20 into a closed position upon a first actuation of movable handle 24. Upon subsequent actuations of movable handle 24, drive assembly 212 can be advanced through disposable loading unit 16 to clamp, staple, and incise the soft tissue positioned intermediate cartridge assembly 18 and anvil assembly 20. In such instruments, as a result of the tissue being clamped at the same time as it is being stapled and incised, a portion of the soft tissue can flow, or 'milk', out of the distal end of the disposable loading unit and, in various circumstances, the soft tissue may not be properly treated by the surgical stapling instrument.

In various embodiments of the present invention, such problems can be ameliorated by utilizing a surgical stapling instrument which can apply a clamping force to soft tissue prior to the staples being deployed from the staple cartridge and/or the drive assembly being advanced within the disposable loading unit. In various circumstances, such embodiments can prevent, or at least inhibit, the soft tissue from milking out of the distal end of the disposable loading unit. In at least one embodiment, a surgical stapling instrument can include an actuator configured to be retracted relative to the distal end of the disposable loading unit to rotate the anvil between an open position and a closed position and clamp the tissue in position. In at least one such embodiment, referring to FIGS. 74-81, disposable loading unit 3016 can include cartridge assembly 3018 and anvil assembly 3020, where anvil assembly 3020 can be rotated toward cartridge assembly 3018 by actuator 3043. In at least one embodiment, anvil assembly 3020 can include, first, at least one pivot tab 3211 which can be rotatably received within an aperture or recess within staple cartridge assembly 3018, for example, and, second, at least one recess 3047 which can be configured to operably receive at least a portion of actuator 3043. When actuator 3043 is pulled in a direction indicated by arrow "P", in at least one embodiment, actuator 3043 can rotate anvil assembly 3020 into a closed position about an axis defined by pivot tabs 3211 and apply a clamping force to the soft tissue.

In various embodiments, as outlined above, actuator 3043 can include at least one projection 3049 which can be configured to engage the sidewalls of recess 3047 and apply a force to anvil assembly 3020. In at least one embodiment, such a force can generate a torque, or force-moment, causing anvil assembly 3020 to rotate about pivot tabs 3211 between an open position, as illustrated in FIG. 76, and a closed position, as illustrated in FIG. 77. In use, as also outlined above, such a torque can apply a clamping pressure or force to tissue positioned intermediate anvil assembly 3020 and staple cartridge assembly 3018. In various embodiments, the torque applied to anvil assembly 3020 can be directly proportional to the force applied by actuator 3043 and the distance between projections 3049 and pivot tabs 3211, i.e., distance "D" (FIG. 77). In at least one embodiment, a disposable loading unit can be designed such that distance D can be maximized, or at least substantially increased, to apply a larger clamping moment or force to the soft tissue. In at least one such embodiment, referring to FIGS. 80 and 81, staple cartridge assembly 3018 can comprise staple cartridge carrier 3216 which can include apertures, or recesses, 3045 which can be configured to allow at least a portion of projections 3049 to extend therethrough such that the distance between projections 3049 and pivot tabs 3211 can be increased.

Figure 75:
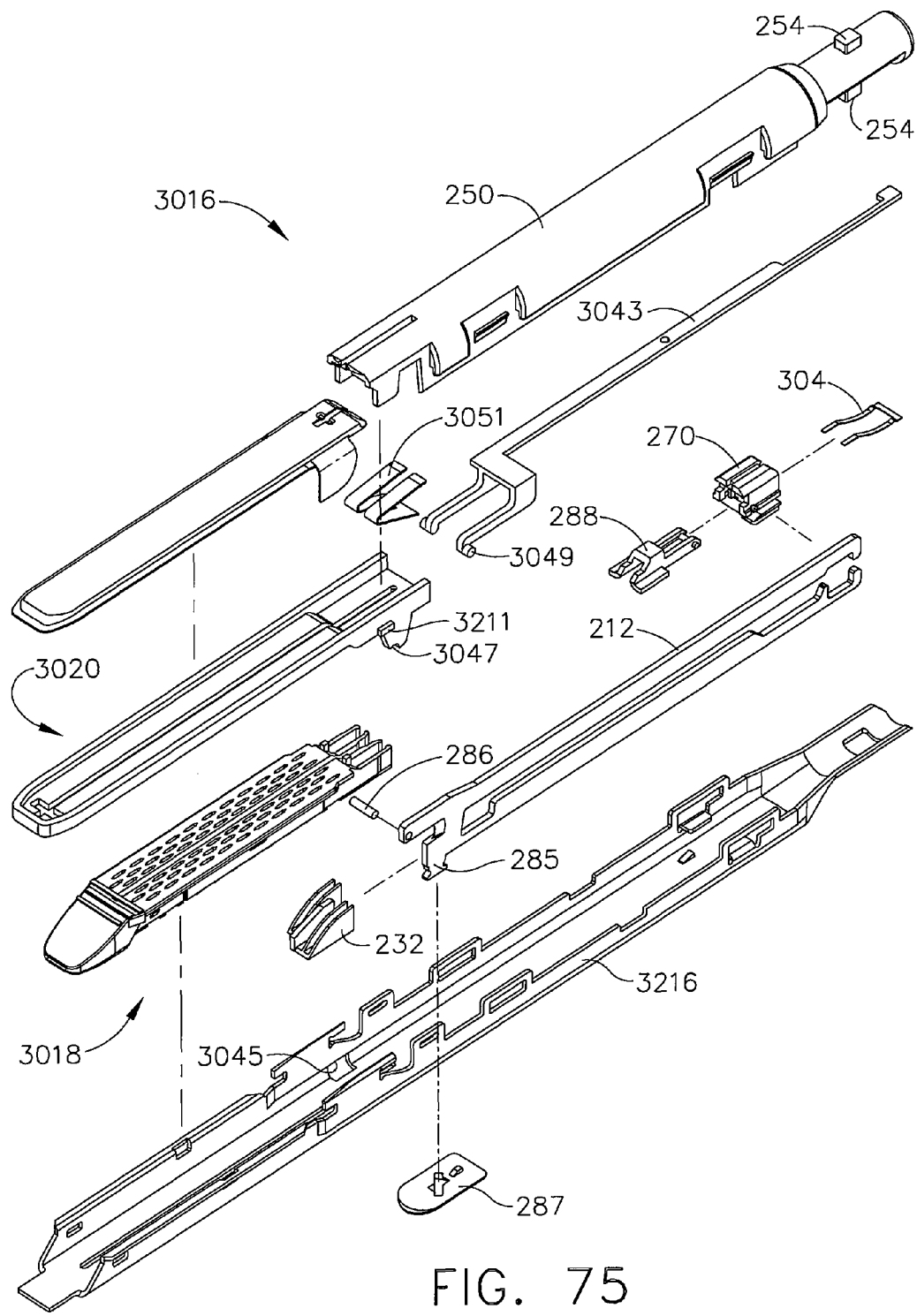
FIG. 75 is an exploded view of the disposable loading unit of FIG. 74.
Figure 78:
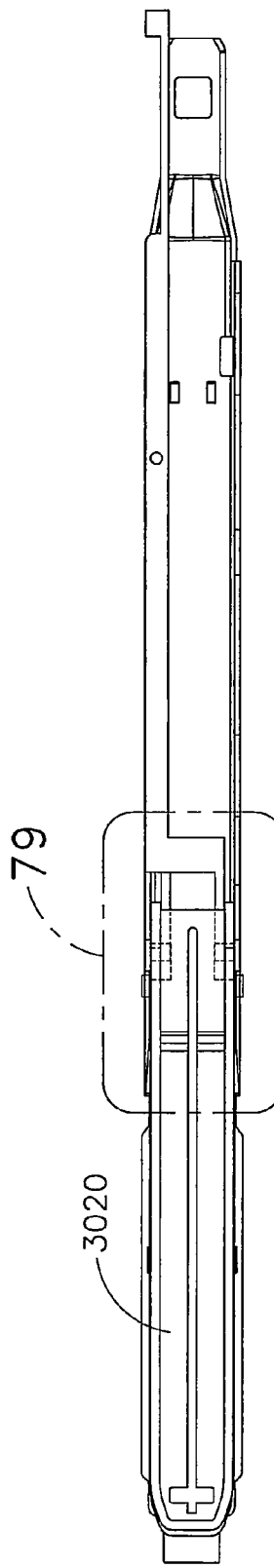
FIG. 78 is a plan view of the disposable loading unit of FIG. 74 with some components removed.
Figure 79:
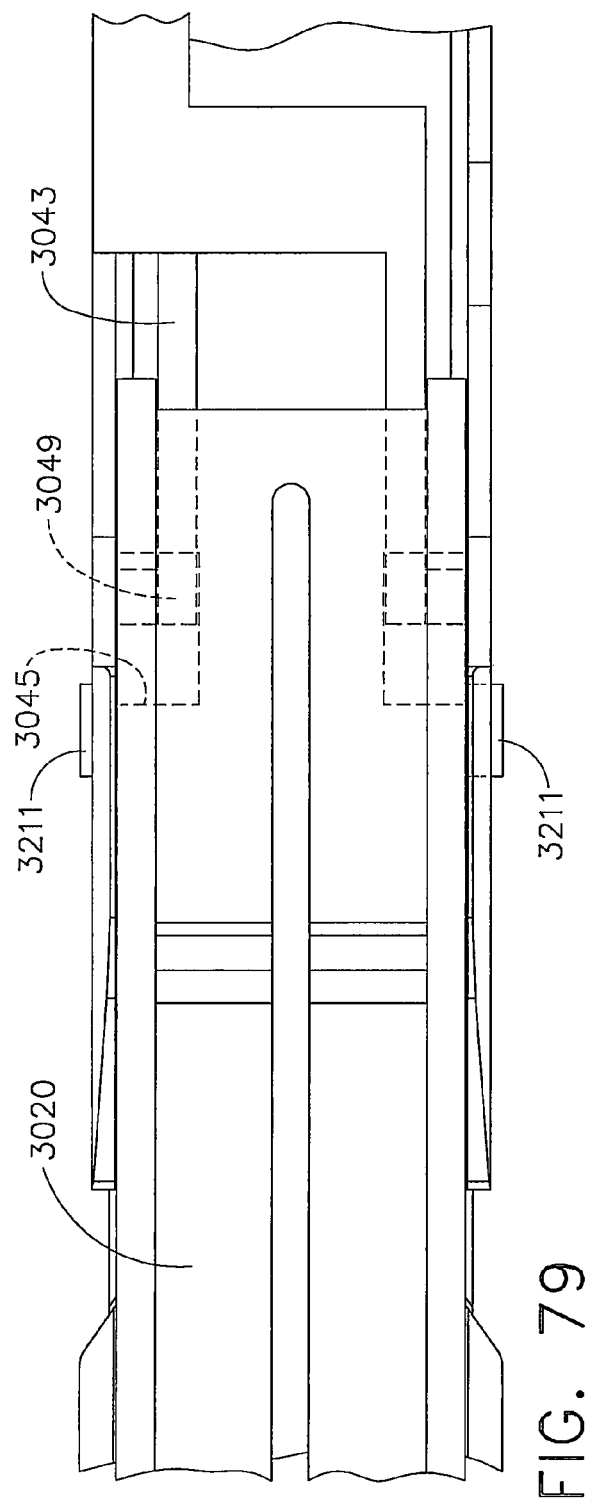
FIG. 79 is a detail view of a portion of the disposable loading unit of FIG. 74.

In various embodiments, referring to FIG. 75, disposable loading unit 3016 can include spring 3051 which can configured to bias anvil assembly 3020 into an open position and, in addition, a spring which can bias actuator 3043 into its most distal position. In use, as outlined above, actuator 3043 can be pulled proximally to pivot anvil assembly 3020 into its closed position. In such circumstances, as illustrated in FIG. 77A, anvil assembly 3020 can resiliently compress spring 3051 such that spring 3051 can return anvil assembly 3020 to its open position when actuator 3043 is released as described in greater detail below. In various embodiments, a surgical instrument can include a trigger, or any other suitable actuation device, which can be manipulated by a surgeon, or other clinician, to pull actuator 3043 proximally and, in at least one embodiment, lock actuator 3043 in its retracted position. In at least one embodiment, referring generally to FIGS. 1 and 9, actuator 3043 can be operably engaged with articulation lever 30 and first articulation link 123 such that, when articulation lever 30 is rotated in a first direction, articulation link 123 and actuator 3043 can be retracted proximally. Similarly, when articulation lever 30 is rotated in a second direction, articulation link 123 and actuator 3043 can be advanced distally. In various embodiments, actuator 3043 can be advanced distally to remove projections 3049 from recesses 3047 and allow spring 3051 to return anvil assembly 3020 to its open position.

In various embodiments, a disposable loading unit can include an actuator comprising a cam configured to operably engage an anvil of the disposable loading unit and apply a compressive pressure or force to soft tissue prior to staples being deployed into the soft tissue. In at least one embodiment, referring to FIGS. 82 and 83, disposable loading unit 4016 can include anvil assembly 4020, staple cartridge assembly 4018, and actuator 4043, where actuator 4043 can be configured to rotate anvil assembly 4020 between an open position, as illustrated in FIG. 82, and a closed position, as illustrated in FIG. 84. In various embodiments, referring to FIGS. 82 and 84, actuator 4043 can include cam 4053 where actuator 4043 can be pulled proximally, i.e., in a direction indicated by arrow "P", such that cam 4053 can engage anvil assembly 4020 and rotate anvil assembly 4020 about an axis defined by pivot tabs 4211. Similar to the above, actuator 4043 can be operable engaged with any suitable trigger, such as articulation lever 30, for example, to motivate actuator 4043.

In various embodiments, an actuator cam can include at least one of a linear, non-linear, arcuate, and/or curvilinear profile. In at least one embodiment, cam 4053 can include an arcuate profile having apex 4055 and initial contact point 4057, for example, where cam 4053 can be configured to engage anvil assembly 4020 such that initial contact point 4057 first contacts anvil assembly 4020. As actuator 4043 is pulled further proximally, cam 4053 can slide relative to anvil assembly 4020 such that various other points of cam 4053 contact anvil assembly 4020 until apex 4055 is in contact with anvil assembly 4020 as illustrated in FIG. 85. At such point, anvil assembly 4020 can be in its closed position. In various embodiments, referring again to FIG. 85, apex 4055 can be positioned proximally relative to pivot tabs 4211, i.e., on the proximal side of axis 4059 and, as a result, anvil assembly 4020 can be prevented from rotating back into its open position until cam 4053 is disengaged from, i.e., moved distally relative to, anvil assembly 4020. Furthermore, the position of apex 4055 relative to pivot tabs 4211 can utilize leverage, or mechanical advantage, to apply an even greater clamping force to the soft tissue.

In various embodiments, as cam 4053 is retracted proximally and anvil assembly 4020 is rotated into its closed position as described above, anvil assembly 4020 can contact soft tissue, for example, positioned intermediate anvil assembly 4020 and staple cartridge assembly 4018. In at least one embodiment, anvil assembly 4020 can apply an initial clamping force to the soft tissue when it initially contacts the tissue and wherein anvil assembly 4020 can apply an increasingly greater force to the soft tissue as anvil assembly 4020 is moved into its final, or closed, position. In various embodiments, the clamping force can be increased in a substantially linear manner. In at least one embodiment, a cam, such as cam 4053, for example, can be configured to drive anvil 4020 in such a manner as to increase the clamping force to the soft tissue in a non-linear manner. In at least one such embodiment, the clamping force can be increased in a geometric manner such that the climax of the clamping force is applied to the soft tissue when anvil assembly 4020 is in its final, or closed, position, for example. As a result of the above, an anvil can apply a clamping force to soft tissue prior to staples being deployed from the staple cartridge, for example, and prevent, or at least inhibit, the soft tissue from flowing, or 'milking', out of the distal end of the disposable loading unit.

In various embodiments, further to the above, a cam can include a profile which utilizes a variable mechanical advantage as the anvil is moved into its closed position. In at least one embodiment, the cam can include a compound profile which includes a first portion for utilizing a first mechanical advantage, or leverage, during the initial movement of the anvil and, in addition, a second portion for utilizing a second mechanical advantage, or leverage, for subsequent movement of the anvil. In at least one such embodiment, a larger mechanical advantage can be utilized during the final movement of the anvil so as to apply a larger clamping force to the soft tissue when the anvil is in its closed position.

In various embodiments, referring to FIGS. 84 and 85, anvil assembly 4020 can include a tissue-contacting surface, such as surface 4063, for example, which can be positioned parallel to, or at least substantially parallel to, a tissue-contacting surface on staple cartridge assembly 4018, such as surface 4065, for example, when anvil assembly 4020 is in its closed position. In at least one embodiment, anvil assembly 4020 and staple cartridge assembly 4018 can be configured such that there is a gap defined between anvil assembly 4020 and staple cartridge assembly 4018 when anvil assembly 4020 is in its closed position. In various embodiments, the distance between tissue-contacting surfaces 4063 and 4065 can be shorter at distal end 4069 of the disposable loading unit as compared to proximal end 4067. In at least one such embodiment, as a result, the distal end of anvil assembly 4020 can trap soft tissue within the disposable loading unit when anvil assembly 4020 is moved into its closed position. In other various embodiments, the gap between tissue-contacting surfaces 4063 and 4065 can have a consistent, or at least a substantially consistent, distance between proximal end 4067 and distal end 4069.

In various embodiments, referring to FIG. 86, an actuator, such as actuator 4043', for example, can include two or more cams 4053 which can be configured to engage at least a portion of anvil assembly 4020 as described above. In at least one embodiment, cams 4053 can extend from a shaft portion 4061' of actuator 4043' such that cams 4053 can be moved relative to anvil assembly 4020 simultaneously. In various embodiments, actuator 4043' can also include at least one hook portion 258 configured to engage first articulation link 123 as outlined further above. In various alternative embodiments, referring to FIG. 87, a disposable loading unit can include two or more actuators, such as actuators 4043", for example, which can each include one or more cams 4053, for example, for pivoting anvil assembly 4020. In at least one such embodiment, each actuator 4043" can include a hook portion 258 which can be operably connected with one or more articulation links, for example, in a surgical stapling instrument.

In various embodiments of the present invention, a surgical stapling instrument can include a disposable loading unit comprising a staple cartridge, an anvil, and a sleeve, wherein the sleeve can be configured to be slid relative to the staple cartridge and the anvil and hold at least one of the anvil and the staple cartridge in position. In at least one embodiment, referring to FIGS. 109 and 110, disposable loading unit 5016 can include at least one sleeve or collar, such as sleeve 5071, for example, which can be slid between a proximal position, as illustrated in FIG. 109, and a distal position, as illustrated in FIG. 110. In at least one embodiment, sleeve 5071 can include an aperture which, when sleeve 5071 is positioned in its distal position, for example, can at least partially encompass or surround anvil assembly 5020 and/or staple cartridge assembly 5018. In various embodiments, sleeve 5071 can be configured to prevent anvil assembly 5020 from prematurely opening. Furthermore, sleeve 5071 can prevent, or at least inhibit, anvil assembly 5020 and staple cartridge assembly 5018 from deflecting when the soft tissue positioned therebetween is stapled and/or incised.

In at least one embodiment, sleeve 5071, for example, can be configured to apply a clamping pressure or force to the soft tissue positioned between anvil assembly 5020 and staple cartridge assembly 5018. In various embodiments, similar to the above, such a clamping pressure or force can be applied before surgical staples are deployed from the staple cartridge and/or the soft tissue is incised. In various embodiments, referring again to FIGS. 109 and 110, sleeve 5071 can further include slots 5079 which can be configured such that, when sleeve 5071 is advanced distally, sleeve 5071 may not contact and/or damage the tissue positioned between anvil assembly 5020 and staple cartridge assembly 5018.

Figure 113:
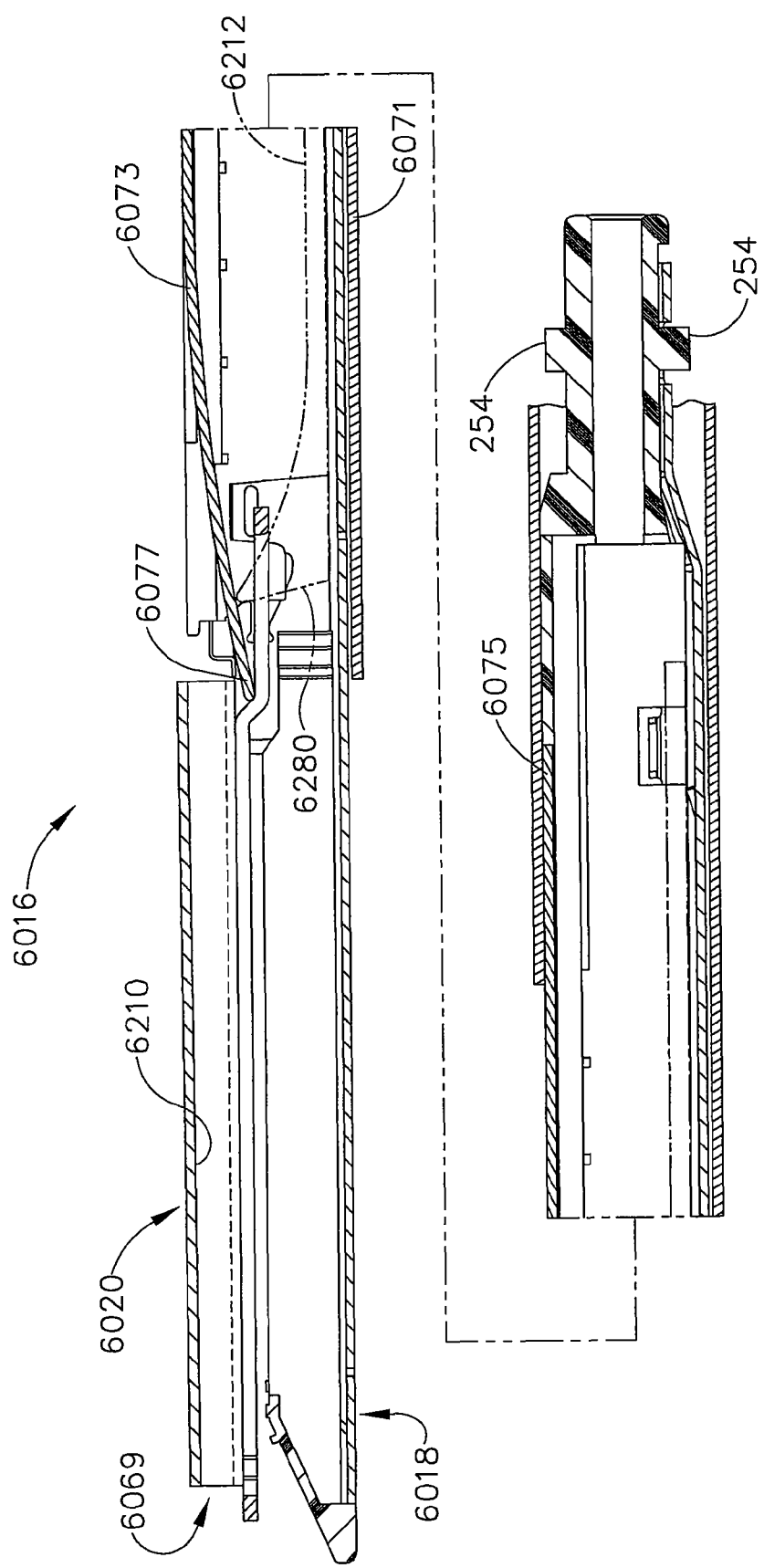

In various embodiments, a surgical stapling instrument can include a cantilever, or tongue, configured to be slid relative to at least one of a staple cartridge and an anvil and engage at least one of the staple cartridge and anvil to hold them in a closed position, for example. In at least one embodiment, referring to FIGS. 111 and 112, disposable loading unit 6016 can include at least one sleeve or collar, such as sleeve 6071, for example, which can be slid between a proximal position, as illustrated in FIG. 111, and a distal position, as illustrated in FIG. 112. In at least one embodiment, sleeve 6071 can include tongue 6073 extending therefrom which can be configured to engage at least a portion of anvil assembly 6020 and apply a force thereto. In various embodiments, such a force can position anvil assembly 6020 against the soft tissue positioned intermediate anvil assembly 6020 and staple cartridge assembly 6018 and clamp the soft tissue therebetween. Referring to FIG. 113, tongue 6073, for example, can comprise any suitable configuration including an arcuate, linear, and/or curvilinear configuration. In at least one embodiment, tongue 6073 can include a curved body comprising proximal end 6075 connected to sleeve 6071 and a distal tip 6077 which can be configured to engage anvil assembly 6020 within anvil cavity 6210. In at least one such embodiment, the force transmitted between tongue 6073 and anvil assembly 6020 can be applied to anvil assembly 6020 through tip 6077 and, as a result, the location in which the force is applied to the soft tissue can be dictated by the position of tip 6077.

In various embodiments, sleeve 6071 can be configured such that it can be advanced between its proximal and distal positions prior to staples being deployed from staple cartridge assembly 6018 and the tissue being incised by drive member 6212, for example. In at least one such embodiment, referring to FIG. 113, tongue 6073 can be slid distally by sleeve 6071 until distal tip 6077 of tongue 6073 contacts anvil assembly 6020 at distal end 6069. Thereafter, similar to the above, drive assembly 6212 can be advanced toward the distal end of the disposable loading unit to staple and/or incise the tissue. In such circumstances, the clamping force applied to the soft tissue by tongue 6073 can be applied at the distal end of the disposable loading unit and the possibility that the tissue may milk out of the distal end of the disposable loading unit can be reduced. In other various embodiments, distal tip 6077 can be advanced toward distal end 6069 as drive member 6212 is advanced toward distal end 6069, for example. In at least one embodiment, distal tip 6077 can be configured to contact anvil assembly 6020 at a location which is positioned directly over, or at least adjacent to, knife blade 6280. In such embodiments, tongue 6073 can support anvil assembly 6020 directly above the location in which staples are deformed against anvil assembly 6020.

Figure 90:
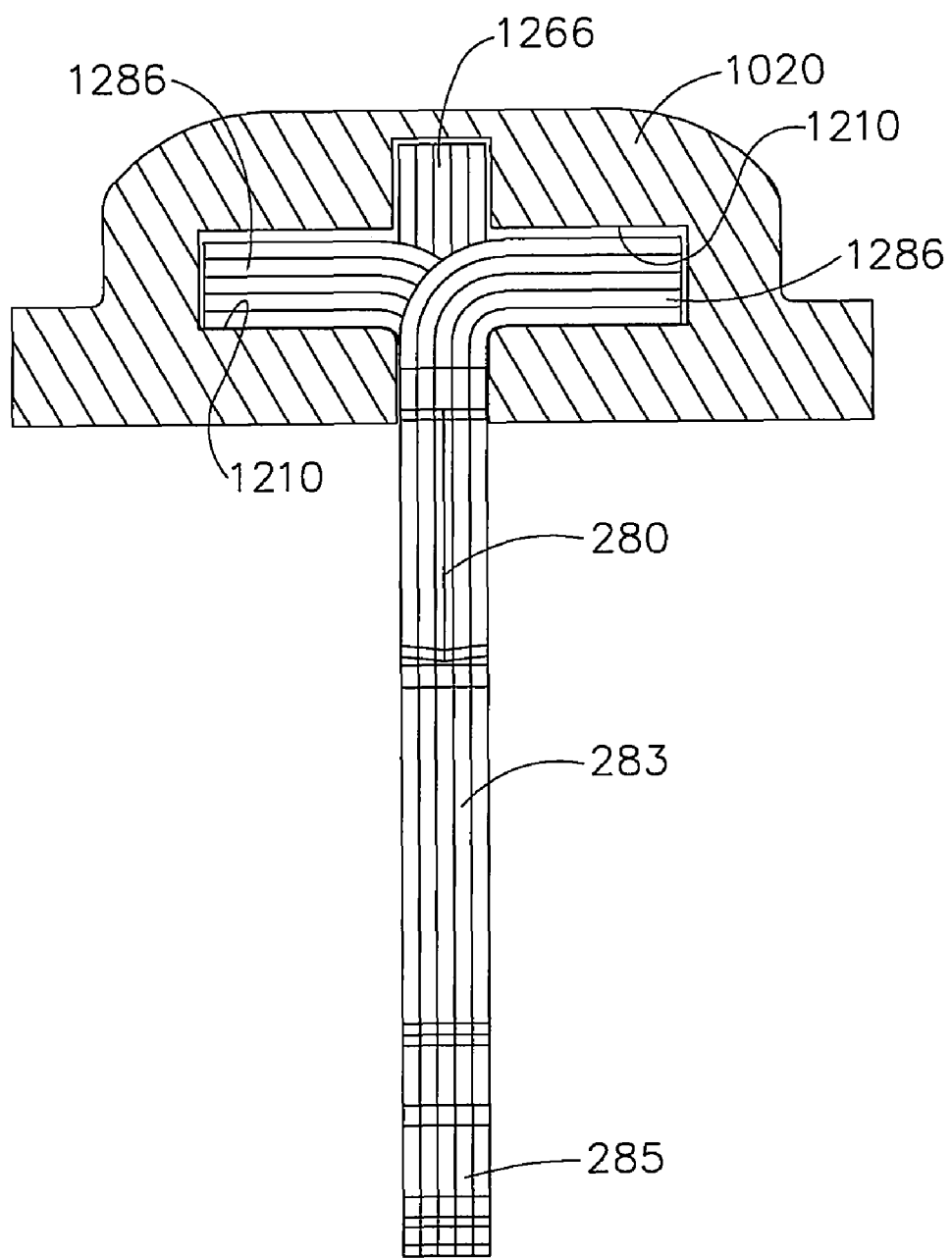
FIG. 90 is a cross-sectional view of a portion of the drive beam of FIG. 88 positioned within a channel of an anvil.

After an anvil of a disposable loading unit has been moved into a closed position, as outlined above, a drive beam can be advanced within the disposable loading unit to eject the staples therefrom and/or incise soft tissue. In various embodiments, a drive beam, such as drive beam 266, for example, can be comprised of a single sheet of material and/or multiple stacked sheets of material. As also outlined above, a drive assembly, such as drive assembly 212, for example, can further comprise a cam roller 286 and a support member 287 which can be configured to retain drive beam to anvil assembly 20 and staple cartridge assembly 18, respectively. In various circumstances, the time and cost to assemble such components to drive beam 266 can be significant. In various embodiments of the present invention, such time and cost can be reduced. More particularly, in at least one embodiment of the present invention, a portion of a drive beam can be deformed, or otherwise integrally formed, so as to create features which can obviate the need for a separately-manufactured cam roller 286 and/or support member 287, for example. In various embodiments, referring to FIGS. 88-90, drive beam 1266 can include integral cam members 1286 which can extend laterally from retention flange 1284. In at least one embodiment, drive beam 1266 can manufactured from a flat, or at least substantially flat, piece of material where the piece of material can be stamped such that cam members 1286 are at least partially separated from retention flange 1284 and extend in a transverse or oblique direction with respect to drive beam 1266. In at least one such embodiment, referring to FIG. 90, cam members 1286 can be sized and configured such that they can slide within anvil channel 1210 and at least assist in holding anvil assembly 1020 in a closed position. In addition to or in lieu of the above, although not illustrated, a portion of drive beam 1266, for example, can be configured to extend laterally from drive beam 1266 so as to retain drive assembly 1212 to a staple cartridge assembly. In at least one embodiment, similar to the above, retention flanges can be at least partially separated from drive beam 1266 during a stamping process such that the integral retention flanges extend in a transverse or oblique direction with respect to drive beam 1266. In various embodiments, as a result of the above, at least one integral cam member and/or at least one integral retention member can be formed during a suitable manufacturing process, such as progression stamping, for example, which can reduce, or even eliminate, the assembly time of additional components to the drive beam.

Figure 49:
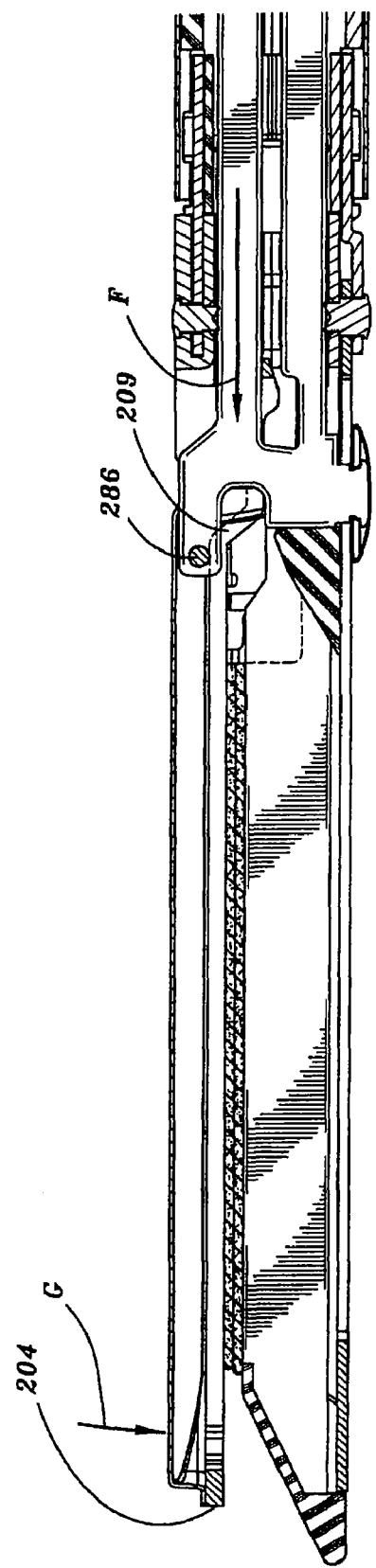
FIG. 49 is a cross-sectional view of the tool assembly of the surgical stapling apparatus shown in FIG. 1 positioned about tissue in the clamped position.
Figure 92:
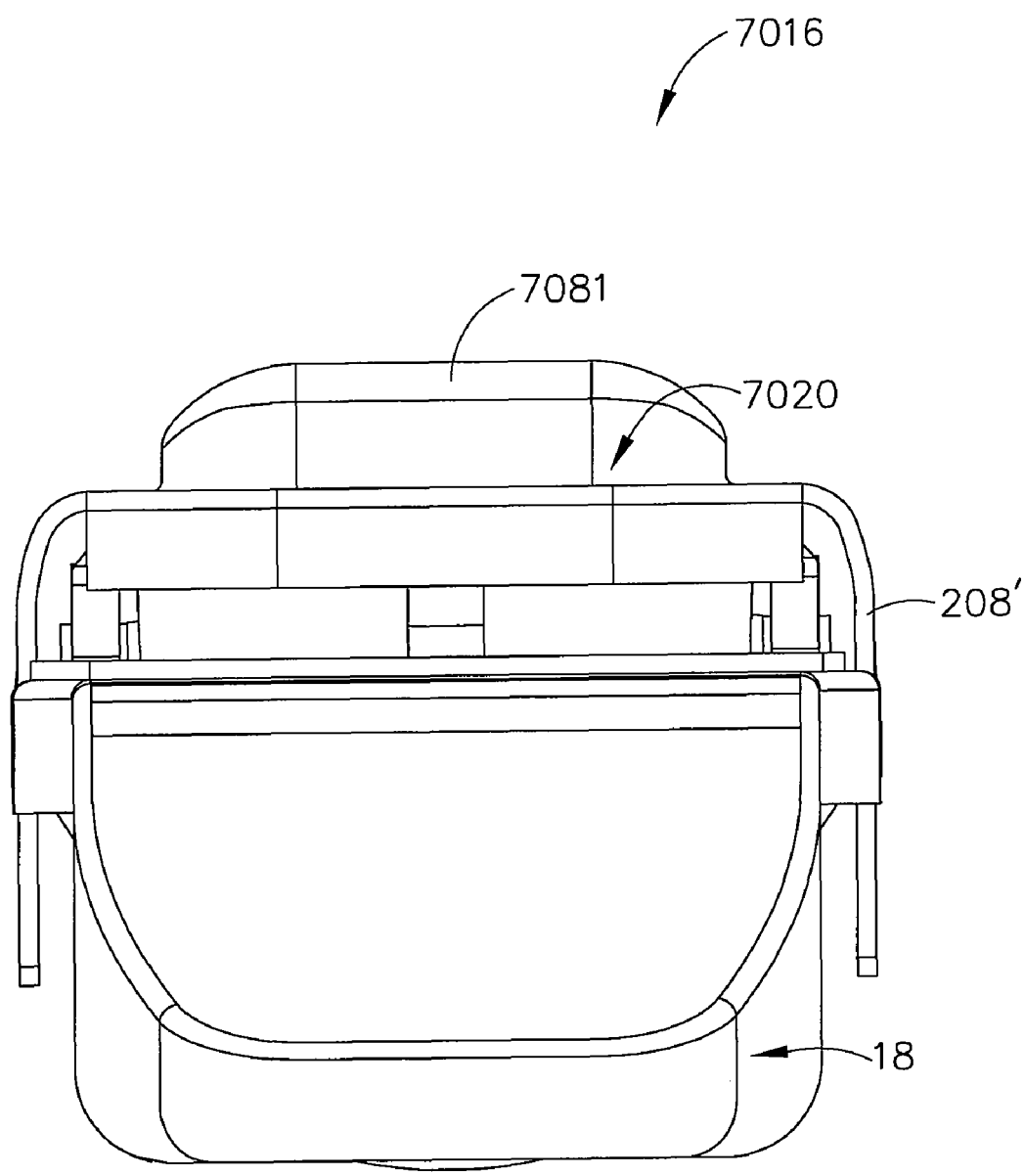
FIG. 92 is an end view of the disposable loading unit of FIG. 91.
Figure 93:
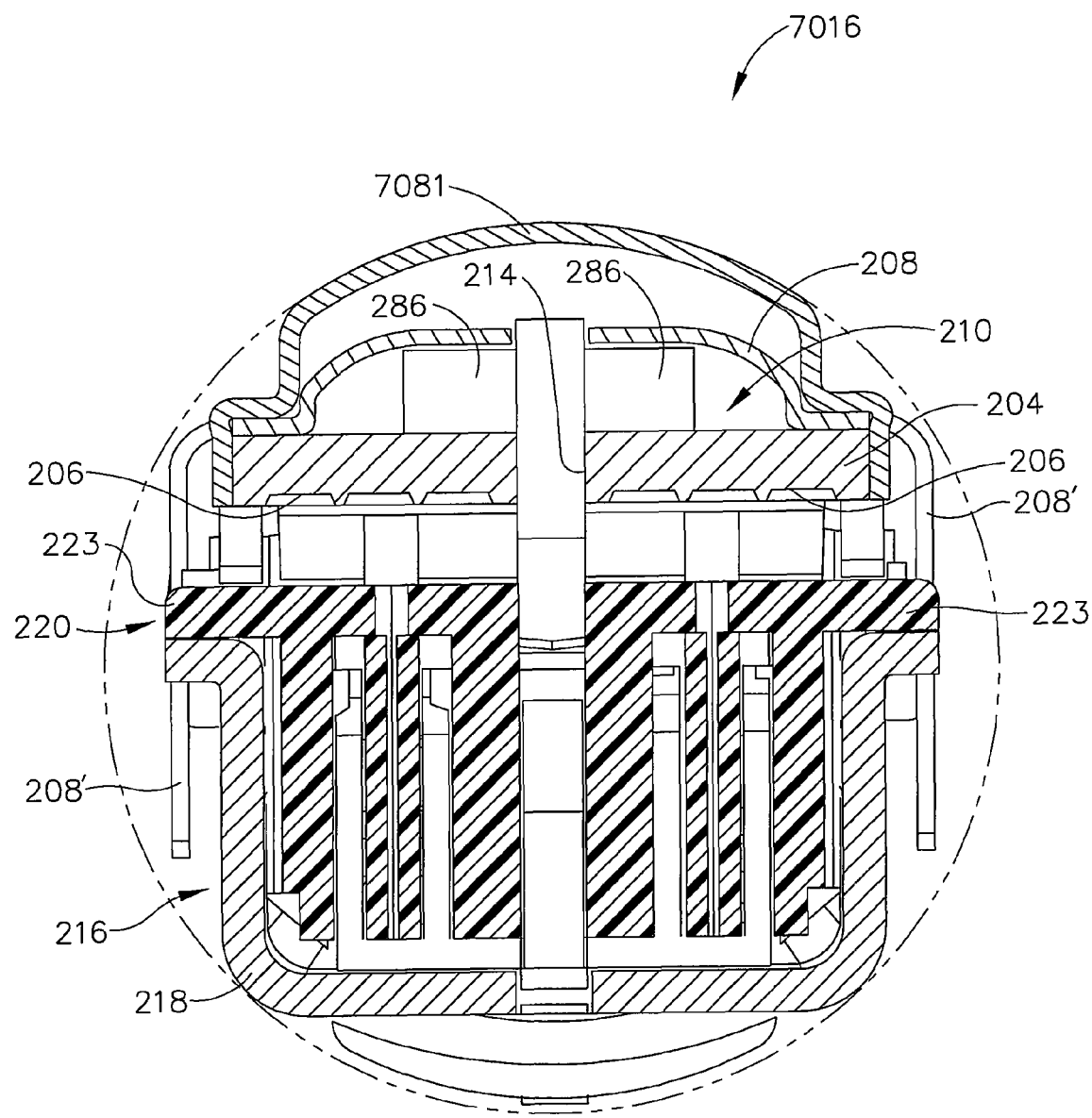
FIG. 93 is a cross-sectional view of the disposable loading unit of FIG. 91.

In various embodiments, referring to FIG. 49, the anvil of a disposable loading unit can include a slot defined therein which can be configured to receive at least a portion of a drive beam. In at least one embodiment, referring to FIGS. 51 and 52, the anvil can include a channel extending therethrough where cam rollers 286 can be configured to engage a sidewall of the channel and apply a force, or forces, to the anvil assembly. In various circumstances, such forces can cause the anvil to elastically and/or plastically deform and, as a result, affect the deployment of the surgical staples into the soft tissue. In various embodiments of the present invention, an anvil can include features which can eliminate, or at least reduce, the deformation of the anvil. In at least one embodiment, an anvil can include a first member having staple pockets for deforming the staples, a first cover plate secured to the first member, and a second cover plate secured to at least one of the first member and the first cover plate, wherein the first and second cover plates can be configured to support the first member. In at least one such embodiment, referring to FIGS. 91-93, disposable loading unit 7016 can include anvil assembly 7020 which can comprise anvil portion 204, first cover plate 208 affixed to anvil portion 204, and second cover plate 7081 affixed to at least one of anvil portion 204 and first cover plate 208. In various embodiments, first cover plate 208 can be welded to anvil portion 204 and, in addition, second cover plate 7081 can be welded to first cover plate 208 and/or anvil portion 204. In at least one embodiment, second cover plate 7081 can strengthen, stiffen, and/or increase the section modulus of the anvil assembly, thereby reducing the possibility that the anvil assembly may unsuitably deform during use.

Figure 91:
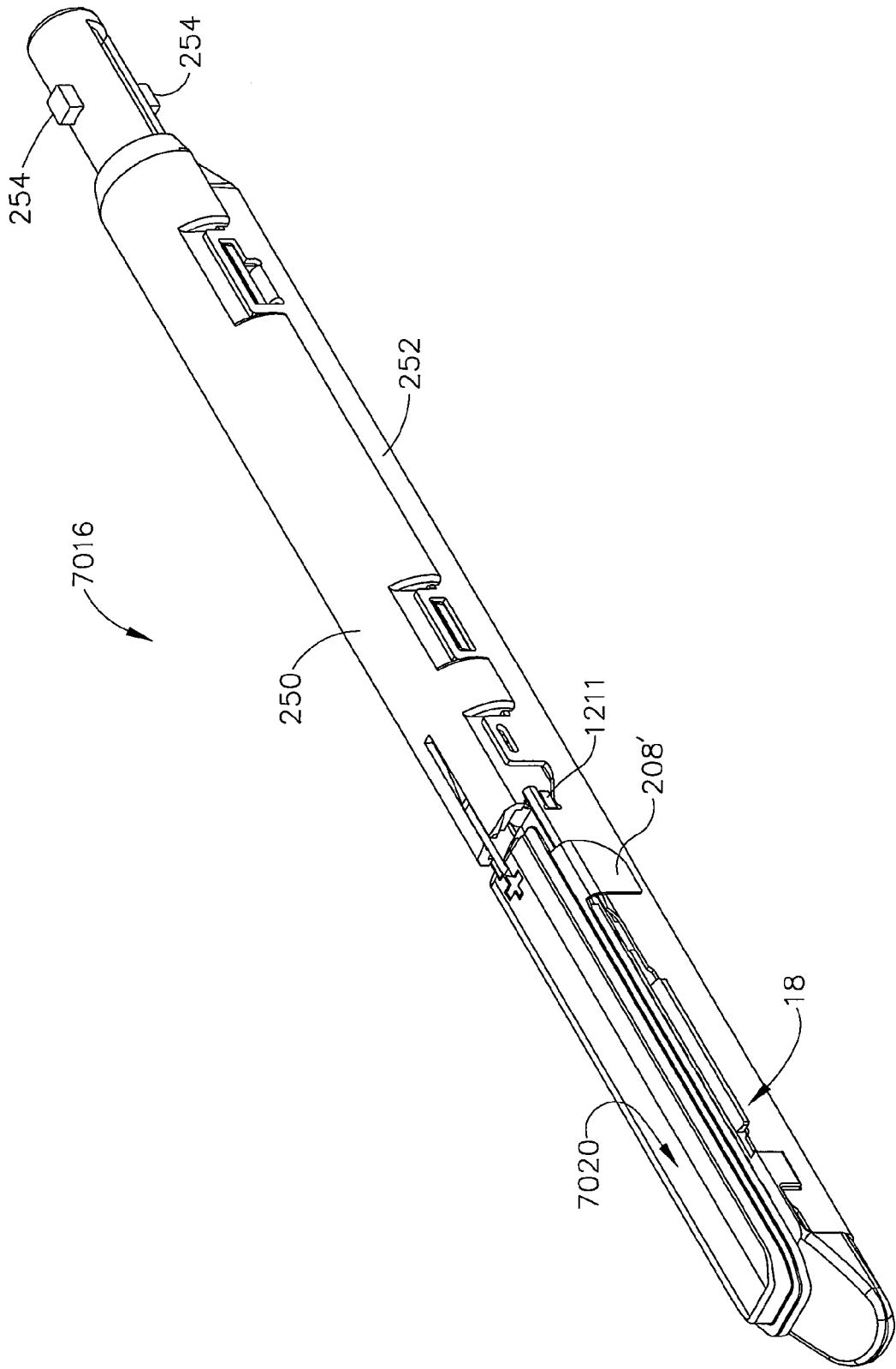
FIG. 91 is a perspective view of a disposable loading unit of an alternative embodiment of a surgical stapling apparatus.
Figure 94:
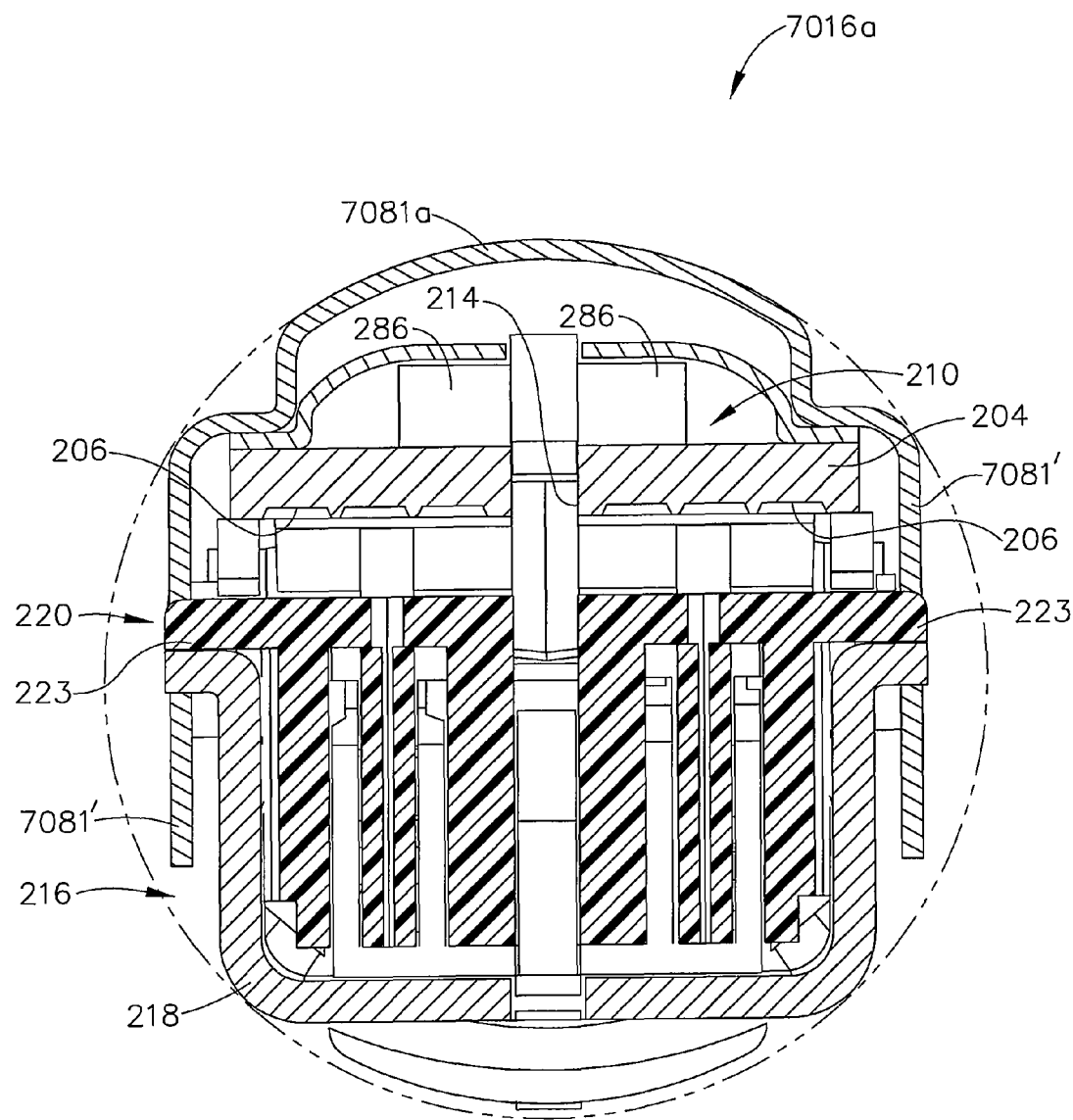
FIG. 94 is a cross-sectional view of an alternative embodiment of a disposable loading unit.

In various embodiments, referring to FIG. 91, first cover plate 208 can include tissue stops 208' extending therefrom. In at least one embodiment, tissue stops 208' can be configured such that, when the anvil and staple cartridge assemblies are positioned relative to soft tissue, tissue stops 208' can prevent, or at least inhibit, the soft tissue from progressing past a certain point in the disposable loading unit. In various embodiments of the present invention, referring to FIG. 94, second cover plate 7081a of disposable loading unit 7016a can include tissue stops 7081' extending therefrom in addition to or in lieu of the above. In various embodiments, a disposable loading unit can include a second cover plate which can be formed from one or more sheets of material. In at least one embodiment, referring to FIG. 95, disposable loading unit 7061b can include second cover plate 7081b, wherein second cover plate 7081b can be formed from a single sheet of material, such as stainless steel, for example. In various embodiments, the sheet of material can be deformed over one or more forming anvils, or mandrels, until it is bent into a suitable shape. In at least one embodiment, the sheet of material can include one or more side edges 7083b which can be positioned against or proximal to central portion 7085b of second cover plate 7081b during the bending process. Thereafter, in at least one such embodiment, side edges 7083b can be affixed to central portion 7085b by any suitable manufacturing process, such as welding, for example. As a result of the above, in various embodiments, second cover plate 7081b can include at least one tissue-contacting edge 7087b which is formed at the bend between two portions of the sheet material. In at least one such embodiment, the tissue-contacting edges 7087b can have a rounded or radiused profile which can be configured such that the edges do not damage soft tissue. In various embodiments, further to the above, an anvil can be formed from a sheet of material wherein the formed anvil can include a central portion having a first side and a second side and at least two flaps oppositely folded to one another with one flap on the first side and one flap on the second side.

Figure 95:
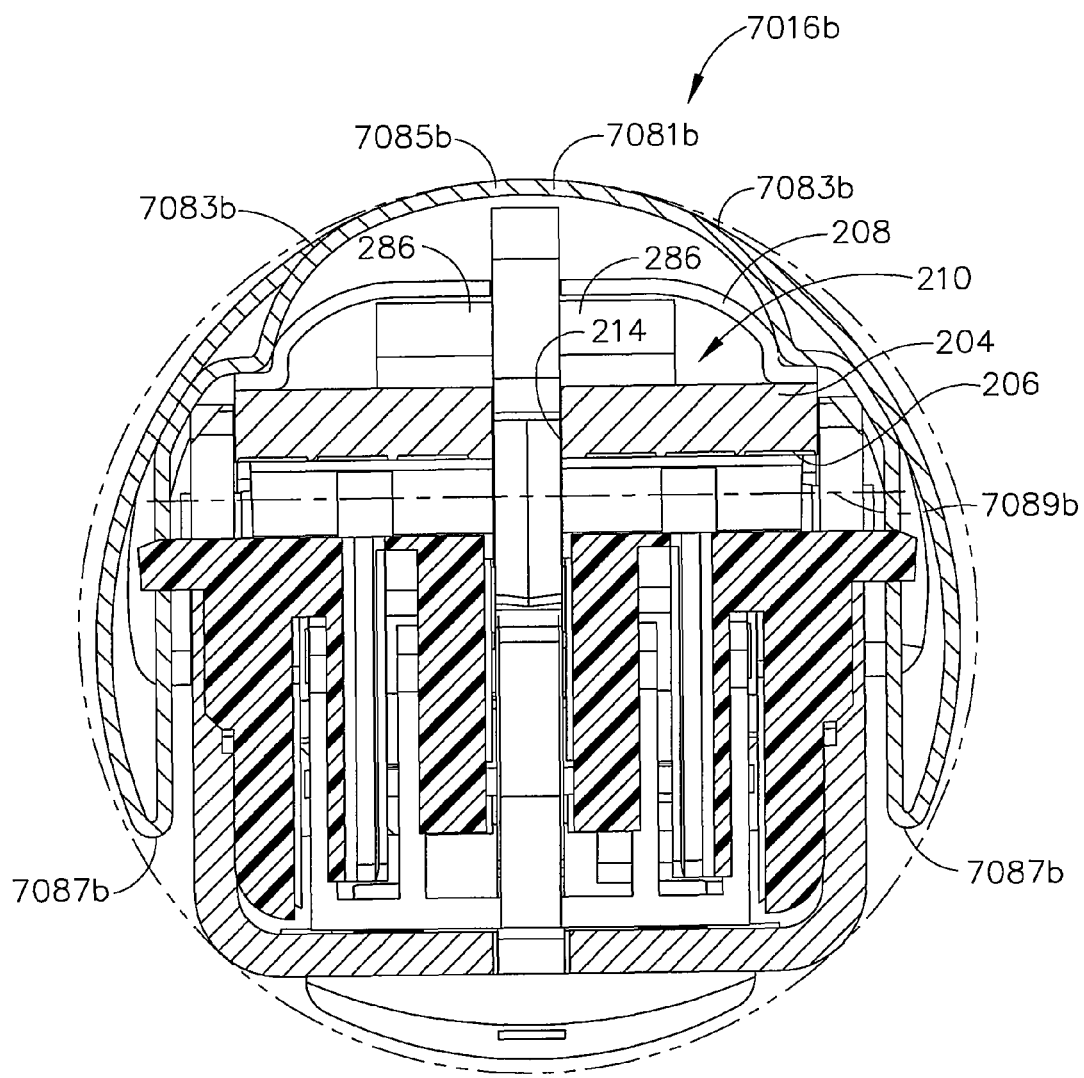
FIG. 95 is a cross-sectional view of a further alternative embodiment of a disposable loading unit.
Figure 96:
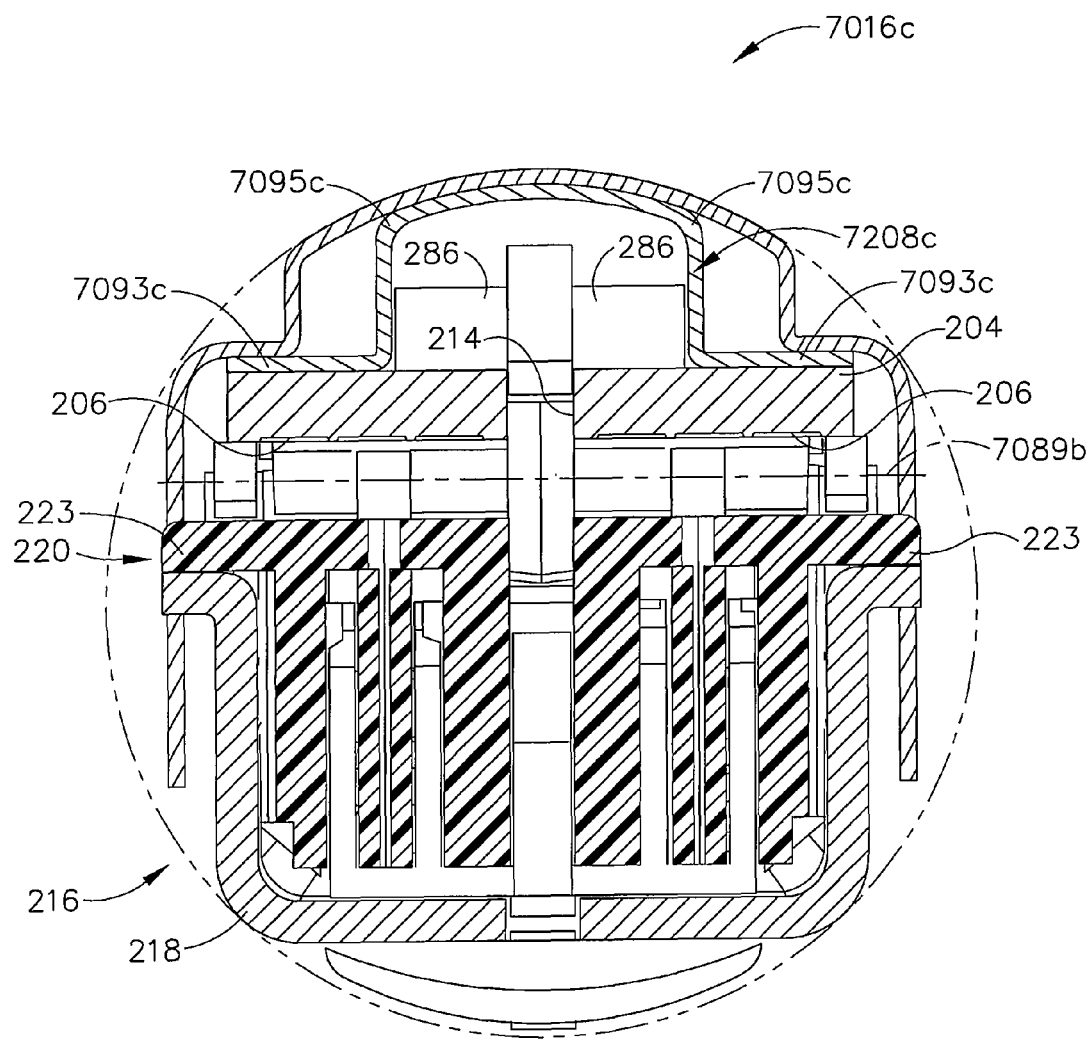
FIG. 96 is a cross-sectional view of another alternative embodiment of a disposable loading unit.

In various embodiments, referring to FIG. 95, first cover plate 208 and anvil member 204 can define anvil cavity 210 therebetween. In at least one embodiment, as described above, cavity 210 can be configured to receive cam actuators 286 and, in various circumstances, first cover plate 208 can be configured such that there are large gaps between cam actuators 286 and the sidewalls of cavity 210. In such an embodiment, however, the configuration of first cover plate 208 may not be optimized so as to maximize the moment of inertia of the anvil assembly with respect to axis 7089b, for example. As known in the art, a device having a larger moment of inertia with respect to an axis can be more resistant to bending or deformation with respect to that axis. Thus, in various embodiments of the present invention, a cover plate of an anvil assembly can be configured such that the gaps between cam actuators 286 and the cover plate can be eliminated, or at least reduced. In at least one embodiment, referring to FIG. 96, first cover plate 7208c can include at least one base portion 7093c and at least one side wall 7095c positioned adjacent to, or in abutting contact with, cam actuators 286. In such embodiments, side walls 7095c can extend in a direction so as to increase the moment of inertia of first cover plate 7208c with respect to axis 7089b. In various embodiments, side wall portions 7095c can be oriented in perpendicular, or at least substantially perpendicular, directions with respect to base portions 7093c.

Figure 97:
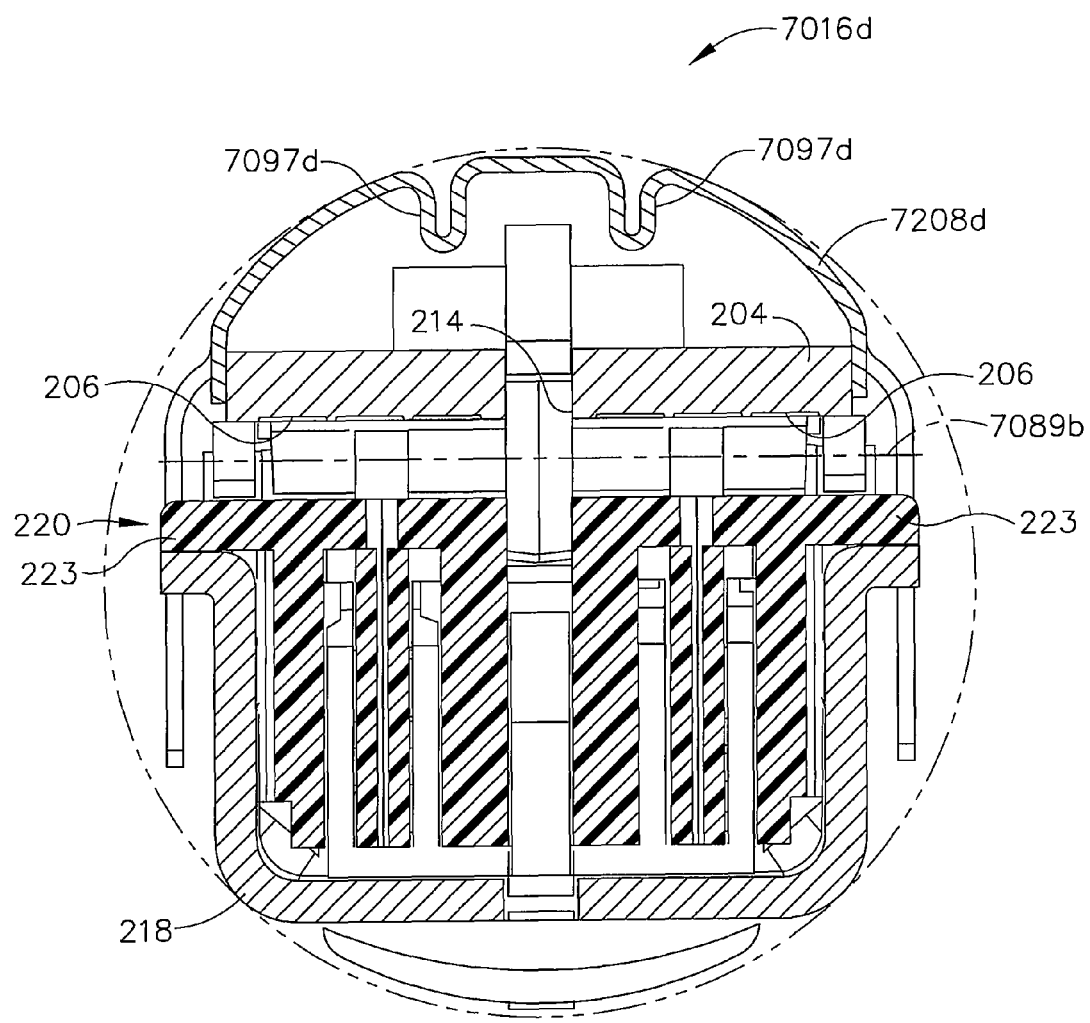
FIG. 97 is a cross-sectional view of an alternative embodiment of a disposable loading unit.

In various embodiments, further to the above, an anvil assembly can include a first and/or second cover plate which can include ribs and/or folds therein which can strengthen or stiffen the anvil assembly. In at least one embodiment, referring to FIG. 97, an anvil assembly of disposable loading unit 7016d can include anvil portion 204 and cover plate 7208d attached to anvil portion 204. In various embodiments, cover plate 7208d can be include ribs or folds 7097d which can increase the moment of inertia of cover plate 7208d with respect to axis 7089b. In at least one embodiment, cover plate 7208d can be manufactured from one or more sheets of material, such as stainless steel, for example, where the sheet, or sheets, can be bent into the configuration illustrated in FIG. 97. As known in the art, the moment of inertia of a cross-section can be increased by increasing the mass of the cross-section and/or increasing the distance between a mass and a reference axis. The ribs and/or folds 7097d, as they can add additional mass at a distance from axis 7089b, can add to the moment of inertia of cover plate 7208d as compared to cover plate 208, for example.

Figure 98:
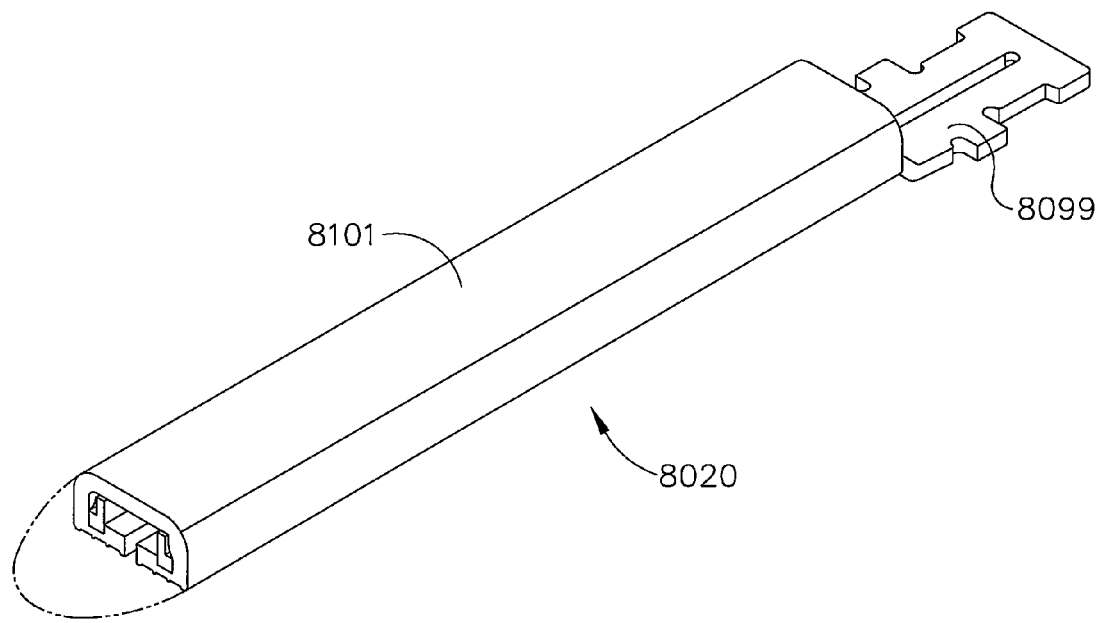
FIG. 98 is a perspective view of an anvil assembly of an alternative embodiment of a disposable loading unit, the anvil assembly including an outer portion and an insert portion.
Figure 99:
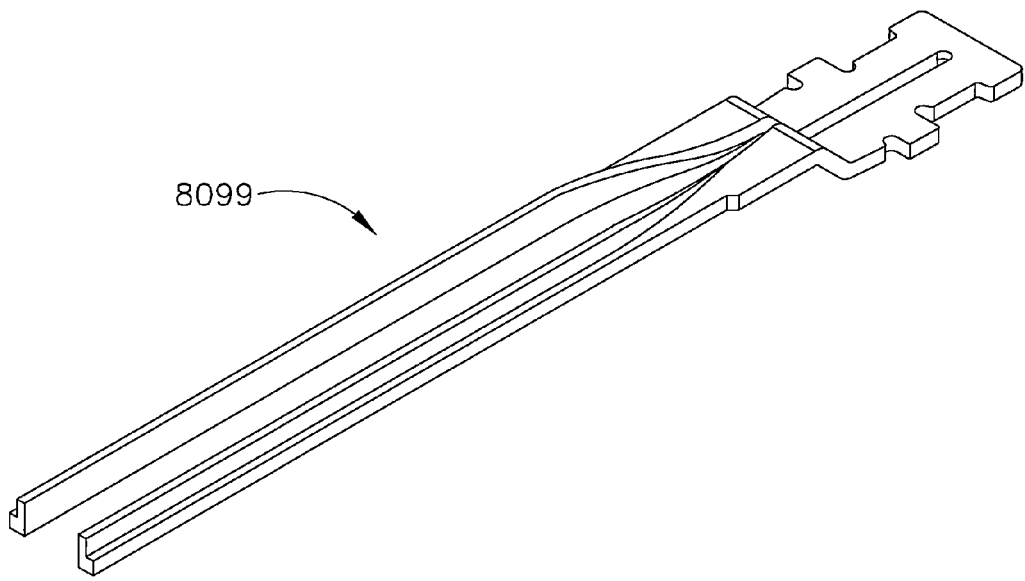
FIG. 99 is a perspective view of the insert portion of FIG. 98.

In various embodiments, as described above, two or more components of an anvil assembly can be welded together. In at least one embodiment of the present invention, two or more components of an anvil assembly can be press-fit together such that the components are retained to one another. In various embodiments, referring to FIGS. 98-101, anvil assembly 8020 can include insert portion 8099 and cover portion 8101 where, referring to FIGS. 98 and 100, insert portion 8099 can be positioned within cavity 8103 defined by cover portion 8101. Thereafter, referring to FIG. 101, at least a portion of cover portion 8101 can be deformed, stamped, or swaged such that at least a portion of insert portion 8099 is captured within cavity 8103. In at least one embodiment, insert portion 8099 can include uneven, rough, and/or corrugated surfaces which can be configured to interlock with portions of cover portion 8101 when it is deformed.

Figure 100:
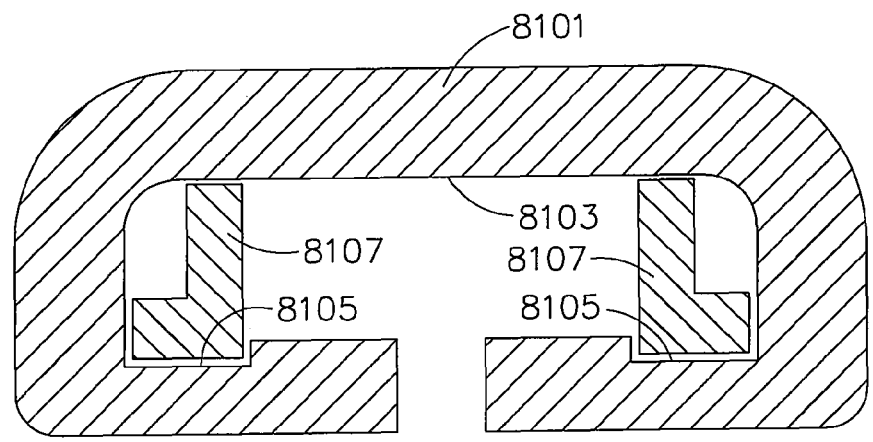
FIG. 100 is a cross-sectional view of the insert positioned within the outer portion of the anvil assembly of FIG. 98.
Figure 101:
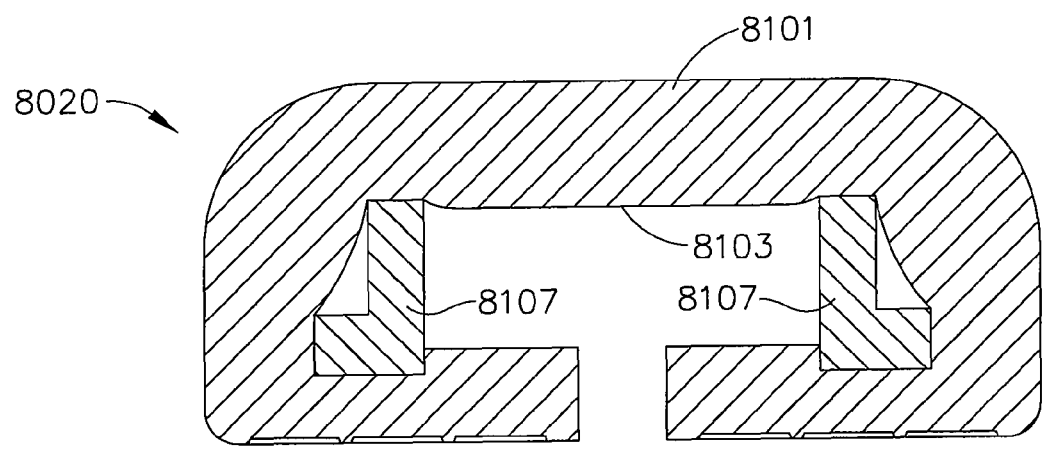
FIG. 101 is a cross-sectional view of the anvil assembly of FIG. 98 illustrating the outer portion after it has been deformed to retain the insert portion therein.

In various embodiments, referring to FIG. 100, cavity 8103 can include slots or grooves 8105 which can be configured to slidably receive tines 8107 of insert portion 8099 therein, wherein cover portion 8101 can be deformed to capture tines, or arms, 8107 in grooves 8105. In at least one embodiment, arms 8107 can be press-fit into grooves 8105 where, in various circumstances, such a press-fit can be sufficient to retain insert portion 8099 within cover portion 8101. In various embodiments, the cover and insert portions of the anvil assembly can be constructed from the same material or different materials. In at least one embodiment, the cover portion can be comprised of a softer or more malleable material than the insert portion. In at least one such embodiment, the cover portion can be at least partially comprised of aluminum, for example, and the insert portion can be at least partially comprised of steel, for example. In either event, the cover portion can be comprised of a material which can be stamped or coined to form the staple-deforming pockets therein. In at least one such embodiment, the cover portion can then be anodized.

Figure 102:
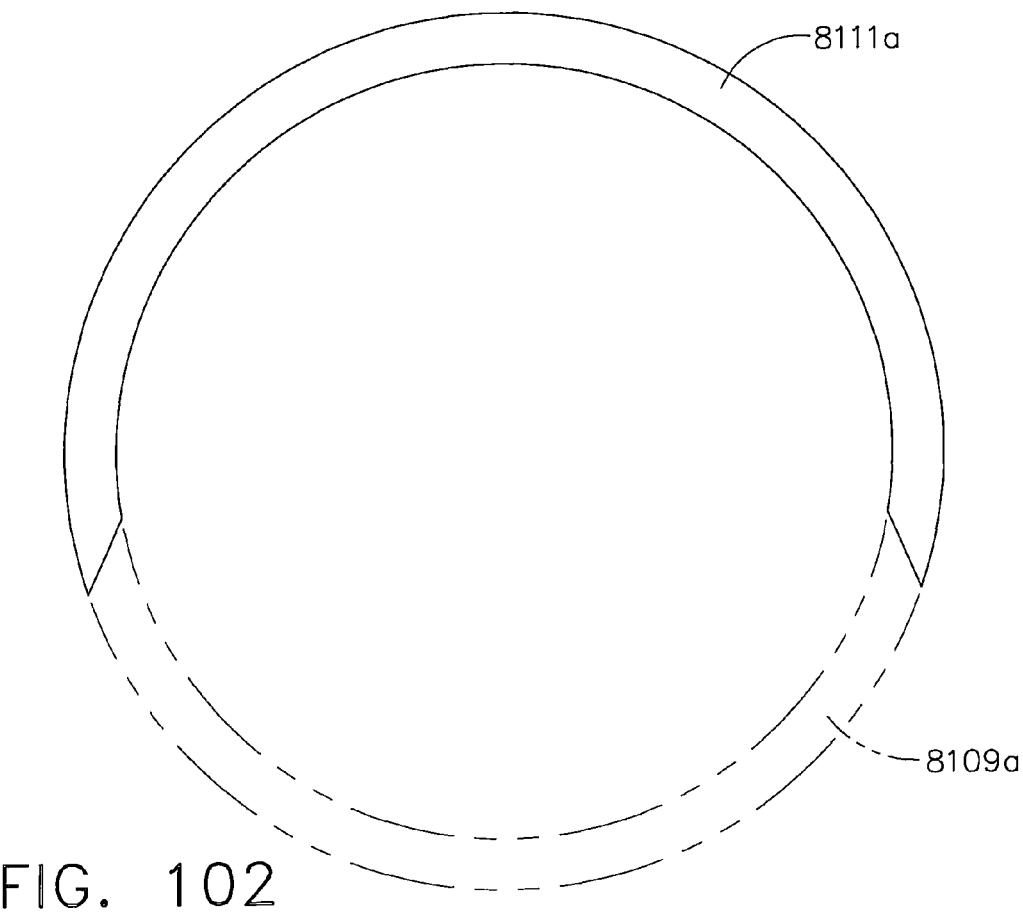
FIG. 102 is a diagram of a piece of tubular stock having removed portions which are illustrated in dash.
Figure 103:
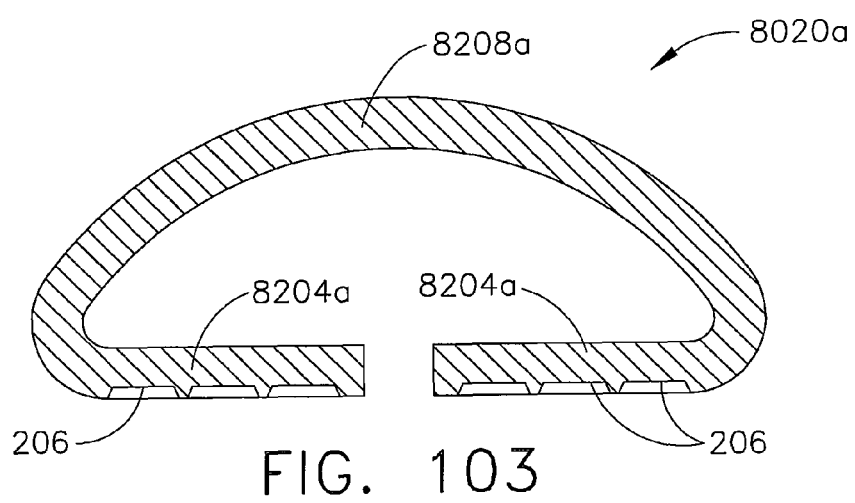
FIG. 103 is a cross-sectional view of an anvil formed from the tubular stock of FIG. 102.

In various embodiments, as described above, an anvil assembly can comprise an anvil portion have staple-deforming pockets therein and a cover plate for supporting the anvil portion. In at least one embodiment, the anvil portion and the cover plate can be integrally formed. Referring to FIGS. 102-103, anvil 8020a can be manufactured from a tube, or annulus, of material where, in at least one embodiment, at least a portion of the tube, such as portion 8109a, for example, can be removed. In at least one such embodiment, the remaining portion of the tube, such as portion 8111a, for example, can be deformed utilizing a stamping or forming process such that anvil 8020a can include co-planar, or at least substantially co-planar, anvil portions 8204a extending from support portion 8208a. In various embodiments, the tube can be at least partially comprised of extruded aluminum and, in at least one embodiment, staple-deforming cavities 206 can be formed in the tube prior to and/or after the portion of the tube is removed.

Figure 105:
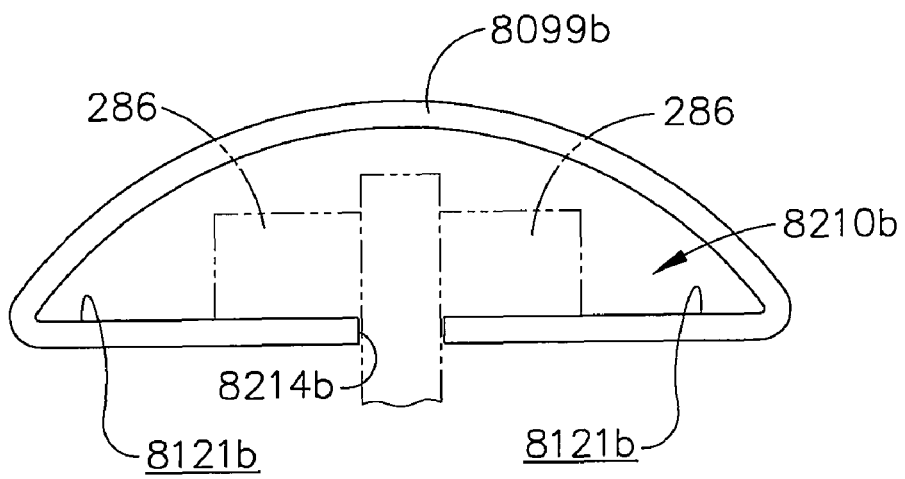
FIG. 105 is an end view of the inner portion of FIG. 104.
Figure 106:
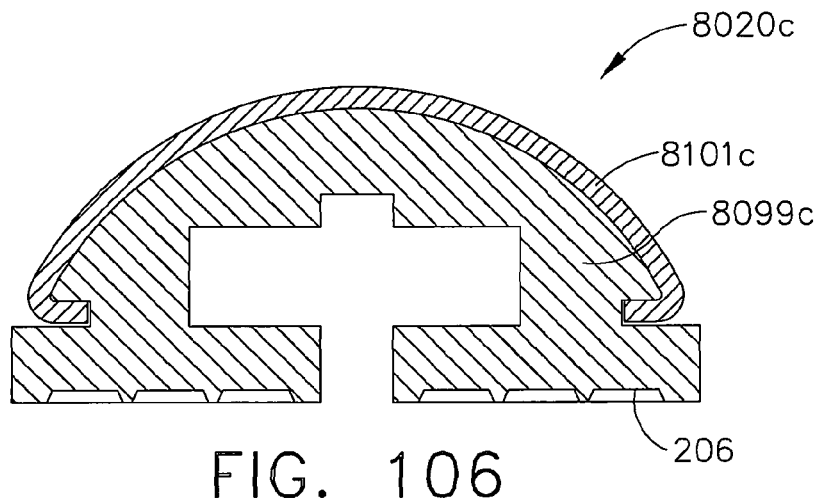
FIG. 106 is a cross-sectional view of an anvil assembly of an alternative embodiment of a disposable loading unit, the anvil assembly including a body and a support plate attached thereto.

In various embodiments, as described above, an anvil assembly can be comprised of two or more components which are press-fit together. In at least one embodiment, referring to FIGS. 105 and 106, anvil assembly 8020b can include a first, or insert, portion 8099b and a second, or cover, portion 8101b, wherein insert portion 8099b can be inserted into cavity 8103b of cover portion 8101b. In at least one embodiment, the outer surface of insert portion 8099b can define a perimeter which is larger than a perimeter defined by an outer surface of outer portion 8101b wherein, as a result, insert portion 8099b can expand outer portion 8101b outwardly when insert portion 8099b is inserted into cavity 8103b. Owing to such co-operating geometries, a significant normal force can be generated between the surfaces of portions 8099b and 8101b. In at least one such embodiment, as a result, a significant pulling force may be required to overcome the friction force between members 8099b and 8101b resulting from the high normal force therebetween.

Figure 107:
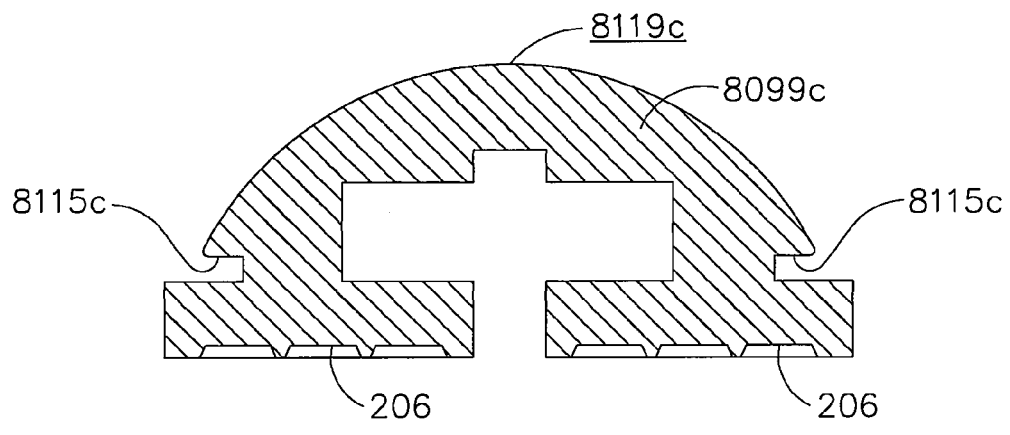
FIG. 107 is a cross-sectional view of the anvil body of FIG. 106.
Figure 108:
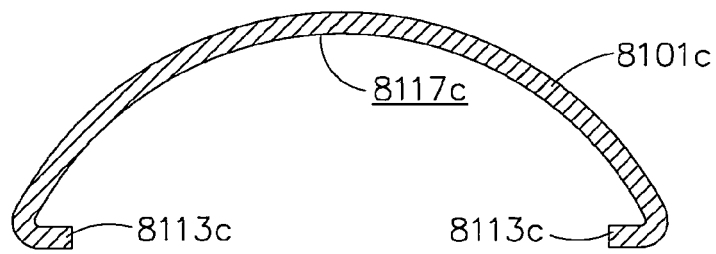
FIG. 108 is a cross-sectional view of the support plate of FIG. 106.

In various embodiments, an anvil assembly can be comprised of two or more components which are snap-fit together. In at least one embodiment, referring to FIGS. 106-108, anvil assembly 8020c can include first portion 8099c and second portion 8101c, where second portion 8101c can be snap-fit to first portion 8099c. Referring to FIG. 109, in at least one embodiment, second portion 8101c can include projections 8113c extending therefrom which can be configured to fit within grooves 8115c. In various embodiments, second portion 8101c can be at least partially comprised of a resilient material, such as stainless steel, for example, which can allow projections 8113c to be displaced outwardly as surface 8117c of second portion 8101c is moved toward surface 8119c of first portion 8099c. Once surface 8117c is positioned against or adjacent to surface 8119c, projections 8113c can be resiliently positioned within, or snapped into, grooves 8115c such that second portion 8101c is retained to first portion 8099c. In at least one embodiment, the first and second portions can be comprised of the same material or they can be comprised of different materials. In at least one embodiment, first portion 8099c can be at least partially comprised of aluminum and second portion 8101c can support the first portion.

In various embodiments, referring to FIG. 86, an anvil can include an anvil member, such as anvil member 4204, for example, which can include ribs or ridges 4153 extending therefrom. In at least one embodiment, ribs 4153 can increase the moment of inertia or cross-sectional modulus of anvil member 4204, for example, such that anvil assembly 4020 is less susceptible to unwanted deformation. In various embodiments, ribs 4153 can extend around the perimeter of anvil member 4204.

In various embodiments, although not illustrated, other components can be assembled to an anvil. In at least one embodiment, a soft or pliable nosepiece, for example, can be assembled to the anvil in order to reduce the possibility that the anvil may damage soft tissue when it is inserted into a surgical site. In at least one such embodiment, the nosepiece, or any other suitable component, can be comprised of any suitable material such as rubber and/or nylon, for example.

Figure 104:
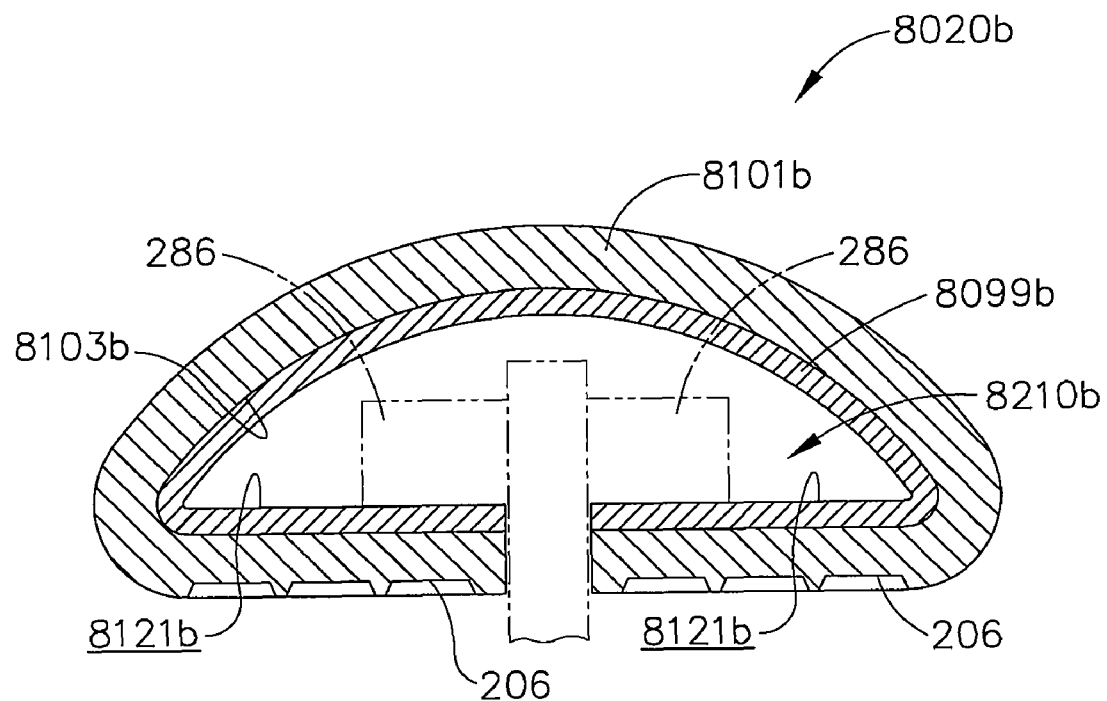
FIG. 104 is a cross-sectional view of an anvil assembly of an alternative embodiment of a disposable loading unit, the anvil assembly including an inner portion press-fit within an outer portion.

In various embodiments, as described above, cam actuators 286, for example, can be configured to engage an anvil assembly and position the anvil assembly against soft tissue positioned intermediate the anvil assembly and a staple cartridge. In at least one embodiment of the present invention, referring to FIGS. 104 and 105, anvil assembly 8020b, for example, can include contact surface, or surfaces, 8121b, wherein cam actuators 286 can be configured to engage contact surfaces 8121b and hold anvil assembly 8020b in a closed position. In various embodiments, contact surfaces 8121b can be configured such that they extend inwardly toward drive beam 1266 such that at least a portion of the contact surfaces are positioned adjacent to, or in contact with, drive beam 1266. In at least one embodiment, as a result, contact surfaces 8121*b* can be configured such that the contact area between cam actuators 286 and contact surfaces 8121*b* can be maximized, or at least increased. As a result of the increased contact area, the stress or pressure applied by actuators 286 to contact surfaces 8121*b* can be reduced and the possibility of galling and/or localized yielding of the anvil assembly can be reduced.

In various circumstances, especially during endoscopic or laparoscopic surgical procedures, for example, at least a portion of a surgical stapling instrument can be inserted through a cannula, or trocar, into a surgical site. Often, an anvil of a disposable loading unit is moved into its closed position before it is inserted into the trocar and then reopened after it has been inserted therethrough. Some disposable loading units having large anvils and/or staple cartridges may not fit, or easily fit, through the trocar even when the anvil is in the closed position. In various embodiments of the present invention, a surgical stapling instrument can include a disposable loading unit having an anvil which can be moved between open, closed, and/or collapsed positions to facilitate the insertion of the disposable loading unit through the trocar. More particularly, in at least one embodiment, an anvil can be moved into a closed position in which the anvil is a first distance away from the staple cartridge, for example, and a collapsed position in which the anvil is closer to the staple cartridge such that the disposable loading unit can be more easily inserted through the trocar.

Figure 114:
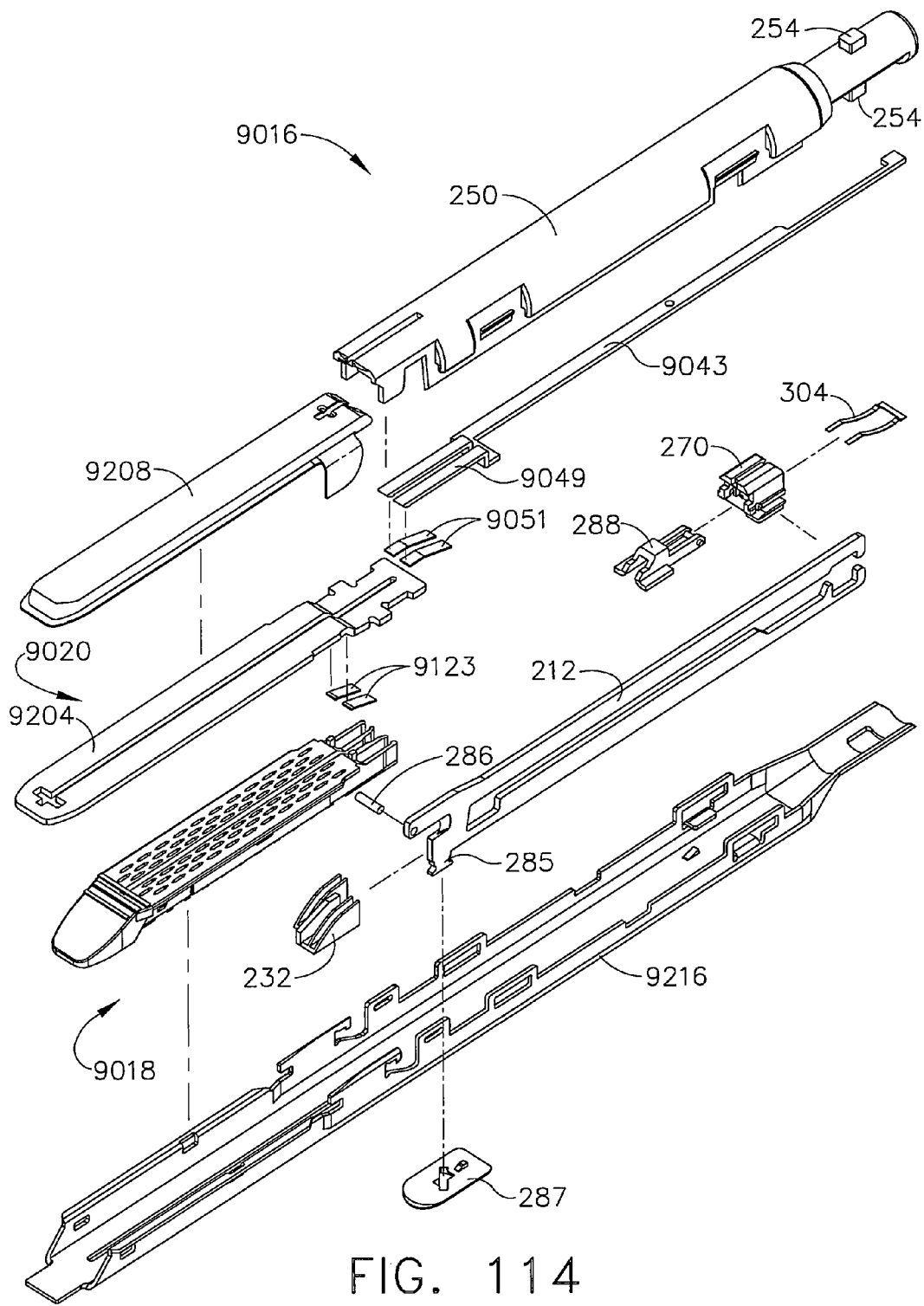
Figure 115:
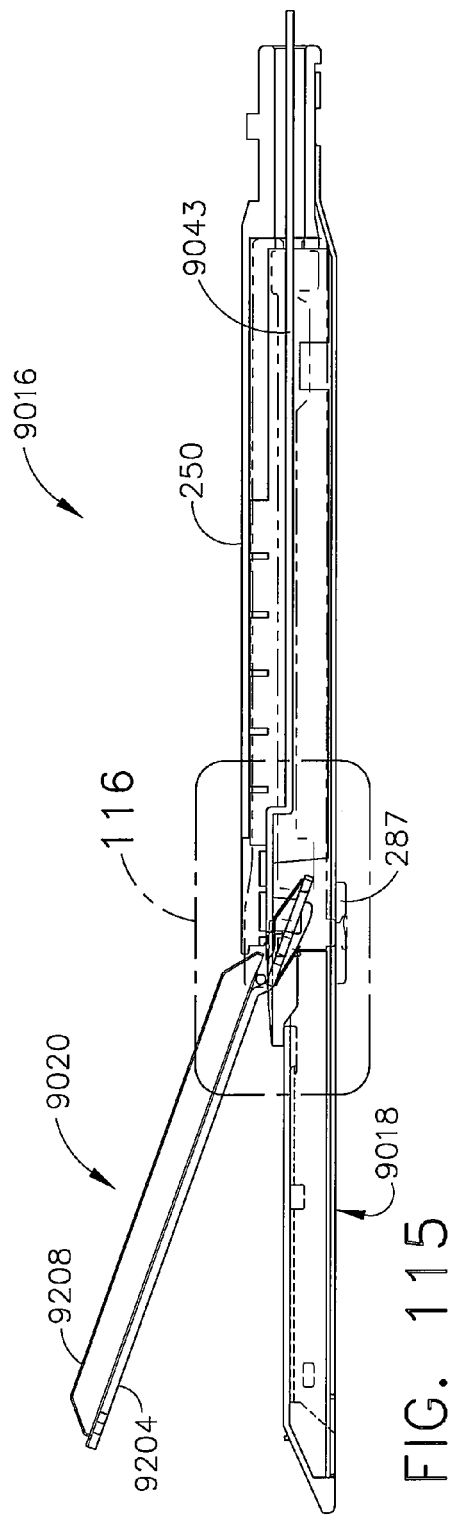
Figure 116:
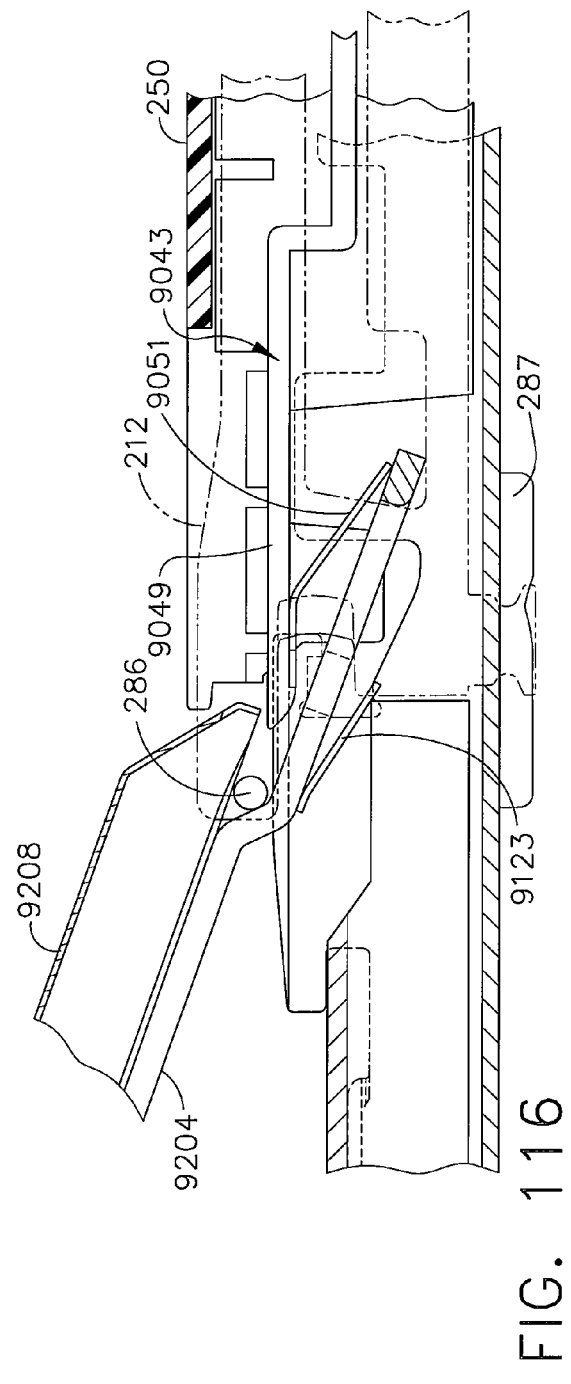
Figure 117:
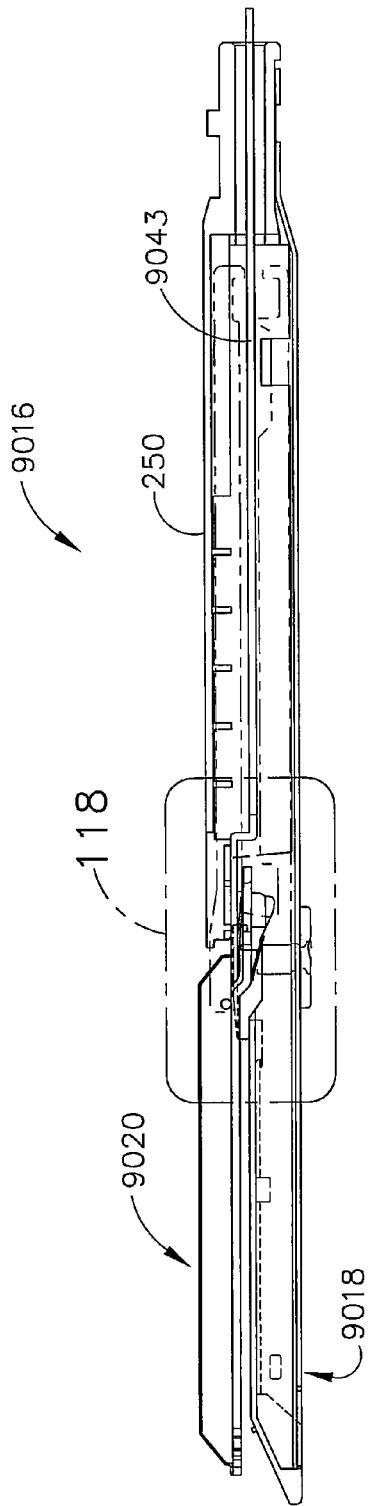
Figure 118:
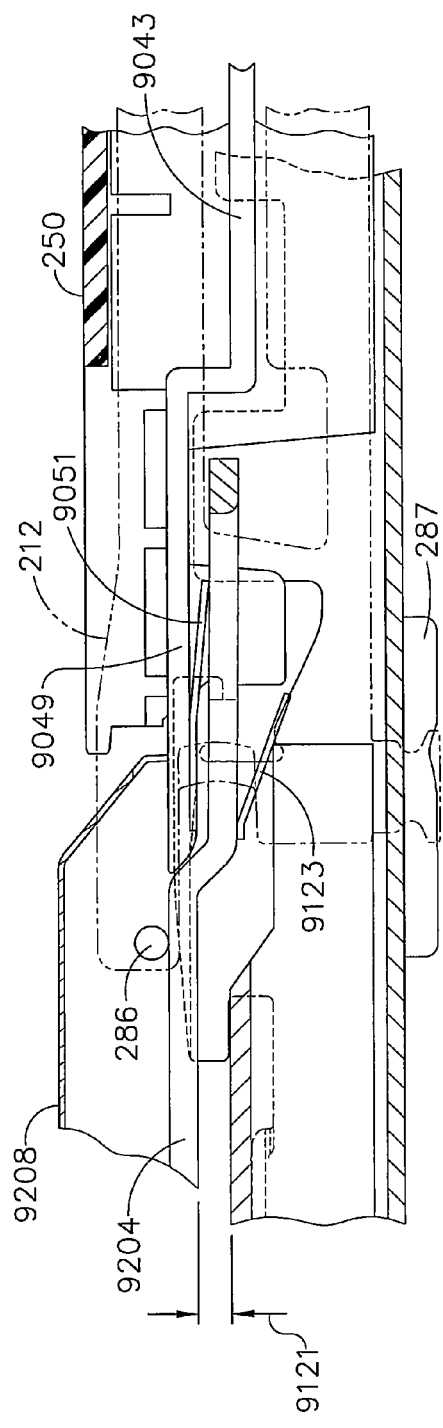

In various embodiments of the present invention, further to the above and referring to FIGS. 114-116, a disposable loading unit 9016 can include anvil assembly 9020 and staple cartridge assembly 9018, wherein anvil assembly 9020 can be rotatably mounted relative to staple cartridge assembly 9018. In use, similar to the above, drive assembly 212 can be advanced distally such that cam actuators 286 can contact anvil member 9204 and rotate anvil assembly 9020 between an open position, as illustrated in FIGS. 115 and 116, and a closed position, as illustrated in FIGS. 117 and 118. When anvil assembly 9020 is rotated toward staple cartridge assembly 9018, in at least one embodiment, anvil assembly 9020 can be configured to compress at least one return spring 9051, for example, in the disposable loading unit.

Figure 119:
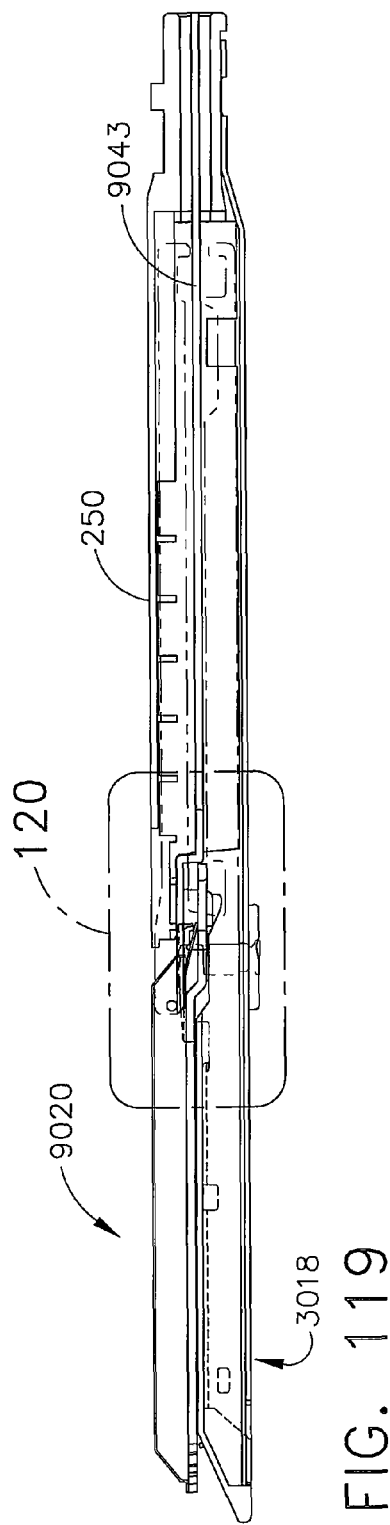
Figure 120:
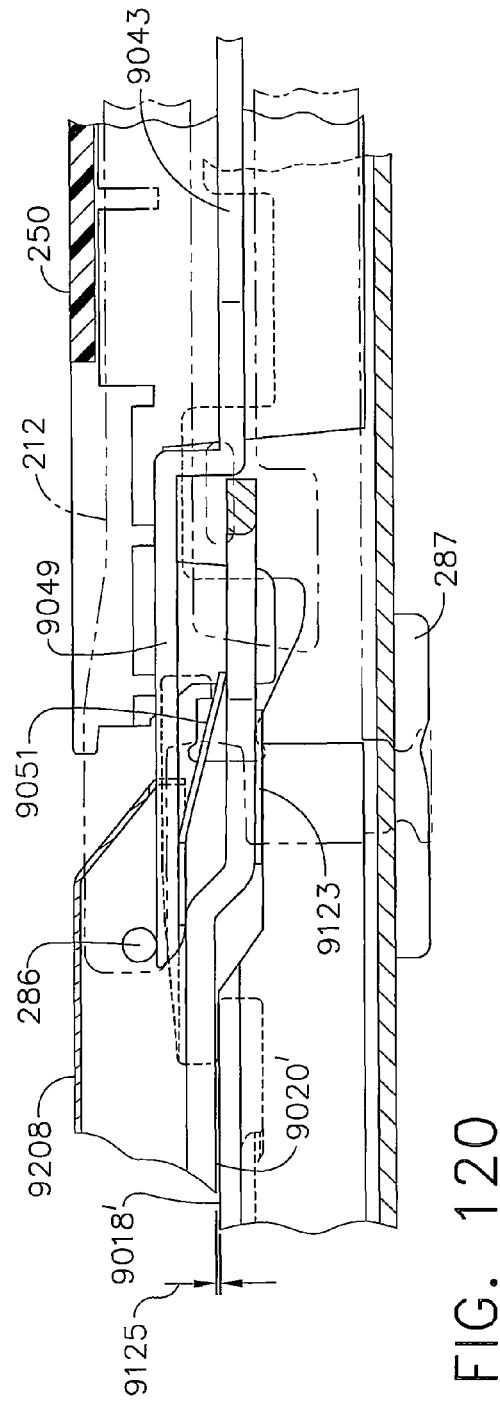

In at least one embodiment, referring to FIG. 118, anvil assembly 9020 can further include tissue-contacting surface 9020' and, similarly, staple cartridge assembly 9018 can include tissue contacting surface 9018'. In various embodiments, tissue-contacting surfaces 9018' and 9020' can be separated by a first distance 9121 when anvil assembly 9020 is in a closed position. In order to move anvil assembly 9020 into a collapsed position, in various embodiments, actuator 9043 can be moved distally, for example, such that portion 9049 of actuator 9043 can contact anvil assembly 9020 and push anvil assembly 9020 toward staple cartridge assembly 9018 as illustrated in FIGS. 119 and 120. In such a collapsed position, in at least one embodiment, tissue-contacting surfaces 9018' and 9020' can be separated by a second distance 9125 which can be shorter than first distance 9121. In various embodiments, actuator 9043 can push anvil assembly 9020 downwardly until surface 9020' at least partially abuts surface 9018'.

Figure 121:
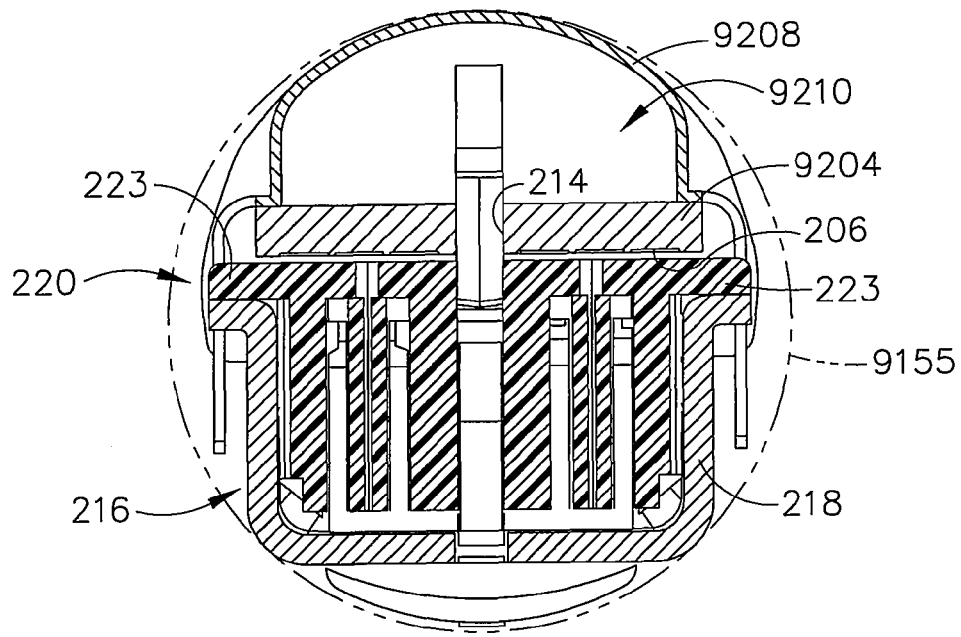
Figure 122:
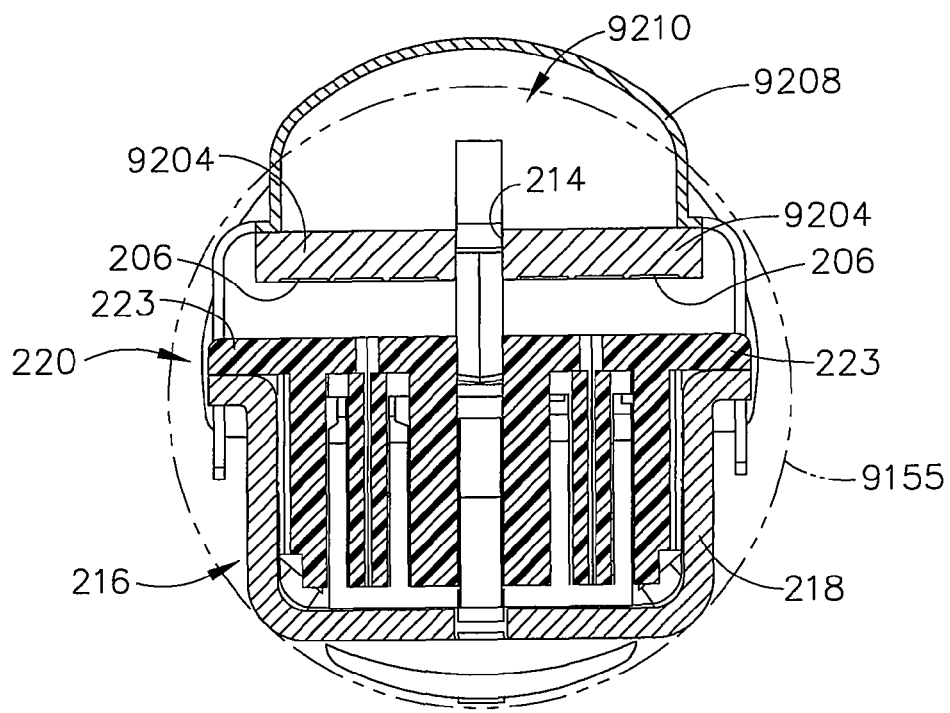

In various embodiments, further to the above, a disposable loading unit can include at least one return spring which can be compressed when the anvil assembly is moved into its collapsed position. In at least one embodiment, referring to FIGS. 116 and 118, disposable loading unit 9016 can include springs 9123 which can be compressed when anvil assembly 9020 is moved between its open and closed positions and, referring to FIGS. 118 and 120, further compressed when anvil assembly is moved into its collapsed position. Once the anvil assembly is in its collapsed position, the disposable loading unit can be inserted into a trocar, which is represented in dash as circle 9155 in FIG. 121. After at least a portion of anvil assembly 9020 and staple cartridge assembly 9018 have passed through the trocar, actuator 9043 can be disengaged from anvil assembly 9020 to allow springs 9123 to move anvil assembly from its collapsed position into its closed position, as illustrated in FIG. 122. Furthermore, cam actuators 286 can be sufficiently disengaged from anvil assembly 9020 to allow springs 9051 to move anvil assembly 9020 into its open position such that the anvil and staple cartridge assemblies can be positioned relative to soft tissue.

In various embodiments, as outlined above, cam actuators 286 can be utilized to move anvil assembly 9020 between an open position and a closed position and, thereafter, actuator 9043 can be utilized to move anvil assembly 9020 between the closed position and a collapsed position. Alternatively, actuator 9043 can be configured such that it can engage anvil assembly 9020 when it is in its open position and move anvil assembly 9020 directly into its collapsed position. In various circumstances, such embodiments can allow a surgeon to more quickly and easily configure a disposable loading unit to be inserted through a trocar. In at least one such embodiment, after at least a portion of the anvil assembly has been inserted through the trocar, the actuator can be sufficiently disengaged from the anvil assembly such that the anvil assembly can be moved directly into is open position and positioned relative to soft tissue, for example. In order to remove the disposable loading unit from the surgical site, the actuator can be reengaged with the anvil assembly to move the anvil assembly into its collapsed position such that the disposable loading unit can be withdrawn through the trocar.

With respect to the disposable loading units and surgical instruments described further above, referring to FIGS. 41 and 42, a disposable loading unit can be inserted into the distal end of a surgical instrument and can be rotated with respect to the surgical instrument in order to operably engage the drive assembly and/or articulation link of the disposable loading unit with the surgical instrument. In at least one embodiment of the present invention, such rotation can unlock the drive assembly and allow the drive assembly to be advanced distally as described above. Referring to FIG. 123, disposable loading unit 10016 can include anvil assembly 10020, shaft assembly 10125, and lockout device 10127, where lockout device 10127 can be engaged with drive assembly 10212 (FIG. 128) prior to disposable loading unit 10016 being rotated relative to elongated body 14 (FIG. 1) of the surgical instrument. In at least one such embodiment, referring to FIG. 124, lockout device 10127 can include key 10131 which can be configured to engage a recess in drive assembly 10212, for example, so as to prevent, or at least inhibit, drive assembly 10212 from being advanced distally prior to disposable loading unit 10016 being rotated. As disposable loading unit 10016 is rotated, key 10131 can be disengaged from drive assembly 10212 and, as a result, drive assembly 10212 can be advanced distally as described above.

In various embodiments, referring to FIGS. 123 and 124, lockout device 10127 can include arms 10129 extending therefrom which, prior to the rotation of disposable loading unit 10016, can be aligned, or at least substantially aligned, with nubs 254 extending from shaft assembly 10125. In at least one embodiment, referring to FIGS. 125 and 126, arms 10129 and nubs 254 can be inserted into slots 10133 in elongated body 14, for example, when disposable loading unit 10016 is inserted into elongated body 14. When disposable loading unit 10016 is rotated, referring to FIG. 127, arms 10129 can be sufficiently confined within slots 10133 such that slots 10133 can hold them in position, whereas nubs 254 can be positioned such that they are not confined within slots 10133 and can be rotated relative to arms 10129. In effect, elongated body 14 can hold lockout device 10127 in position and, when shaft assembly 10125 is rotated with disposable loading unit 10016, drive assembly 10212 can be rotated away from key 10131 of lockout device 10127.

To detach disposable loading unit 10116 from elongated member 14, disposable loading unit 10016, and shaft assembly 10125, can be rotated in an opposite direction such that nubs 254 are at least substantially realigned with arms 10129 and, as a result, nubs 254 and arms 10129 can be withdrawn from slots 10133. Such circumstances can typically arise after the disposable loading unit has been used, or expended, and the surgeon, or other clinician, desires to assemble a new disposable loading unit to the elongated body. In various circumstances, though, the surgeon, or other clinician, may become confused as to whether a disposable loading unit has been previously expended. In various embodiments of the present invention, the lockout device described above, or any other suitable lockout device disclosed herein, can be utilized to prevent, or at least inhibit, an expended disposable loading unit from being reassembled to the elongated body of the surgical instrument.

In various embodiments, referring to FIG. 128, disposable loading unit 10016 can further include biasing spring 10135, actuator 10137, and actuator plate 10139 extending from actuator 10137, wherein actuator plate 10139 can be configured to operably engage spring 10135. After disposable loading unit 10116 has been operably engaged with elongated portion 14, as described above, drive assembly 10212 can be advanced distally to staple and/or incise tissue. In at least one embodiment, actuator 10137 can be operably attached to drive assembly 10212 such that, when drive assembly 10212 is advanced, drive assembly 10212 can pull actuator 10137 and actuator plate 10139 distally as well. Once drive assembly 10212 has been sufficiently advanced, referring to FIG. 129, actuator plate 10139 can be sufficiently disengaged from biasing spring 10135 so as to release biasing spring 10135 from a compressed state and allow biasing spring 10135 to apply a biasing force against lockout device 10127. However, at such point, as lockout device 10127 is held in position by elongated member 14, as described above, the biasing force applied by spring 10135 cannot move, or at least substantially move, lockout device 10127, at least as long as disposable loading unit 10016 remains engaged with elongated member 14.

In various embodiments, the disengagement of actuator plate 10139 from biasing spring 10135 can occur before, or at the exact moment, in which a staple can de deployed from the staple cartridge and/or the cutting member can incise the tissue. In at least one such embodiment, a surgeon could advance and retract drive assembly 10212 in order to position anvil assembly 10020 relative to soft tissue without triggering the lockout assembly described above. After actuator 10137 has been sufficiently advanced to disengage plate 10139 from spring 10135, drive assembly 10212 can be further advanced distally such that, referring again to FIG. 129, actuator 10137 and/or actuator plate 10139 can abut a shoulder, for example, within the disposable loading unit. In at least one such embodiment, the shoulder can prevent actuator 10137 and actuator plate 10139 from being advanced further within the disposable loading unit. Upon further advancement of drive assembly 10212, however, actuator 10137 can become operably detached from drive assembly 10212 such that the advancement of drive assembly 10212 is not transmitted to actuator 10137.

After disposable loading unit 10016 has been disengaged from elongated member 14, referring to FIG. 130, biasing spring 10135 can move, or rotate, locking device 10127 into a position in which arms 10129 are no longer aligned with nubs 254. In at least one such embodiment, such a disposable loading unit 10016 cannot be readily reassembled to elongated member 14 as arms 10129 and nubs 254 would not both fit within slots 10133 owing to their relative misalignment. In various embodiments, such disposable loading units can provide the surgeon, or other clinician, with immediate feedback that they are attempting to assemble an expended, or possibly defective, disposable loading unit to a surgical instrument. Such embodiments can ameliorate the circumstances where an at least partially expended disposable loading unit is reassembled to a surgical instrument and reinserted into a surgical site only for the surgeon to then discover that the disposable loading unit has been expended. In various embodiments, drive assembly 10212 and actuator 10137 can be configured such that, in the event that drive assembly 10212 is retracted, drive assembly 10212 may not cause actuator 10137 to reengage biasing spring 10135 and return biasing spring 10135 to its compressed state.

Figure 64:
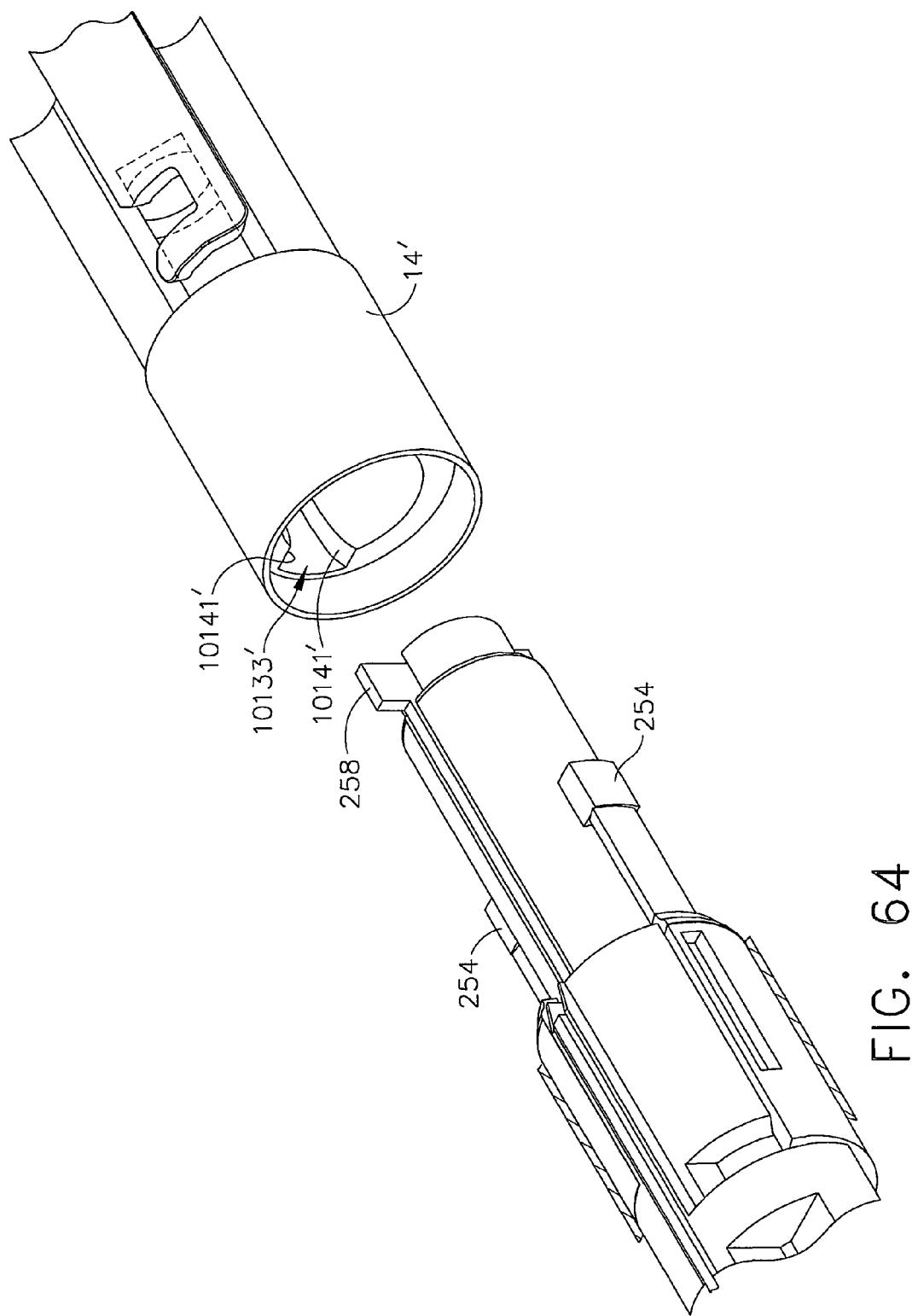
FIG. 64 is a partial perspective view of an elongated body and a disposable loading unit of an embodiment of a surgical stapling apparatus.

In various embodiments, referring primarily to FIG. 126, slots 10133 of elongated member 14 can include a substantially rectangular profile which extends along the length thereof. While suitable for its intended purpose, circumstances may arise where it may be difficult to assemble the disposable loading unit to the elongated member. More particularly, in at least one embodiment, the disposable loading unit can be configured such that a surgeon, or other clinician, can not readily observe whether nubs 254 are aligned with slots 10133 and the surgeon may have spend time to precisely align nubs 254 with slots 10133 before assembling the disposable loading unit to elongated member 14. In at least one embodiment of the present invention, referring to FIG. 64, elongated member 14' can include slots 10133' having radiused and/or beveled ends 10141' which can facilitate the insertion of nubs 254 into slots 10133' and reduce the time and/or effort that a surgeon must expend to align and assemble the disposable loading unit to the surgical instrument.

As described above, a disposable loading unit can be detached from a surgical instrument after it has been at least partially expended and a new disposable loading unit can be attached to the surgical instrument such that the surgical instrument can be reused. In various embodiments, previous disposable loading units have included a housing, an anvil assembly, and a staple cartridge assembly, as outlined above, and, in addition, a staple driver for deploying staples from the staple cartridge assembly and a cutting member for incising tissue. When the staple cartridge assemblies of such disposable loading units are at least partially expended, the remainder of the disposable loading unit, such as the housing, the anvil assembly, the staple driver, and the cutting member, for example, are typically discarded along with the expended staple cartridge assembly. As a result, significant cost and undue waste can be expended to replace such previous disposable loading units.

In various embodiments of the present invention, a disposable loading unit can include a replaceable staple cartridge. In at least one embodiment, referring to FIGS. 131-135, disposable loading unit 11016 can include anvil assembly 11020, staple cartridge channel 11216, and staple cartridge 11018, wherein staple cartridge 11018 can be removably attached to staple cartridge channel 11216. In at least one embodiment, as a result, a first staple cartridge 11018 can be replaced with a second staple cartridge 11018, or another suitable staple cartridge, such that one or more of the various other portions of the disposable loading unit can be reused. In various embodiments, referring to FIG. 132, staple cartridge 11018 can be snap-fit into staple cartridge channel 11216 such that staple cartridge 11018 can be reliably retained within, yet easily removed from, staple cartridge channel 11216.

In at least one embodiment, staple cartridge 11018 can include body portion 11143 having at least one staple cavity for removably storing at least one staple therein and, in addition, cartridge pan 11145 which can be attached to body portion 11143. In various embodiments, cartridge pan 11145 can be snap-fit and/or press-fit to body portion 11143 to prevent, or at least inhibit, the staples within the staple cavities from falling out of the bottom of body portion 11143. In at least one embodiment, body portion 11143 and/or cartridge pan 11145 can include one or more projections 11147 and/or apertures 11149 which can be configured to retain body portion 11143 and cartridge pan 11145 to one another. In various embodiments, cartridge pan 11145 can further include projections or dimples 11151, for example, which can be configured to engage staple cartridge channel 11216 and retain staple cartridge 11018 thereto.

In various embodiments, as described above, staple driver 232 and cutting member 280 can be advanced distally to deploy staples from the staple cartridge and incise soft tissue. Thereafter, in at least one embodiment of the present invention, staple driver 232 and cutting member 280 can be retracted relative to the staple cartridge such that, when the staple cartridge is replaced, staple driver 232 and cutting member 280 can be advanced distally once again into the new staple cartridge. In various embodiments, the staple driver and/or cutting member can remain in the spent staple cartridge as the staple cartridge is being removed and the new staple cartridge can include a new staple driver positioned therein. In at least one such embodiment, each staple cartridge can include a staple driver and a cutting member positioned therein such that the staple driver and cutting member of a spent staple cartridge do not have to be reused. Such embodiments can be useful when the staple driver and the cutting member can be damaged and/or dulled during their use. In various embodiments, the staple driver and the cutting member can comprise an assembly. In at least one such embodiment, the cutting member can be snap-fit and/or press-fit into the staple driver. In other embodiments, the cutting member can be comprised of a plastic material, for example, which is overmolded onto the cutting member.

As described above, an anvil assembly of a disposable loading unit can include one or more pockets therein for deforming at least one staple when it is ejected from the staple cartridge. In various embodiments of the present invention, an anvil can be attached to the disposable loading unit such that it cannot be readily detached from the disposable loading unit eventhough the staple cartridge may be readily removable. In various circumstances, however, the anvil may become worn after a single use and/or multiple uses. In at least one embodiment of the present invention, at least a portion of an anvil assembly can be configured such that it can be detached from disposable loading unit and replaced with a new portion of the anvil assembly. In at least one such embodiment, the anvil assembly and the staple cartridge can both be replaced before a disposable loading unit is reused. In various embodiments, further to the above, a disposable loading unit can include a staple cartridge channel, or at least a portion of a staple cartridge channel, which is detachable from the disposable loading unit. In at least one such embodiment, the staple cartridge channel, or a portion of the staple cartridge channel, can be replaced along with a staple cartridge.

When a staple cartridge and/or anvil of a disposable loading unit is replaced, in various embodiments of the present invention, the staple cartridge and anvil can be replaced with an identical, or at least nearly identical, staple cartridge and anvil. In at least one such embodiment, for example, a 30 mm staple cartridge can be replaced with another 30 mm staple cartridge. In at least one embodiment, however, the staple cartridge and/or anvil can be replaced with a different staple cartridge and anvil. In at least one such embodiment, a 30 mm staple cartridge can be replaced with a 45 mm staple cartridge. Such embodiments may be particularly useful when the anvil assembly and/or staple cartridge channel are also replaced to accommodate the different staple cartridge. Other embodiments are envisioned in which a staple cartridge is replaced with a staple cartridge having a different quantity and/or arrangement of staples stored therein. In such embodiments, similar to the above, at least a portion of the anvil assembly can be replaced to accommodate such a staple cartridge. In various embodiments, sets of anvils and staple cartridges can be provided for and/or with a disposable loading unit. In at least one such embodiment, a rigid anvil can be provided for use with a staple cartridge containing staples which will require a large force to deform the staples. In other various embodiments, an anvil can be provided having specialized staple-deforming pockets which are particularly designed to deform a particular staple, such as staples with long staple legs, for example. In at least one embodiment, the anvil and staple cartridge can include corresponding indicia, such as colors, numbers, and/or symbols, etc. which can allow a surgeon, or other clinician, to readily identify matching pairs of anvils and staple cartridges.

Several of the disposable loading unit embodiments described above have been exemplified with an anvil having a distal end which is movable relative to a distal end of a staple cartridge. In various alternative embodiments, although not illustrated, a disposable loading unit can include an anvil and a staple cartridge wherein the anvil can include a distal end which is pivotably mounted relative to the staple cartridge at its distal end. In at least one embodiment, the disposable loading unit can include an actuator which can be displaced distally to engage the anvil and rotate the anvil between an open position and a closed position. In at least one such embodiment, the staple cartridge can include a staple cartridge and/or a cutting member which can be displaced from a position located near the distal end of the anvil to a proximal end of the anvil. In at least one such embodiment, as a result, a surgeon can more readily observe whether soft tissue has been properly positioned between and/or treated within the staple cartridge and anvil.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A disposable loading unit for a surgical stapling instrument, comprising:
 a staple cartridge carrier configured to operably support a staple cartridge, wherein said staple cartridge carrier comprises a carrier outer surface;
 an anvil comprising at least one staple deforming cavity, wherein said anvil is rotatably movable between a first position and a second position, and wherein said anvil comprises an anvil outer surface; and
 a sleeve comprising:
  a longitudinal axis;
  a distal end;
  an aperture, wherein said sleeve is configured to be slid along said carrier outer surface and said anvil outer surface, and wherein at least a portion of said staple cartridge carrier and said anvil are configured to be positioned within said aperture such that said sleeve can hold said anvil in said second position;
  a first slot extending along said longitudinal axis on a first side of said sleeve, wherein said first slot comprises:
   a first open end opening toward said distal end; and
   a first closed proximal end;
  a second slot extending along a second side of said sleeve, wherein said second slot is aligned with said first slot, and wherein said second slot comprises:
   a second open end opening toward said distal end; and
   a second closed proximal end; and
 a staple cartridge positioned within said staple cartridge carrier, wherein said staple cartridge and said anvil define a tissue gap therebetween when said anvil is in said second position, and wherein said first slot and said second slot are aligned with said tissue gap.

2. The disposable loading unit of claim 1, wherein said sleeve is configured to contact said anvil and rotate said anvil between said first and second positions.

3. The disposable loading unit of claim 1, further comprising a shaft, wherein said staple cartridge carrier and said anvil extend from said shaft, and wherein said shaft comprises an end configured to be attached to the surgical stapling instrument.

4. The disposable loading unit of claim 3, further comprising a drive member configured to be advanced and retracted relative to said anvil and said staple cartridge carrier.

5. A disposable loading unit for a surgical stapling instrument, comprising:
 a staple cartridge carrier configured to operably support a staple cartridge;
 an anvil rotatable between a first position and a second position, wherein said anvil comprises:
  at least one staple deforming cavity;
  a proximal end comprising an opening;
  a distal end;
  an outer cover comprising an outer surface;
  an inner drive surface; and
  an elongate cavity defined between said outer cover and said inner drive surface;
 a sleeve comprising an aperture, wherein said sleeve is configured to be slid around said staple cartridge carrier and said outer surface of said cover, and wherein at least a portion of said staple cartridge carrier and said anvil are configured to be positioned within said aperture such that said sleeve can hold said anvil in said second position;
 a drive member comprising a cutting edge configured to incise tissue; and
 a cantilevered tongue extending from said sleeve, wherein said tongue is configured to be slide relative to said staple cartridge channel and said anvil, and wherein said tongue is configured to enter into said elongate cavity through said opening in said proximal end of said anvil and engage said inner drive surface of said anvil to hold said anvil in said second position.

6. The disposable loading unit of claim 3, further comprising said staple cartridge.

7. The disposable loading unit of claim 5, further comprising a shaft, wherein said staple cartridge carrier and said anvil extend from said shaft, and wherein said shaft comprises an end configured to be attached to the surgical stapling instrument.

8. The disposable loading unit of claim 5, wherein said sleeve is configured to contact said anvil and rotate said anvil between said first and second positions.

9. A disposable loading unit for a surgical stapling instrument, said disposable loading unit comprising:
 a first jaw, comprising:
  a staple cartridge comprising a plurality of staples;
  a first tissue-compression surface; and
  a first outer surface;
 a second jaw rotatable between a first position and a second position, wherein said second jaw comprises:
  an anvil comprising at least one staple deforming cavity;
  a second tissue-compression surface; and
  a second outer surface; and
 a sleeve, comprising:
  a distal end;
  an aperture defined by an aperture sidewall, wherein said sleeve is configured to be slid along said first outer surface and said second outer surface, and wherein at least a portion of said first jaw and said second jaw are configured to be positioned within said aperture such that said aperture sidewall can hold said second jaw in said second position;

a first slot extending along a first side of said sleeve, wherein said first slot comprises:
a first open end opening toward said distal end; and
a first closed proximal end;
a second slot extending along a second side of said sleeve, wherein said second slot is aligned with said first slot, and wherein said second slot comprises:
a second open end opening toward said distal end; and
a second closed proximal end;
wherein said first tissue-compression surface and said second tissue- compression surface define a tissue gap therebetween when said second jaw is in said second position, and wherein said first slot and said second slot are aligned with said tissue gap.

10. The disposable loading unit of claim 9, further comprising a shaft, wherein said first jaw and said second jaw extend from said shaft, and wherein said shaft comprises an end configured to be attached to the surgical stapling instrument.

11. The disposable loading unit of claim 9, wherein said sleeve is configured to contact said second jaw and rotate said second jaw between said first and second positions.

12. A disposable loading unit for a surgical fastening instrument, said disposable loading unit comprising:
a first jaw, comprising:
a plurality of fasteners; and
a first tissue-compression surface;
a second jaw rotatable between a first position and a second position, wherein said second jaw comprises a second tissue-compression surface; and
a sleeve, comprising:
a first cantilever comprising a first distal end configured to engage said first jaw;
a second cantilever comprising a second distal end configured to engage said second jaw;
an aperture defined by an aperture sidewall, wherein at least a portion of said first jaw and said second are configured to be positioned within said aperture;
a first slot defined between said first cantilever and said second cantilever, wherein said first slot comprises:
a first open distal end; and
a first closed proximal end;
a second slot defined between said first cantilever and said second cantilever, wherein said second slot is positioned opposite said first slot, and wherein said second slot comprises:
a second open distal end; and
a second closed proximal end; and
wherein said first tissue-compression surface and said second tissue- compression surface define a tissue gap therebetween when said second jaw is in said second position, and wherein said first slot and said second slot are aligned with said tissue gap.

13. The disposable loading unit of claim 9, further comprising a shaft, wherein said first jaw and said second jaw extend from said shaft, and wherein said shaft comprises an end configured to be attached to the surgical fastening instrument.

14. The disposable loading unit of claim 12, wherein said sleeve is configured to contact said second jaw and rotate said second jaw between said first and second positions.

15. A disposable loading unit for a surgical stapling instrument, said disposable loading unit comprising:
a first jaw comprising a staple cartridge, wherein said staple cartridge comprises a plurality of staples;
a second jaw rotatable between a first position and a second position, wherein said second jaw comprises:
an anvil comprising a plurality of staple deforming cavities;
a proximal end comprising an opening;
a distal end;
an outer cover comprising an outer surface;
an inner drive surface; and
an elongate cavity defined between said outer cover and said inner drive surface;
a drive member comprising a cutting edge configured to incise tissue; and
a sleeve, comprising:
a first portion configured to engage said first jaw; and
a cantilevered tongue configured to engage said second jaw, wherein said tongue is configured to enter into said elongate cavity through said opening in said proximal end of said anvil and engage said inner drive surface of said anvil to hold said anvil in said second position.

16. The disposable loading unit of claim 15, further comprising a shaft, wherein said first jaw and said second jaw extend from said shaft, and wherein said shaft comprises an end configured to be attached to the surgical stapling instrument.

17. The disposable loading unit of claim 15, wherein said sleeve is configured to contact said second jaw and rotate said second jaw between said first and second positions.

18. A disposable loading unit for a surgical fastening instrument, said disposable loading unit comprising:
a first jaw comprising a plurality of fasteners;
a second jaw rotatable between a first position and a second position, wherein said second jaw comprises:
a proximal end comprising an opening;
a distal end;
an outer cover comprising an outer surface;
an inner drive surface; and
an elongate cavity defined between said outer cover and said inner drive surface;
a drive member comprising a cutting edge configured to incise tissue; and
a jaw closure actuator, comprising:
a first portion configured to engage said first jaw; and
a cantilevered beam configured to engage said second jaw, wherein said beam is configured to enter into said elongate cavity through said opening in said proximal end of said anvil and engage said inner drive surface of said anvil to move said anvil into said second position.

19. The disposable loading unit of claim 18, further comprising a shaft, wherein said first jaw and said second jaw extend from said shaft, and wherein said shaft comprises an end configured to be attached to the surgical stapling instrument.

20. The disposable loading unit of claim 18, wherein said jaw closure actuator is configured to contact said second jaw and rotate said second jaw between said first and second positions.

* * * * *